(12) United States Patent
Vater et al.

(10) Patent No.: US 7,879,991 B2
(45) Date of Patent: Feb. 1, 2011

(54) CGRP BINDING NUCLEIC ACIDS

(75) Inventors: Axel Vater, Berlin (DE); Christian Maasch, Berlin (DE); Florian Jarosch, Berlin (DE); Mathias Bell, Berlin (DE); Steffen Helmling, Brookline, MA (US); Bernd Eschgfäller, Basel (CH); Elisabeth Moyroud, Graz (AT); Sandra Stark, Berlin (DE); Sven Klussmann, Berlin (DE); Thorsten Ruppert, Berlin (DE); Gregor Bahrenberg, Aachen-Brand (DE); Clemens Gillen, Roetgen (DE); Klaus Schiene, Düsseldorf (DE)

(73) Assignee: NOXXON Pharma AG, Berlin (DE)

( * ) Notice: Subject to any disclaimer, the term of this patent is extended or adjusted under 35 U.S.C. 154(b) by 869 days.

(21) Appl. No.: 10/513,490

(22) PCT Filed: May 6, 2003

(86) PCT No.: PCT/EP03/04746

§ 371 (c)(1),
(2), (4) Date: Mar. 22, 2006

(87) PCT Pub. No.: WO03/093472

PCT Pub. Date: Nov. 13, 2003

(65) Prior Publication Data

US 2006/0183700 A1    Aug. 17, 2006

(30) Foreign Application Priority Data

May 6, 2002   (DE)   ............................... 102 20 188
Nov. 4, 2002  (DE)   ............................... 102 51 246

(51) Int. Cl.
    *C07H 21/04*   (2006.01)
(52) U.S. Cl. ................. 536/24.5; 536/24.1; 536/24.31; 514/44
(58) Field of Classification Search ............. None
    See application file for complete search history.

(56) References Cited

U.S. PATENT DOCUMENTS 6,207,816 B1 * 3/2001 Gold et al. ................. 536/24.1
6,682,886 B1 * 1/2004 Gold ........................... 435/6
2002/0164707 A1 * 11/2002 Adamou et al. ............ 435/69.1

FOREIGN PATENT DOCUMENTS

WO     WO 92/14843     9/1992

OTHER PUBLICATIONS

Herbison et al. Sexually dimorphic expression of calcitonin gene-related peptide (CGRP) mRNA in rat medial preoptic nucleus. Molecular Brain Research 1995, vol. 34: 143-148.*
Novials et al. Reduction of Islet Amylin Expression and Basal Secretion by Adenovirus-Mediated Delivery of Amylin Antisese cDNA. Pancreas 1998, vol. 17, No. 2: 182-186.*
Pohl et al. Gene therapy of pain: emerging strategies and furture directions. European Journal of Pharmacology 429 2001, pp. 39-48.*
Rusconi et al., "TNA Aptamers as Reversible Antagonists of Coagulation Factor IXa", Nature, Sep. 5, 2002, vol. 419, MacMillion Journals Ltd., London Great Britain.
Brain et al., "CGRP Receptors: A Headache to Study, But Will Antagonists Prove Therapeutic in Migraine", Trends in Pharmacological Sciences, Feb. 2002, vol. 23, No. 2.
Famulok et al., "Aptamers as Tools in Molecular Biology and Immunology", 1999, vol. 243, Seiten 123-136.
Williams et al., "Bioactive and Nuclease-Resistant L-DNA Ligand of Vasopressin", Proceedings of the National Academy of Sciences of USA, National Academy of Science, Oct. 1997, pp. 11285-11290, vol. 94, Washington, DC.
Edvinsson et al., "Characterisation of the Effects of a Non-Peptide CGRP Receptor Antagonist in SK-N-MC Cells and Isolated Human Cerebral Arteries", 2001, vol. 415, pp. 39-44, European Journal of Pharmacology.
Search Report for PCT/EP 03/04746, dated Sep. 16, 2004.

* cited by examiner

*Primary Examiner*—Kimberly Chong
(74) *Attorney, Agent, or Firm*—MDIP LLC

(57) ABSTRACT

The invention relates to an antagonist for CGRP and amylin, whereby the antagonist is a nucleic acid and said nucleic acid binds to CGRP or amylin. Said nucleic acid preferably comprises an L-nucleotide.

25 Claims, 74 Drawing Sheets

Aligned sequences (+) strand

```
5' GGAGCTCAGCCTTCACTGCGAAGTGACGCACGTATGACGTATAGTTTCCATTTTGGACTCCTGGGCACCACGGTCGGATCCAC  168x
5' GGAGCTCAGCCTTCACTGCGAAGTGATGCACGTATGACGTATAGTTTCCATTTTGGACTCCTGGGCACCACGGTCGGATCCAC  1x
5' GGAGCTCAGCCTTCACTGC--AGTGACGCACGTATGACGTATAGTTTCCATTTTGGACTCCTGGGCACCACGGTCGGATCCAC  2x
5' GGAGCTCAGCCTTCACTGCAAAGTGACGCACGTATGACGTATAGTTTCCATTTTGGACTCCTGGGCACCACGGTCGGATCCAC  5x
5' GGAGCTCAGCCTTCACTGCGAAGTGACGCACGTATTATAGTTTCCATTTTGGACTCCTGGGCACCACGGTCGGATCCAC  1x
5' GGAGCTCAGCCTTCACTGCTAAGTGACGCACGTATGACGTATAGTTTCCATTTTGGACTCCTGGGCACCACGGTCGGATCCAC  1x
5' GGAGCTCAGCCCTTCACTGCGAAGTGACGACGCACGTATGACGTATAGTTTCCGTTTTGGACTCCTGGGCACCACGGTCGGATCCAC  1x
5' GGAGCTCAGCCTTCACTGCGAAGTGACGCACGTACGTATGACGTATAGTTTCCATTTTGGACTCCTGGGCACCACGGTCGGATCCAC  1x
   FF primer (19)                                                    REV primer (20)
```

The order of the 8 clones:

| | SEQ ID NO: |
|---|---|
| 666 | 1 |
| 711 | 2 |
| 732 | 3 |
| 669 | 4 |
| 670 | 5 |
| 781 | 6 |
| 836 | 7 |
| 748 | 8 |

Fig. 3 nucleic acid 732 [SEQ ID NO:10]

nucleic acid 732-029 [SEQ ID NO:12]

icid 732-26 [SEQ ID NO:11]

nucleic acid 732-100 [SEQ ID NO:15]

nucleic acid 732-108 [SEQ ID NO:18]

nucleic acid 732-045 [SEQ ID NO:13]

nucleic acid 732-096 [SEQ ID NO:14]

Sequences

```
                                                                                                            SEQ ID NO:
666      GGAGCTCAGCCTTCACTGCGAAGTGACGCACGTATGATAGTTTCCATTTTGGACTCCTGGGCACCACGGTCGGATCCAC         9
732      GGAGCTCAGCCTTCACTGCGAAG---TGACGCACGTATGATAGTTTCCATTTTGGACTCCTGGGCACCACGGTCGGATCCAC       10
732_026  GG----CAGCCTTCACTGCGAG---TGACGCACGTATGATAGTTTCCATTTTGGACTCCTG---------------------CC       11
732_029  GG----CTCAGCCTTCACTGCAG---TGACGCACGTATGATAGTTTCCATTTTGGACTCCTGGGC-----------------C        12
732_045  CG----CTCAGCCTTCACTGCAG---TGACGCACGTATGATAGTTTCCATTTTGGACTCCTG--------------------CG       13
732_096  CG----CTCAGCCTTCACTGCAG---TGACGCACGTATGATAGTTTCCATTTGGACTCCTGGGC------------------G        14
732_100  GG----CAGCCTTC-CTGCAG---GACGCACGTATGATAGTTTCC--TTTGGACTCCTG-----------------------CC       15
732_103  GG----CAGCCTTG-CTGCAG---CACGCACGTATGATAGTTTCC--TTTGGACTCCTG-----------------------CC       16
732_104  GG----CAGCCTTC-CTGCAG---GACGCACGTATGATAGTTTGC--TTTGCACTCCTG-----------------------CC       17
732_109  GG----CAGCCTTG-CTGCAG---CACGCAC-TATGATAGTTTCC--TTTGGACTCCTG-----------------------CC       18

732_070a  GGCAGCCTTCACTG  [SEQ ID NO:19]
732_070b  CAGTGACGCACGTATGATAGTTTCCATTTTGGACTCCTGCC₃₄  [SEQ ID NO:20]
732_071a  GGCAGCCTTCACTGCAGTGACGCACGTATGATAGTTTCCAAG  [SEQ ID NO:21]
732_071b  CTTGGACTCCTGCC₃₄  [SEQ ID NO:22]
```

Fig. 18

| Selection-round | STAR-RNA Selection 02, Neutravidin-Agarose, room temperature | | | | |
|---|---|---|---|---|---|
| | Pre-column [%] | Empty-column [%] | Eluted fraction [%] | RNA:Peptide-ratio | Peptide-concentration [nM] |
| 1 |  |  | 0,8 | 0,5 | 10000 |
| 2 | 0,74 | 0,34 | 0,13 | 0,5 | 10000 |
| 3 | 0,92 | 0,33 | 0,45 | 0,5 | 10000 |
| 4 | 0,31 | 0,45 | 0,69 | 0,5 | 10000 |
| 5 | 2,59 | 0,15 | 2 | 0,5 | 10000 |
| 6 | 2,3 | 0,24 | 12 | 0,5 | 10000 |
| 7 | 0,72 | 0,48 | 9 | 0,5 | 10000 |
| 8 | 0,9 | 0,27 | 25 | 0,5 | 10000 |
| 9 | 1,5 | 0,5 | 32 | 0,5 | 10000 |
| 10 | 0,9 | 0,6 | 25 | 0,5 | 10000 |

Fig. 29

| STAR-RNA Selection 02s rounds 6s-15d, Neutravidin-Agarose, room temperature | | | | | |
|---|---|---|---|---|---|
| Selection-round | Pre-column [%] | Empty-column [%] | Eluted fraction [%] | RNA:Peptide-ratio | Peptide-concentration [nM] |
| 6s | 0,8 | 0,5 | 6,2 | 0,5 | 1000 |
| 7s | 0,23 | 0,1 | 1,7 | 0,5 | 1000 |
| 8s | 0,2 | 0,4 | 1,7 | 0,5 | 100 |
| 9s | 0,5 | 0,1 | 2,1 | 0,5 | 31,6 |
| 10s | 2,6 | 0,04 | 1,1 | 1 | 3,16 |
| 11s | 0,13 | 0,4 | 2,8 | 5 | 3,16 |
| 12s | 0,9 | 0,1 | 2,3 | 5 | 3,16 |
| 13s | 0,2 | 0,09 | 1,2 | 5 | 1 |
| 14s | 0,3 | 0,06 | 1,6 | 5 | 1 |
| 15d | 1,5 | 0,4 | 3,3 | 1 | 1 |

Fig. 31

| STAR-RNA Selection 02MW rounds 8MW-12MW, Streptavidin ultra link and Neutravidin-Agarose | | | | | |
|---|---|---|---|---|---|
| Selection-round | Pre-column [%] | Empty-column [%] | Eluted fraction [%] | RNA:Peptide-ratio | Peptide-concentration [nM] |
| 8MW | 0,7 | 0,08 | 8,5 | 0,5 | 1000 |
| 9MW | 0,6 | 0,1 | 7 | 0,5 | 100 |
| 10MW | 0,4 | 0,02 | 7,1 | 0,5 | 10 |
| 11MW | 0,2 | 0,2 | 4 | 5 | 3,16 |
| 12MW | 0,3 | 0,09 | 1 | 5 | 3,16 |

Fig. 33

STAR-RNA Selection 02xx rounds 10xx-15xx, matrix switch, 37°C

| Selection-round | Pre-column [%] | Empty-column [%] | Eluted fraction [%] | RNA:Peptide-ratio | Peptide-concentration [nM] |
|---|---|---|---|---|---|
| 10xx | 1,6 | 0,16 | 1,5 | 0,5 | 316 |
| 11xx | 1 | 0,5 | 2,7 | 0,5 | 31,6 |
| 12xx | 0,1 | 0,2 | 1,2 | 5 | 31,6 |
| 13xx | 0,5 | 0,7 | 1,3 | 0,5 | 10 |
| 14xx | 1,4 | 0,2 | 2,3 | 0,5 | 1 |
| 15xx | 1 | 0,4 | 4,2 | 0,5 | 3,16 |

Fig. 35

STAR-RNA Selection 03: Parallel 2-step-ligation, Neutravidin-Agarose, room temperature

| Selection-round | Pre-column [%] | Empty-column [%] | Eluted fraction [%] | RNA:Peptide-ratio | Peptide-concentration [nM] |
|---|---|---|---|---|---|
| 1 |  |  | 0,63 | 0,5 | 10000 |
| 2 | 0,62 | 1,5 | 5,47 | 0,5 | 10000 |
| 3 | 3,85 | 2,4 | 0,24 | 0,5 | 10000 |
| 4 | 1,33 | 0,13 | 4,2 | 0,5 | 10000 |
| 5 | 0,1 | 0,25 | 12,1 | 0,5 | 10000 |
| 6 | 1 | 0,44 | 10,7 | 0,5 | 1000 |
| 7 | 0,1 | 0,2 | 1,8 | 0,5 | 100 |
| 8 | 0,2 | 0,2 | 1,7 | 0,5 | 10 |
| 9 | 0,5 | 0,1 | 2,1 | 5 | 3,16 |
| 10 | 0,7 | 0,07 | 2,4 | 5 | 3,16 |
| 11 | 0,8 | 0,5 | 6 | 1 | 1 |

Fig. 37

Spiegelmer STAR-R02-15xx-A11, 37°C

STAR-R03-11-F10, 25°C

| clone # | Sequence | SEQ ID No |
|---|---|---|
| STAR-R02-10-224 | GGACCAACAUGUGAAGAACAUACGGUGGAAGAAACGAUUGUUAGACAGG | 93 |
| STAR-R02-10-225 | GGACAAACCUUGUGUAGAAGGGGUAAUAUACAGUAGUGUAGGAGGACAGG | 94 |
| STAR-R02-10-227 | GGACGUAAUGAUCCGGCGAUAAGUCCAGGAUGUCAGGCCGGAGAGACAGG | 95 |
| STAR-R02-10-228 | GGACGAAUGAAGUACGGCGACGGGUGCACCGGGUGUGAAGUUAGCCGACAGG | 96 |
| STAR-R02-10-229 | GGACGUGUUGAUGCAGCGGGUGAACAUUCACAAACAUCCCUAGCGACAGG | 97 |
| STAR-R02-10-230 | GGACGAUAGUGGUGCUGUAAUUCACCGGAGGGUGGCGAGGGACAGG | 98 |
| STAR-R02-10-231 | GGACAGUGCUGGUGUGCCUGAAUUGCAUAUAAGCAGUGAACACCCGACAGG | 99 |
| STAR-R02-10-232 | GGACCAACAUGUGAAAAACAUACGGUGGAAGAAACGAUUGUUAGAGACAGG | 100 |
| STAR-R02-10-234 | GGACCAAGUAAACCCUGUGAGCCUUGUAAGCGUGUAAAGCGGUGGAAGGACAGG | 101 |
| STAR-R02-10-235 | GGACGACAUGUCCGGGAACAUACGGUGAAAAGAAACGAUUGUCGGACAGG | 102 |
| STAR-R02-10-237 | GGACUAGUGAGCGUGGAGGGCCUCACAAACGAAAGUCCGGGACAGG | 103 |
| STAR-R02-10-239 | GGACGAUUGCGUAGUGAAGUGAAGCAUACGGUGAAAGAAACGAUAUCGGACAGG | 104 |
| .GGACUAUACGGUGAAAGAACGUGAGGCGUUAGGAGGAAACGCUAGGACAGG | 105 |
| STAR-R02-10-240 | GGACGAACGUGCUGGUGCAGCGGUGACUUAGUCGAACACCCCUGGGGACAGG | 106 |
| STAR-R02-10-243 | GGACGCCAAAAUCAGGAAGGAGAGAAAAGGAAAUGCGUAGCGCGACAGG | 107 |
| STAR-R02-10-244 | GGACAAUCCUGUGUGGAGUAGGGGGCCUAGUAGCCUAGUGGACAGG | 108 |
| STAR-R02-10-248 | GGACGAUCCUGUGUGGAGUAGGGGGCCUAGUAGCCUAGUGGACAGG | 109 |
| STAR-R02-10-249 | GGACCUUUAGCUGCGUAGUGGAAAGAAGGUGGCAGCCUCCGACAGG | 110 |
| STAR-R02-10-250 | GGACUUGAUGACGCGAGUAACGUCGUCUCAAUCAAGGAGACAGG | 111 |
| STAR-R02-10-251 | GGACCAGUGGUGACGGUGACGCGGCCUGGGCGCGCAGCGCCGGACGUCGACAGG | 112 |
| STAR-R02-10-252 | GGACAGAGGAACGUAGUAGGGGUAGAGGAAAUAAACCACCCUCUCUGGAGACAGG | 113 |
| STAR-R02-10-254 | GGACUAUAUUAAGGCCGGGUAGAGAUACGCCCUGGCGCCUAGGAACAAGGCGACAGG | 114 |
| STAR-R02-10-255 | GGACUGAUCCUGUGUGGAGUAGCGGAGUAGGGGCCCAGUGGCCUAGUGGCCGACAGG | 115 |
| STAR-R02-10-257 | GGACGAUCCUGUGAUGCAGCGGUGGACAUUCACAAACAUCCCUGGCGACAGG | 116 |
| STAR-R02-10-258 | GGACGUGUUGAUGCAGCGGUGGACAUUCACAAACAUCCCUGGCGACAGG | 117 |
| STAR-R02-10-259 | GGACCCUGCUCGAUGAGAGAGAAGCGAUUCCCGGUGAAAGAACGAUGGACAGG | 118 |
| STAR-R02-10-261 | GGACAUACGAUCGAAGACGACAGAAGCGAUCCCGUGCUCGUAGCGGAUGGGACAGG | 119 |
| STAR-R02-10-263 | GGACGAUCCUGUGGAGUAGGUGGUGGAUCCAAGAGGUCUAGUAGACCUAGGACAGG | 120 |
| STAR-R02-10-264 | GGACAGUGAUGGCGCAGCGGUGUAACCAAGAGGUAGAACGGAGACAGG | 121 |
| STAR-R02-10-266 | GGACUGAUUCUCAGAGAAUACGAUGAAAGAAGCGAUUCAGUCUGGACAGG | 122 |
| STAR-R02-10-267 | | |

Fig. 43

| clone # | sequence | SEQ ID No |
|---|---|---|
| STAR-R02-10-268 | GGACACAACUCGAAGGAGAUGGAGGUAGGACAGCGGGGUUGUGACAGG | 123 |
| STAR-R02-10-270 | GGACCAACAUGUGAAAGCAUACGGUGAAAGAAACGAUUGUUGAGACAGG | 124 |
| STAR-R02-10-271 | GGACGUGAUGGCCAGCGACUGACACAAGGAUCAGAACGCCCCGACAGG | 125 |
| STAR-R02-10-272 | GGACGAACUGGUAGGGUGGCUGCCCUAUACGAUGAAAGAAGCGAGACAGG | 126 |
| STAR-R02-10-274 | GGACUUGAUGACGCGAGUUAACGUCGCUGUCUCUCAAUCAAGGGACAGG | 127 |
| STAR-R02-10-275 | GGACGACUGAUGGCGCGUCGUAAGGAGAUGGUAGGUAGGACAGCGGACAGG | 128 |
| STAR-R02-10-276 | GGACACAACUCGAAGGAGAUGGAGGUAGGACAGCGGGAGUUGUGACAGG | 129 |
| STAR-R02-10-278 | GGACGAUUGCGUAGUGGGAGCAUACGGUGAAAGAAACGAUAUCGACAGG | 130 |
| STAR-R02-10-280 | GGACAUAUGGUGAAAAGAAACAAUACUCCGUUAGUAGGAGUGGACAGG | 131 |
| STAR-R02-10-283 | GGACGUGUUGAUGCAGCAGCAGUAAACGGCAGUUACGAACAUCCGGCGACAGG | 132 |
| STAR-R02-10-286 | GGACGUGUUGAUGACCAGCAGUACGGCUGAUGGAGAAAACCGCUAAGGACGUAGACAGG | 133 |
| STAR-R02-10-287 | GGACACUCUCAGCGCGGUGAAUAAACGCCCCCUGUAACAGAUGACAGG | 134 |
| STAR-R02-10-288 | GGACAACGAAGUAAACCUUAGGCGACCCGCAUGAAGGCGGUUGGACAGG | 135 |
| STAR-R02-10-289 | GGACAUACGGUGAAAGAAACGAUUCGGAACUUCGAAUCCGAUGGACAGG | 136 |
| STAR-R02-10-291 | GGACGAAUGAAACGCGCACCGGGAGCGUGAAGUUAGCGUGAGACAGG | 137 |
| STAR-R02-10-292 | GGACCAACAUGUAAAGACGGUGAAGAACAUACGGUGAAGAAUGUUGAGACAGG | 138 |
| STAR-R02-10-293 | GGACGACAUGUUCCGAGAACAUACGGUGAACAUAACGGUGAAAUAAACGAUUGUCAGACAGG | 139 |
| STAR-R02-10-294 | GGACCAACAUGUAAGACAUAAGAGCGUACGGCUUGCCAGGGGUCAGACAGG | 140 |
| STAR-R02-10-295 | GGACGACCCAUCAAGAAGAUGAAGAGCGUACGCCUUGCGCAGGGGUCAGACAGG | 141 |
| STAR-R02-10-296 | GGACCGUGUGUUAGUCUGCGGAUAUAAAAACACUGCUGUCUAUGGGACAGG | 142 |
| STAR-R02-10-297 | GGACGAGGUGCUGGCGGCCUGCCUAAGCCUUGUAAAGCGGUGGAAGGACAGG | 143 |
| STAR-R02-10-298 | GGACCAAGUAAACCCUGUAAGCCUUGUAAGCGGACGACGGAAGGGACAGG | 144 |
| STAR-R02-10-300 | GGACAACCCGUCAAGGAUGAAGAGCGUACGCUUGCCAGGUUCGACAGG | 145 |
| STAR-R02-10-303 | GGACGAGAUGGCGUAAUAAGAGUGGGCGAAAAUAGCGAAAGCCCGACAGG | 146 |
| STAR-R02-10-304 | GGACUCUCUGAUGGCGCGAGACGCGGAGAGAAUAUACGCCACUGUCGUGAGACAGG | 147 |
| STAR-R02-10-307 | GGACGAACGAGCAUGGGGGUGAGACGGCGCUAGUUCGGGAUCCGCGGGACAGG | 148 |
| STAR-R02-10-310 | GGACGACGAGGAAUUGGUGGGGAUGGGGUGAGGAUCCGAAAAGAACGGGACAGG | 149 |
| STAR-R02-10-311 | GGACGAUCAUAGUGAGACAUACGGUGAAAGACGUGAAAAGACAAACACCCUGGACAGG | 150 |
| STAR-R02-10-314 | GGACGUGAUGGUCAGCGAGUAUCGGGUUAAGACGCGUUAAGACAAACACCCCUGGACAGG | 151 |
| STAR-R02-10-315 | GGACAUACGAUGAGAGAAGCGAUUCCCGCUGCUAACGGGAUGUCGACAGG | 152 |

Fig. 44

| clone # | sequence | SEQ ID No |
|---|---|---|
| STAR-R02-10-318 | GGACAUACGAUGAAAGAAGCGAUCCCGCUGACGGGAUGUCGACAGG | 153 |
| STAR-R02-12MW-A1 | GGACGACAUGUUCCGAACAUACGGUGAAAGAAACGAUUAUCGGACAGG | 154 |
| STAR-R02-12MW-A4 | GGACGACAUGCUCCAGGAGCAACAUACGGUGAAAGAAACGAUUGUCGGACAGG | 155 |
| STAR-R02-12MW-A5 | GGACGACAUGUUCCAGGAACAUACGGUGAAAGAAACGAUUGUCGGACAGG | 156 |
| STAR-R02-12MW-B5 | GGACGAUAUGUUCCAAGAACAUACGGUGAAAGAAACGAUUGUCGGACAGG | 157 |
| STAR-R02-12MW-D2 | GGACAUACGAUGAAAGAAGCGAUUCCCGCUGACGGGAUGUCGACAGG | 158 |
| STAR-R02-12MW-E1 | GGACUACAAGCCAACAAAUCCUUGCCCACUGAGGAUCUGCUGUCGACAGG | 159 |
| STAR-R02-12MW-E3 | GGACUCAUACGGUGAAAGAAACGAUUCGUCUUGUGACGAUGAGGACAGG | 160 |
| STAR-R02-12MW-E4 | GGACAUACGGUUCGGGAAAGAAACGAUACGGUGAAAGAAACGAUUGUCGGACAGG | 161 |
| STAR-R02-12MW-F3 | GGACAUACGGUGAAAGAAACGAUACGAAUUGUGUCCCGACAGG | 162 |
| STAR-R02-12MW-F4 | GGACGAUUGCAUACUAAAGCAUACGGUGAAAGAAACGAUAUCGGACAGG | 163 |
| STAR-R02-12MW-F6 | GGACUCAUACGGUGAAAGAAACGAUUCGUCUUAACGAUGAGGACAGG | 164 |
| STAR-R02-12MW-G1 | GGACUAAGUGAGCCAAGUCAGCGGAUGUCCAUAACUUGUCGACAGG | 165 |
| STAR-R02-12MW-H1 | GGACAUACGGUGAAAGAAACGAUAAUUAUGUUCCUGUCCAAGACAGG | 166 |
| STAR-R02-12MW-H2 | GGACGAUUGCACAAUGAGANACGAUACGGUGAAAGAAACGAUAUCGGACAGG | 167 |
| STAR-R02-15d-A1 | GGACGACAUGUUCUAUGAACAUACGGUGAAAGAAACGAUAUCGGACAGG | 168 |
| STAR-R02-15d-A10 | GGACGACAUGCAUAGUAAGAGACAUACGGUGAAAGAAACGAUUGUCGGACAGG | 169 |
| STAR-R02-15d-A12 | GGACGACAUGUUCCAGGAACAUACGGUGAAAGAAACGAUAUCGGACAGG | 170 |
| STAR-R02-15d-A2 | GGACGACAUGUUCUAGGAAGAAGACAUACGGUGAAAGAAACGAUUGUCGGACAGG | 171 |
| STAR-R02-15d-A9 | GGACAUACGAUGAAGAAGAAGCGAUUCCCGCUACUAGGAUGUCGGACAGG | 172 |
| STAR-R02-15d-B11 | GGACCAACAUGCAAAGAAGCGAUACAAUCGGUGAAAGAAACGAUUGUGACAGG | 173 |
| STAR-R02-15d-B3 | GGACAUACGGUGAAAGAAAAAAGCAUACGGUGAAACUUCGAUUCCGAUGGACAGG | 174 |
| STAR-R02-15d-C10 | GGACGAUUGCAUAAUAAAGCAUACGGUGAAAGAAACGAUAUCGGACAGG | 175 |
| STAR-R02-15d-C9 | GGACGACAUGUUCUAAGGAACAUACGGUGAAAGAAACGAUUGUCGGACAGG | 176 |
| STAR-R02-15d-D10 | GGACGACAUGUUCCAAGGAACAUACGGUGAAAGAAACGAUUGUCGGACAGG | 177 |
| STAR-R02-15d-D7 | GGACGACAUGGAAGAGCAUACGGUGAAAGAAACGAUUCGUUGAGACAGG | 178 |
| STAR-R02-15d-D9 | GGACAACAACAUGUGCAUACGGUGAAACGAUACGAAUAUCGGACAGG | 179 |
| STAR-R02-15d-E11 | GGACGAUUGCAUAGUGGUCAUACGGUGAAAGCAUAGGUGAAAGAAACGAUAUCGGACAGG | 180 |
| STAR-R02-15d-E12 | GGACGACAUGUUCAAAGAACAUACGGUGAAAGAAACGAUAUCGGACAGG | 181 |
| STAR-R02-15d-E3 | GGACCAUACGAUGAAAGAAGAGCGAUACUGCACCAGAAGCAGUUGGGACAGG | 182 |

Fig. 45

| clone # | sequence | SEQ ID No |
|---|---|---|
| STAR-R02-15d-F8 | GGACGAUUGCAUUAAGAGCAUACGGUGAAAGAAGAUAUCGGACAGG | 183 |
| STAR-R02-15d-F9 | GGACGACAUGUUCCGAGAACAUACGGUGAAAGAACGAUUGUCGGACAGG | 184 |
| STAR-R02-15d-G1 | GGACGAUUGCAUAGUAGAAGCAUACGGUGAAAGAAACGAUAUCGGACAGG | 185 |
| STAR-R02-15d-G12 | GGACUCAUACGGUGAAAGAAACGAUUCGUCUUGACGAUGAGGACAGG | 186 |
| STAR-R02-15d-G2 | GGACAUACGAUGAAAGAAGCGAUUCCCGUACUAGCGGAUGUCGGACAGG | 187 |
| STAR-R02-15d-H1 | GGACGACAUGUCCCAGAACAUACGGUGAAAGAAACGAUUGUCGGACAGG | 188 |
| STAR-R02-15d-H7 | GGACAUACGGUGAAAGAACGAUAUCGGACUUGAGUCCGAUGGACAGG | 189 |
| STAR-R02-15d-H9 | GGACGAUUGCAUAAUAAGAGCAUACGGUGAAAGAACGAUAUCGGACAGG | 190 |
| STAR-R02-15xx-A11 | GGACUGAUGCGGCGCGUCAAAAACGCCGAUAGGGUGAGGGACAGG | 191 |
| STAR-R02-15xx-A7 | GGACUGAUGCGGCGCGUCUUAAAAAAACGCCGAUGGGUGAGGGACAGG | 192 |
| STAR-R02-15xx-B10 | GGACUCAUACGGUGAAAGAAACGAUUCGUCUAGCGACGAUGAGGACAGG | 193 |
| STAR-R02-15xx-B7 | GGACUCAUACGGUGAAAGAAACGAUUCGUCUUAGCGNCGAUGAGGACAGG | 194 |
| STAR-R02-15xx-C7 | GGACUGAUGGCGCGGUNCAAAAAACCCGAUAGGGUGAGGGACAGG | 195 |
| STAR-R02-15xx-C9 | GGACUGAUGGCGCGGUCUCAAAAAACGCCGUAGGGUGAGGGACAGG | 196 |
| STAR-R02-15xx-D8 | GGACAGACGAUGGCGCGUCGUAAAAUCAUCGGAAGGGAUGGAGGACAGG | 197 |
| STAR-R02-15xx-E9 | GGACUGAUGGCGCGGUCGUAAAUAUACGCCGAUAACUGGGAAGUGGACAGG | 198 |
| STAR-R02-15xx-F12 | GGACUGAUGGCGCGGUCCUAUACGCCGAAAGGGAGAGGGAGACAGG | 199 |
| STAR-R02-15xx-F7 | GGACUGAUGGCGCGGUCUUAAAAACGCCGAUAAGGGUGAGGGACAGG | 200 |
| STAR-R02-15xx-G10 | GGACAGACGAUGGCCAUGAAAGAAACCAUCGGAAGGGAUGAGGACAGG | 201 |
| STAR-R02-15xx-G12 | GGACUCAGACGAUGAAAGAAACGAUUCGUCUUAGGACGAUGAGGACAGG | 202 |
| STAR-R02-15xx-G7 | GGACAGACGAUGNCCGUAAACAUCGGGAAAGGGCAUGGAGGGUACAGG | 203 |
| STAR-R03-11-A4 | GGACGACAUGUUCGAGAACAUACGGUGAAAGAAACGAUUGCGGACACAGG | 204 |
| STAR-R03-11-A6 | GGACGACAUGUUCCGAGAACAUACGGUGAAAGAAACCCCGUACAGCGGACAGG | 205 |
| STAR-R03-11-A7 | GGACGACAUGUUCAAAAGAACAUACGGUGAAAGAACGAUUGUCGGACAGG | 206 |
| STAR-R03-11-B10 | GGACAUACGGUGAAAGAACAUGAAAGAUAUUAUGUCCCGAGACAGG | 207 |
| STAR-R03-11-B7 | GGACAUACGGUGAAAGAACGAUUCUCGCUAGCGAGAUGUCGACAGG | 208 |
| STAR-R03-11-C12 | GGACGACAUGUUCCAGGAACAUACGGAACAUAGGAAGAAACGAUUGUCGGACAGG | 209 |
| STAR-R03-11-C6 | GGACGACAUGUUCGAGAAACAUACGGUGAAAGAAACGAUUGUCGGACAGG | 210 |
| STAR-R03-11-C7 | GGACAUACGGUGAAAGAAACGGAUUCGAUUACCAAUCCGAUGGACAGG | 211 |
| STAR-R03-11-C8 | GGACUCAUACGGUGAAAGAACGAUUCGUCGUUAGCGACGAUGAGGACAGG | 212 |

Fig. 46

| clone # | sequence | SEQ ID No |
|---|---|---|
| STAR-R03-11-C9 | GGACGACAUGUUCCAAGAACACAUACGGUGAAAGAAACGAUUGUCGGACACAGG | 213 |
| STAR-R03-11-D5 | GGACGACAUGUUCAUAGAACAUACGGUGAAAGAAACGAUUGUCAGACACAGG | 214 |
| STAR-R03-11-E11 | GGACGACAUGUUCUAGGAACAUACGGUGAAAGAAACGAUUGUCGGACACAGG | 215 |
| STAR-R03-11-E5 | GGACGACAUGUUCCAUGGAACAUACGGUGAAACGGUGAAAGAAACGAUUGUCGGACACAGG | 216 |
| STAR-R03-11-E6 | GGACGACAUGUUCAGGGAACAUACGGUGAAAGAAACGAUUGUCGGACACAGG | 217 |
| STAR-R03-11-E7 | GGACAGACGAUGCCCUUAAAUCACGGGAAAGGGAUGGAGGGACACAGG | 218 |
| STAR-R03-11-E8 | GGACGACAUGUUCUAGGAACAUACGGUGAAAGAAGCGAUUGUCGGACACAGG | 219 |
| STAR-R03-11-F10 | GGACAUACGGUGAAAGAAACGAUACAUAAUUAUGUGUCCCGAGACACAGG | 220 |
| STAR-R03-11-F5 | GGACGUCCAUACGGUGAAAGAAACGAUAGGGAUAGACUCCCUUGGACACAGG | 221 |
| STAR-R03-11-F6 | GGACAUACGGUGAAAGAAACGAUUCGGAACUUCGAUUCCGAUGGACACAGG | 222 |
| STAR-R03-11-F7 | GGACGACAUGUUCUACGAACAUACGGUGAAAGAAACGAUUGUCGGACACAGG | 223 |
| STAR-R03-11-G10 | GGACCAACGCCUUAAGCAACAAACCCCACUACACUACACUACCUUAAGCGUCGAGCGACACAGG | 224 |
| STAR-R03-11-G12 | GGACAUACGGUGAAAGAAACGAUUCCCACUACGGAUUCCCACUACGGAUUGUCGGACACAGG | 225 |
| STAR-R03-11-G4 | GGACGACAUGUUCAAGGAACAUACGGUGAAAGAAACGAUUGUCGGACACAGG | 226 |
| STAR-R03-11-G8 | GGACGACAUGUUCAGAGAACAUACGGUGAAAGAAACGAUUGUCAGACACAGG | 227 |
| STAR-R03-11-G9 | GGACAUACGAUGAAGAAGCGAUUCCCGUUGCUAGCGGUGAUGCGACACAGG | 228 |
| STAR-R03-11-H12 | GGACCAUUAUCCCCAGGAUAUACGGUGAAAGAAACGAUAUGGACACAGG | 229 |
| STAR-R03-11-H5 | GGACGACAUGUUCAAGAACAUACGGUGAAAGAAACGAUUGUCGGACACAGG | 230 |
| STAR-R03-11-H9 | GGACGACAUGUUCAGAACAUACGGUGAAAGAAACGAUUGUCGGACACAGG | 231 |
| STAR-R03-11-F10-45-001 | CGGGACAUACGGUGAAAGAAACGAUACAUAAUUAUGUGUCCCG | 232 |
| STAR-R03-11-C12-48-001 | GGCCGACAUGUUCCCAGGAACAUACGGUGAAAGAAACGAUUGUCGUCC | 233 |

NOX-504 [SEQ ID NO:250]
GGACUGAUGGCGCGGUCCUAUUACGCCGA-AAGGGAGAGGGG-AGACAGG

NOX-504-ad3 [SEQ ID NO:251]
GGACUGAUGGCGCGGUCCUAUUACGCCGA-AAGGGAGAGGGG-AGCACGG

Grt2-STAR-504-5-B0.1-C10 [SEQ ID NO:252]
GGACUGAUGGCGCGGUCCUAUUACGCCGAGAAGGGAGUGGGGAGCACGG

Fig. 63

| | | |
|---|---|---|
| L097 | GGACUGAUGGCGCGGUCCUAUUACGCCGAGAAGGGAGUGGGGGA | [SEQ ID NO:253] |
| L102 | GGACUGAUGGCGCGGUCCUAUUACGCCGAGAAGGGAGAGGGG-A | [SEQ ID NO:254] |
| L103 | GGACUGAUGGCGCGGUCCUAUUACGCCGA-AAGGGAGAGGGGGA | [SEQ ID NO:255] |
| L104 | GGACUGAUGGCGCGGUCCUAUUACGCCGA-AAGGGAGUGGGG-A | [SEQ ID NO:256] |
| L105 | GGACUGAUGGCGCGGUCCUAUUACGCCGA-AAGGGAGUGGGGGA | [SEQ ID NO:257] |
| L106 | GGACUGAUGGCGCGGUCCUAUUACGCCGAGAAGGGAGUGGGG-A | [SEQ ID NO:258] |
| L107 | GGACUGAUGGCGCGGUCCUAUUACGCCGAGAAGGGAGAGGGGGA | [SEQ ID NO:259] |
| L108 | GGACUGAUGGCGCGGUCCUAUUACGCCGAGUAGGGAGUGGGGGA | [SEQ ID NO:260] |
| L109 | GGACUGAUGGCGCGGUCCUAUUACGCCGAGAAGGGUGUGGGGGA | [SEQ ID NO:261] |

Fig. 65

SEQUENCE LISTING

```
<160> NUMBER OF SEQ ID NOS: 286

<210> SEQ ID NO 1
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: clone 666
<220> FEATURE:
<221> NAME/KEY: misc_feature
<223> OTHER INFORMATION: all pyrimidines 2'-fluoro modified

<400> SEQUENCE: 1
ggagcucagc cuucacugcg aagugacgca cguaugauag uuuccauuuu ggacuccugg      60
gcaccacggu cggauccac                                                  79

<210> SEQ ID NO 2
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: clone 711
<220> FEATURE:
<221> NAME/KEY: misc_feature
<223> OTHER INFORMATION: all pyrimidines 2'-fluoro modified

<400> SEQUENCE: 2
```
ggagcucagc cuucacugcg aagugaugca cguaugauag uuuccauuuu ggacuccugg    60
gcaccacggu cggauccac                                                79

<210> SEQ ID NO 3
<211> LENGTH: 77
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: clone 732
<220> FEATURE:
<221> NAME/KEY: misc_feature
<223> OTHER INFORMATION: all pyrimidines 2'-fluoro modified

<400> SEQUENCE: 3
ggagcucagc cuucacugca gugacgcacg uaugauaguu uccauuuugg acuccgggc    60 accacggucg gauccac                                                  77

<210> SEQ ID NO 4
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: clone 669
<220> FEATURE:
<221> NAME/KEY: misc_feature
<223> OTHER INFORMATION: all pyrimidines 2'-fluoro modified

<400> SEQUENCE: 4
ggagcucagc cuucacugca aagugacgca cguaugauag uuuccauuuu ggacuccugg   60
gcaccacggu cggauccac                                                79

<210> SEQ ID NO 5
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: clone 670
<220> FEATURE:
<221> NAME/KEY: misc_feature
<223> OTHER INFORMATION: all pyrimidines 2'-fluoro modified

<400> SEQUENCE: 5
ggagcucagc cuucacugcg aagugacgca cguauuauag uuuccauuuu ggacuccugg   60
gcaccacggu cggauccac                                                79

<210> SEQ ID NO 6
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: clone 781
<220> FEATURE:
<221> NAME/KEY: misc_feature
<223> OTHER INFORMATION: all pyrimidines 2'-fluoro modified

<400> SEQUENCE: 6
ggagcucagc cuucacugcu aagugacgca cguaugauag uuuccauuuu ggacuccugg    60
gcaccacggu cggauccac    79

<210> SEQ ID NO 7
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: clone 836
<220> FEATURE:
<221> NAME/KEY: misc_feature
<223> OTHER INFORMATION: all pyrimidines 2'-fluoro modified

<400> SEQUENCE: 7
ggagcucagc cuucacugcg aagugacgca cguaugauag uuuccguuuu ggacuccugg    60
gcaccacggu cggauccac    79

<210> SEQ ID NO 8
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: clone 748
<220> FEATURE:
<221> NAME/KEY: misc_feature
<223> OTHER INFORMATION: all pyrimidines 2'-fluoro modified

<400> SEQUENCE: 8
ggagcucagc cuucacugcg aagugacgua cguaugauag uuuccauuuu ggacuccugg    60
gcaccacggu cggauccac    79

<210> SEQ ID NO 9
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 666
<220> FEATURE:
<221> NAME/KEY: misc_feature
<223> OTHER INFORMATION: all pyrimidines 2'-fluoro modified

<400> SEQUENCE: 9
ggagcucagc cuucacugcg aagugacgca cguaugauag uuuccauuuu ggacuccugg    60
gcaccacggu cggauccac    79

<210> SEQ ID NO 10
<211> LENGTH: 77
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732
<220> FEATURE:
<221> NAME/KEY: misc_feature
<223> OTHER INFORMATION: all pyrimidines 2'-fluoro modified

```
<400> SEQUENCE: 10
ggagcucagc cuucacugca gugacgcacg uaugauaguu uccauuuugg acuccugggc       60
accacggucg gauccac                                                      77

<210> SEQ ID NO 11
<211> LENGTH: 55
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_026
<220> FEATURE:
<221> NAME/KEY: misc_feature
<223> OTHER INFORMATION: all pyrimidines 2'-fluoro modified

<400> SEQUENCE: 11
ggcagccuuc acugcaguga cgcacguaug auaguuucca uuuggacuc cugcc            55

<210> SEQ ID NO 12
<211> LENGTH: 59
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_029
<220> FEATURE:
<221> NAME/KEY: misc_feature
<223> OTHER INFORMATION: all pyrimidines 2'-fluoro modified

<400> SEQUENCE: 12
ggcucagccu ucacugcagu gacgcacgua ugauaguuuc cauuuggac uccugggcc        59

<210> SEQ ID NO 13
<211> LENGTH: 55
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_045
<220> FEATURE:
<221> NAME/KEY: misc_feature
<223> OTHER INFORMATION: all pyrimidines 2'-fluoro modified

<400> SEQUENCE: 13
cgcagccuuc acugcaguga cgcacguaug auaguuucca uuuggacuc cugcg            55

<210> SEQ ID NO 14
<211> LENGTH: 59
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_096
<220> FEATURE:
<221> NAME/KEY: misc_feature
<223> OTHER INFORMATION: all pyrimidines 2'-fluoro modified

<400> SEQUENCE: 14
cgcucagccu ucacugcagu gacgcacgua ugauaguuuc cauuuggac uccugggcg        59
```

```
<210> SEQ ID NO 15
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_100
<220> FEATURE:
<221> NAME/KEY: misc_feature
<223> OTHER INFORMATION: all pyrimidines 2'-fluoro modified

<400> SEQUENCE: 15
ggcagccuuc cugcaggacg cacguaugau aguuccuuuu ggacuccugc c        51

<210> SEQ ID NO 16
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_103
<220> FEATURE:
<221> NAME/KEY: misc_feature
<223> OTHER INFORMATION: all pyrimidines 2'-fluoro modified

<400> SEQUENCE: 16
ggcagccuug cugcagcacg cacguaugau aguuccuuu ggacuccugc c         51

<210> SEQ ID NO 17
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_104
<220> FEATURE:
<221> NAME/KEY: misc_feature
<223> OTHER INFORMATION: all pyrimidines 2'-fluoro modified

<400> SEQUENCE: 17
ggcagccuuc cugcaggacg cacguaugau aguuugcuuu gcacuccugc c        51

<210> SEQ ID NO 18
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_108
<220> FEATURE:
<221> NAME/KEY: misc_feature
<223> OTHER INFORMATION: all pyrimidines 2'-fluoro modified

<400> SEQUENCE: 18
ggcagccuug cugcagcacg cacuaugaua guuuccuuug gacuccugcc          50

<210> SEQ ID NO 19
<211> LENGTH: 14
<212> TYPE: RNA
<213> ORGANISM: Artificial Sequence
<220> FEATURE:
<223> OTHER INFORMATION: CGRP-binding nucleic acid
```

-continued

```
<220> FEATURE:
<221> NAME/KEY: misc_feature
<223> OTHER INFORMATION: laboratory code: sequence 732_070a
<220> FEATURE:
<221> NAME/KEY: misc_feature
<223> OTHER INFORMATION: all pyrimidines 2'-fluoro modified

<400> SEQUENCE: 19
ggcagccuuc acug                                                          14

<210> SEQ ID NO 20
<211> LENGTH: 41
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_070b
<220> FEATURE:
<221> NAME/KEY: misc_feature
<223> OTHER INFORMATION: all pyrimidines except for 3'-terminal C
      2'-fluoro modified

<400> SEQUENCE: 20
cagugacgca cguaugauag uuuccauuuu ggacuccugc c                             41

<210> SEQ ID NO 21
<211> LENGTH: 42
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_071a
<220> FEATURE:
<221> NAME/KEY: misc_feature
<223> OTHER INFORMATION: all pyrimidines 2'-fluoro modified

<400> SEQUENCE: 21
ggcagccuuc acugcaguga cgcacguaug auaguuucca ag                            42

<210> SEQ ID NO 22
<211> LENGTH: 14
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: sequence 732_071b
<220> FEATURE:
<221> NAME/KEY: misc_feature
<223> OTHER INFORMATION: all pyrimidines except for 3'-terminal C
      2'-fluoro modified

<400> SEQUENCE: 22
cuuggacucc ugcc                                                          14

<210> SEQ ID NO 23
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: family #1
<220> FEATURE:
<221> NAME/KEY: misc_feature
```

<223> OTHER INFORMATION: all pyrimidines 2'-fluoro modified

<400> SEQUENCE: 23
gggaauucga gcucgguacc uuaacccgua uggggucacu guuucgauuu cauucgccuu    60
aucgagccga uucacuugcg cugcaggcau gaagcuugg    99

<210> SEQ ID NO 24
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: family #2
<220> FEATURE:
<221> NAME/KEY: misc_feature
<223> OTHER INFORMATION: all pyrimidines 2'-fluoro modified

<400> SEQUENCE: 24
gggaauucga gcucgguacc uuguuaccca cuguuuagua ucucgcgaua cucauuaccg    60
agacacaguc ccauuacugc cugcaggcau gaagcuugg    99

<210> SEQ ID NO 25
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: family #3
<220> FEATURE:
<221> NAME/KEY: misc_feature
<223> OTHER INFORMATION: all pyrimidines 2'-fluoro modified

<400> SEQUENCE: 25
gggaauucga gcucgguacc gcacuuucgu uacauacgau auacugggcu auagcuauc    60 cuugugccua cagguacugc ugcaggcaug aagcuugg    98

<210> SEQ ID NO 26
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: family #4
<220> FEATURE:
<221> NAME/KEY: misc_feature
<223> OTHER INFORMATION: all pyrimidines 2'-fluoro modified

<400> SEQUENCE: 26
gggaauucga gcucgguacc uacugcucga cuaauugucu aguacaauau gcuuaccaca    60
uuaucuguua gugagcuccc ugcaggcaug aagcuugg    98

<210> SEQ ID NO 27
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: family #5
<220> FEATURE:

<221> NAME/KEY: misc_feature
<223> OTHER INFORMATION: all pyrimidines 2'-fluoro modified

<400> SEQUENCE: 27
gggaauucga gcucgguacc uuguucugac ucuguuuaug cguuuccgc gucuuuaccg    60 gacuccuucu uccccagugc cugcaggcau gaagcuugg                          99

<210> SEQ ID NO 28
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: family #6
<220> FEATURE:
<221> NAME/KEY: misc_feature
<223> OTHER INFORMATION: all pyrimidines 2'-fluoro modified

<400> SEQUENCE: 28
gggaauucga gcucgguacc uaucgucgaa cauucgaucu guuuuacgu aaguaacuuu    60 accguccucg uuuucccgc cugcaggcau gaagcuugg                           99

<210> SEQ ID NO 29
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: family #7
<220> FEATURE:
<221> NAME/KEY: misc_feature
<223> OTHER INFORMATION: all pyrimidines 2'-fluoro modified

<400> SEQUENCE: 29
gggaauucga gcucgguacc aaacaucacu uacaugugcu cugcguuuuu ugcauaguuu   60
uuuggucgag cgcuuccucc cugcaggcau gaagcuugg                          99

<210> SEQ ID NO 30
<211> LENGTH: 96
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: family #8
<220> FEATURE:
<221> NAME/KEY: misc_feature
<223> OTHER INFORMATION: all pyrimidines 2'-fluoro modified

<400> SEQUENCE: 30
gggaauucga gcucgguacc gcggagucug ucacaagauc ucguccuuau cguugaugua   60
ucguacaagu cuuugcccug caggcaugaa gcuugg                             96

<210> SEQ ID NO 31
<211> LENGTH: 97
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: family #9

```
<220> FEATURE:
<221> NAME/KEY: misc_feature
<223> OTHER INFORMATION: all pyrimidines 2'-fluoro modified
<220> FEATURE:
<221> NAME/KEY: misc_feature
<222> LOCATION: (31)..(31)
<223> OTHER INFORMATION: any nucleotide
<220> FEATURE:
<221> NAME/KEY: misc_feature
<222> LOCATION: (51)..(51)
<223> OTHER INFORMATION: any nucleotide

<400> SEQUENCE: 31
gggaauucga gcucgguacc uaauacgacu nacuauaggg aauucgagcu ngguaccuua    60
acccguaugg gguuacugcu gcaggcauga agcuugg                            97

<210> SEQ ID NO 32
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: familiy #10
<220> FEATURE:
<221> NAME/KEY: misc_feature
<223> OTHER INFORMATION: all pyrimidines 2'-fluoro modified

<400> SEQUENCE: 32
gggaauucga gcucgguacc aaugccugcu uuguuugag uuuccuuca cacuagggau     60 ggauaauaca guccuuaccc ugcaggcaug aagcuugg                           98

<210> SEQ ID NO 33
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156750.seq
<220> FEATURE:
<221> NAME/KEY: misc_feature
<223> OTHER INFORMATION: all pyrimidines 2'-fluoro modified

<400> SEQUENCE: 33
gggaauucga gcucgguacc uuaacccgua uggggucacu guuucgauuu cauucgccuu    60
cucgagcuga uucacuugcg cugcaggcau gaagcuugg                           99

<210> SEQ ID NO 34
<211> LENGTH: 100
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156701.seq
<220> FEATURE:
<221> NAME/KEY: misc_feature
<223> OTHER INFORMATION: all pyrimidines 2'-fluoro modified

<400> SEQUENCE: 34
gggaauucga gcucgguacc uuaacccgua uggggucacu gguuucgauu ucauucgccu    60
uaucgagcug auucacuugc gcugcaggca ugaagcuugg                         100
```

```
<210> SEQ ID NO 35
<211> LENGTH: 100
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156698.seq
<220> FEATURE:
<221> NAME/KEY: misc_feature
<223> OTHER INFORMATION: all pyrimidines 2'-fluoro modified

<400> SEQUENCE: 35
gggaauucga gcucgguacc uuaacccgua uggggucac uguuucgauu ucauucgccu      60
uaucgagcug auucacuugc gcugcaggca ugaagcuugg                          100

<210> SEQ ID NO 36
<211> LENGTH: 100
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156707.seq
<220> FEATURE:
<221> NAME/KEY: misc_feature
<223> OTHER INFORMATION: all pyrimidines 2'-fluoro modified

<400> SEQUENCE: 36
gggaauucga gcucgguacc uuaacccgua uggggucacu guuucgauuu ucauucgccu     60
uaucgagcug auucacuugc gcugcaggca ugaagcuugg                          100

<210> SEQ ID NO 37
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: KN-158_06b_D06_x_046
<220> FEATURE:
<221> NAME/KEY: misc_feature
<223> OTHER INFORMATION: all pyrimidines 2'-fluoro modified
<220> FEATURE:
<221> NAME/KEY: misc_feature
<222> LOCATION: (64)..(64)
<223> OTHER INFORMATION: any nucleotide
<220> FEATURE:
<221> NAME/KEY: misc_feature
<222> LOCATION: (66)..(66)
<223> OTHER INFORMATION: any nucleotide

<400> SEQUENCE: 37
gggaauucga gcucgguacc cuaacccgua uggggucacu guuucgauuu cauucgccuu     60
aucnancuga uucacuugcg cugcaggcau gaagcuugg                           99

<210> SEQ ID NO 38
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: KN-158_06b_D12_x_094
<220> FEATURE:
<221> NAME/KEY: misc_feature
```

<223> OTHER INFORMATION: all pyrimidines 2'-fluoro modified

<400> SEQUENCE: 38
gggaauucga gcucgguacc cuaacccgua uggggucacu guuucgauuu cauucgccuu    60
aucgagcuga uucacuugcg cugcaggcau gaagcuugg    99

<210> SEQ ID NO 39
<211> LENGTH: 100
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_h03_m13-fp
<220> FEATURE:
<221> NAME/KEY: misc_feature
<223> OTHER INFORMATION: all pyrimidines 2'-fluoro modified
<220> FEATURE:
<221> NAME/KEY: misc_feature
<222> LOCATION: (27)..(27)
<223> OTHER INFORMATION: any nucleotide

<400> SEQUENCE: 39
gggaauucga gcucgguacc uuaaccngua uggggucacu guuucgauuu cauucgccuu    60
aucgagcuga auucacuugc gcugcaggca ugaagcuugg    100

<210> SEQ ID NO 40
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_f12_m13-fp
<220> FEATURE:
<221> NAME/KEY: misc_feature
<223> OTHER INFORMATION: all pyrimidines 2'-fluoro modified
<220> FEATURE:
<221> NAME/KEY: misc_feature
<222> LOCATION: (72)..(72)
<223> OTHER INFORMATION: any nucleotide

<400> SEQUENCE: 40
gggaauucga gcucgguacc uuaacccgua uggggucacu guuucgauuu cauucgccuu    60
aucgagcuga uncacuugcg cugcaggcau gaagcuugg    99

<210> SEQ ID NO 41
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code. 156703.seq
<220> FEATURE:
<221> NAME/KEY: misc_feature
<223> OTHER INFORMATION: all pyrimidines 2'-fluoro modified

<400> SEQUENCE: 41
gggaauucga gcucgguacc uuguuaccca cuguuuagua ucucgcgaua cucauuaccg    60
agacacaguc ccauuacugc cugcaggcau gaagcuugg    99

<210> SEQ ID NO 42
<211> LENGTH: 98

```
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156719.seq
<220> FEATURE:
<221> NAME/KEY: misc_feature
<223> OTHER INFORMATION: all pyrimidines 2'-fluoro modified

<400> SEQUENCE: 42
gggaauucga gcucgguacc gcacuuucgu uacauacgau auacugggcu auagucuauc    60
cuugugccua cagguacugc ugcaggcaug aagcuugg                            98

<210> SEQ ID NO 43
<211> LENGTH: 96
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156718.seq
<220> FEATURE:
<221> NAME/KEY: misc_feature
<223> OTHER INFORMATION: all pyrimidines 2'-fluoro modified

<400> SEQUENCE: 43
gggaauucga gcucgguacc gcacuuucgu uacauacgau auacugggcu auagucuauc    60
cuugugccua cagguugcug caggcaugaa gcuugg                              96

<210> SEQ ID NO 44
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156736.seq
<220> FEATURE:
<221> NAME/KEY: misc_feature
<223> OTHER INFORMATION: all pyrimidines 2'-fluoro modified

<400> SEQUENCE: 44
gggaauucga gcucgguacc gcacuuucgu uacauacgau auacugggcu auagucuauc    60
ccugugccua cagguacugc ugcaggcaug aagcuugg                            98

<210> SEQ ID NO 45
<211> LENGTH: 96
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: KN-158_06b_B10_x_077
<220> FEATURE:
<221> NAME/KEY: misc_feature
<223> OTHER INFORMATION: all pyrimidines 2'-fluoro modified

<400> SEQUENCE: 45
gggaauucga gcucgguacc gcacuuucgu uacauacgau auacugggcu auuguauccu    60
ugugccuaca gguacugcug caggcaugaa gcuugg                              96

<210> SEQ ID NO 46
```

```
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_f07_m13-fp
<220> FEATURE:
<221> NAME/KEY: misc_feature
<223> OTHER INFORMATION: all pyrimidines 2'-fluoro modified

<400> SEQUENCE: 46
gggaauucga gcucgguacc gcacuuucgu ugcauacgau auaccgggcu auagucuauc    60
cuugugccua cagguacugc ugcaggcaug aagcuugg                           98

<210> SEQ ID NO 47
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156695.seq
<220> FEATURE:
<221> NAME/KEY: misc_feature
<223> OTHER INFORMATION: all pyrimidines 2'-fluoro modified

<400> SEQUENCE: 47
gggaauucga gcucgguacc uacugcucga cuaauugucu aguacaauau gcuuaccaca    60
uuaucuguua gugagcuccc ugcaggcaug aagcuugg                           98

<210> SEQ ID NO 48
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156673.seq
<220> FEATURE:
<221> NAME/KEY: misc_feature
<223> OTHER INFORMATION: all pyrimidines 2'-fluoro modified

<400> SEQUENCE: 48
gggaauucga gcucgguacc uuguucugac ucuguuuaug cguuuccgc gucuuuaccg     60 gacuccuucu uccccagugc cugcaggcau gaagcuugg                          99

<210> SEQ ID NO 49
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156706.seq
<220> FEATURE:
<221> NAME/KEY: misc_feature
<223> OTHER INFORMATION: all pyrimidines 2'-fluoro modified

<400> SEQUENCE: 49
gggaauucga gcucgguacc uuguucugac ucuguuuaug cguuuacgc gucuuuaccg     60 gacuccucuu ccccagugcc ugcaggcaug aagcuugg                           98
```

```
<210> SEQ ID NO 50
<211> LENGTH: 97
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156761.seq
<220> FEATURE:
<221> NAME/KEY: misc_feature
<223> OTHER INFORMATION: all pyrimidines 2'-fluoro modified

<400> SEQUENCE: 50
gggaauucga gcucgguacc uuguucugac ucuguuuaug cguuuacgcg ucuuuaccgg      60
acuccuucuu cccagugccu gcaggcauga agcuugg                              97

<210> SEQ ID NO 51
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156738.seq
<220> FEATURE:
<221> NAME/KEY: misc_feature
<223> OTHER INFORMATION: all pyrimidines 2'-fluoro modified

<400> SEQUENCE: 51
gggaauucga gcucgguacc uaucgucgaa cauucgaucu guuuuacgu aaguaacuuu      60 accguccucg uuuuucccgc cugcaggcau gaagcuugg                            99

<210> SEQ ID NO 52
<211> LENGTH: 100
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156730.seq
<220> FEATURE:
<221> NAME/KEY: misc_feature
<223> OTHER INFORMATION: all pyrimidines 2'-fluoro modified

<400> SEQUENCE: 52
gggaauucga gcucgguacc uaucgucgaa cauucgaucu guuuuacgu uaaguaacuu      60 uaccguccuc guuuuucccg ccugcaggca ugaagcuugg                           100

<210> SEQ ID NO 53
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_f04_m13-fp.abi
<220> FEATURE:
<221> NAME/KEY: misc_feature
<223> OTHER INFORMATION: all pyrimidines 2'-fluoro modified

<400> SEQUENCE: 53
gggaauucga gcucgguacc uaucgucgaa cauucgaucu guuuuacgu aaguaacuuu      60 accguccucg uuuuucccgc cugcaggcau gaagcuugg                            99
```

```
<210> SEQ ID NO 54
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_f06_m13-fp.abi
<220> FEATURE:
<221> NAME/KEY: misc_feature
<223> OTHER INFORMATION: all pyrimidines 2'-fluoro modified

<400> SEQUENCE: 54
gggaauucga gcucgguacc uaucgucgaa cauucgaucu guuuuuacgu aaguaacugu      60
accguccucg uuuuuccucc cugcaggcau gaagcuugg                            99

<210> SEQ ID NO 55
<211> LENGTH: 100
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_g02_m13-fp.abi
<220> FEATURE:
<221> NAME/KEY: misc_feature
<223> OTHER INFORMATION: all pyrimidines 2'-fluoro modified

<400> SEQUENCE: 55
gggaauucga gcucgguacc uauugucgaa cauucgaucu guuuuuacgu aaguaacuuu      60
accguccucg uuuuucccg ccugcaggca ugaagcuugg                            100

<210> SEQ ID NO 56
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156697.seq
<220> FEATURE:
<221> NAME/KEY: misc_feature
<223> OTHER INFORMATION: all pyrimidines 2'-fluoro modified

<400> SEQUENCE: 56
gggaauucga gcucgguacc aaacaucacu uacaugugcu cugcguuuuu ugcauaguuu      60
uuuggucgag cgcuuccucc cugcaggcau gaagcuugg                            99

<210> SEQ ID NO 57
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156712.seq
<220> FEATURE:
<221> NAME/KEY: misc_feature
<223> OTHER INFORMATION: all pyrimidines 2'-fluoro modified

<400> SEQUENCE: 57
gggaauucga gcucgguacc agacaucacu uacaugugcu cugcguuuuu ugcaucguuu      60
uuuggucgag cgcuuccucc cugcaggcau gaagcuugg                            99
```

<210> SEQ ID NO 58
<211> LENGTH: 96
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156745.seq
<220> FEATURE:
<221> NAME/KEY: misc_feature
<223> OTHER INFORMATION: all pyrimidines 2'-fluoro modified

<400> SEQUENCE: 58
gggaauucga gcucgguacc gcggagucug ucacaagauc ucguccuuau cguugaugua    60
ucguacaagu cuuugcccug caggcaugaa gcuugg                              96

<210> SEQ ID NO 59
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_e07_m13-fp.abi
<220> FEATURE:
<221> NAME/KEY: misc_feature
<223> OTHER INFORMATION: all pyrimidines 2'-fluoro modified

<400> SEQUENCE: 59
gggaauucga gcucgguacc aaugccugcu uuguuugag uuuccuuca cacuagggau     60 ggauaauaca gucccuaccc ugcaggcaug aagcuugg                            98

<210> SEQ ID NO 60
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_e05_m13-fp.abi
<220> FEATURE:
<221> NAME/KEY: misc_feature
<223> OTHER INFORMATION: all pyrimidines 2'-fluoro modified

<400> SEQUENCE: 60
gggaauucga gcucgguacc aaugccugcu uuguuugag uuuuucuuca cacuagggau    60
ggauaauaca gucccuaccc ugcaggcaug aagcuugg                            98

<210> SEQ ID NO 61
<211> LENGTH: 91
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_e08_m13-fp.abi
<220> FEATURE:
<221> NAME/KEY: misc_feature
<223> OTHER INFORMATION: all pyrimidines 2'-fluoro modified

<400> SEQUENCE: 61
gggaauucga gcucgguacc cuuuguuuug aguuuucccu guacacuagg gauggauaau    60 acaguccccua cccugcaggc augaagcuug g                                        91

<210> SEQ ID NO 62
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156678.seq
<220> FEATURE:
<221> NAME/KEY: misc_feature
<223> OTHER INFORMATION: all pyrimidines 2'-fluoro modified

<400> SEQUENCE: 62
gggaauucga gcucgguacc uguuacagug uuguacuagu ucuaguguuu gguugaugua        60
cucccguaac uuauccugcc ugcaggcaug aagcuugg                                98

<210> SEQ ID NO 63
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156758.seq
<220> FEATURE:
<221> NAME/KEY: misc_feature
<223> OTHER INFORMATION: all pyrimidines 2'-fluoro modified

<400> SEQUENCE: 63
gggaauucga gcucgguacc uaaacgacua cgaccugaug cuggaaguua auuuguaacu        60
guguuacaua cagucgcgug cugcaggcau gaagcuugg                               99

<210> SEQ ID NO 64
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156708.seq
<220> FEATURE:
<221> NAME/KEY: misc_feature
<223> OTHER INFORMATION: all pyrimidines 2'-fluoro modified

<400> SEQUENCE: 64
gggaauucga gcucgguacc uuaaugguug acugauucuu ccuugccaac ugugcuuagc        60
uguuacaguu uaucaugugc cugcaggcau gaagcuugg                               99

<210> SEQ ID NO 65
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156693.seq
<220> FEATURE:
<221> NAME/KEY: misc_feature
<223> OTHER INFORMATION: all pyrimidines 2'-fluoro modified

<400> SEQUENCE: 65
gggaauucga gcucgguacc aagagaugau caagcgucgu ucuaaucaug aguugugucu        60
accccuaacu gccaauucgc ugcaggcaug aagcuugg    98

<210> SEQ ID NO 66
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156751.seq
<220> FEATURE:
<221> NAME/KEY: misc_feature
<223> OTHER INFORMATION: all pyrimidines 2'-fluoro modified

<400> SEQUENCE: 66
gggaauucga gcucgguacc uuaaacacca gugccugcuc ucaaugaugu uguuucuuc    60 augcgugucg ugagaucuuc cugcaggcau gaagcuugg    99

<210> SEQ ID NO 67
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156759.seq
<220> FEATURE:
<221> NAME/KEY: misc_feature
<223> OTHER INFORMATION: all pyrimidines 2'-fluoro modified

<400> SEQUENCE: 67
gggaauucga gcucgguacc gugaaccugu aacuuuguca gccgcacggu aauuuguuc    60 ucgauuaauc ccgagagccc ugcaggcaug aagcuugg    98

<210> SEQ ID NO 68
<211> LENGTH: 78
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156733.seq
<220> FEATURE:
<221> NAME/KEY: misc_feature
<223> OTHER INFORMATION: all pyrimidines 2'-fluoro modified

<400> SEQUENCE: 68
gggaauucga gcucgguacc aaacggcagc acucgcacuu auucguggac gauuugagg    60 uuaauguacg cuugcccc    78

<210> SEQ ID NO 69
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156710.seq
<220> FEATURE:
<221> NAME/KEY: misc_feature
<223> OTHER INFORMATION: all pyrimidines 2'-fluoro modified

<400> SEQUENCE: 69

```
gggaauucga gcucgguacc uaucguugaa cauucgaucu guuuuuacgu aaguaacuuu    60
accguccucg uuuuucccgc cugcaggcau gaagcuugg                          99
```

<210> SEQ ID NO 70
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156760.seq
<220> FEATURE:
<221> NAME/KEY: misc_feature
<223> OTHER INFORMATION: all pyrimidines 2'-fluoro modified

<400> SEQUENCE: 70

```
gggaauucga gcucgguacc cugcaguuuc agauuuaacg auuagcuucu ggauggguau    60
uggcacaucu uacccuuugg cugcaggcau gaagcuugg                          99
```

<210> SEQ ID NO 71
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156755.seq
<220> FEATURE:
<221> NAME/KEY: misc_feature
<223> OTHER INFORMATION: all pyrimidines 2'-fluoro modified

<400> SEQUENCE: 71

```
gggaauucga gcucgguacc auuuggcuag guaaccgaca acuucaaucg cuacuucacu    60
uggagucuug gcuauccauc cugcaggcau gaagcuugg                          99
```

<210> SEQ ID NO 72
<211> LENGTH: 97
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156714.seq
<220> FEATURE:
<221> NAME/KEY: misc_feature
<223> OTHER INFORMATION: all pyrimidines 2'-fluoro modified

<400> SEQUENCE: 72

```
gggaauucga gcucgguacc uuucugcgac uguugccgca aucuucaacc uugcgugauu    60
aagccacgua ucgucuugcu gcaggcauga agcuugg                            97
```

<210> SEQ ID NO 73
<211> LENGTH: 97
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156690.seq
<220> FEATURE:
<221> NAME/KEY: misc_feature
<223> OTHER INFORMATION: all pyrimidines 2'-fluoro modified

<400> SEQUENCE: 73
gggaauucga gcucgguacc ucauccucau caaacaguag cguuaucauu guguaguaac    60
ccaaagcgcu gccauucccu gcaggcauga agcuugg    97

<210> SEQ ID NO 74
<211> LENGTH: 95
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156681.seq
<220> FEATURE:
<221> NAME/KEY: misc_feature
<223> OTHER INFORMATION: all pyrimidines 2'-fluoro modified

<400> SEQUENCE: 74
gggaauucga gcucgguacc ggauggaaca cgcaguuugu cuuaguucgu ugaugaaacc    60
uuuucaacgc uucgcccugc aggcaugaag cuugg    95

<210> SEQ ID NO 75
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156739.seq
<220> FEATURE:
<221> NAME/KEY: misc_feature
<223> OTHER INFORMATION: all pyrimidines 2'-fluoro modified

<400> SEQUENCE: 75
gggaauucga gcucgguacc uauacugcuc acuuugaauu caaucaccgu ucgcgcugcu    60
aacucacuau uucccuuggc cugcaggcau gaagcuugg    99

<210> SEQ ID NO 76
<211> LENGTH: 92
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: 156682.seq
<220> FEATURE:
<221> NAME/KEY: misc_feature
<223> OTHER INFORMATION: all pyrimidines 2'-fluoro modified

<400> SEQUENCE: 76
gggaauucga gcucgguacc aggugauugc uuucuuaacu uuguuagacu ucgaccauca    60
gugucgcccu caccugcagg caugaagcuu gg    92

<210> SEQ ID NO 77
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_d04_m13-fp.abi
<220> FEATURE:
<221> NAME/KEY: misc_feature
<223> OTHER INFORMATION: all pyrimidines 2'-fluoro modified -continued

```
<400> SEQUENCE: 77
gggaauucga gcucgguacc aaugccugcu uuguuugag uuuuccuuca cacuagggau    60
ggauaauaca gucccuaccc ugcaggcaug aagcuugg                          98

<210> SEQ ID NO 78
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_a01_m13-fp.abi
<220> FEATURE:
<221> NAME/KEY: misc_feature
<223> OTHER INFORMATION: all pyrimidines 2'-fluoro modified

<400> SEQUENCE: 78
gggaauucga gcucgguacc uacaaucguu accugcucgc uuuaaucuug gauccuaucc    60
gauuuagauc uucccacuac cugcaggcau gaagcuugg                          99

<210> SEQ ID NO 79
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_c01_m13-fp.abi
<220> FEATURE:
<221> NAME/KEY: misc_feature
<223> OTHER INFORMATION: all pyrimidines 2'-fluoro modified

<400> SEQUENCE: 79
gggaauucga gcucgguacc augcaggugc ccccuuuggu uuuuccaaa ggcacaucag    60 aaaguucucg aauuuccgua cugcaggcau gaagcuugg                          99

<210> SEQ ID NO 80
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_c05_m13-fp.abi
<220> FEATURE:
<221> NAME/KEY: misc_feature
<223> OTHER INFORMATION: all pyrimidines 2'-fluoro modified
<220> FEATURE:
<221> NAME/KEY: misc_feature
<222> LOCATION: (35)..(35)
<223> OTHER INFORMATION: any nucleotide
<220> FEATURE:
<221> NAME/KEY: misc_feature
<222> LOCATION: (61)..(61)
<223> OTHER INFORMATION: any nucleotide

<400> SEQUENCE: 80
gggaauucga gcucgguacc accugcaauu ccaunccguu cucccauaug ucuuaggcuu    60
nugguguucu cgucuuggguc cugcaggcau gaagcuugg                         99

<210> SEQ ID NO 81
<211> LENGTH: 99
<212> TYPE: RNA
<213> ORGANISM: Artificial Sequence
```

<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_a12_m13-fp.abi
<220> FEATURE:
<221> NAME/KEY: misc_feature
<223> OTHER INFORMATION: all pyrimidines 2'-fluoro modified

<400> SEQUENCE: 81
gggaauucga gcucgguacc uuuacguaac auuguacccc uucagccgcu ggcugucgca    60
cauaugauag uucucggauu cugcaggcau gaagcuugg                          99

<210> SEQ ID NO 82
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_a06_m13-fp.abi
<220> FEATURE:
<221> NAME/KEY: misc_feature
<223> OTHER INFORMATION: all pyrimidines 2'-fluoro modified

<400> SEQUENCE: 82
gggaauucga gcucgguacc acaggacgcu guugauccuc gguaaaucgg uauguaagua    60
uucgaaguau gugugcccccc ugcaggcaug aagcuugg                          98

<210> SEQ ID NO 83
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_c10_m13-fp.abi
<220> FEATURE:
<221> NAME/KEY: misc_feature
<223> OTHER INFORMATION: all pyrimidines 2'-fluoro modified

<400> SEQUENCE: 83
gggaauucga gcucgguacc uacugcucga cuaauugucu aguacaauau gcuuaccaca    60
uuaucuguua gugagcuccc ugcaggcaug aagcuugg                           98

<210> SEQ ID NO 84
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_b05_m13-fp.abi
<220> FEATURE:
<221> NAME/KEY: misc_feature
<223> OTHER INFORMATION: all pyrimidines 2'-fluoro modified

<400> SEQUENCE: 84
gggaauucga gcucgguacc agacaucacu uacaugugcu cugcguuuuu ugcaucguuu    60
uuuggucgag cgcuuccucc cugcaggcau gaagcuugg                          99

<210> SEQ ID NO 85
<211> LENGTH: 99
<212> TYPE: RNA

```
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_c09_m13-fp.abi
<220> FEATURE:
<221> NAME/KEY: misc_feature
<223> OTHER INFORMATION: all pyrimidines 2'-fluoro modified

<400> SEQUENCE: 85
gggaauucga gcucgguacc uaucgucgaa cauucgaucu guuuuuacgu aaguaacuuu      60
accguccucg uuuuucccgc cugcaggcau gaagcuugg                            99

<210> SEQ ID NO 86
<211> LENGTH: 96
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_b09_m13-fp.abi
<220> FEATURE:
<221> NAME/KEY: misc_feature
<223> OTHER INFORMATION: all pyrimidines 2'-fluoro modified

<400> SEQUENCE: 86
gggaauucga gcucgguacc ucuugcacgc auuaacugau ugcucuuuca ugacuuacaa      60
cucccuuugc uagcccccug caggcaugaa gcuugg                               96

<210> SEQ ID NO 87
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_a02_m13-fp.abi
<220> FEATURE:
<221> NAME/KEY: misc_feature
<223> OTHER INFORMATION: all pyrimidines 2'-fluoro modified

<400> SEQUENCE: 87
gggaauucga gcucgguacc gcuuaagaca uauucuuccu acccucuauu gggucuuuac      60
gggcuuacuu uccuagggcg cugcaggcau gaagcuugg                            99

<210> SEQ ID NO 88
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_g10_m13-fp.abi
<220> FEATURE:
<221> NAME/KEY: misc_feature
<223> OTHER INFORMATION: all pyrimidines 2'-fluoro modified

<400> SEQUENCE: 88
gggaauucga gcucgguacc agacaucacu uacaugugcu cugcguuuuu ugcaucguuu      60
uuuggucgag cgcuucccuc cugcaggcau gaagcuugg                            99

<210> SEQ ID NO 89
<211> LENGTH: 98
```

<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_f11_m13-fp.abi
<220> FEATURE:
<221> NAME/KEY: misc_feature
<223> OTHER INFORMATION: all pyrimidines 2'-fluoro modified

<400> SEQUENCE: 89
gggaauucga gcucgguacc uuguucugac acuguuuaug cguuuacgc gucuuuaccg     60 ggcuccuucu ucccagugcc ugcaggcaug aagcuugg                            98

<210> SEQ ID NO 90
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_h02_m13-fp.abi
<220> FEATURE:
<221> NAME/KEY: misc_feature
<223> OTHER INFORMATION: all pyrimidines 2'-fluoro modified

<400> SEQUENCE: 90
gggaauucga gcucgguacc aauguaccau aguguuacau ugggcuugga auacagucuc     60
gacugaauuc gguucccgg cugcaggcau gaagcuugg                             99

<210> SEQ ID NO 91
<211> LENGTH: 98
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_h07_m13-fp.abi
<220> FEATURE:
<221> NAME/KEY: misc_feature
<223> OTHER INFORMATION: all pyrimidines 2'-fluoro modified

<400> SEQUENCE: 91
gggaauucga gcucgguacc ugcgagcaua gacccacagu cuuuugcgau ucguuuucaa     60 acguuucgu gcguauuccc ugcaggcaug aagcuugg                              98

<210> SEQ ID NO 92
<211> LENGTH: 99
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: kn-158-6_h05_m13-fp.abi
<220> FEATURE:
<221> NAME/KEY: misc_feature
<223> OTHER INFORMATION: all pyrimidines 2'-fluoro modified

<400> SEQUENCE: 92
gggaauucga gcucgguacc aaaugguauu ggcccgagac ugugcuuucg cacaguuaau     60
caauaguuug cgauuguucc cugcaggcau gaagcuugg                            99

<210> SEQ ID NO 93

```
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02_10-224

<400> SEQUENCE: 93
ggaccaacau gugaagaaca uacgguggaa gaaacgauug uuagacagg                49

<210> SEQ ID NO 94
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR_R02-10-225

<400> SEQUENCE: 94
ggacaaaccu guguagaagg ggguaauaua caguagguag ggagggacag g             51

<210> SEQ ID NO 95
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-227

<400> SEQUENCE: 95
ggacguaaug auccggcgau aaguccagga ugucaggccg gagagacagg               50

<210> SEQ ID NO 96
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-228

<400> SEQUENCE: 96
ggacgaauga aguacggcgc accgggggug ugaaguuagc gugagacagg               50

<210> SEQ ID NO 97
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-229

<400> SEQUENCE: 97
ggacguguug augcagcggg ugaacauuca caaacauccc uagcgacagg               50

<210> SEQ ID NO 98
<211> LENGTH: 50
<212> TYPE: RNA
<213> ORGANISM: Artificial Sequence
<220> FEATURE:
```

```
<223> OTHER INFORMATION: CGRP-binding nucleic acid
<220> FEATURE:
<221> NAME/KEY: misc_feature
<223> OTHER INFORMATION: laboratory code: STAR-R02-10-230

<400> SEQUENCE: 98
ggacgauagu ggugugucgu uaauucaccg ggaggguggc gagggacagg            50

<210> SEQ ID NO 99
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-231

<400> SEQUENCE: 99
ggacagugcu ggugcggcug auugcauaua agcagugaac acccgacagg            50

<210> SEQ ID NO 100
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-232

<400> SEQUENCE: 100
ggaccaacau gugaaaaaca uacgguggaa gaaacgauug uugagacagg            50

<210> SEQ ID NO 101
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-234

<400> SEQUENCE: 101
ggaccaagua aacccuguga gccuugguaa agcggguggg aagggacagg            50

<210> SEQ ID NO 102
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-235

<400> SEQUENCE: 102
ggacgacaug uuccgggaac auacggugaa agaaacgauu gucggacagg            50

<210> SEQ ID NO 103
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-237
```

<400> SEQUENCE: 103
ggacuaguga gcgugggagg gccucacaaa acgaaaaguc cggggacagg          50

<210> SEQ ID NO 104
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-239

<400> SEQUENCE: 104
ggacgauugc guaguggaag cauacgguga aagaaacgau aucggacagg          50

<210> SEQ ID NO 105
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-240

<400> SEQUENCE: 105
ggacuauacg gugaaagaaa cgaggcguua ggaggaaacg cuaggacagg          50

<210> SEQ ID NO 106
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR_R02-10-243

<400> SEQUENCE: 106
ggacgaacgu gcuggugcag cgugacuuag ucgaacaccc cuggggacag g         51

<210> SEQ ID NO 107
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-244

<400> SEQUENCE: 107
ggacgccaaa aucaggaagg gagagaaaag gaaugcguac ggcgacagg           49

<210> SEQ ID NO 108
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-248

<400> SEQUENCE: 108
ggacaauccu guggaguagg gugggggccu aguaggccua gugggacagg          50

```
<210> SEQ ID NO 109
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-249

<400> SEQUENCE: 109
ggacgauccu guggaguagg gugggggccu aguaggccua gugggacagg        50

<210> SEQ ID NO 110
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-250

<400> SEQUENCE: 110
ggacuuuagc ugcguaguag ggaaaagaag ggugggcag cuccgacagg         50

<210> SEQ ID NO 111
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-251

<400> SEQUENCE: 111
ggacuugaug acgcgaguua acgucgcugu cucucaauca aggagacagg        50

<210> SEQ ID NO 112
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-252

<400> SEQUENCE: 112
ggaccagugg ugacgcggcu ggggcgccac agcgccggac gucgacagg         49

<210> SEQ ID NO 113
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-254

<400> SEQUENCE: 113
ggacagagga acguaguagg guaagguagg augaggggguu ccucgacagg       50

<210> SEQ ID NO 114
<211> LENGTH: 50
```

<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-255

<400> SEQUENCE: 114
ggacuauuua agggccggua gagaaauaaa ccacccucuc uggagacagg                50

<210> SEQ ID NO 115
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-257

<400> SEQUENCE: 115
ggacugaugg cgcgggauua cgccgcuggc gcuaggaaca aggcgacagg                50

<210> SEQ ID NO 116
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-258

<400> SEQUENCE: 116
ggacgauccu guggaguagg guggggggccc agugggccua ugggacagg                50

<210> SEQ ID NO 117
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-259

<400> SEQUENCE: 117
ggacguguug augcagcggg uggacauuca caaacauccc uggcgacagg                50

<210> SEQ ID NO 118
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-261

<400> SEQUENCE: 118
ggacccugcu cgagaggacg agcauacggu gaaagaaacg augggacagg                50

<210> SEQ ID NO 119
<211> LENGTH: 50
<212> TYPE: RNA
<213> ORGANISM: Artificial Sequence
<220> FEATURE:
<223> OTHER INFORMATION: CGRP-binding nucleic acid

```
<220> FEATURE:
<221> NAME/KEY: misc_feature
<223> OTHER INFORMATION: laboratory code: STAR-R02-10-263

<400> SEQUENCE: 119
ggacauacga ugagagaagc gauucccgcu gcugacggga ugucgacagg            50

<210> SEQ ID NO 120
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-264

<400> SEQUENCE: 120
ggacgauccu guggaguagg guggggucu aguagaccua gugggacagg             50

<210> SEQ ID NO 121
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-266

<400> SEQUENCE: 121
ggacagugau ggcgcagcug uaaccaagag guuagaacgc uggagacagg            50

<210> SEQ ID NO 122
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-267

<400> SEQUENCE: 122
ggacugauuc ucagagaaua cgaugaaaga agcgauucag ucuggacagg            50

<210> SEQ ID NO 123
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-268

<400> SEQUENCE: 123
ggacacaacu cgaaggagau gguagguagg acagcgggggg uugugacagg           50

<210> SEQ ID NO 124
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-270
```

```
<400> SEQUENCE: 124
ggaccaacau gugaaaagca uacggugaaa gaaacgauug uugagacagg           50

<210> SEQ ID NO 125
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-271

<400> SEQUENCE: 125
ggacgugaug gcgcagcgac ugacacaaag gaucaggaac gccccgacag g         51

<210> SEQ ID NO 126
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-272

<400> SEQUENCE: 126
ggacgaacug guaggguggc ugcccuauac gaugaaagaa gcgagacagg           50

<210> SEQ ID NO 127
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-274

<400> SEQUENCE: 127
ggacuugaug acgcgaguua acgucgcugu cucucaauca aggggacagg           50

<210> SEQ ID NO 128
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-275

<400> SEQUENCE: 128
ggacgacuga uggcgcgguc guguaauaaa acaacgccgc uggcgacagg           50

<210> SEQ ID NO 129
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-276

<400> SEQUENCE: 129
ggacacaacu cgaaggagau gguagguagg acagcgggag uugugacagg           50
```

```
<210> SEQ ID NO 130
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-278

<400> SEQUENCE: 130
ggacgauugc guagugggag cauacgguga aagaaacgau aucggacagg        50

<210> SEQ ID NO 131
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-280

<400> SEQUENCE: 131
ggacauaugg ugaaaagaaa caauacuccg uuagugagga guuggacagg        50

<210> SEQ ID NO 132
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-283

<400> SEQUENCE: 132
ggacguguug augcagcgag ugaacauuca cgaacauccc uggcgacagg        50

<210> SEQ ID NO 133
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-286

<400> SEQUENCE: 133
ggacguguug acgcagcguu acggcuaagg accguagaac guuagacagg        50

<210> SEQ ID NO 134
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-287

<400> SEQUENCE: 134
ggacacuguc agcgcgguga ugagaaaacg ccccuguaac agaugacagg        50

<210> SEQ ID NO 135
<211> LENGTH: 50
<212> TYPE: RNA
```

<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-288

<400> SEQUENCE: 135
ggacaacgaa guaaaccuua ggcgacccgc augaaggcgg gguggacagg        50

<210> SEQ ID NO 136
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-289

<400> SEQUENCE: 136
ggacauacgg ugaaagaaac gauucggaac uucgaauccg auggacagg         49

<210> SEQ ID NO 137
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-291

<400> SEQUENCE: 137
ggacgaauga aguacggcgc accgggagcg ugaaguuagc gugagacagg         50

<210> SEQ ID NO 138
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-292

<400> SEQUENCE: 138
ggaccaacau guaaagagca uacgguggaa gaaacgauug uugagacagg         50

<210> SEQ ID NO 139
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-293

<400> SEQUENCE: 139
ggacgacaug uuccgagaac auacggugaa auaaacgauu gucagacagg         50

<210> SEQ ID NO 140
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:

```
<221> NAME/KEY: misc_feature
<223> OTHER INFORMATION: laboratory code: STAR-R02-10-294

<400> SEQUENCE: 140
ggaccaacau guaagagcau acgguggaag aaacgauugu uagacagg              48

<210> SEQ ID NO 141
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-295

<400> SEQUENCE: 141
ggacgaccca ucaaggauga agagcguacg cuugcgcagg ggucgacagg            50

<210> SEQ ID NO 142
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-296

<400> SEQUENCE: 142 ggaccuguu agugcugcgg auauaaaaac acugcugucu augggacagg            50

<210> SEQ ID NO 143
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-297

<400> SEQUENCE: 143
ggacgaggug cuggcgcugc cuaugcccga uuggguaaaa cgccgacagg            50

<210> SEQ ID NO 144
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-298

<400> SEQUENCE: 144
ggaccaagua aacccuguaa gccuuggua agcgggu ggg aagggacagg             50

<210> SEQ ID NO 145
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-300

<400> SEQUENCE: 145
```
ggacaacccg ucaaggauga agagcguacg cuugcgcagg guucgacagg        50

<210> SEQ ID NO 146
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-303

<400> SEQUENCE: 146
ggacgagaug ggcguaauaa gaugggggaaa auagccgaaa gcccgacagg        50

<210> SEQ ID NO 147
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-304

<400> SEQUENCE: 147
ggacucucug auggcgcgga gagaauauua cgccacuguc gugagacagg        50

<210> SEQ ID NO 148
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-307

<400> SEQUENCE: 148
ggacgaacga gcauggacgc gggugaggag agggcgcuag uucggacagg        50

<210> SEQ ID NO 149
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-310

<400> SEQUENCE: 149
ggacgacgag gaauuggugg gggauggggu gaggauccuc gcgggacagg        50

<210> SEQ ID NO 150
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-311

<400> SEQUENCE: 150
ggacgauugc auagugagag cauacgguga aagaaacgau aucggacagg        50

```
<210> SEQ ID NO 151
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-314

<400> SEQUENCE: 151
ggacgugaug gugcagcgua gucgguuaag acaaacaccc cugggacagg        50

<210> SEQ ID NO 152
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-315

<400> SEQUENCE: 152
ggacauacga ugagagaagc gauucccgcu gcuaacggga ugucgacagg        50

<210> SEQ ID NO 153
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-10-318

<400> SEQUENCE: 153
ggacauacga ugaaagaagc gauucccgcu gcugacggga ugucgacagg        50

<210> SEQ ID NO 154
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-A1

<400> SEQUENCE: 154
ggacgacaug uucccggaac auacggugaa agaaacgauu aucggacagg        50

<210> SEQ ID NO 155
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-A4

<400> SEQUENCE: 155
ggacgacaug cuccaggagc auacggugaa agaaacgauu gucggacagg        50

<210> SEQ ID NO 156
<211> LENGTH: 50
<212> TYPE: RNA
<213> ORGANISM: Artificial Sequence
```

```
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-A5

<400> SEQUENCE: 156
ggacgacaug uuccaggaac auacggugaa agaaacgauu gucggacagg            50

<210> SEQ ID NO 157
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-B5

<400> SEQUENCE: 157
ggacgauaug uuccaagaac auacggugaa agaaacgauu gucggacagg            50

<210> SEQ ID NO 158
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-D2

<400> SEQUENCE: 158
ggacauacga ugaaagaagc gauucccgcu gcuagcggga ugucgacagg            50

<210> SEQ ID NO 159
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-E1

<400> SEQUENCE: 159
ggacuacaag ccaacaaauc cuugcccacu gaggaucugc ugucgacagg            50

<210> SEQ ID NO 160
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-E3

<400> SEQUENCE: 160
ggacucauac ggugaaagaa acgauucguc uugugacgau gaggacagg             49

<210> SEQ ID NO 161
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
```

<223> OTHER INFORMATION: laboratory code: STAR-R02-12MW-E4

<400> SEQUENCE: 161
ggacgacaug uucggggaac auacggugaa agaaacgauu gucggacagg            50

<210> SEQ ID NO 162
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-F3

<400> SEQUENCE: 162
ggacauacgg ugaagaaac gauacgcaau uuguguguc ccgacagg                48

<210> SEQ ID NO 163
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-F4

<400> SEQUENCE: 163
ggacgauugc auacuaaaag cauacgguga aagaaacgau aucggacagg            50

<210> SEQ ID NO 164
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-F6

<400> SEQUENCE: 164
ggacucauac ggugaaagaa acgauucguc uuaacgacga ugaggacagg            50

<210> SEQ ID NO 165
<211> LENGTH: 47
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-G1

<400> SEQUENCE: 165
ggacuaagug agccaaguca gcgggauguc cauaacuugu cgacagg               47

<210> SEQ ID NO 166
<211> LENGTH: 52
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-H1

<400> SEQUENCE: 166
ggacauacgg ugaaagaaac gauacauaau uuauguuccu guccaagaca gg         52

<210> SEQ ID NO 167
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-12MW-H2
<220> FEATURE:
<221> NAME/KEY: misc_feature
<222> LOCATION: (18)..(18)
<223> OTHER INFORMATION: any nucleotide

<400> SEQUENCE: 167
ggacgauugc acaauganag cauacgguga agaaacgau aucggacagg              50

<210> SEQ ID NO 168
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-A1

<400> SEQUENCE: 168
ggacgacaug uucuaugaac auacggugaa agaaacgauu gucggacagg             50

<210> SEQ ID NO 169
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-15d-A10

<400> SEQUENCE: 169
ggacgauugc auaguaagag cauacgguga agaaacgau aucggacagg              50

<210> SEQ ID NO 170
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-A12

<400> SEQUENCE: 170
ggacgacaug uuccaggaac auacggugaa aaaaacgauu gucggacagg             50

<210> SEQ ID NO 171
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-A2

<400> SEQUENCE: 171
ggacgacaug uucuaggaac auacggugaa agaaacgauu guuggacagg         50

<210> SEQ ID NO 172
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-A9

<400> SEQUENCE: 172
ggacauacga ugaaagaagc gauucccgcu acuagcggga ugucgacagg         50

<210> SEQ ID NO 173
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-B11

<400> SEQUENCE: 173
ggaccaacau gcaaagagca uacggugaaa gaaacgauug uugagacagg         50

<210> SEQ ID NO 174
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-B3

<400> SEQUENCE: 174
ggacauaugg ugaaagaaac aauucggaac uucgauuccg auggacagg          49

<210> SEQ ID NO 175
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-C10

<400> SEQUENCE: 175
ggacgauugc auaauaaaag cauacgguga agaaacgau aucggacagg          50

<210> SEQ ID NO 176
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-C9

<400> SEQUENCE: 176
ggacgacaug uucuaagaac auacggugaa agaaacgauu gucggacagg         50

<210> SEQ ID NO 177

```
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-D10

<400> SEQUENCE: 177
ggacgacaug uuccaaggaa cauacgguga aagaaacgau ugucggacag g          51

<210> SEQ ID NO 178
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-D7

<400> SEQUENCE: 178
ggaccaacau gugaagagca uacggugaaa gaaacgauug uugagacagg            50

<210> SEQ ID NO 179
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-D9

<400> SEQUENCE: 179
ggacgauugc auagugggug cauacgguga aagaaacgau aucggacagg            50

<210> SEQ ID NO 180
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-E11

<400> SEQUENCE: 180
ggacgauugc auaguaaaag cauacgguga aagaaacgau aucggacagg            50

<210> SEQ ID NO 181
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-E12

<400> SEQUENCE: 181
ggacgacaug uucaaagaac auacggugaa agaaacgauu gucggacagg            50

<210> SEQ ID NO 182
<211> LENGTH: 50
<212> TYPE: RNA
<213> ORGANISM: Artificial Sequence
<220> FEATURE:
```

-continued

<223> OTHER INFORMATION: CGRP-binding nucleic acid
<220> FEATURE:
<221> NAME/KEY: misc_feature
<223> OTHER INFORMATION: laboratory code: STAR-R02-15d-E3

<400> SEQUENCE: 182
ggaccauacg augaaagaag cgauacugca ccagaagcag uugggacagg    50

<210> SEQ ID NO 183
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-F8

<400> SEQUENCE: 183
ggacgauugc auuaagagca uacggugaaa gaaacgauau cggacagg    48

<210> SEQ ID NO 184
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-F9

<400> SEQUENCE: 184
ggacgacaug uuccgagaac auacggugaa agaaacgauu gucggacagg    50

<210> SEQ ID NO 185
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-G1

<400> SEQUENCE: 185
ggacgauugc auaguagaag cauacgguga aagaaacgau aucggacagg    50

<210> SEQ ID NO 186
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-G12

<400> SEQUENCE: 186
ggacucauac ggugaaagaa acgauucguc uugacgacga ugaggacagg    50

<210> SEQ ID NO 187
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-G2

```
<400> SEQUENCE: 187
ggacauacga ugaaagaagc gauucccguu acuagcggga ugucgacagg          50

<210> SEQ ID NO 188
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-H1

<400> SEQUENCE: 188
ggacgacaug uucccagaac auacggugaa agaaacgauu gucggacagg          50

<210> SEQ ID NO 189
<211> LENGTH: 47
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-H7

<400> SEQUENCE: 189
ggacauacgg ugaaagaaac gauucggacu ugaguccgau ggacagg             47

<210> SEQ ID NO 190
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15d-H9

<400> SEQUENCE: 190
ggacgauugc auaauaagag cauacgguga aagaaacgau aucggacagg          50

<210> SEQ ID NO 191
<211> LENGTH: 48
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: STAR-R02-15xx-A11

<400> SEQUENCE: 191
ggacugaugg cgcggucuca aaaaacgccg auagggugag gggacagg            48

<210> SEQ ID NO 192
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-A7

<400> SEQUENCE: 192
ggacugaugg cgcggucuua aaaaacgccg augggugag gggacagg             48
```

```
<210> SEQ ID NO 193
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-B10

<400> SEQUENCE: 193
ggacucauac ggugaaagaa acgauucguc uagcgacgau gaggacagg           49

<210> SEQ ID NO 194
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-B7
<220> FEATURE:
<221> NAME/KEY: misc_feature
<222> LOCATION: (37)..(37)
<223> OTHER INFORMATION: any nucleotide

<400> SEQUENCE: 194
ggacucauac ggugaaagaa acgauucguc uuagcgncga ugaggacagg          50

<210> SEQ ID NO 195
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-C7
<220> FEATURE:
<221> NAME/KEY: misc_feature
<222> LOCATION: (17)..(17)
<223> OTHER INFORMATION: any nucleotide

<400> SEQUENCE: 195
ggacugaugg cgcggunuca aaaaacgccg auagggugag gggacagg            48

<210> SEQ ID NO 196
<211> LENGTH: 48
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: STAR-R02-15xx-C9

<400> SEQUENCE: 196
ggacugaugg cgcggucuca aaaaacgccg cuagggugag gggacagg            48

<210> SEQ ID NO 197
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-D8
```

```
<400> SEQUENCE: 197
ggacagacga uggccguaaa ucaucgggaa aggggaugga gggacagg                    48

<210> SEQ ID NO 198
<211> LENGTH: 52
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-E9

<400> SEQUENCE: 198
ggacugaugg cgcggucgau aaauacgccc gugaacuggg aaguggaca gg                52

<210> SEQ ID NO 199
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-F12

<400> SEQUENCE: 199
ggacugaugg cgcgguccua uuacgccgaa agggagaggg gagacagg                    48

<210> SEQ ID NO 200
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-F7

<400> SEQUENCE: 200
ggacugaugg cgcggucuua aaaaacgccg auagggugag gggacagg                    48

<210> SEQ ID NO 201
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-G10

<400> SEQUENCE: 201
ggacagacga uggccauaaa ucaucgggaa aggggaugga gggacagg                    48

<210> SEQ ID NO 202
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-G12

<400> SEQUENCE: 202
ggacucauac ggugaaagaa acgauucguc uuaggacgau gaggacagg                   49
```

<210> SEQ ID NO 203
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R02-15xx-G7
<220> FEATURE:
<221> NAME/KEY: misc_feature
<222> LOCATION: (13)..(13)
<223> OTHER INFORMATION: any nucleotide

<400> SEQUENCE: 203
ggacagacga ugnccguaaa ucaucgggaa agggcaugga ggguacagg        49

<210> SEQ ID NO 204
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-A4

<400> SEQUENCE: 204
ggacgacaug uucgcagaac auacggugaa agaaacgauu gucggacagg        50

<210> SEQ ID NO 205
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-A6

<400> SEQUENCE: 205
ggacauacgg ugaaagaaac gauucccgcu acuagcggga ugucgacagg        50

<210> SEQ ID NO 206
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-A7

<400> SEQUENCE: 206
ggacgacaug uucaaaagaa cauacgguga aagaaacgau gucggacag g        51

<210> SEQ ID NO 207
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-B10

<400> SEQUENCE: 207
ggacauacgg ugaaagaaac gauacaugau uuauguuguc ccgagacagg        50

<210> SEQ ID NO 208
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-B7

<400> SEQUENCE: 208
ggacauacgg ugaaagaaac gauucucgcu gcuagcgaga ugucgacagg     50

<210> SEQ ID NO 209
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-C12

<400> SEQUENCE: 209
ggacgacaug uucccaggaa cauacgguga aagaaacgau ugucggacag g     51

<210> SEQ ID NO 210
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-C6

<400> SEQUENCE: 210
ggacgacaug uucggagaac auacggugaa agaaacgauu gucggacagg     50

<210> SEQ ID NO 211
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-C7

<400> SEQUENCE: 211
ggacauacgg ugaaagaaac gauucggauu accaauccga uggacagg     48

<210> SEQ ID NO 212
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-C8

<400> SEQUENCE: 212
ggacucauac ggugaaagaa acgauucguc uuagcgacga ugaggacagg     50

<210> SEQ ID NO 213
<211> LENGTH: 50

```
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-C9

<400> SEQUENCE: 213
ggacgacaug uuccaagaac auacggugaa agaaacgauu gucggacagg         50

<210> SEQ ID NO 214
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-D5

<400> SEQUENCE: 214
ggacgacaug uucauagaac auacggugaa agaaacgauu gucagacagg         50

<210> SEQ ID NO 215
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-E11

<400> SEQUENCE: 215
ggacgacaug uucuaggaac auacggugaa agaaacgauu gucggacagg         50

<210> SEQ ID NO 216
<211> LENGTH: 51
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-E5

<400> SEQUENCE: 216
ggacgacaug uuccauggaa cauacgguga aagaaacgau ugucggacag g       51

<210> SEQ ID NO 217
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-E6

<400> SEQUENCE: 217
ggacgacaug uucagggaac auacggugaa agaaacgauu gucggacagg         50

<210> SEQ ID NO 218
<211> LENGTH: 48
<212> TYPE: RNA
<213> ORGANISM: Artificial Sequence
<220> FEATURE:
<223> OTHER INFORMATION: CGRP-binding nucleic acid
```

```
<220> FEATURE:
<221> NAME/KEY: misc_feature
<223> OTHER INFORMATION: laboratory code: STAR-R03-11-E7

<400> SEQUENCE: 218
ggacagacga uggccuuaaa ucaucgggaa aggggaugga gggacagg            48

<210> SEQ ID NO 219
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-E8

<400> SEQUENCE: 219
ggacgacaug uucuaggaac auacgaugaa agaagcgauu gucggacagg          50

<210> SEQ ID NO 220
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-F10

<400> SEQUENCE: 220
ggacauacgg ugaaagaaac gauacauaau uuauguuguc ccgagacagg          50

<210> SEQ ID NO 221
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-F5

<400> SEQUENCE: 221
ggacguccau acggugaaag aaacgauagg gauagacucc cuuggacagg          50

<210> SEQ ID NO 222
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-F6

<400> SEQUENCE: 222
ggacauacgg ugaaagaaac gauucggaac uucgauuccg auggacagg           49

<210> SEQ ID NO 223
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-F7
```

<400> SEQUENCE: 223
ggacgacaug uucuacgaac auacggugaa agaaacgauu gucggacagg          50

<210> SEQ ID NO 224
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-G10

<400> SEQUENCE: 224
ggaccaacgc uuaagcaaac cccacuuaca cuuaagcguc gagcgacagg          50

<210> SEQ ID NO 225
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-G12

<400> SEQUENCE: 225
ggacauacgg ugaaagaaac gauucccacu acuagcggga ugucgacagg          50

<210> SEQ ID NO 226
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-G4

<400> SEQUENCE: 226
ggacgacaug uucaaggaac auacggugaa agaaacgauu gucggacagg          50

<210> SEQ ID NO 227
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-G8

<400> SEQUENCE: 227
ggacgacaug uucagagaac auacggugaa agaaacgauu gucagacagg          50

<210> SEQ ID NO 228
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-G9

<400> SEQUENCE: 228
ggacauacga ugaaagaagc gauucccguu gcuagcggga ugucgacagg          50

<210> SEQ ID NO 229
<211> LENGTH: 49
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-H12

<400> SEQUENCE: 229
ggaccauuau cccccaggau auacggugaa agaaacgaua ugggacagg            49

<210> SEQ ID NO 230
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-H5

<400> SEQUENCE: 230
ggacgacaug uucaaagaac auacggugaa agaaacgauu gucggacagg           50

<210> SEQ ID NO 231
<211> LENGTH: 50
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-H9

<400> SEQUENCE: 231
ggacgacaug uucagagaac auacggugaa agaaacgauu gucggacagg           50

<210> SEQ ID NO 232
<211> LENGTH: 45
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-F10-45-001

<400> SEQUENCE: 232
cgggacauac ggugaaagaa acgauacaua auuuauguug ucccg                45

<210> SEQ ID NO 233
<211> LENGTH: 48
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: STAR-R03-11-C12-48-001

<400> SEQUENCE: 233
ggccgacaug uucccaggaa cauacgguga aagaaacgau ugucgucc             48

<210> SEQ ID NO 234
<211> LENGTH: 79
<212> TYPE: RNA

```
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: G 12

<400> SEQUENCE: 234
ggagcucagc cuucacugca ucgaggcgau ccaaguugua ggaaugggu ggcuuggagg      60 gcaccacggu cggauccag                                                 79

<210> SEQ ID NO 235
<211> LENGTH: 78
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: G 12a

<400> SEQUENCE: 235
ggagcucagc cuucacugca ucgaggcauc caaguuauag gaauagggug gcuugaaggg     60
caccacgguc ggauccag                                                  78

<210> SEQ ID NO 236
<211> LENGTH: 78
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: G 12b

<400> SEQUENCE: 236
ggagcucagc cuucacugca ucgaggcauc caaguuauag gaauagggug gcuugaaggg     60
caccacgguc ggauccag                                                  78

<210> SEQ ID NO 237
<211> LENGTH: 78
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: G 12c

<400> SEQUENCE: 237
ggagcucagc cuucacugca ucgaggcgau ccaaguugag gaaugggug gcuuggaggg      60 caccacgguc ggauccag                                                  78

<210> SEQ ID NO 238
<211> LENGTH: 81
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: G 12d

<400> SEQUENCE: 238
ggagcucagc cuucacugca ucgaaggcga uccaaguugu aagaauggg guggcuugga     60
```
gggcaccacg gucggaucca g                                                  81

<210> SEQ ID NO 239
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: G 12e

<400> SEQUENCE: 239
ggagcucagc cuucacugca ucgaggcgau ccaaguugua ggaauuggau gacuuggagg        60
gcaccacggu cggauccag                                                     79

<210> SEQ ID NO 240
<211> LENGTH: 80
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: G 12f

<400> SEQUENCE: 240
ggagcucagc cuucacugca ucgagggcga uccaaguugu aggaaugggg uggcuuggag        60
ggcaccacgg ucggauccag                                                    80

<210> SEQ ID NO 241
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: G 12g

<400> SEQUENCE: 241
ggagcucagc cuucacugca ucgaagcgau ccaaguugua ggaauggggu agcuuggagg        60
gcaccacggu cggauccag                                                     79

<210> SEQ ID NO 242
<211> LENGTH: 78
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: H 08a

<400> SEQUENCE: 242
ggagcucagc cuucacugcg ggugggaggg uggaugguga agaacgagcg cugaccgcgg        60
caccacgguc ggauccag                                                      78

<210> SEQ ID NO 243
<211> LENGTH: 78
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: H 08b

<400> SEQUENCE: 243
ggagcucagc cuucacugcg gguggagggg uggauggugg agaacgagca cugaccucgg    60
caccacgguc ggauccag                                                 78

<210> SEQ ID NO 244
<211> LENGTH: 79
<212> TYPE: RNA
<213> ORGANISM: Artificial Sequence
<220> FEATURE:
<223> OTHER INFORMATION: CGRP-binding nucleic acid
<220> FEATURE:
<221> NAME/KEY: misc_feature
<223> OTHER INFORMATION: laboratory code: H 03a

<400> SEQUENCE: 244
ggagcucagc cuucacugcc auugaggaua ugccgcgggu ccgcauggag uggguguugg    60
gcaccacggu cggauccag                                                79

<210> SEQ ID NO 245
<211> LENGTH: 42
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: STAR-R02-15xx-014
      (= NOX-504-014)

<400> SEQUENCE: 245
ggacugaugg cgcgguccua uuacgccgaa agggagaggg ga                       42

<210> SEQ ID NO 246
<211> LENGTH: 42
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: NOX-504-089

<400> SEQUENCE: 246
ggacugaugg cgcgguccua uuacgccgau agggugaggg ga                       42

<210> SEQ ID NO 247
<211> LENGTH: 73
<212> TYPE: DNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: NOX-504-ad3-18%-Bibliothek
<220> FEATURE:
<221> NAME/KEY: misc_feature
<223> OTHER INFORMATION: laboratory code: NOX-504-ad3-18%-Bibliothek
      (reverser ssDNA-Strang)
<220> FEATURE:
<221> NAME/KEY: misc_feature
<222> LOCATION: (1)..(2)
<223> OTHER INFORMATION: O-methylated nucleotide
<220> FEATURE:
<221> NAME/KEY: misc_feature
<222> LOCATION: (7)..(44)
<223> OTHER INFORMATION: other nucleotides at a mutation rate of 0.18

-continued

```
<400> SEQUENCE: 247
ccgtgctccc ctctcccttt cggcgtaata ggaccgcgcc atcagtccta tagtgagtcg      60
tattagtagt cgc                                                         73

<210> SEQ ID NO 248
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: laboratory code:  STAR-1 Reverse Primer Ribo U
      (=STAR-1 Reverse Matrix)
<220> FEATURE:
<221> NAME/KEY: misc_feature
<223> OTHER INFORMATION: DNA with ribonucleotides at positions 12 and 18

<400> SEQUENCE: 248
gcgagttcag cucagcgucc gtgc                                             24

<210> SEQ ID NO 249
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: laboratory code: STAR-1 N+1 Reverse Matrix
      Ribo I
<220> FEATURE:
<221> NAME/KEY: misc_feature
<223> OTHER INFORMATION: DNA with ribonucleotides at positions 12 and 18
<220> FEATURE:
<221> NAME/KEY: misc_feature
<222> LOCATION: (18)..(18)
<223> OTHER INFORMATION: inosin

<400> SEQUENCE: 249
gcgagttcag cucagcgncc gtgc                                             24

<210> SEQ ID NO 250
<211> LENGTH: 48
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: NOX-504

<400> SEQUENCE: 250
ggacugaugg cgcgguccua uuacgccgaa agggagaggg gagacagg                   48

<210> SEQ ID NO 251
<211> LENGTH: 48
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: NOX-504-ad3

<400> SEQUENCE: 251
ggacugaugg cgcgguccua uuacgccgaa agggagaggg gagcacgg                   48
```

```
<210> SEQ ID NO 252
<211> LENGTH: 50
<212> TYPE: RNA
<213> ORGANISM: Artificial Sequence
<220> FEATURE:
<223> OTHER INFORMATION: CGRP-binding and/or amylin-binding nucleic acid

<400> SEQUENCE: 252
ggacugaugg cgcgguccua uuacgccgag aagggagugg gggagcacgg                50

<210> SEQ ID NO 253
<211> LENGTH: 44
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: L097

<400> SEQUENCE: 253
ggacugaugg cgcgguccua uuacgccgag aagggagugg ggga                      44

<210> SEQ ID NO 254
<211> LENGTH: 43
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: L102

<400> SEQUENCE: 254
ggacugaugg cgcgguccua uuacgccgag aagggagagg gga                       43

<210> SEQ ID NO 255
<211> LENGTH: 43
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: L103

<400> SEQUENCE: 255
ggacugaugg cgcgguccua uuacgccgaa agggagaggg gga                       43

<210> SEQ ID NO 256
<211> LENGTH: 42
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: L104

<400> SEQUENCE: 256
ggacugaugg cgcgguccua uuacgccgaa agggaguggg ga                        42

<210> SEQ ID NO 257
<211> LENGTH: 43
<212> TYPE: RNA
<213> ORGANISM: Artificial Sequence
<220> FEATURE:
<223> OTHER INFORMATION: CGRP-binding and/or amylin-binding nucleic acid
<220> FEATURE:
```

```
<221> NAME/KEY: misc_feature
<223> OTHER INFORMATION: laboratory code: L105

<400> SEQUENCE: 257
ggacugaugg cgcgguccua uuacgccgaa agggaguggg gga              43

<210> SEQ ID NO 258
<211> LENGTH: 43
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: L106

<400> SEQUENCE: 258
ggacugaugg cgcgguccua uuacgccgag aagggagugg gga              43

<210> SEQ ID NO 259
<211> LENGTH: 44
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: L107

<400> SEQUENCE: 259
ggacugaugg cgcgguccua uuacgccgag aagggagagg ggga             44

<210> SEQ ID NO 260
<211> LENGTH: 44
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: L108

<400> SEQUENCE: 260
ggacugaugg cgcgguccua uuacgccgag uagggagugg ggga             44

<210> SEQ ID NO 261
<211> LENGTH: 44
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: L109

<400> SEQUENCE: 261
ggacugaugg cgcgguccua uuacgccgag aagggugugg ggga             44

<210> SEQ ID NO 262
<211> LENGTH: 42
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: NOX-504-095

<400> SEQUENCE: 262
```

```
ggacugaugg cgcgguccua uuacgccgag agggaguggg ga                    42

<210> SEQ ID NO 263
<211> LENGTH: 42
<212> TYPE: RNA
<213> ORGANISM: Artificial Sequence
<220> FEATURE:
<223> OTHER INFORMATION: CGRP-binding and/or amylin-binding nucleic acid
<220> FEATURE:
<221> NAME/KEY: misc_feature
<223> OTHER INFORMATION: laboratory code: NOX-504-096

<400> SEQUENCE: 263
ggacugaugg cgcgguccua uuacgccgau aggguguggg ga                    42

<210> SEQ ID NO 264
<211> LENGTH: 79
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (20)..(59)
<223> OTHER INFORMATION: n is a, c, g, or t

<400> SEQUENCE: 264
ggagctcagc cttcactgcn nnnnnnnnn nnnnnnnnnn nnnnnnnnnn nnnnnnnng    60 gcaccacggt cggatccac                                              79

<210> SEQ ID NO 265
<211> LENGTH: 38
<212> TYPE: DNA
<213> ORGANISM: Artificial
<220> FEATURE:
<223> OTHER INFORMATION: synthetic

<400> SEQUENCE: 265
tctaatacga ctcactatag gagctcagcc ttcactgc                         38

<210> SEQ ID NO 266
<211> LENGTH: 20
<212> TYPE: DNA
<213> ORGANISM: Artificial
<220> FEATURE:
<223> OTHER INFORMATION: synthetic

<400> SEQUENCE: 266
gtggatccga ccgtggtgcc                                             20

<210> SEQ ID NO 267
<211> LENGTH: 100
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (21)..(80)
<223> OTHER INFORMATION: n is a, c, g, or t

<400> SEQUENCE: 267
gggaattcga gctcggtacc nnnnnnnnnn nnnnnnnnnn nnnnnnnnnn nnnnnnnnnn   60
nnnnnnnnnn nnnnnnnnnn ctgcaggcat gcaagcttgg                       100
```

<210> SEQ ID NO 268
<211> LENGTH: 37
<212> TYPE: DNA
<213> ORGANISM: Artificial
<220> FEATURE:
<223> OTHER INFORMATION: synthetic

<400> SEQUENCE: 268
taatacgact cactataggg aattcgagct cggtacc                                37

<210> SEQ ID NO 269
<211> LENGTH: 20
<212> TYPE: DNA
<213> ORGANISM: Artificial
<220> FEATURE:
<223> OTHER INFORMATION: synthetic

<400> SEQUENCE: 269
gggaattcga gctcggtacc                                                   20

<210> SEQ ID NO 270
<211> LENGTH: 20
<212> TYPE: DNA
<213> ORGANISM: Artificial
<220> FEATURE:
<223> OTHER INFORMATION: synthetic

<400> SEQUENCE: 270
ccaagcttgc atgcctgcag                                                   20

<210> SEQ ID NO 271
<211> LENGTH: 50
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (5)..(44)
<223> OTHER INFORMATION: n is a, c, g, or t

<400> SEQUENCE: 271
ggacnnnnnn nnnnnnnnnn nnnnnnnnnn nnnnnnnnnn nnnngacagg                  50

<210> SEQ ID NO 272
<211> LENGTH: 78
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (7)..(46)
<223> OTHER INFORMATION: n is a, c, g, or t

<400> SEQUENCE: 272
cctgtcnnnn nnnnnnnnnn nnnnnnnnnn nnnnnnnnnn nnnnnngtcc tatagtgagt       60
cgtattagta gtgcgaag                                                     78

<210> SEQ ID NO 273
<211> LENGTH: 29
<212> TYPE: DNA
<213> ORGANISM: Artificial
<220> FEATURE:
<223> OTHER INFORMATION: synthetic

<400> SEQUENCE: 273

```
gcgactacta atacgactca ctataggac                                          29

<210> SEQ ID NO 274
<211> LENGTH: 25
<212> TYPE: RNA
<213> ORGANISM: Artificial
<220> FEATURE:
<223> OTHER INFORMATION: synthetic

<400> SEQUENCE: 274
gcgacuacua auacgacuca cuaua                                              25

<210> SEQ ID NO 275
<211> LENGTH: 17
<212> TYPE: DNA
<213> ORGANISM: Artificial
<220> FEATURE:
<223> OTHER INFORMATION: synthetic

<400> SEQUENCE: 275
gtcctatagt gagtcgt                                                       17

<210> SEQ ID NO 276
<211> LENGTH: 24
<212> TYPE: DNA
<213> ORGANISM: Artificial
<220> FEATURE:
<223> OTHER INFORMATION: syntehtic

<400> SEQUENCE: 276
gcgagttcag ctcagcgtcc tgtc                                               24

<210> SEQ ID NO 277
<211> LENGTH: 18
<212> TYPE: DNA
<213> ORGANISM: Artificial
<220> FEATURE:
<223> OTHER INFORMATION: synthetic

<400> SEQUENCE: 277
acgctgagct gaactcgc                                                      18

<210> SEQ ID NO 278
<211> LENGTH: 17
<212> TYPE: DNA
<213> ORGANISM: Artificial
<220> FEATURE:
<223> OTHER INFORMATION: synthetic

<400> SEQUENCE: 278
cgctgagctg aactcgc                                                       17

<210> SEQ ID NO 279
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (18)..(18)
<223> OTHER INFORMATION: n is riboinosine

<400> SEQUENCE: 279
gcgagttcag ctcagcgncc tgtc                                               24
```

```
<210> SEQ ID NO 280
<211> LENGTH: 20
<212> TYPE: RNA
<213> ORGANISM: Artificial
<220> FEATURE:
<223> OTHER INFORMATION: synthetic

<400> SEQUENCE: 280
cauacgguga aagaaacgau                                              20

<210> SEQ ID NO 281
<211> LENGTH: 50
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (14)..(16)
<223> OTHER INFORMATION: n is a, c, g, or u

<400> SEQUENCE: 281
ggacgacaug uucnnngaac auacggugaa agaaacgauu gucggacagg             50

<210> SEQ ID NO 282
<211> LENGTH: 51
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (14)..(17)
<223> OTHER INFORMATION: n is a, c, g, or u

<400> SEQUENCE: 282
ggacgacaug uucnnnngaa cauacgguga aagaaacgau ugucggacag g           51

<210> SEQ ID NO 283
<211> LENGTH: 37
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (14)..(14)
<223> OTHER INFORMATION: n is a, c, g, or u
<220> FEATURE:
<221> NAME/KEY: misc_feature
<222> LOCATION: (26)..(28)
<223> OTHER INFORMATION: n is a, c, g, or u
<220> FEATURE:
<221> NAME/KEY: misc_feature
<222> LOCATION: (32)..(32)
<223> OTHER INFORMATION: n is a, c, g, or u

<400> SEQUENCE: 283
gauggcgcgg ucunaaaaaa cgccgnnngg gngaggg                           37

<210> SEQ ID NO 284
<211> LENGTH: 79
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (20)..(59)
<223> OTHER INFORMATION: n is a, c, g, or u
```

```
-continued

<400> SEQUENCE: 284
ggagcucagc cuucacugcn nnnnnnnnnn nnnnnnnnnn nnnnnnnnnn nnnnnnnnng        60
gcaccacggu cggauccag                                                     79

<210> SEQ ID NO 285
<211> LENGTH: 48
<212> TYPE: RNA
<213> ORGANISM: Artificial
<220> FEATURE:
<223> OTHER INFORMATION: synthetic

<400> SEQUENCE: 285
ggacugaugg cgcgguccua uuacgccgaa agggagaggg gagcacgg                     48

<210> SEQ ID NO 286
<211> LENGTH: 42
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (30)..(30)
<223> OTHER INFORMATION: n is G or absent

<400> SEQUENCE: 286
ggacugaugg cgcgguccua uuacgccgan dagggagwgg gr                           42
```

CGRP BINDING NUCLEIC ACIDS

The present invention relates to antagonists of CGRP and amylin, antagonists of the CGR receptor, nucleic acids binding CGRP and amylin, the use of such nucleic acids as antagonists of CGRP and/or of the CGR receptor system or respectively amylin, the use of one of the abovementioned nucleic acids for producing a drug, a composition, in particular pharmaceutical composition, comprising said nucleic acid(s), a complex comprising CGRP or respectively amylin and one of said nucleic acids, the use of said nucleic acids for proving CGRP or respectively amylin, as well as a process for screening CGRP antagonists and amylin antagonists and a kit for proof of CGRP or respectively amylin.

It was Hippocrates who described the visual symptoms of migraine, and these headaches, as discovered on papyrus, were also not unfamiliar to Egyptian medicine. During the 17th century it was recognised that the vessels of the body play a significant role in migraine headache. At that time it was already known that migraine, apart from the gravity of attacks, is benign and hereditary, and depends on the seasons, air pressure and the consumption of certain foodstuffs (Willis, T., Cerebri anatome, Martin Allestry, London, 1664). According to Willis (Willis, T., Cerebri anatome, Martin Allestry, London, 1664) headache is resolved through a slowly developing vasospasm, which beings in the periphery of the arterial system. An added important aspect of migraine-pathophysiology surfaced in the 19th century. Liveing (Liveing, E., Churchill, London, 1873, 1-512) attributed migraine to a dysfunction of the brain, which arose from "nerve storms" inside the brain. He believed that there was a relationship between migraine and epilepsy, since both are determined by releases of the central nervous system. The studies undertaken by Ray and Wolff (Ray, B. S. et al., 1940, Arch. Surg., 41, 813-856) demonstrate that only the major cerebral arteries of the base of the skull and the meningeal (dural) arteries and veins are sensitive to harmful stimuli. This directed interest to the intercranial vessel walls as a putative source of pain in headaches.

According to the IHS Classification of 1998 there are chiefly two groups of migraine: migraine with and migraine without aura. Earlier dividing into simple, classic and complicated migraine was abandoned.

Migraine today is understood as a neurovascular functional disorder, by which approximately 10% of the adult population are afflicted. This condition is characterised by attacks of intensive recurring headaches (Doods, H., 2001, Current opinion in investigational Drugs 2 (9), 1261-1268), nausea and excessive sensitivity to external stimuli such as light and noise. The often half-side headaches (haemicrania) are pulsing and pounding and usually occur on one side. Frequently the side of the headaches changes from one occurrence of migraine to the other or even during an attack. The attack is often accompanied by additional symptoms. Those affected complain of loss of appetite, nausea and vomiting. They are particularly sensitive to light and noise and have an extremely sensitive reaction to smell and exhibit nerve and sight disorders. In between migraine attacks the headaches disappear. Before and after attacks mood and appetite, fluid balance and bowel function can alter.

The pathophysiology of migraine is under constant discussion. The prevalent current opinion is that migraine is a neurovascular illness, whose trigger mechanism is possibly localised in the CNS. This triggering leads finally to vasodilation with subsequent activation of trigeminal afferent sensory neurones and central 'nociceptive' neurones in higher pain centres (Hargreaves, R. J. et al., 1999, Can. J. Neurol. Sci. 26, 512-519). There is some evidence and indication confirming the participation of CGRP in migraine. CGRP is abundant in trigeminal sensory nerves and is one of the most potent known vasodilators. Furthermore, the CGRP1 receptor is expressed on endothelial cells of the meningeal arteries. It is assumed that CGRP takes up a key role as mediator of meningeal vasodilation. Aside from these physiological observations there are animal studies, which support participation of the CGRP1 receptor in migraine. The stimulation of the trigeminal ganglion in anaesthetised rats leads to meningeal vasodilation, which can be inhibited by the aCGRP antagonist CGRP8-37 (Kurosawa, M. et al., 1995, Br. J. Pharmacol. 114, 1397-1402). This experiment implies a heightened CGRP level following trigeminal stimulation, as already described in 1993 by Goadsby and Edvinsson (Goadsby, P. et al., 1993, Ann. Neurol., 33, 48-56).

The result of analysis of CGRP plasma concentrations in human samples was that the concentration of CGRP in the plasma is an important parameter in migraine diagnosis. Increased plasma concentrations were found in patients with acute migraine, in patients with cluster headache and in humans following trigeminal stimulation (Edvinsson, L. et al., 1994, Cephalalgia 14, 320-327). In agreement with the animal studies just described the increased CGRP concentrations, which are described in migraine patients, can be reduced by Sumatriptan or Dihydroergotamin (Goadsby, P. et al., 1993, Ann. Neurol. 33, 48-56).

Within the scope of migraine therapy, in particular acute migraine and prior to forming of the full-blown form of the migraine headache, taking 1-1.5 g of acetyl salicyl acid (e.g. aspirin) still counts as a choice. In addition, a further 1 to 1.5 g of Paracetamol can be added to acetyl salicyl acid. Alternatives to acetyl salicyl acid are NSAIDs, i.e. non-steroidal anti-inflammatory active substances, and non-steroidal anti-rheumatics, such as e.g. Naproxen, Diclofenac or Ibuprofen.

The so-called triptanes, which currently represent the most potent therapeutics for acute treatment of modest to serious migraine attacks (Tepper, S. J. et al., 1999, CNS Drugs 12, 403-417; Doods, H., 2001, Current opinion in investigational Drugs 2 (9), 1261-1268), have proven particularly effective in the treatment of migraine.

Due to their high specificity for $5HT_{1BD}$ receptors and over long-term use they also enable therapy of acute migraine attacks which is safe and highly effective, and, in accordance with contraindications, all in all low in side effects also. If the risks and secondary costs are observed by way of the serious ergotamine side effects or respectively insufficiently treated migraine attacks, the use of these admittedly at the time most expensive, but also most potent migraine acute therapeutics is in many cases justified. In the trigeminovascular system so significant for migraine, triptanes also inhibit the release of vasoactive and algogenic neuropeptides (CGRP, neurokinines) from nociceptive trigeminal nerve endings, thereby preventing the initiation or respectively maintaining of neurogenic inflammation of perivascular, and particularly dura arteries, the suspected origin of the migraine headache. After successful introduction of Sumatriptan a few new triptanes were developed and launched. These are distinguished chiefly at the commencement of effect and oral bioavailability. Although triptanes are effective and are well tolerated, there are limitations to this class of substance. The occurrence of chest pressure, tightness/strain and angst often indicate angina pectoris in up to 15% of patients (Doods, H., 2001, Current opinion in investigational Drugs 2 (9), 1261-1268; Brown, E. G. et al. Eur. Neurol., 31, 339-344). The use of Sumatriptan is also connected with myocardial infarction (Ottervanger, J. P. et al., 1993, Lancet, 341, 861-862) and cardiac arrest in cardiovascular risk patients (Kelly, K. M., 1995, Neurology, 45, 1211-1213). It was also observed that administering Sumatriptan, Rizatriptan (Merck & Co. Inc.) and Zolmitriptan (Glaxo Wellcome plc/AstraZenecaplc) induced a minor increase in blood pressure (De Hoon, J. N. J. M. et al., 2000, Clin. Pharmacol. Ther., 68, 418-426). The vasoconstrictory effectiveness of triptanes on the coronary system could be clearly shown in vitro and in vivo, although it appears that triptanes work selectively on cerebral vessels (Doods, H., 2001, Current opinion in investigational Drugs 2 (9), 1261-1268).

A further group of active ingredients to be used is ergotamines.

The release of CGRP in primary headaches, the pharmacology of the trigeminovascular system, the concept of neurogenic inflammation (Moskowitz, M. A. et al., 1993, Brain Metab. Rev. 5, 159-177) and the answer to triptanes (Humphrey, P. P. A. et al., 1991, Trends Pharmacol. Sci., 12, 444-446) are key elements in the pathology of migraine (Edvinsson, L., 2001, Pharmacology & Toxicology 89, 65-73). The latest pharmacological research has accordingly been concentrated on this neuropeptide.

The 37 amino acid-long neuropeptide aCGRP, calcitonin gene-related peptide, was identified in 1982 as an extremely potent vasodilator (Amara et al., 1982, Nature 298, 240-244). CGRP originates through alternative splicing of the CGRP gene. Aside from aCGRP there is a second CGRP, ssCGRP, which has a high sequence homology to the abovementioned, yet is transcribed by another gene. Both peptides show similar biological effects such as vasodilation, raised blood pressure, hypotonia and tachycardia. aCGRP and calcitonin originate through alternative splicing of the calcitonin gene (Amara, G. S. et al., 1982, Nature 298, 240-244). The structure for hCGRP was determined in part by $^1$H-NMR. The peptide comprises a defined N-terminal loop, formed by the amino acids 2 to 7 by linking two cysteines via a disulphide bridge, to which approximately three windings of an α helix attach. In the direction of C terminus is attached a poorly defined kink, which itself again terminates in an unstable structure on the C terminus (Breeze, A. L. et al., 1991, Biochemistry, 30, 575-582). In addition, the C terminal phenylalanine is present in amidised form.

Ergotamine preparations are classic pharmaceuticals for arresting a migraine attack, which are however not quite unproblematic because of possible side effects. The danger of getting used to and triggering an additional permanent headache grows with increasing intake frequency. For this reason not more than 6 mg ergotamine tartrate and per migraine attack not more than 4 mg should be taken per week. It is also a good idea with migraine headache if the use of mixed preparations (e.g. ergotamine tartrate with caffeine or Prophyphenazon, Codein, Paracetamol etc.) is strictly avoided. One to 1.5 mg of dihydroergotamine (Hydergin®) can also be tried i. m. or slowly i. v. at this stage of therapy. Particularly with pronounced vegetative migraine side effects the addition of 1-2 mg Flunitrazepam (Rohypnol®, a sleeping pill) is highly proven. Above all also from the point of view of saving on painkillers, especially as patients in this situation anyway have the need to lie down. If the migraine headaches are accompanied by nausea and vomiting (possibly also already prior to the expected appearance of these symptoms), the administration of Metoclopramid (Paspertin®) is highly effective. It is advantageous to take this substance before an analgesic, because Metoclopramid increases bowel activity and thus requires resorption of additionally administered substances. Alternatively, the dopamine antagonist Domperidon (Motilium®) can also be used here.

A series of CGRP antagonists and derivates derived therefrom is known from the prior art. For example, a quinine analogon as CGRP antagonist is described in the international patent application with publication number WO 97/09046. But these compounds show only a weak affinity for the human CGRP receptor in the micromolar region and are therefore not of great importance.

A first potent non-peptidic CGRP receptor antagonist is the compound BIBN-4096BS, as described in DE 19911039. This substance is a lys-tyr-dipeptide derivative and has a high affinity for the human CGRP1 receptor ($K_i$=14.4 pM). In trials on cerebral vessels BIBN-4096BS was able to reverse the CGRP-arranged vasodilation (Doods, H. et al., 2000, Br. J. Pharmacol., 129, 420-423). Even though high doses of CGRP are cardioprotective, the α-CGRP antagonist BIBN-4096BS had no negative effect on myocardial infarcts or the releases of creatin phosphatkinase.

Based on the structure of BIBN-4096BS a cyclopropyl derivative was developed, in which the dipeptide core was replaced by a cyclopropyl ring. This compound is the object of international patent application with publication number WO 01/32648. Further CGRP receptor antagonists are the object of international patent application with publication number WO 01/32649, which describes naphthalene, piperidine, imidazole and quinazoline as CGRP receptor antagonists.

Further classes of structure, which are the object of tests, to utilise them as CGRP receptor antagonists are 3,4-dinitrobenzamine, such as described for example in international patent application with the publication number WO 98/09630, as well as 4-sulfinylbenzanilide, as described in international patent application with the publication number WO 98/56779. However, detailed binding analyses show that these substances have irreversible binding properties. In addition to this, they have, in particular some agents of 4-sulfinylbenzanilide, restrictions such that they have comparatively little solubility and oral availability as well as a short half value time of ca. 10 minutes, which excludes intensive in vivo-characterising.

The object of the present invention was to provide an agent suitable for treating migraine and the associated pattern of other illnesses. A further underlying object of the present invention is to provide an antagonist for CGRP and the CGR receptor system. In addition, an object of the present invention is to provide a process, with which CGRP antagonists, in particular within the scope of a screening method, can be supplied. Finally, it is an object of the present invention to provide further uses for the antagonists.

According to the present invention the task is solved in a first aspect solved by an antagonist of CGRP, whereby the antagonist is a nucleic acid and preferably binds the nucleic acid to CGRP.

In an embodiment it is provided that the CGRP is α-CGRP.

In an alternative embodiment it is provided that the CGRP is β-CGRP.

In a second aspect the object according to the present invention is solved by an antagonist of amylin, whereby the antagonist is a nucleic acid and preferably binds the nucleic acid to amylin.

In a third aspect the task is solved according to the present invention by an antagonist of the CGR receptor, whereby the antagonist is a nucleic acid and whereby preferably the nucleic acid binds to a ligand of the receptor and whereby more preferably the ligand is CGRP.

In an embodiment it is provided that the ligand is α-CGRP.

In an alternative embodiment it is provided that the is ligand β-CGRP.

In a fourth aspect the object according to the present invention is solved by an antagonist of the amylin-receptor, whereby the antagonist is a nucleic acid and whereby preferably the nucleic acid binds to a ligand of the receptor and whereby more preferably the ligand is amylin.

In a further embodiment of the various aspects of the present invention it is provided that the nucleic acid comprises at least one L nucleotide.

In a preferred embodiment of the various aspects of the present invention it is provided that the antagonist is a L nucleic acid.

In a fifth aspect the task is solved according to the present invention by a nucleic acid, which binds to CGRP.

In an embodiment it is provided that the CGRP is α-CGRP.

In an alternative embodiment it is provided that CGRP is β-CGRP.

In a sixth aspect the task is solved according to the present invention by a nucleic acid, which binds to amylin or an amyloid polypeptide.

In a seventh aspect the task is solved according to the present invention by a nucleic acid with a sequence, whereby the sequence is selected from the group comprising the sequences according to SEQ ID No. 1 to SEQ ID No. 247 and SEQ ID No. 250 to SEQ ID No. 263.

In an embodiment of the various aspects of the invention it is provided that the nucleic acid comprises at least one L nucleotide.

In an embodiment of the various aspects of the invention it is provided that the nucleic acid is a L nucleic acid.

In a further embodiment of the various aspects of the invention it is provided that the nucleic acid is selected from the group comprising DNA, RNA and combinations thereof.

In yet another embodiment of the various aspects of the invention it is provided that the $K_D$ value of the nucleic acid is less than 0.5 μM, preferably less than 0.1 μM, more preferably less than 0.05 μM and most preferably less than 0.01 μM.

In yet another embodiment of the various aspects of the present invention it is provided that the $K_D$ value of the nucleic acid is more than 100 μM, preferably more than 10 μM, more preferably more than 1 μM and most preferably more than 0.01 μM.

In an embodiment of the various aspects of the present invention it is provided that the inventive nucleic acids, independent of possible further characteristics and properties, have a $IC_{50}$ value, whereby the $IC_{50}$ value is preferably 0.5-30 μM, more preferably 0.5-10 μM, even more preferably 0.5-3 μM and most preferably 1-2 μM.

In an embodiment of the various aspects of the invention it is provided that the nucleic acid comprises a minimal binding motif.

In a further embodiment of the various aspects of the invention it is provided that the nucleic acid has a length, whereby the length is selected from the group, which comprises lengths of 15 to 150 nucleotides, 20 to 100 nucleotides, 20 to 80 nucleotides, 20 to 60 nucleotides, 20 to 50 nucleotides and 30 to 50 nucleotides, and the length most preferably 25 to 45 nucleotides.

In yet another embodiment of the various aspects of the invention it is provided that the nucleic acid has a two-, three- or multi-part structure.

In an eighth aspect the task is solved according to the present invention by the use of one of the inventive nucleic acids as an antagonist of CGRP and/or of the CGRP receptor system.

In a ninth aspect the task is solved according to the present invention by the use of a nucleic acid according to the present invention as an antagonist of amylin and/or of the amylin receptor system.

In a tenth aspect the task is solved according to the present invention by the use of one of the inventive nucleic acids for manufacturing a drug.

In an eleventh aspect the task is solved according to the present invention by the use of an inventive antagonist for manufacturing a drug.

In an embodiment of the uses according to both present aspects it is provided that the drug is for treatment and/or prevention of an illness, selected from the group comprising migraine, cluster headaches, loss of appetite, nausea, vomiting, neurogenic inflammation, in particular neurogenic inflammation imparted by other neuropeptides, vasodilation, raised blood pressure, hypotonia, tachycardia, illnesses attributed to activation of trigeminal afferent sensory neurons and central "nociceptive" neurones, in particular higher pain centres, and chronic inflammatory pains, and/or for treating pain, in particular chronic pain, acute pain, inflammatory pain, visceral pain and neuropathic pain.

In an embodiment it is provided that the nucleic acid or the antagonist binds to CGRP.

In an embodiment according to the ninth and tenth aspect of the present invention it is provided that the drug is for treatment and/or prevention of an illness, selected from the group comprising high blood pressure, diabetes, stomach evacuation disorders, diabetic gastroparesis, polydipsia, and degeneration and/or decline and/or functional loss of Langerhans' pancreatic islet cells, in particular diabetes mellitus. In a preferred embodiment diabetes on such, in which amylin distribution is highly regulated, as is the case in an early form of diabetes. In a further preferred embodiment diabetes is one such, in which amylin plaques occur, as is the case in a late form of diabetes.

In a particularly preferred embodiment it is provided that the nucleic acid or the antagonist binds on amylin or an amyloid polypeptide.

In a twelfth aspect the task is solved according to the present invention by a composition comprising an inventive nucleic acid and preferably a pharmaceutically acceptable carrier.

In a thirteenth aspect the task is solved according to the present invention by a composition comprising an inventive antagonist and preferably a pharmaceutically acceptable carrier.

In a fourteenth aspect the task is solved according to the present invention by a complex comprising CGRP and at least an inventive nucleic acid.

In a fifteenth aspect the task is solved according to the present invention by a complex comprising amylin and at least an inventive nucleic acid.

In a sixteenth aspect the task is solved according to the present invention by the use of an inventive nucleic acid for proving CGRP, preferably α-CGRP or β-CGRP and most preferably human α-CGRP or β-CGRP.

In a seventeenth aspect the task is solved according to the present invention by a method for screening CGRP antagonists comprising the following steps:
  providing a candidate CGRP antagonist,
  providing an inventive nucleic acid,
  providing a test system, which emits a signal in the presence of a CGRP antagonist, and
  determining whether the candidate CGRP antagonist is a CGRP antagonist.

In an embodiment it is provided that the CGRP is α-CGRP and/or β-CGRP, preferably human α-CGRP and/or β-CGRP.

In an eighteenth aspect the task is solved according to the present invention by a method for screening CGRP agonists comprising the following steps:
  providing CGRP, preferably immobilised CGRP,
  providing an inventive nucleic acid, preferably a marked inventive nucleic acid,
  addition of a candidate CGRP agonist, and
  determining whether the candidate CGRP agonist is a CGRP agonist.

In an embodiment it is provided that this determining results from establishing whether the nucleic acid is driven out by the candidate CGRP agonist.

In a nineteenth aspect the task is solved according to the present invention by a kit for proof of CGRP, preferably α-CGRP or β-CGRP, comprising at least an inventive nucleic acid.

In a twentieth aspect the task is solved according to the present invention by the use of a nucleic acid according to the present invention for proving amylin and/or amyloid polypeptides and/or amyloid plaques.

In a twenty-first aspect the task is solved according to the present invention by a method for screening amylin antagonists comprising the following steps:
  providing a candidate amylin antagonist,
  providing a nucleic acids according to the present invention,
  providing a test system, which emits a signal in the presence of an amylin antagonist, and
  determining whether the candidate amylin antagonist is an amylin antagonist.

In a twenty-second aspect the task is solved according to the present invention by a method for screening amylin agonists comprising the following steps:
  providing amylin,
  providing a nucleic acid according to the present invention, preferably a marked nucleic acid according to the present invention,
  adding a candidate amylin agonist, and
  determining whether the candidate amylin agonist is an amylin agonist.

In an embodiment it is provided that this determining results from establishing whether the nucleic acid is driven out by the candidate amylin agonist.

In a twenty-third aspect the task is solved according to the present invention by a kit for proof of amylin, comprising a nucleic acid according to the present invention.

The surprising knowledge of the present invention that it is possible to generate nucleic acids specifically binding to CGRP. Since there is extensive evidence for the fact that CGRP participates in the occurrence of pain and in the formation of migraine in its various forms, it thus results that such nucleic acids can be used as antagonists for CGRP or respectively the CGR receptor system and to that extent also as pharmaceutical substances in the treatment of illnesses of the pattern of migraine. It is particularly noteworthy that CGRP is a comparatively small peptide, against which binding nucleic acids can be generated only with difficulty. The amino acid sequence of human aCGRP and ssCGRP are differentiated into three amino acids, while the amino acid sequence of aCGRP and ssCGRP and the rat are differentiated into one amino acid. The different sequences are described in Hakala and Vihinen (Hakala J. M. L. and Vihinen M., 1994, protein Engineering 7 (9), 1069-1075. (Accession numbers: human aCGRP P06881, human ssCGRP P10092, rat aCGRP PO1256, rat ssCGRP P10093.

This application is supported substantially on the observation that CGRP is adequately present in neural tissue and in particular in somatic sensory cells and is frequently co-expressed with other neuropeptides, such as for example substance P, and other results of pain and migraine research mentioned hereinbelow.

Immunocytochemical studies show that substance P is almost always associated with CGRP in small DRG neurones (dorsal root ganglion), whereas CGRP is observed also without substance P (Wiesenfeld-Hallin, Z. et al., 1984, Neurosci. Lett. 52, 199-203). The release of CGRP in the periphery leads to vasodilation and together with other neuropeptides, such as substance P, for neurogenic inflammation. CGRP is also released in the dorsal bump of the spinal cord as an answer to harmful stimulations in the periphery and thus constitutes an applications and examination site for application of the inventive nucleic acids, antagonists and agents.

The CGRP1 antagonist CGRP8-37 was tested in different pain models. In order to antagonise endogenous CGRP an anti-CGRP antiserum was tested in various pain models after being given intrathecally. The creation of aCGRP-deficient mice and behavioural experiments complete the picture. The anti-nociceptive effect of CGRP8-37 could assist in different pain models such as phenylquinone-induced (PQ) writhing (Saxen, M. A. et al., 1994, Life Sciences 55, 1665-1674), acetic acid-induced writhing (Friese, N. et al., 1997, Regulatory peptides 70, 1-7), visceral pain (colorectal distension model, Plourde, V. et al., 1997, Am. J. Physio, 36, G191-G196), burn pain (heat-induced hyperalgesia, Lofgren, O. et al., 1997, Neuropeptides 31, 601-607), and neuropathic pain (spinal hemisection, Bennett, A. D. et al., 2000, Pain 86, 163-175). In mouse-tail flick, a model for acute pain, no effect was observed.

To block the effect of the spinal released CGRP's an antiserum was tested in different models for chronic pain. In chronic-inflammatory pain models, such as for example adjuvant-induced arthritis (Kuraishi, Y. et al., 1988, Neurosci. Lett. 92, 325-329) or carrageenin-induced hyperalgesia (Kawamura, M. et al., 1989, Brain Res. 497, 199-203), the anti-CGRP antiserum exhibited an anti-nociceptive effect. This antiserum can also prevent repeated stress-induced hyperalgesia in rats (Satoh, M. et al., 1992, Pain 49, 273-278).

The anti-nociceptive effects, which are observed both with the truncated peptide CGRP8-37 and also with the antiserum, go well together with the hyperalgesia observed in aCGRP-deficient knockout mice (Salmon, A.-M. et al., 1999, Neuroreport 10, 849-954). Compared to $CGRP^{+/+}$ mice $CGRP^{-/-}$ mice show reduced hyperalgesia with chronic inflammatory pain, which was resolved by formalin or capsaicin injections in the rear paw (Salmon, A.-M. et al., 2001, Nature 56, 357-358). A second aCGRP-deficient mouse was created to test the role of calcitonin. The $CGRP^{-/-}$ mice are born normal, are fertile and live a normal life. These mice develop in a chronic arthritis model (kaolin-carragenin mix was injected into the knee joint) as compared to the wild type, no secondary hyperalgesia (Zhang, L. et al., 2001, Pain 89, 265-273).

As a result of these results α-CGRP antagonists can also be used effectively for treating chronic inflammatory and visceral pain, as the disclosed CGRP antagonists or respectively the inventive nucleic acids.

As used herein the term CGR receptor basically designates each CGRP receptor. Preferred CGRP receptors are the abovementioned CGRP1 receptors and CGRP2 receptors, to which the inventive nucleic acids bind or respectively for which the disclosed nucleic acids display antagonists. Here, the receptor CGRP1 is one such for α-CGRP and CGRP2 is one such for β-CGRP.

Additional knowledge underlying the present invention is that also antagonists can be produced on the basis of nucleic acids against amylin, or respectively the nucleic acids binding on CGRP, which have an antagonistic effect on CGRP or respectively on the CGRP receptor, interact with amylin and in this respect have antagonistic activity.

Amylin is a 37 amino acid-long peptide hormone. It is secreted both in diabetic and in healthy individuals along with insulin from the β-cells of Langerhans' islets. Amylin was first discovered in 1987 and is currently the third active hormone of the pancreas, which contributes to controlling blood sugar levels. Amylin prevents excessively rapid emptying of the stomach and in this way retards glucose uptake after meals. In addition it could be demonstrated that amylin inhibits both glucagon and somatostatin secretion. Just like other members of the calcitonin-like peptides amylin binds to a G protein-coupled receptor. And just like the other members of the G protein-coupled receptors, which bind calcitonin-like peptides, the amylin receptor is composed of different subunits, containing, apart from the calcitonin receptor gene product (CTR), either the protein RAMP1 (receptor activity-modifying protein 1) or the protein RAMP3 (receptor activity modifying protein 3). Both isoforms form the amylin receptor; but there are also reports that RAMP 2 can participate in building the receptor (G. Christopoulos et al. Mol Pharmacol. 1999 July; 56(1): 235-42 and N. Tilakaratne J Pharmacol Exp Ther 2000 July; 294(1): 61-72).

Besides, it causes a feeling of fullness and thirst, apparently through interaction with the central nervous system. Binding sites for amylin were found in the kidney rind (in particular in the region of the juxtaglomerular apparatus) (Hayden, M. R. (2002). "Islet amyloid, metabolic syndrome, and the natural progressive history of type 2 diabetes mellitus." Jop 3 (5): 126-38). Activating the rennin angiotensin aldosteron system, which inter alia regulates blood pressure and excretion of sodium, was likewise falls described (Cooper, M. E., P. G. McNally, et al. (1995). "Amylin stimulates plasma rennin concentration in humans." Hypertension 26 (3): 460-4). In patients, suffering from diabetes mellitus, heightened sensitivity to the constituents of the systemic rennin angiotensin system was established (Carlsson, P. O. (2001). "The rennin-angiotensin system in the endocrine pancreas." Jop 2 (1): 26-32 2001).

Amylin levels in the blood are increased in patients with type 2 diabetes mellitus, overweight patients with insulin resistance and in patients with restricted glucose tolerance.

Increased amylin production, which constantly represents a concomitant form of increased insulin production, frequently leads to the formation of amyloid plaques in the pancreas. These plaques widen out from the Langerhans' islets containing β cells over the whole pancreas, as was able to be shown in transgenic mice, which express human amylin and form typical amyloid deposits (Wang, F., R. L. Hull, et al. (2001). "Islet amyloid develops diffusely throughout the pancreas before becoming severe and replacing endocrine cells." diabetes 50 (11): 2514-20). It is described variously in the literature that amyloid plaques especially let the β cells of the pancreas die off, or at least impair them in their function as insulin producer (Jaikaran, E. T. and A. Clark (2001). "Islet amyloid and type 2 diabetes: from molecular misfolding to islet pathophysiology." Biochim Biophys Acta 1537 (3): 179-203). Resulting from this for Jaikaran and Clark (2001) (Jaikaran, E. T. and A. Clark (2001). "Islet amyloid and type 2 diabetes: from molecular misfolding to islet pathophysiology." Biochim Biophys Acta 1537 (3): 179-203) is the consequence that plaque formation is a procedure which can be stopped by new therapeutic interventions (Jaikaran, E. T. and A. Clark (2001). "Islet amyloid and type 2 diabetes: from molecular misfolding to islet pathophysiology." Biochim Biophys Acta 1537 (3): 179-203). However, it has not been finally explained whether the deposits of the amyloid polypeptides toxic for β cells represents only a simultaneously occurring phenomenon, a strengthening or even a trigger for the course of type 2 diabetes mellitus. It is clear that the amyloid plaques are observed in over 70% of patients (Hayden, M. R. (2002). "Islet amyloid, metabolic syndrome, and the natural progressive history of type 2 diabetes mellitus." Jop 3 (5): 126-38). Other sources speak of over 90% (Scrocchi, L. A., Y. Chen, et al. (2002). "Design of peptide-based inhibitors of human islet amyloid polypeptide fibrillogenesis." J Mol Biol 318 (3): 697-706) to over 95% (Kapurniotu, A., A. Schmauder, et al. (2002). "Structure-based design and study of non-amyloidogenic, double N-methylated IAPP amyloid core sequences as inhibitors of IAPP amyloid formation and cytotoxicity." J Mol Biol 315 (3): 339-50).

Also in the case of patients with renal failure, taking part in dialysis programs, increased concentrations of amyloid polypeptides in the blood were proven (de Koning, E. J., K. A. Fleming, et al. (1995). "High prevalence of pancreatic islet amyloid in patients with end-stage renal failure on dialysis treatment." J Pathol 175 (2): 253-8).

Other groups also have already tried to prevent the development of fibrils from amylin. Scrocchi et al. and Kapurniotu et al. (2002) report a peptidic antagonist of fibril formation (Scrocchi, L. A., Y. Chen, et al. (2002). "Design of peptide-based inhibitors of human islet amyloid polypeptide fibrillogenesis." J Mol Biol 318 (3): 697-706) (Kapurniotu, A., A. Schmauder, et al. (2002). "Structure-based design and study of non-amyloidogenic, double N-methylated IAPP amyloid core sequences as inhibitors of IAPP amyloid formation and cytotoxicity." J Mol Biol 315 (3): 339-50).

As a result of the abovedescribed involvement of amylin in a series of biological processes corresponding applications can arise for treating and/or preventing organisms, in particular mammals, and, quite particularly preferred, humans. The corresponding illnesses are in particular high blood pressure and diabetes, in particular diabetes mellitus.

As in the case of CGRP receptors, herein also designated as CGR receptor system, the nucleic acids or respectively the antagonists of amylin according to the present invention are also those of the amylin receptor, also designated here as an amylin-receptor system. The amylin and/or the amylin receptor is preferably amylin or respectively amylin receptor from human or rat. Amylin receptors are described as such for example in Christopoulos G, Perry K J, Morfis M, Tilakaratne N, Gao Y, Fraser N J, Main M J, Foord S M, Sexton P M. Multiple amylin receptors arise from receptor activity-modifying protein interaction with the calcitonin receptor gene product. Mol Pharmacol. 1999 July; 56(1): 235-42; Tilakaratne N, Christopoulos G, Zumpe E T, Foord S M, Sexton P M. Amylin receptor phenotypes derived from human calcitonin receptor/RAMP coexpression exhibit pharmacological differences dependent on receptor isoform and host cell environment; Tilakaratne N, Christopoulos G, Zumpe E T, Foord S M, Sexton P M. J Pharmacol Exp Ther 2000 July; 294(1): 61-72.

The inventive nucleic acids or respectively antagonists can thus be used for inhibiting the physiological effect of amylin, in particular inhibiting the amyloid-dependent stimulating of the rennin angiotensin aldosteron system or the effect on the central nervous system. Also, such nucleic acids or respectively antagonists can be employed tp prevent amyloid plaques, for example in the pancreas. It is also within the scope of the present invention that the amyloid plaques are dispersed with use of the inventive antagonists or respectively nucleic acids. Belonging to the group of the inventive nucleic acids, which bind to amylin or respectively represent an amylin receptor antagonist, are in particular those nucleic acids with the SEQ ID No. 191 to SEQ ID No. 196.

The nucleic acids according to the present invention should also comprise those nucleic acids which are substantially homologous to the sequences specifically disclosed herein. The term substantially homologous is to be understood herein such that the homology is at least 75%, preferably 85%, more preferably 90% and most preferably more than 95, 96, 97, 98 or 99%.

The term inventive nucleic acid or nucleic acid according to the present invention should also comprise those nucleic acids which make up part of the nucleic acid sequences disclosed herein or respectively comprise nucleic acids to the extent that said parts are involved with the binding of CGRP. This type of nucleic acids can be derived from those disclosed herein, for example by shortening or truncating. The shortening should refer either to one or both ends of the herein disclosed nucleic acids. The shortening can also refer to a nucleotide sequence within the respective nucleic acid or respective nucleic acid sequence, i.e. they can refer to one or more nucleotides between the 5'- or respectively the 3'-terminal nucleotide. In that context shortening should include the deletion of as little as a single nucleotide from the sequence of the nucleic acids disclosed herein. Shortening can also affect more than one area of the inventive nucleic acid(s). Examples for shortening of the nucleic acids are given in the exemplary section of the present description.

The nucleic acids according to the present invention can either be D nucleic acids or L nucleic acids. The nucleic acids are preferably L nucleic acids. It is also possible that one or more parts of the nucleic acid are configured as D nucleic acid(s), or at least one or more parts of the nucleic acid are designed as L nucleic acid. The term "part" of the nucleic acid should describe as little as one nucleotide. Such nucleic acids are generally designated herein as D or respectively L nucleic acid.

It is also within the scope of the present invention that the inventive nucleic acids are part of a longer nucleic acid, whereby this longer nucleic acid comprises several parts, whereby at least one part is a nucleic acid according to the present invention or a part thereof. The other part or the other parts of these longer nucleic acids can be either a D nucleic acid or an L nucleic acid. Any combination can be used in conjunction with the present invention. This other part or respectively these other parts of the longer nucleic acid can have a function, which is different to binding and especially to binding to CGRP. A possible function comprises interaction with other molecules, e.g. for the purposes of allowing immobilising, cross-linking, proof or amplification.

The L nucleic acids are thus nucleic acids, comprising L nucleotides, preferably completely comprising L nucleotides.

D nucleic acids are thus those nucleic acids comprising D nucleotides, preferably completely comprising D nucleotides.

Independently of whether the inventive nucleic acid comprises D nucleotides, L nucleotides or a combination of both, whereby the combination is e.g. a random combination or a defined sequence of successions of nucleotides, comprising at least a L nucleotide or respectively a D nucleotide, the nucleic acid can comprise one or more desoxyribonucleotide(s), ribonucleotide(s) or combinations thereof.

The configuring of the inventive nucleic acids as L nucleic acid is associated with advantages for a number of reasons. The L nucleic acids are enantiomers of the naturally occurring nucleic acids. The D nucleic acids however are not very stable in aqueous solutions and in particular in biological systems or biological samples as a result of the broad distribution of nucleases. Naturally occurring nucleases, in particular nucleases of animal cells or tissues or cell or body fluids, are not in a position to break down L nucleic acids. As a result of this the biological half-life value of the L nucleic acid in such systems, including the human and animal body, is essentially prolonged. Conditional on the absence of the decomposition capacity of L nucleic acids no nuclease decomposition products are created and in this respect no side effects attributed to the latter are observed. This aspect distinguishes the L nucleic acid from all those other compounds used in therapy for illnesses which tailor to the presence of CGRP.

It is also within the scope of the present invention that the inventive nucleic acids, independently of whether they are present as D nucleic acids, L nucleic acids or D, L nucleic acids, or whether they are present as DNA or RNA, can be present as single-strand or double-strand nucleic acids. Typically the inventive nucleic acids are single-strand nucleic acids, which exhibit a defined secondary structure as a result of the primary sequence and also can form tertiary structures. The inventive nucleic acids can however also be present as double-stranded in the sense that two complementary strands are paired with one another as a result of hybridising. This lends the nucleic acid a stability which is of advantage when the nucleic acid is present in the naturally occurring D form instead of the L form.

The inventive nucleic acids can also be modified. A particularly advantageous modification in connection with the present invention constitutes configuring the inventive nucleic acid(s), in which at least one, preferably more and most preferably all pyrimidine nucleotides forming the nucleic acid have a 2'-fluoro group at the 2' position of the ribose section of each nucleotide. Other modifications represent for example those with PEG.

Further examples for modifying the inventive nucleic acids can be those modifications which affect a single nucleotide of the nucleic acid and are well known in the prior art. Corresponding examples are described, inter alia, in Kusser, W. (2000) J Biotechnol 74, 27-38; Aurup, H. et al., 1994, Nucleic Acids Res 22, 20-4; Cummins, L. L. et al, 1995, Nucleic Acids Res 23, 2019-24; Eaton, B. E. et al., 1995, Chem Biol 2, 633-8; Green, L. S. et al., 1995, Chem Biol 2, 683-95; Kawasaki, A. M. et al., 1993, J Med Chem 36, 831-41; Lesnik, E. A. et al., 1993, Biochemistry 32, 7832-8; Miller, L. E. et al., 1993, J Physiol 469, 213-43.

The nucleic acids according to the present invention can be formed as a single-, two-, three- or multi-part form. Of the multi-part form the two-part or bipartite form is particularly preferred. A multi-part form of an inventive nucleic acid is herein in particular that which comprises at least two nucleic acid strands. Both these nucleic acid strands form a functional unit, whereby the functional unit is a ligand or binding molecule for a target molecule. The at least two strands can be derived from one of the inventive nucleic acids or are derived from splitting an inventive nucleic acid binding to the target molecule, to form two or more strands, or from synthesis of a nucleic acid, corresponding to a first part of the inventive complete nucleic acid and a further nucleic acid, corresponding to a second part of the inventive complete nucleic acid. It should be noted that both the splitting and the synthesis can be applied to produce a multi-part nucleic acid, comprising more than both abovedescribed strands. It should also be stated concerning the multi-part forms of the inventive nucleic acid that at least two nucleic acid strands are typically different to two strands, which are complementary to one another and hybridise with one another, even though a certain degree of complementarity can exist between the different nucleic acid (parts).

The nucleic acids according to the present invention typically have a high affinity to the target molecule. A possibility of determining the affinity, expressed as a binding constant, of the inventive nucleic acids is to use the so-called Biacore device, known to the specialists in this field and described for example in Jönsson, U. et al., 1991, Biotechniques, 11 (5), 620. The affinities were also measured by isothermal titration calorimetry (ITC), as described in the examples and in Haq, I. & Ladburg, J., 2000, J. Mol. Recognit. 13 (4): 188. In this respect the herein described affinity values are to be understood as measured by isothermal titration calorimetry, whereby the temperature for single measuring was 25° C., as long as no contrary data are compiled. A further method employed is applied manually; this is a bead assay, as abovementioned. Hereby constant concentrations of radioactively marked nucleic acid are combined with different concentrations of biotinylated target molecule such as for example a target peptide. After a defined period the formed complexes are removed via addition of beads charged with streptavidin from the solution and each quantity of radioactivity is determined. The binding constants can be determined from the received values via corresponding placing into graphs. This bead assay is described in greater detail inter alia in Example 3. Insofar as reference is made herein to an inventive nucleic acid, all inventive nucleic acids or respectively all nucleic acids disclosed herein should be understood, as long as no contrary data are compiled.

It is also within the scope of the present invention that the inventive sequences originate either fully or partly from the randomised part of the members of a nucleic acid library, which are used as starting material for the selection process.

It is however also within the scope of the present invention that the inventive sequences originate either fully or partly from the non-randomised part of the members of the nucleic acid library, which serves as starting material for the selection process. Such a non-randomised part is for example the part used as binding site for the amplification primer.

The inventive nucleic acids can be utilised to create or produce a drug. This type of drug contains at least one of the inventive nucleic acids, optionally together with further pharmaceutically active compounds, whereby the inventive nucleic acid(s) preferably itself functions as pharmaceutically active compound. By way of example one of the inventive nucleic acids could be combined with another active ingredient, which influences the concentration of CGRP or respectively amylin. In general the combination of the inventive nucleic acids with the other active ingredient seems beneficial particularly when both components of CGRP or respectively amylin and their release are affected by different work mechanisms. A combination advantageous in this sense could comprise for example one of the inventive nucleic acids as well as a triptane, such as for example sumatriptane, since both substances react to different work mechanisms. With a migraine attack a combi-preparation and its effect could be presented as follows: CGRP occurring in the plasma is removed by an inventive nucleic acid and at the same time the CGRP release is reduced/hindered by triptanes. Such drugs include at least one pharmaceutically acceptable carrier in preferred embodiments. Such carriers can be e.g. water, buffer, starch, sugar, gelatine and the like. Such carriers are known to specialists in the field.

The illnesses, for which the inventive nucleic acids and the CGRP antagonists identified under their use can be used, are substantially those which belong to the pattern of migraine, in particular migraine with and without aura, simple migraine, classic migraine and complicated migraine. Inter alia there are headaches, in particular repetitive headaches, nausea, vomiting, excessive sensitivity to external stimuli such as light and noise, loss of appetite and disorders of the fluid balance. The headache is particularly one which occurs in patients as pulsing and throbbing. Typically these headaches occur to one side. Other illnesses, which can be identified with use of the inventive nucleic acids and the candidate CGRP antagonists identified on the basis of their use, are vasodilation, raised blood pressure, hypotonia and tachycardia, in particular those forms of the abovementioned illnesses, observed in conjunction with migraine, in particular a migraine attack. Other illnesses, which can be provided using the inventive nucleic acid or respectively the candidate CGRP antagonists identified using the inventive method, are those illnesses which are associated with activation of trigeminal afferent sensory neurones, with activation of central nociceptive neurones and combinations of activation of both neurone classes. In particular, these neurones are those which are assigned higher pain centres. Other illnesses in the abovementioned sense are, apart from acute pain, those illnesses associated with chronic inflammatory pain. Examples of such chronic inflammatory pain in particular are those which are caused by CGRP along with other neuropeptides, such as for example substance P.

The inventive nucleic acids can also be employed as starting material for the design of pharmaceutically active ingredients (Engl. drug design). Fundamentally, there are two possible approaches here. One approach consists of screening libraries of compounds, whereby such libraries of compounds are preferably libraries of low-molecular compounds (Engl. low or small molecules). Such libraries are known to specialists in this field. Alternatively, according to the present invention the nucleic acids can e used for rational design of active ingredients.

The rational design of active ingredients can take its starting point from any of the nucleic acids according to the present invention and comprises a structure, in particular a three-dimensional structure, similar to the structure of the inventive nucleic acid(s) or identical to the part of the structure of the inventive nucleic acid(s), which imparts binding to CGRP or respectively amylin. In each case such a structure still shows the same or at least a similar binding behaviour as the inventive nucleic acid(s). In either another step or as an alternative step with the rational design of active ingredients the preferably three-dimensional structure of those parts of the nucleic acids binding to CGRP or respectively amylin by chemical groups are mimicked, which are preferably different to nucleotides and nucleic acids. By way of this copying, also known as mimicry, a compound can be constructed which is different to the nucleic acid or respectively the nucleic acids, as was used as starting materials for the rational design of the active ingredient. Such a compound or active ingredient is preferably a small molecule (Engl. small molecule) or a peptide.

In the case of the screening of compound libraries, as with use of a competitive test, which are known to specialists in the field, suitable CGRP analogs, CGRP agonists, CGRP antagonists, amylin analogs, amylin agonists or amylin antagonists are found. Such competitive assays can be constructed as follows.

The inventive nucleic acid, preferably a spiegelmer, configured as L nucleic acid binding target molecule, is coupled to a fixed phase. In order to identify CGRP analogs neuropeptides provided with marking are added to the test system. A potential analogon would compete with the CGRP molecules, binding to the spiegelmer, which would be accompanied by a drop in the signal received from the corresponding marking. The screening on agonists or antagonists may comprise the use of a cell culture test system, known to the specialists in the field. In principle the same approaches can be employed using amylin.

In a further aspect the inventive nucleic acids can be used for target validating as a result of their characteristic binding behaviour to CGRP or respectively amylin. The inventive nucleic acids can be used in an ex vivo organ model for studying the function of CGRP or respectively amylin. There are basically two ex vivo models, in which CGRP agonists/antagonists can be tested. In the guinea pig atrium antagonists for the CGRP2 receptor can be tested, and in the rats vas deferens model antagonists can be checked with respect to their specificity for the CGRP receptor.

In a further aspect of the invention this relates to a complex comprising CGRP or respectively amylin and at least one of the inventive nucleic acids. It has been surprisingly found that the inventive nucleic acids are relatively rigid and take on a precisely defined structure, and in this respect also impart a comparatively rigid structure on the target molecule, i.e. the CGRP or respectively amylin itself, whereby both the CGRP and the amylin are generally comparatively flexible as a result of its length.

The kit according to the present invention can comprise at least one or more of the inventive nucleic acids. In addition, the kit can include at least one or more positive or negative controls. For example, CGRP or respectively amylin can be used as positive controls, against which the inventive nucleic acid was selected, or binds to the latter, preferably in liquid form. As a negative control inter alia a peptide can be used, which behaves similarly to CGRP with respect to its biophysical properties or respectively amylin, which is not however recognised by the inventive nucleic acids, or a peptide with same amino acid composition though from CGRP or respectively amylin of a different sequence.

Furthermore the kit can comprise one or more buffers. The different constituents can be present in the kit in dry or lyophilised form, or dissolved in a fluid. The kit can have one or more containers, which again can contain one or more of the constituents of the kit. Preferably, the vessels contain reaction preparations, as required for one-off carrying out of an experiment using one or more constituents of the kit.

It is further within the scope of the present invention that the inventive nucleic acids can be used as proof of the target molecule such as CGRP or respectively amylin or respectively the resulting structures such as for example amyloidal plaques or fibrils. For this the nucleic acids can be marked directly or indirectly. The marking is preferably selected from the group comprising radioactive markings, fluorescent markings or markings suitable for magnetic resonance spectroscopy, such as for example europium.

The inventive nucleic acids, antagonists or the drugs containing the latter can be applied both systemically and locally. In the case of use of amylin antagonists or respectively corresponding nucleic acids for example local administering is feasible in terms of an injection in the pancreas. It is also within the scope of the present invention to take up the antagonists or respectively nucleic acids in biocompatible gels as deposits, which are then released in the stomach region or in the pancreas.

The present invention is explained further by means of the following figures and examples, from which further characteristics, embodiments and advantages will emerge, and in which:

FIG. 2A shows the CGRP concentration and the associated percentage binding of the F-RNA pools used in each selection round, and FIG. 2B shows a graphic illustration of the values given in FIG. 2A;

FIG. 3 shows the result of sequence analysis of the nucleic acids binding CGRP contained within the scope of Example 1;

FIG. 18 shows the sequences of the initial sequences and the shortened sequences of the nucleic acids binding CGRP of Example 2;

Figure 24:
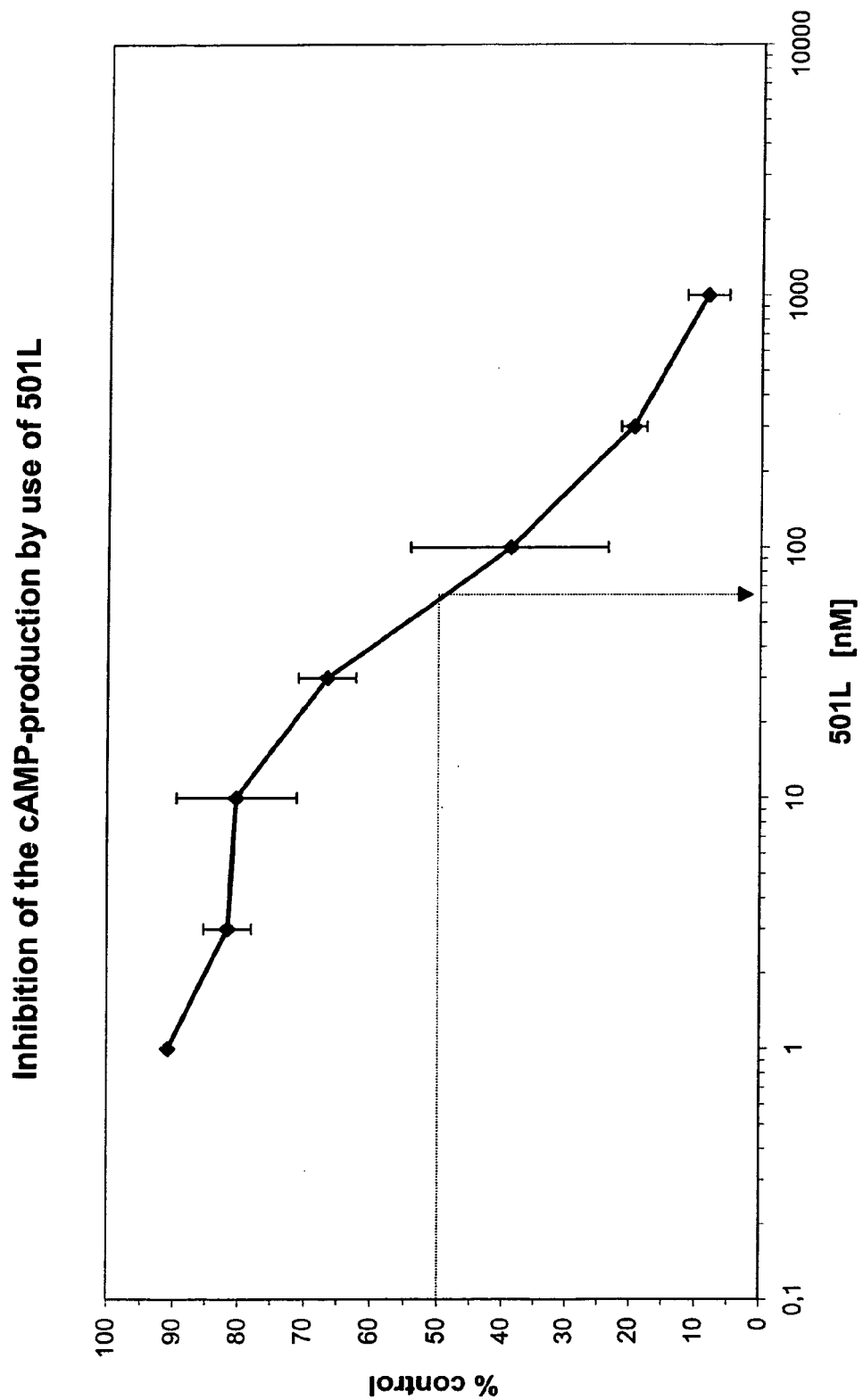
Figure 25:
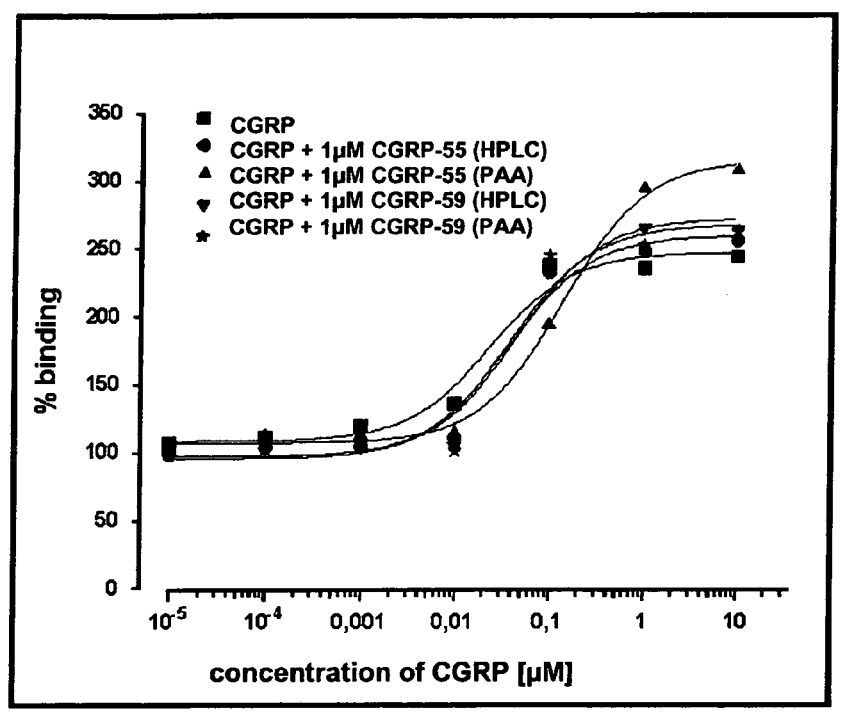
Figure 26:
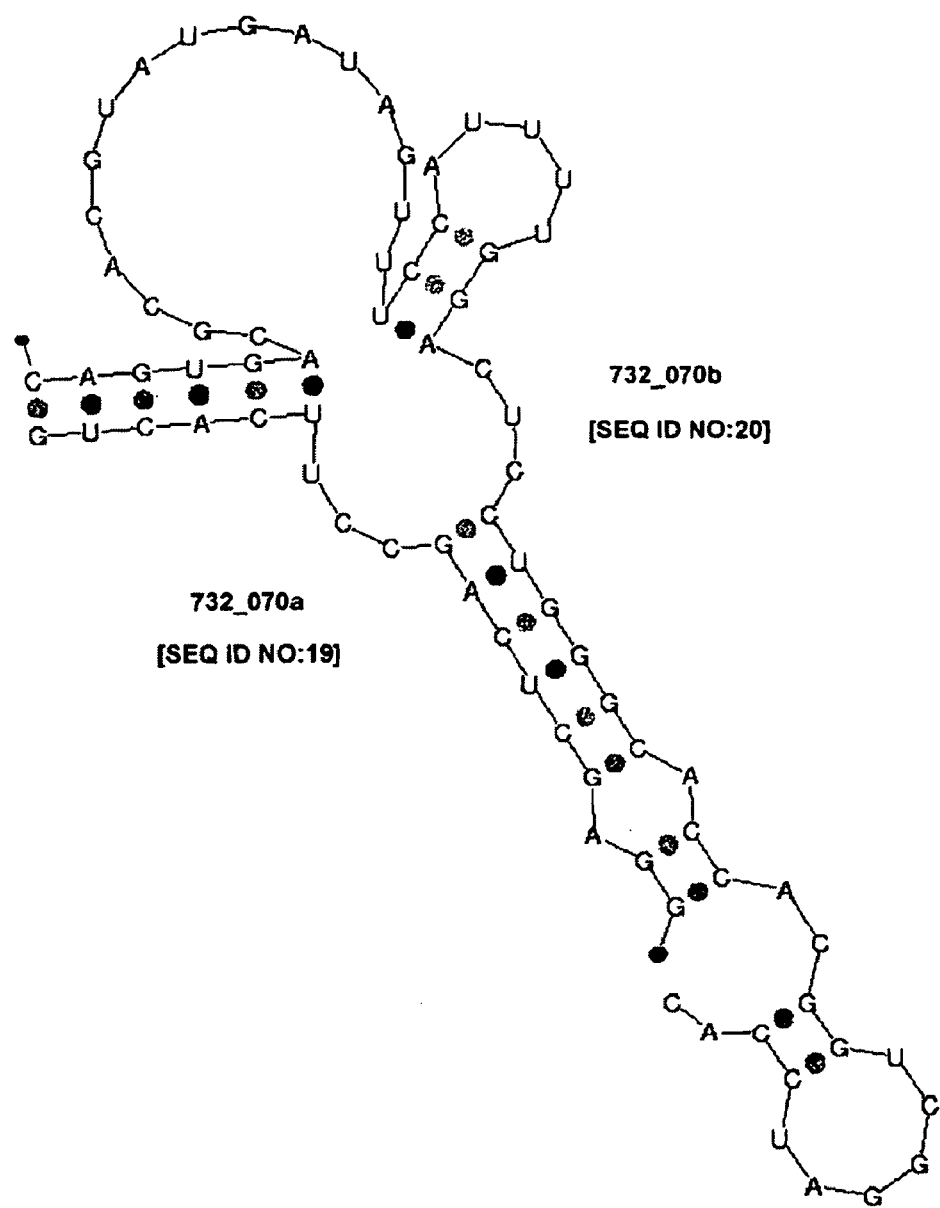
Figure 27:
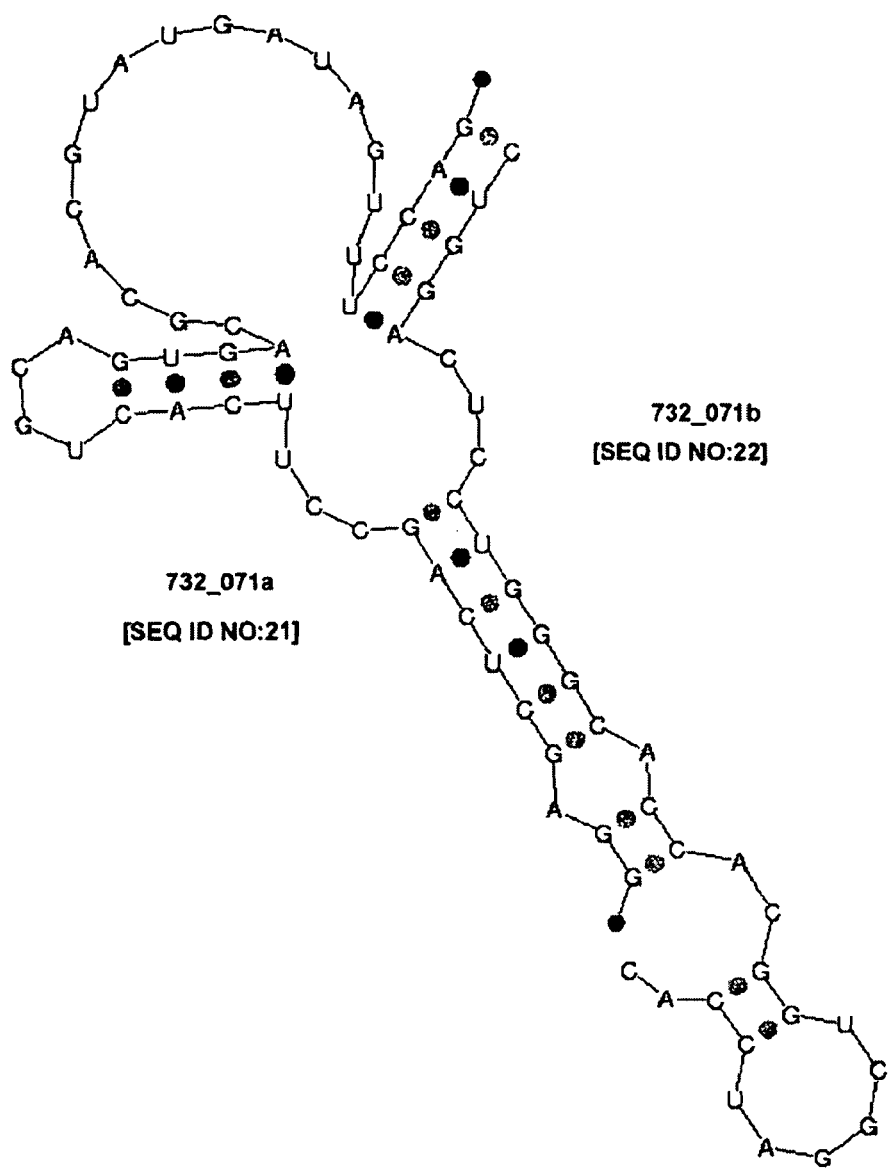
Figure 28:
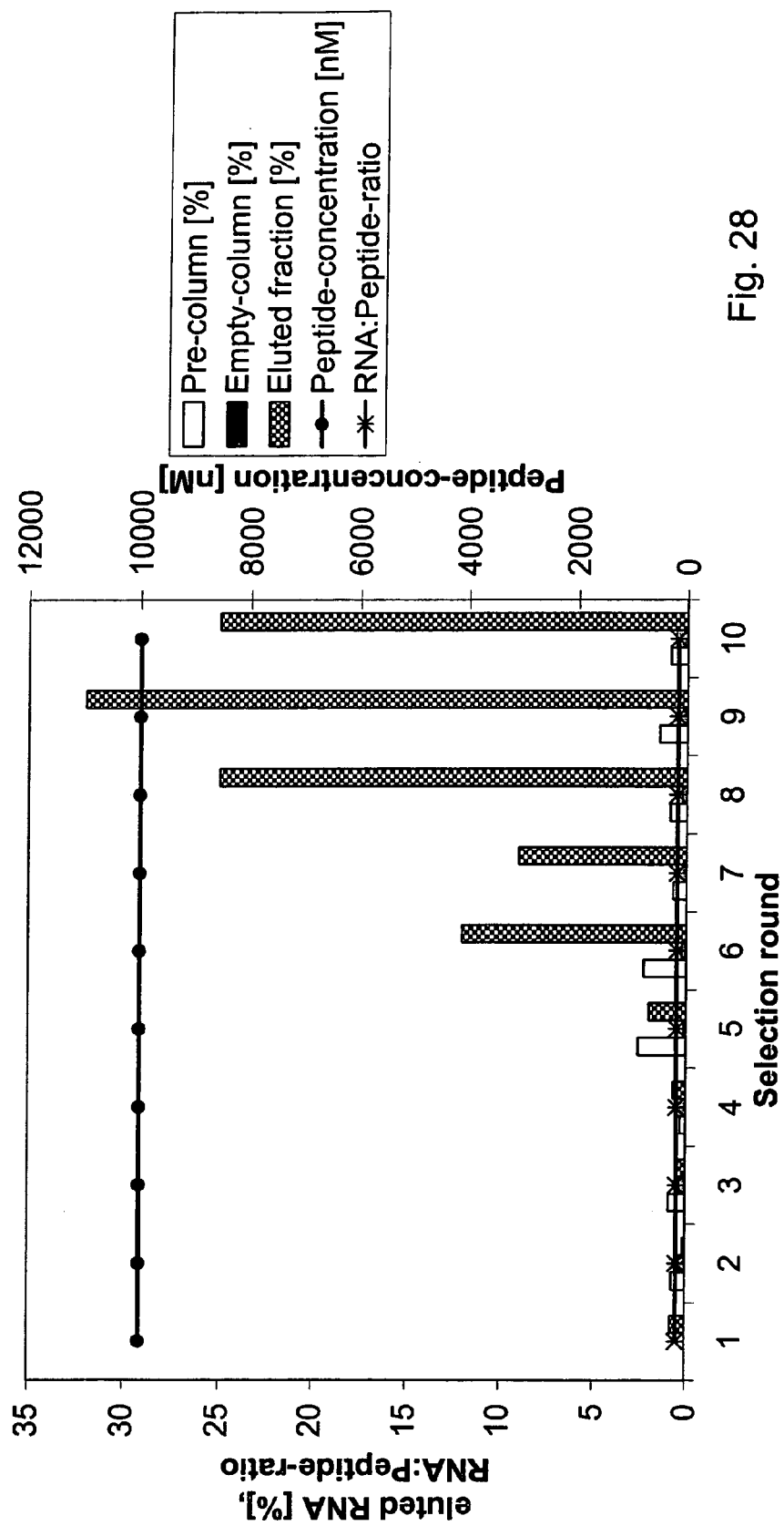
Figure 30:
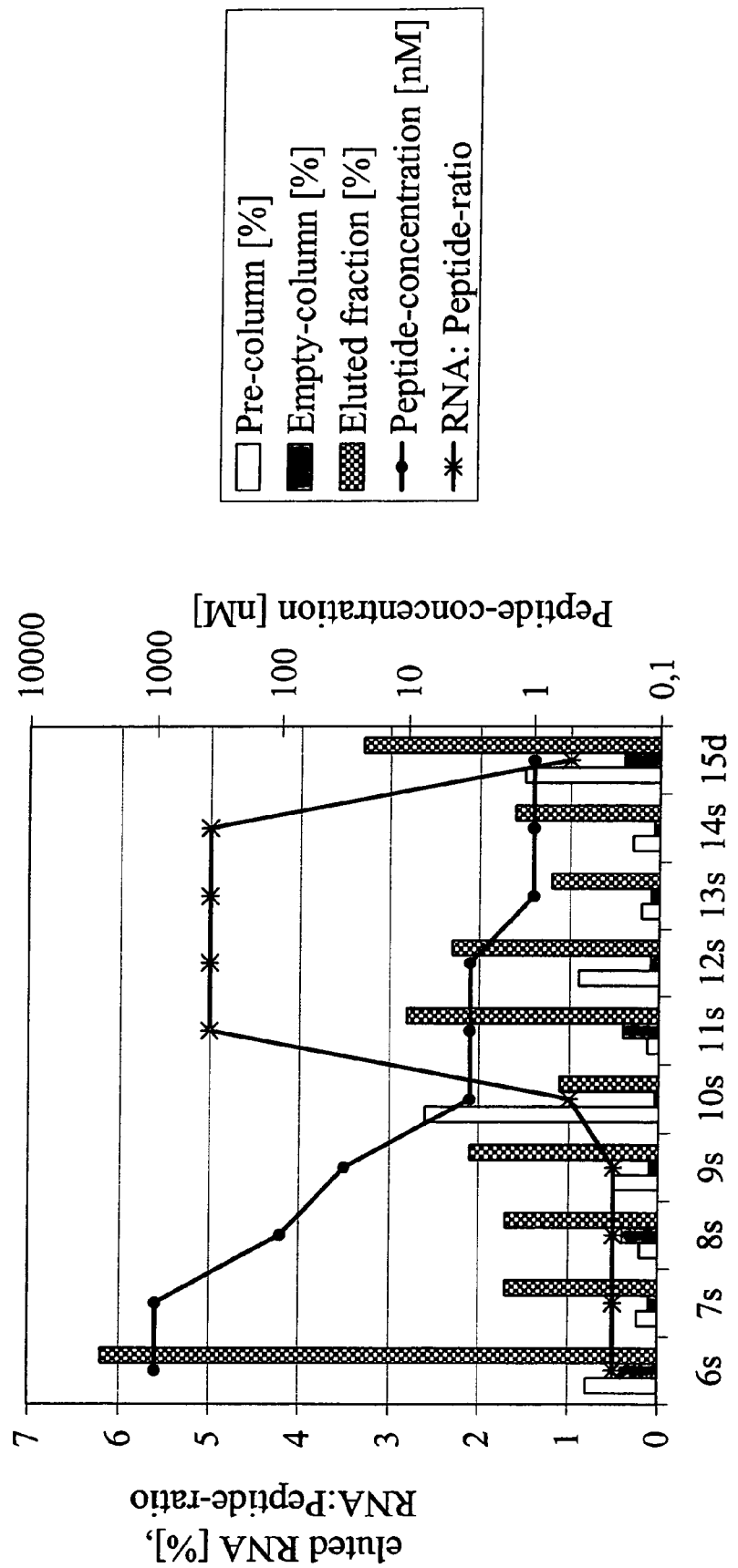
Figure 32:
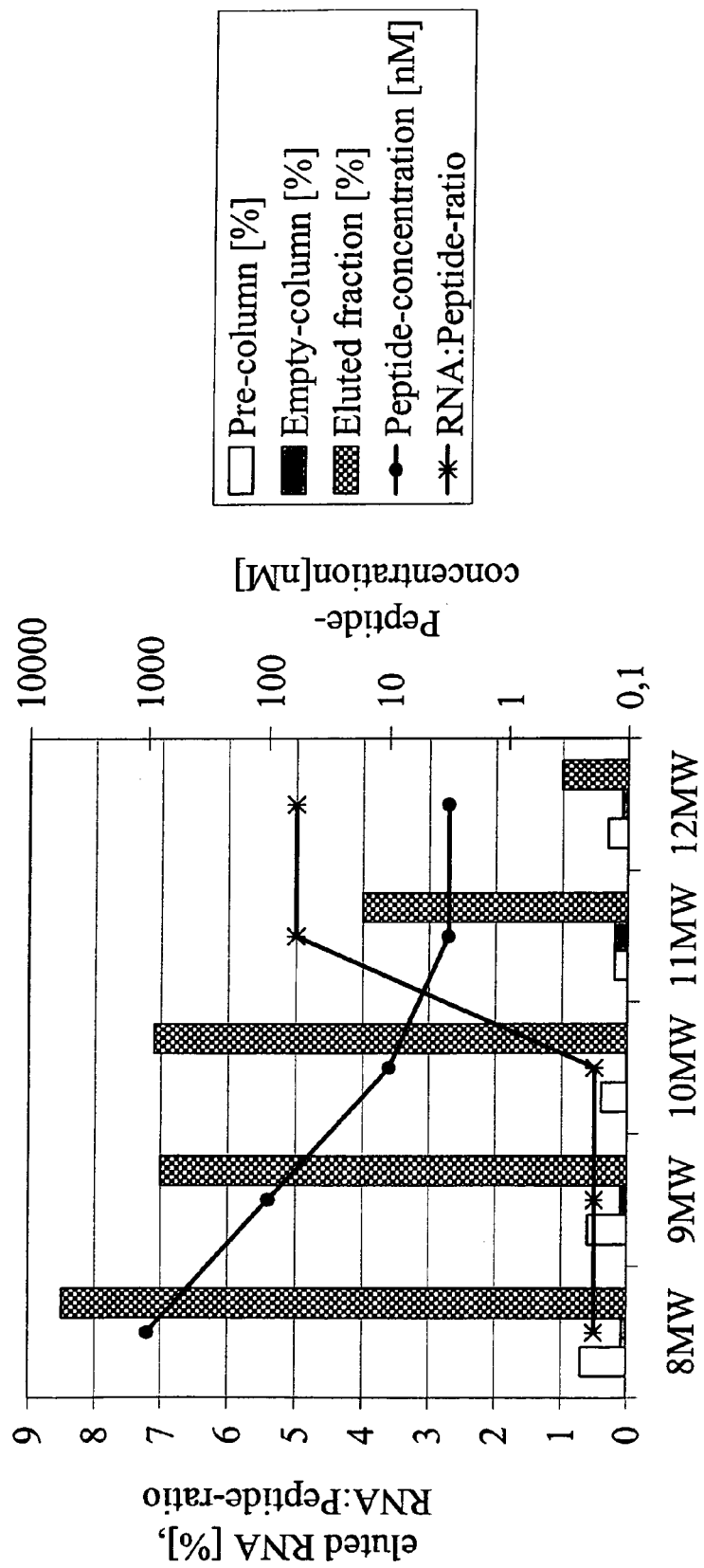
Figure 34:
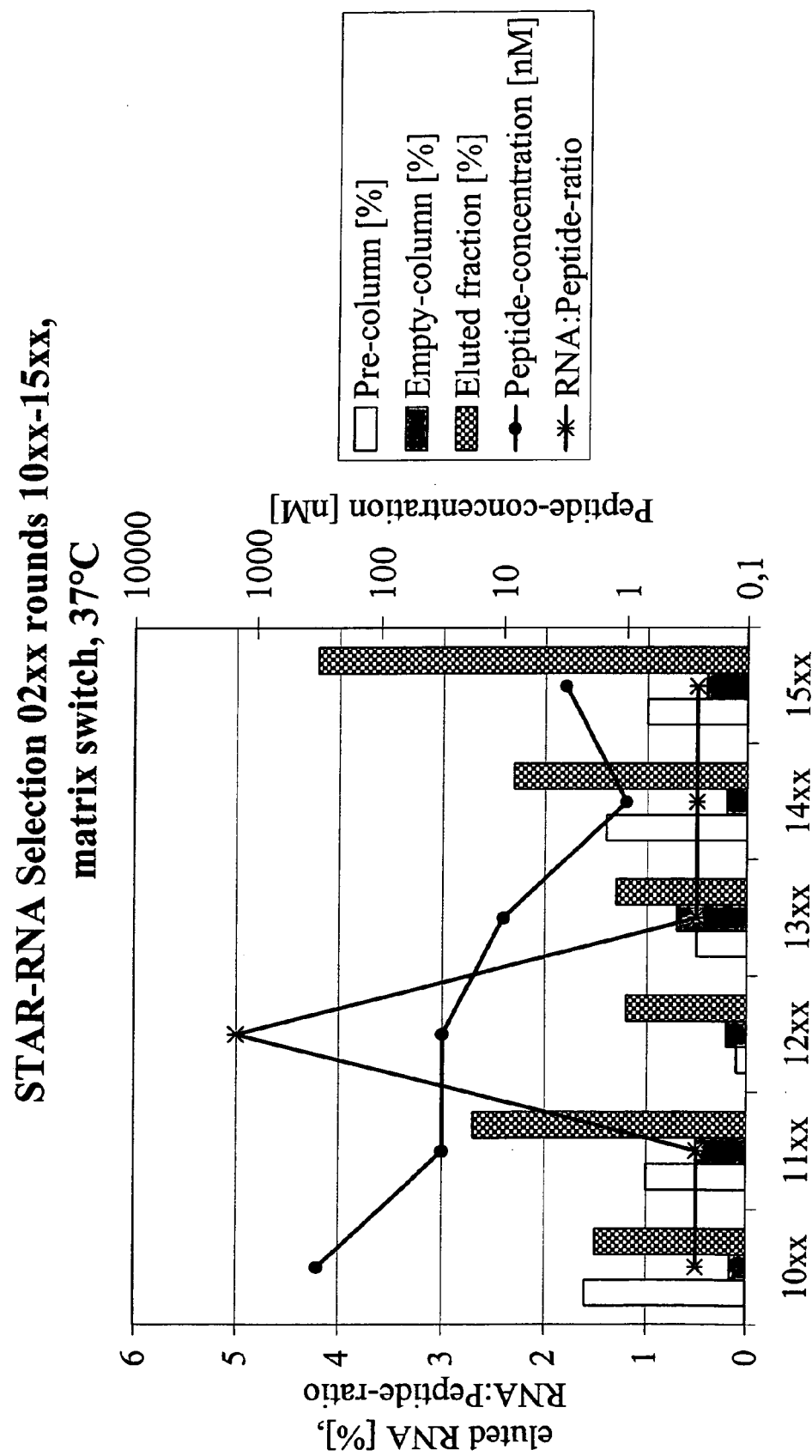
Figure 36:
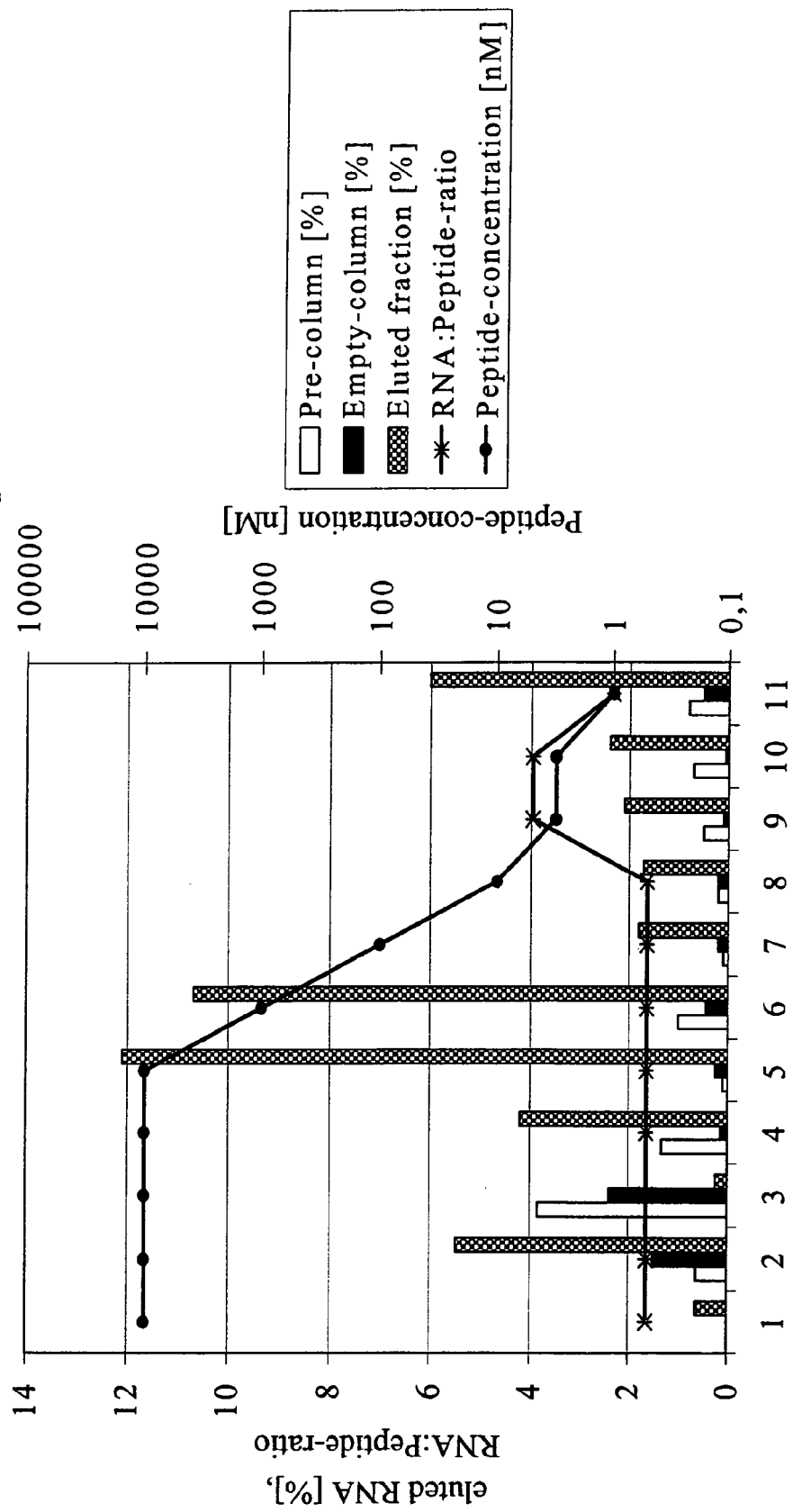
Figure 38:
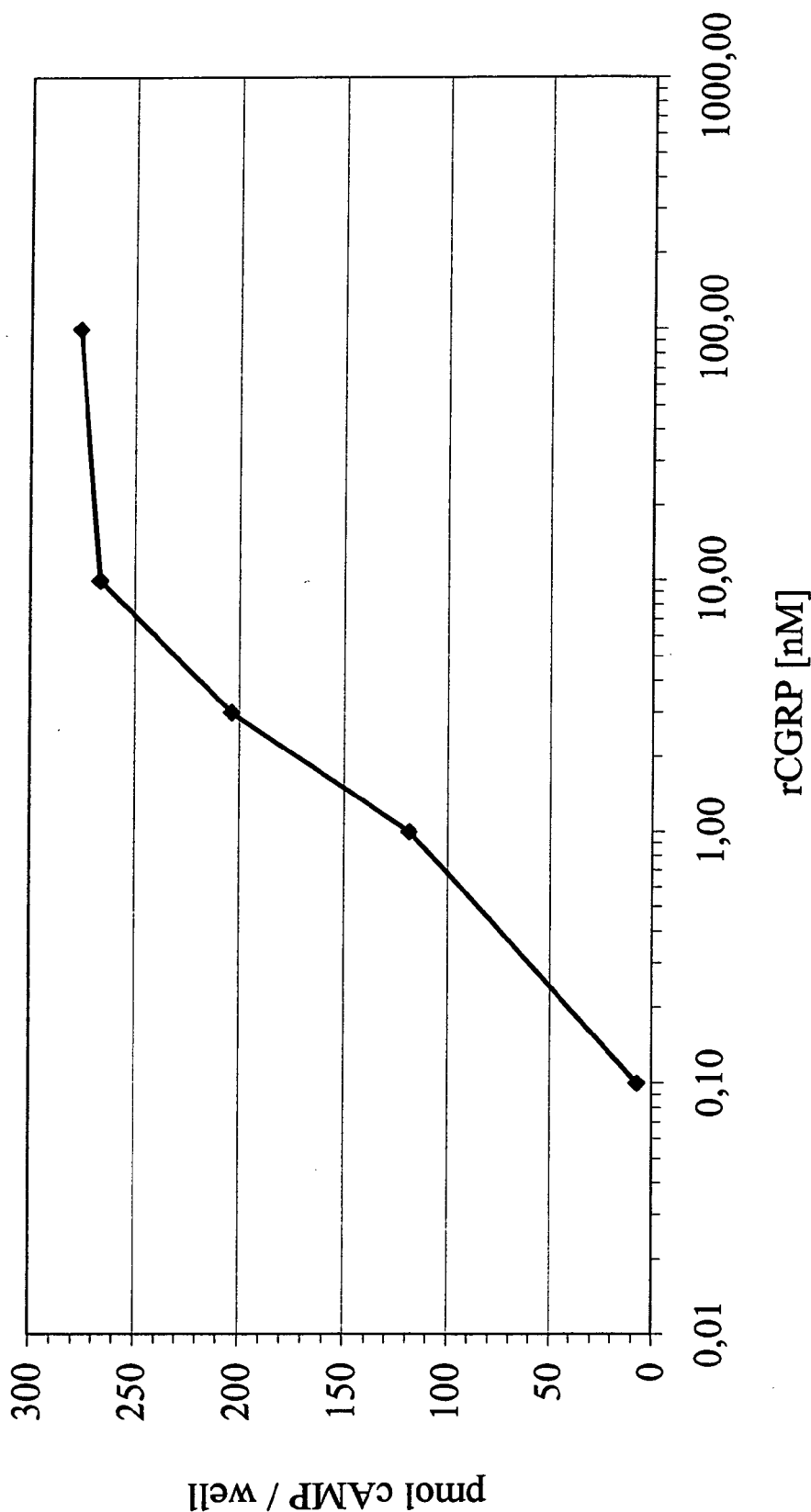

FIG. 24 shows the inhibition of cAMP production by spiegelmers binding rat CGRP, FIG. 25 shows binding studies with the various purified spiegelmers 732_045 (55mer) and 732_096 (59mer) in the [$^{35}$S] GTPyS assay, FIGS. 26-27 show the secondary structure of different nucleic acids binding to CGRP, as produced within the scope of Example 2 and which are combined from more than one nucleic acid strand, FIGS. 28, 30, 32, 34, 36 graphically show the course of the conditions of different selection rounds, FIGS. 29, 31, 33, 35, 37 show in table form the course of the conditions of different selection rounds, FIG. 38 shows the dose effect curve for CGRP, FIG. 39 to 42 show the course of the calorimetric determining of the binding constants of different nucleic acids binding CGRP;

FIG. 43 to 47 show the sequences of different nucleic acids binding CGRP, contained within the scope of Example 4, and FIGS. 48 and 49 show the sequences of different nucleic acids binding CGRP, contained within the scope of Example 3.

Figure 50:
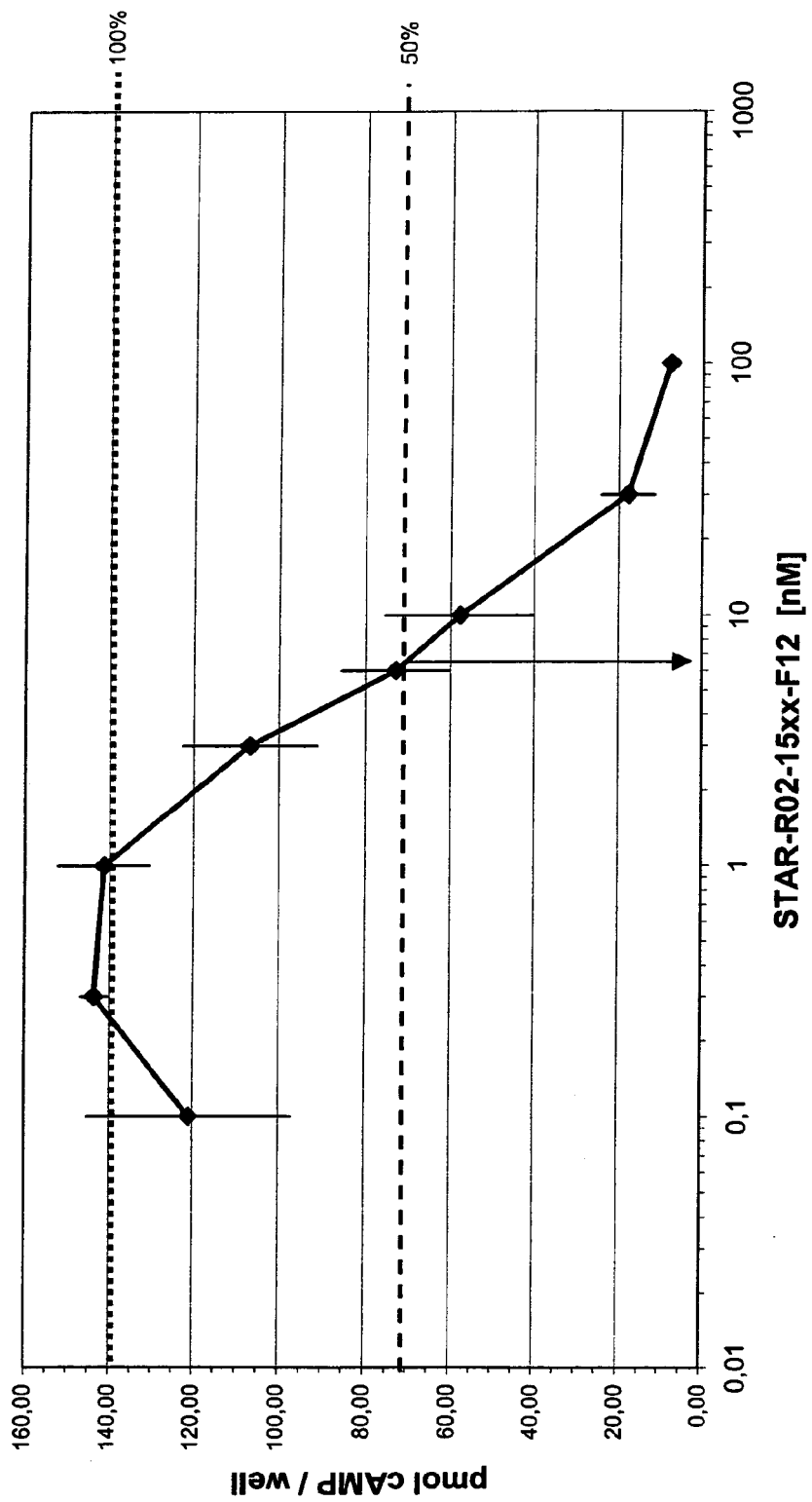
Figure 51:
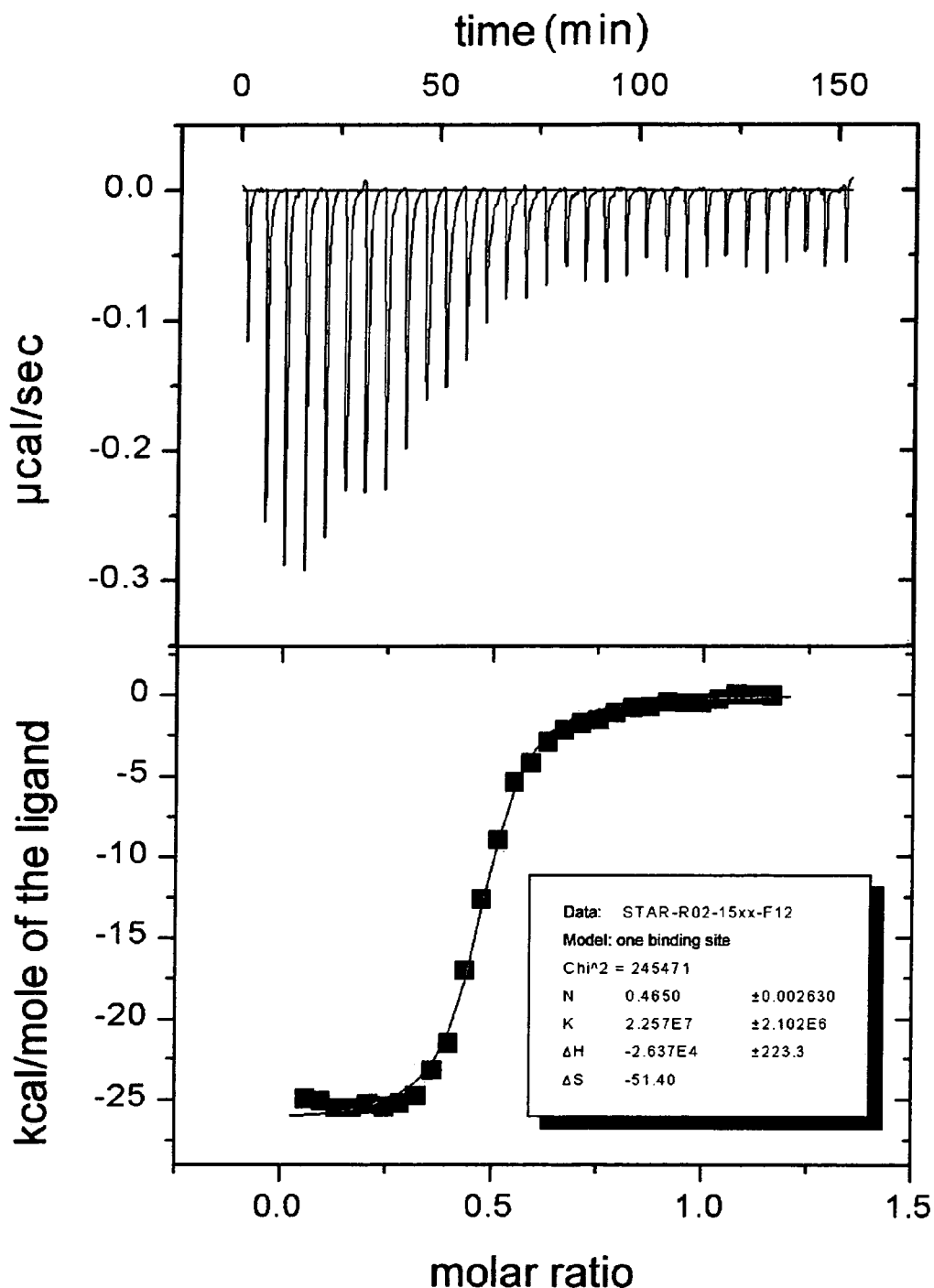
Figure 52:
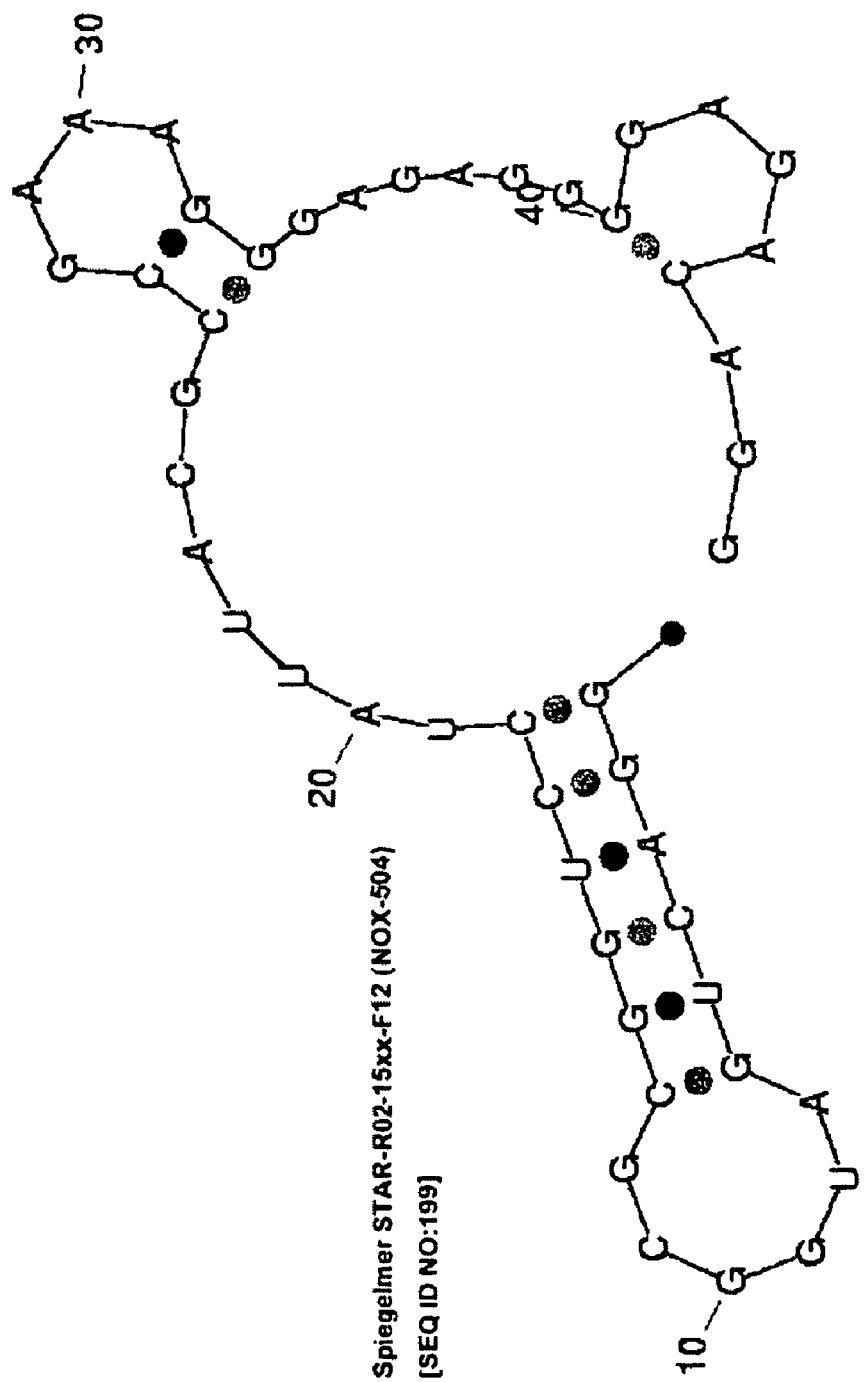
Figure 53:
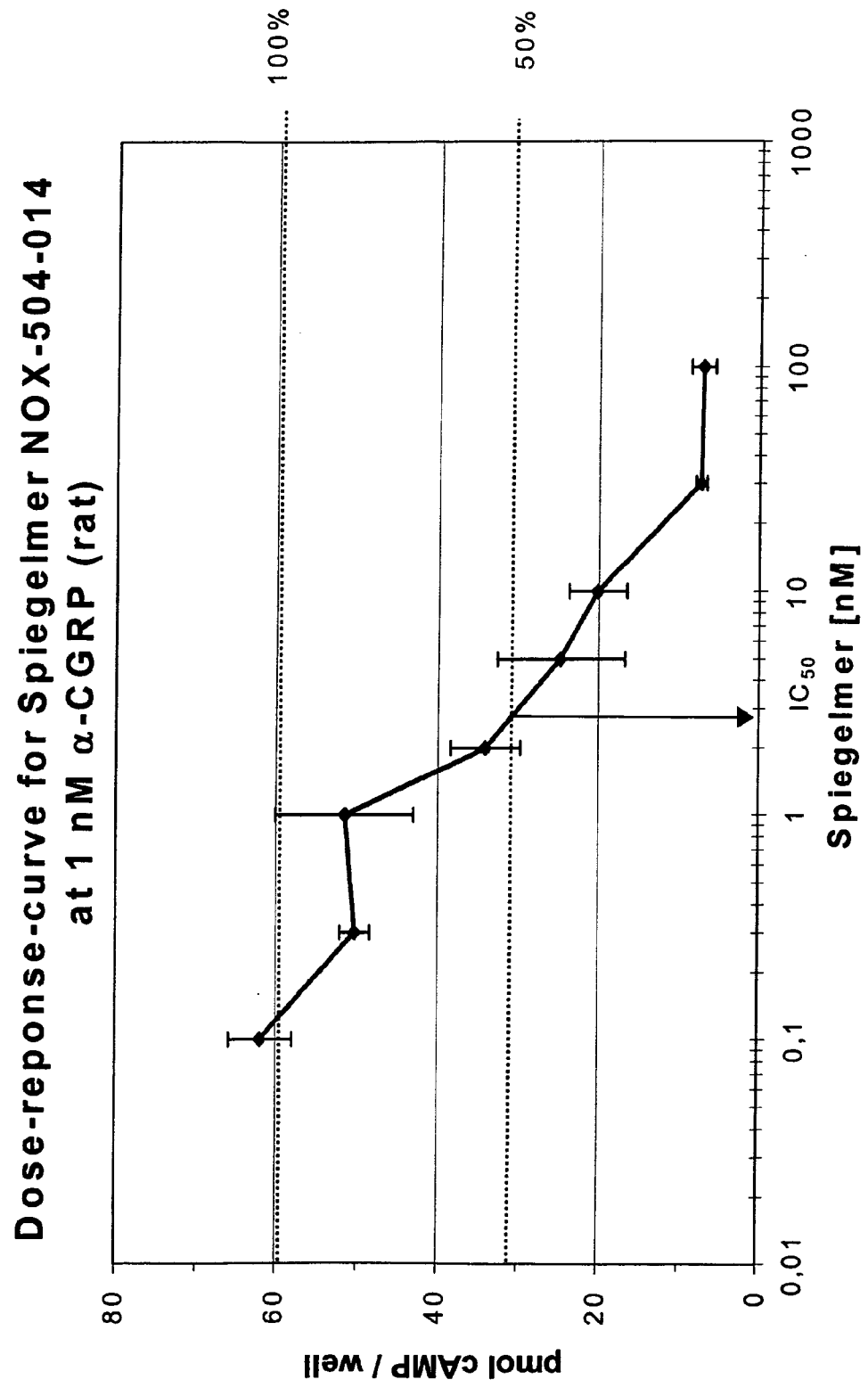
Figure 54:
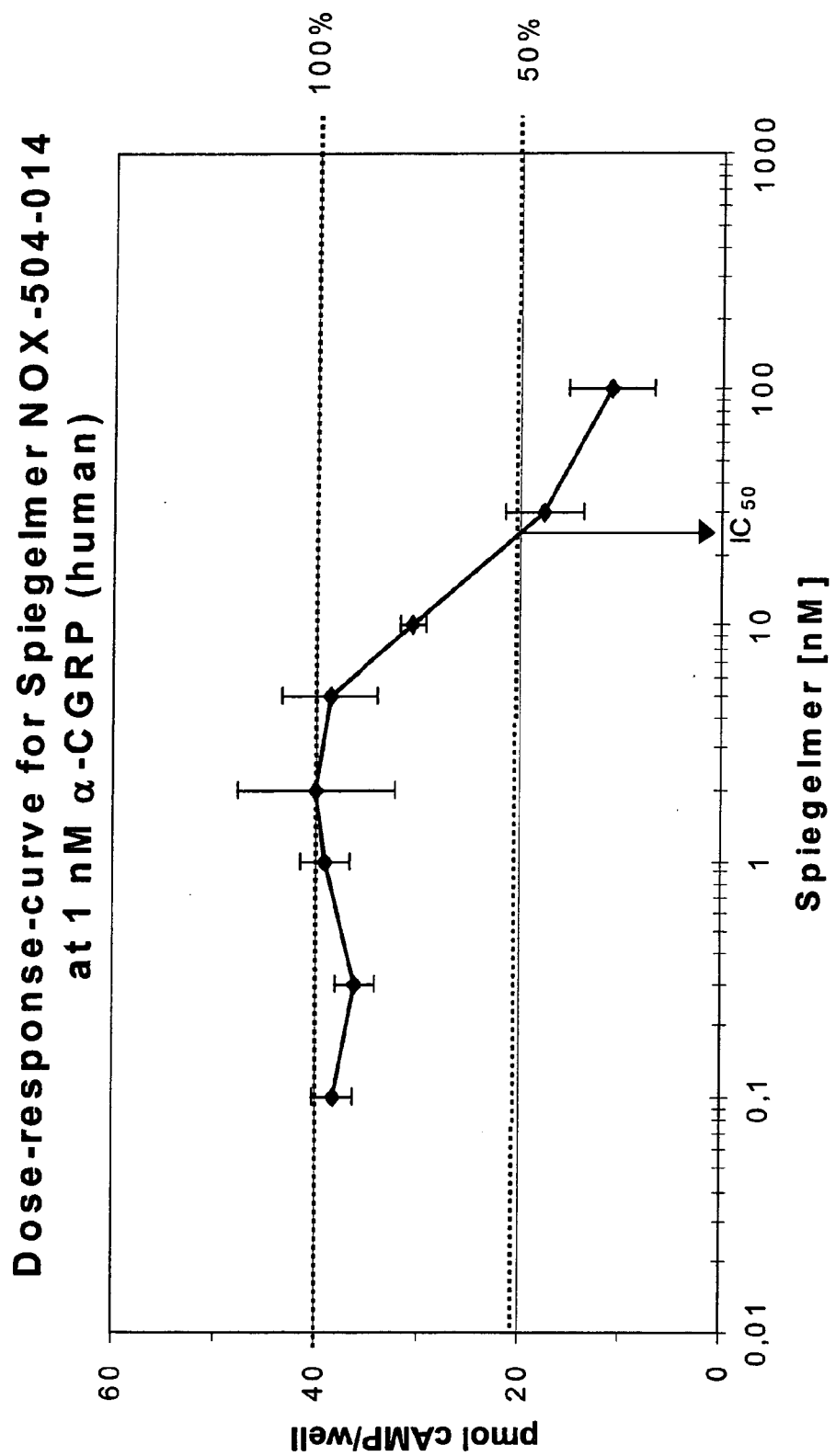
Figure 55:
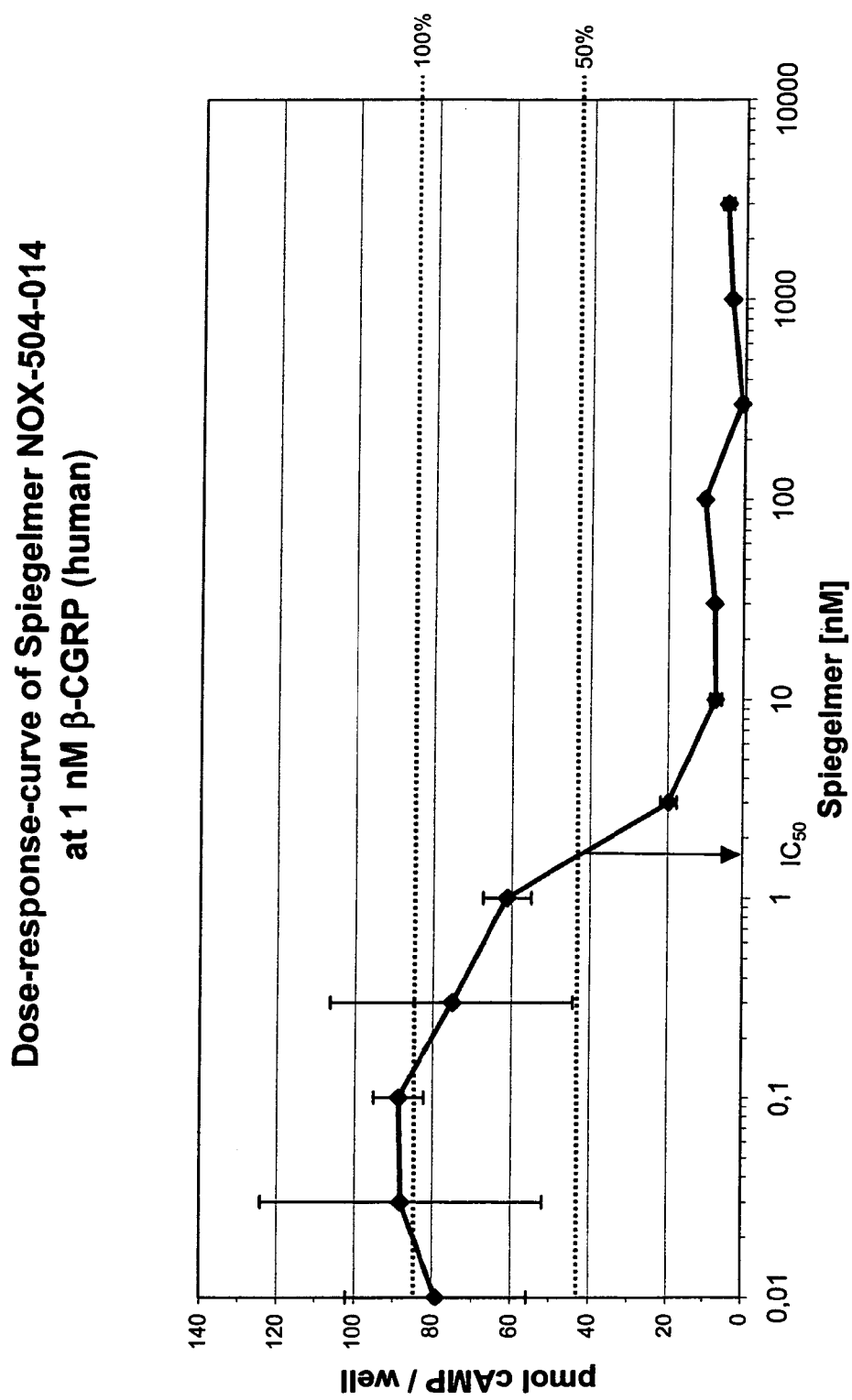
Figure 56:
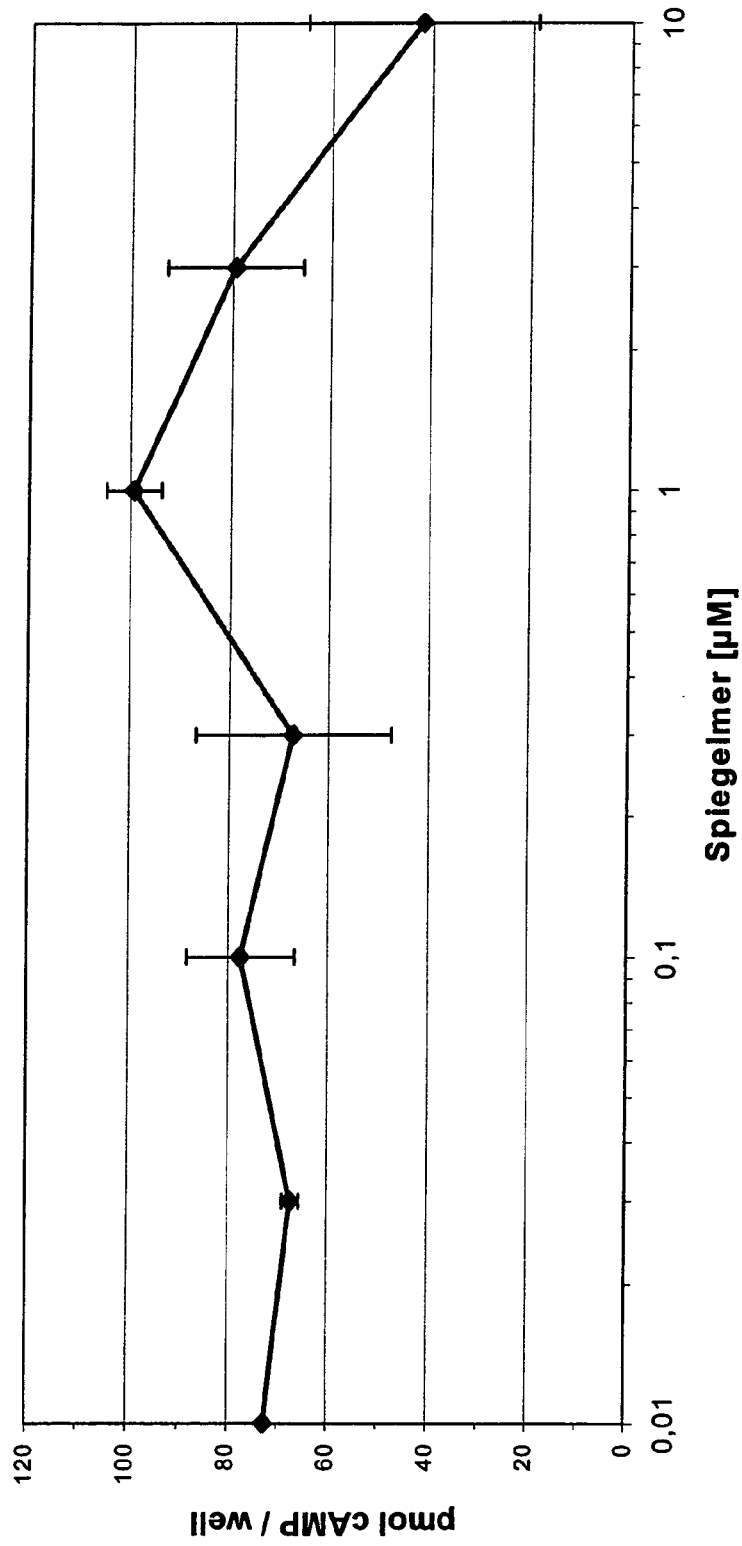
Figure 57:
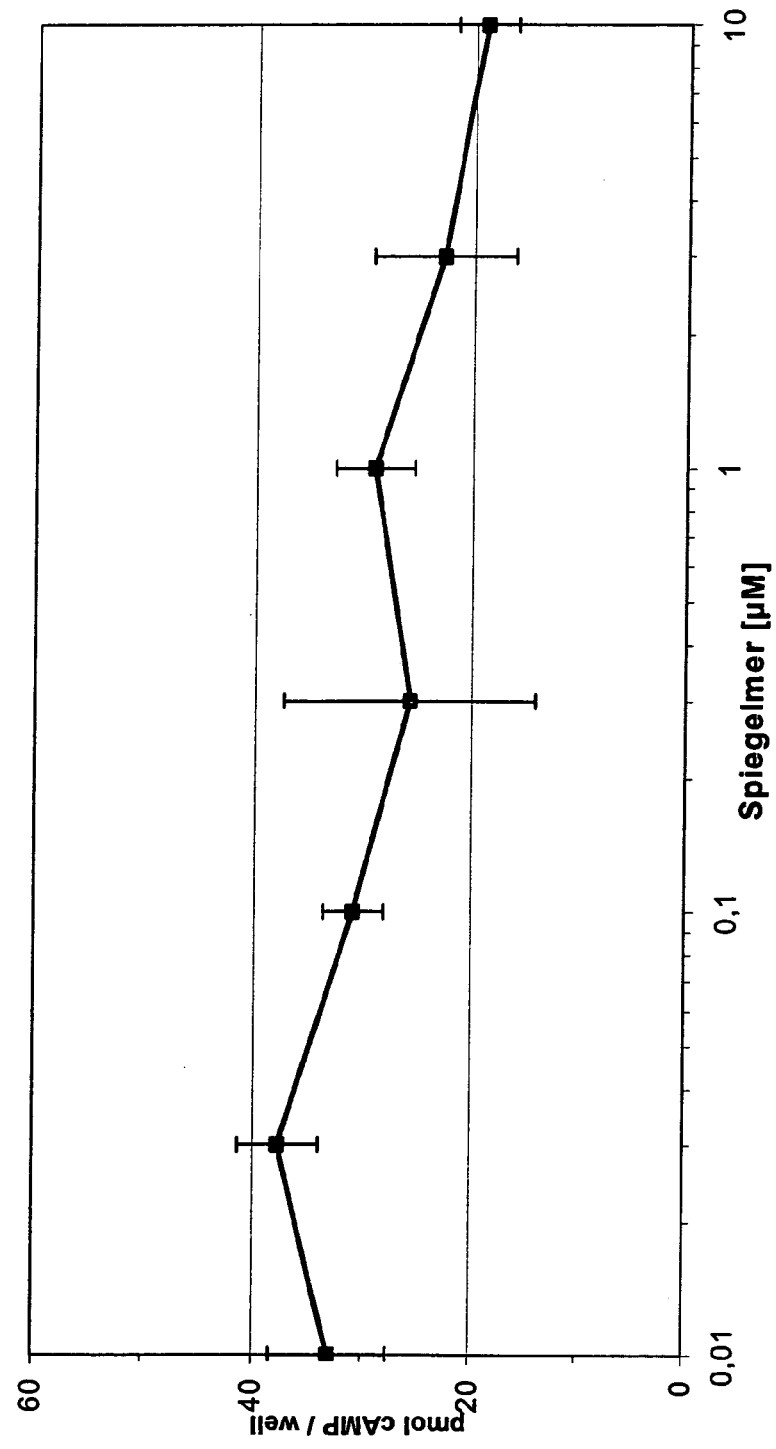
Figure 58:
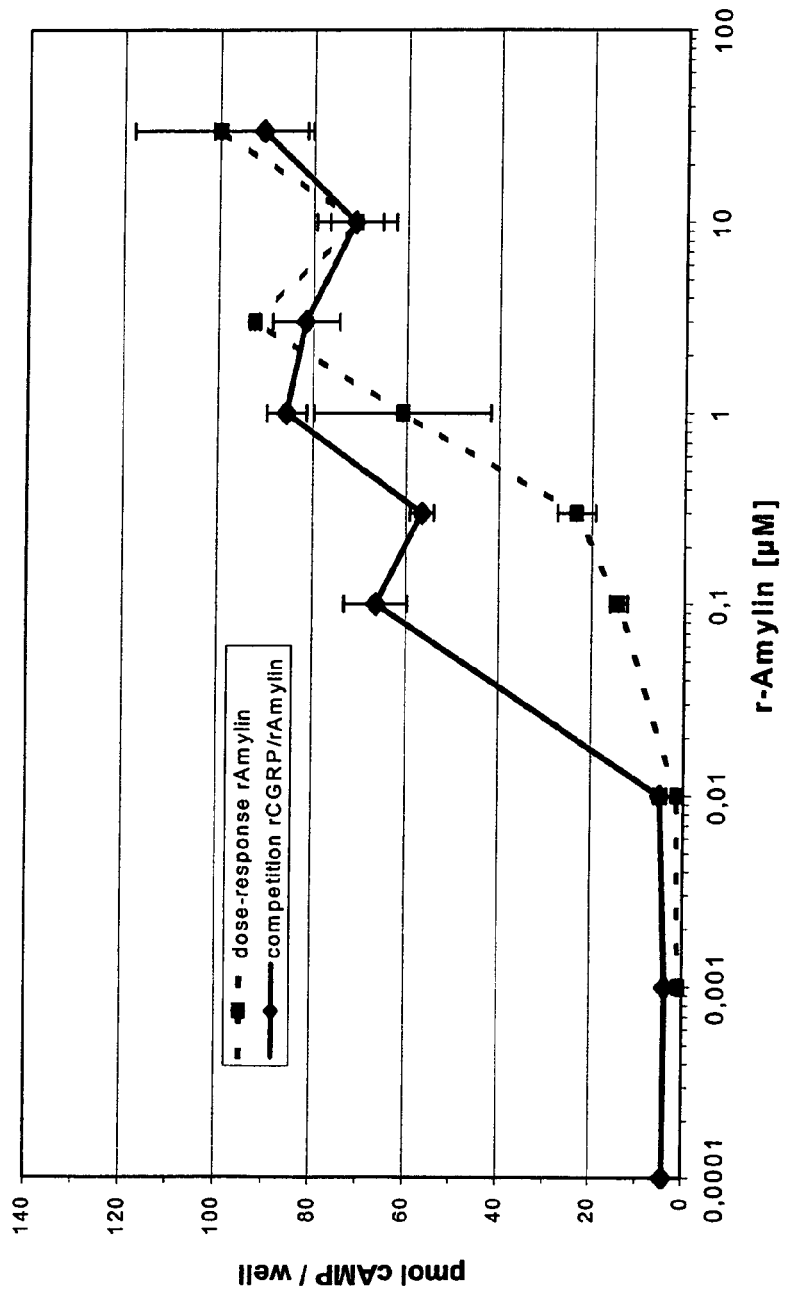
Figure 59:
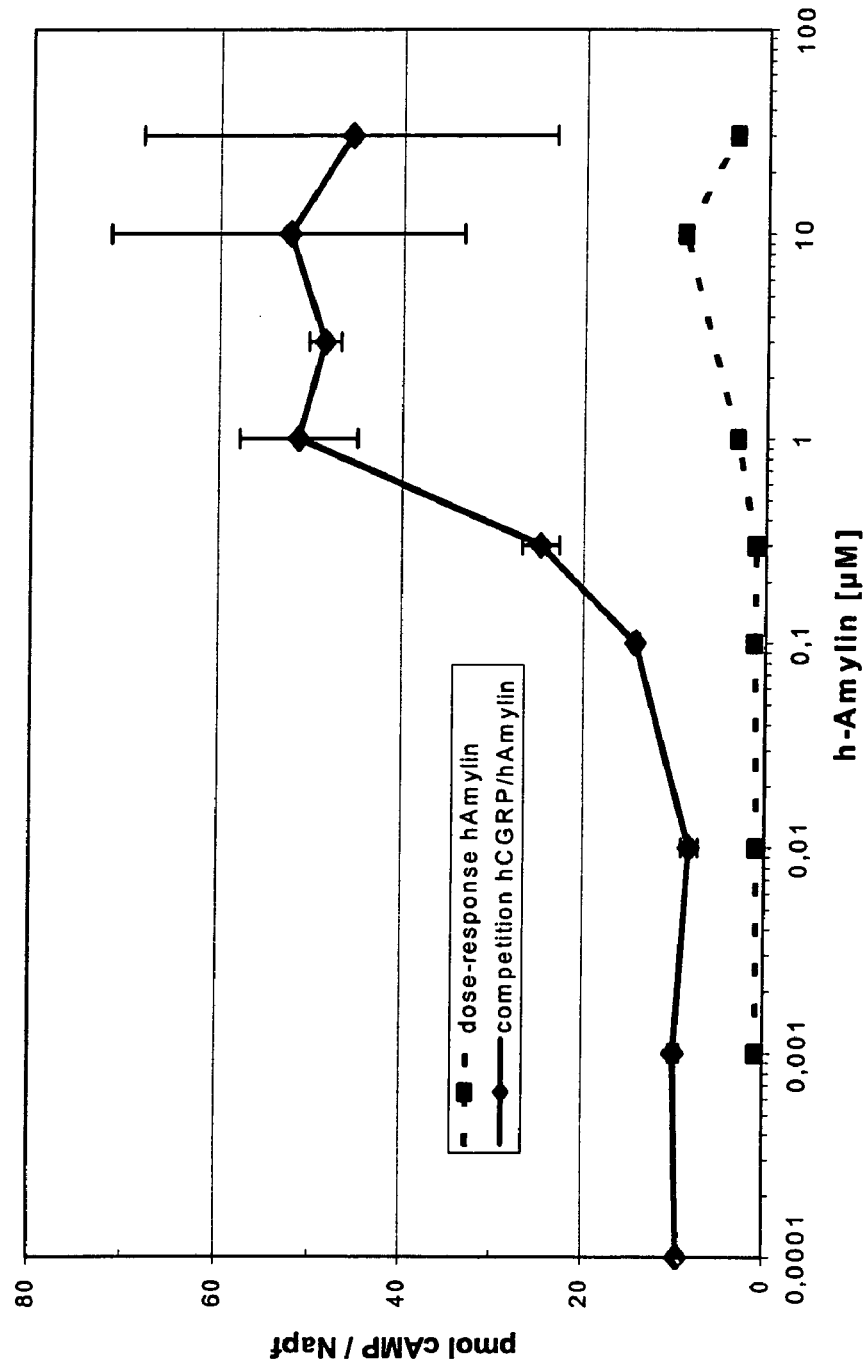
Figure 60:
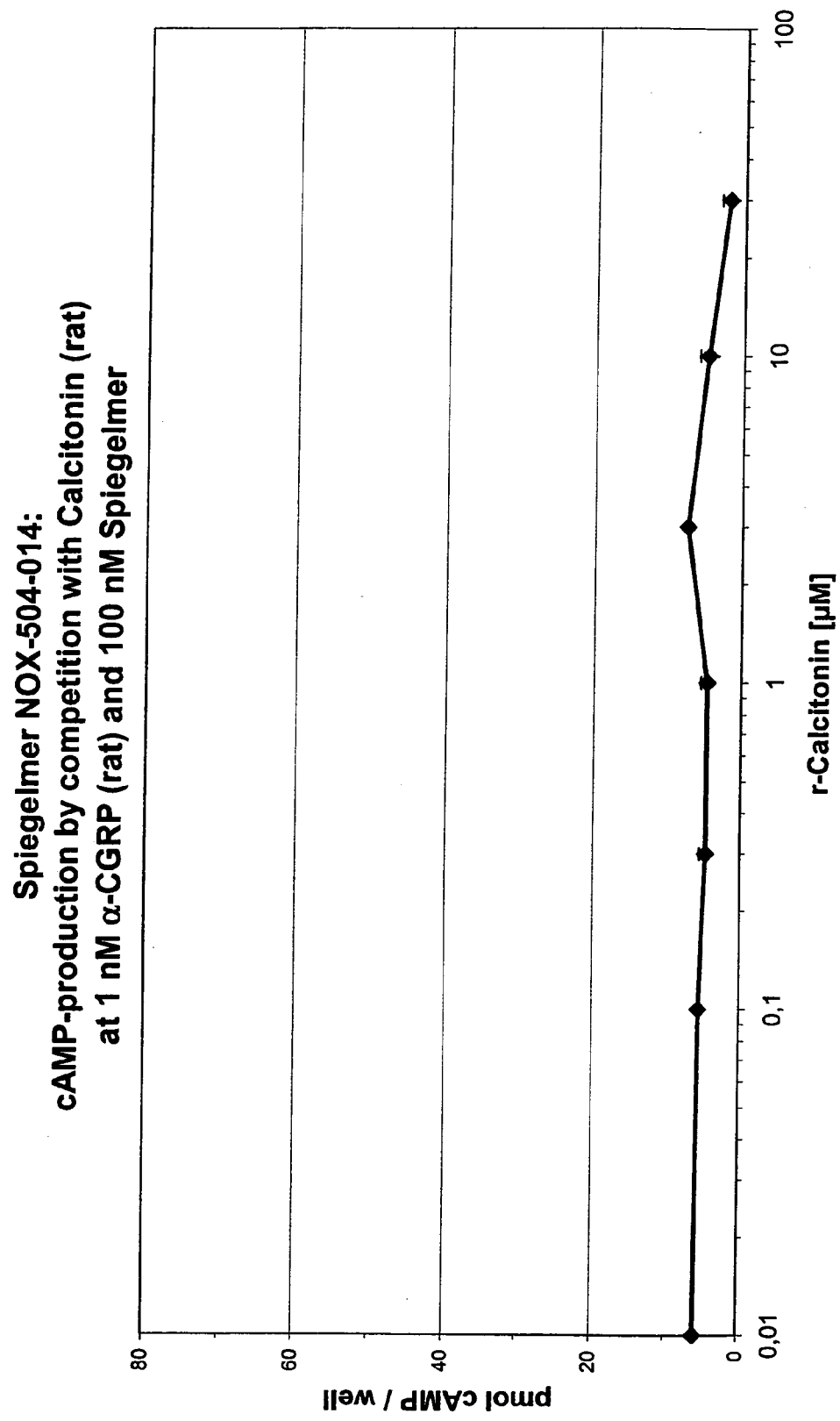
Figure 61:
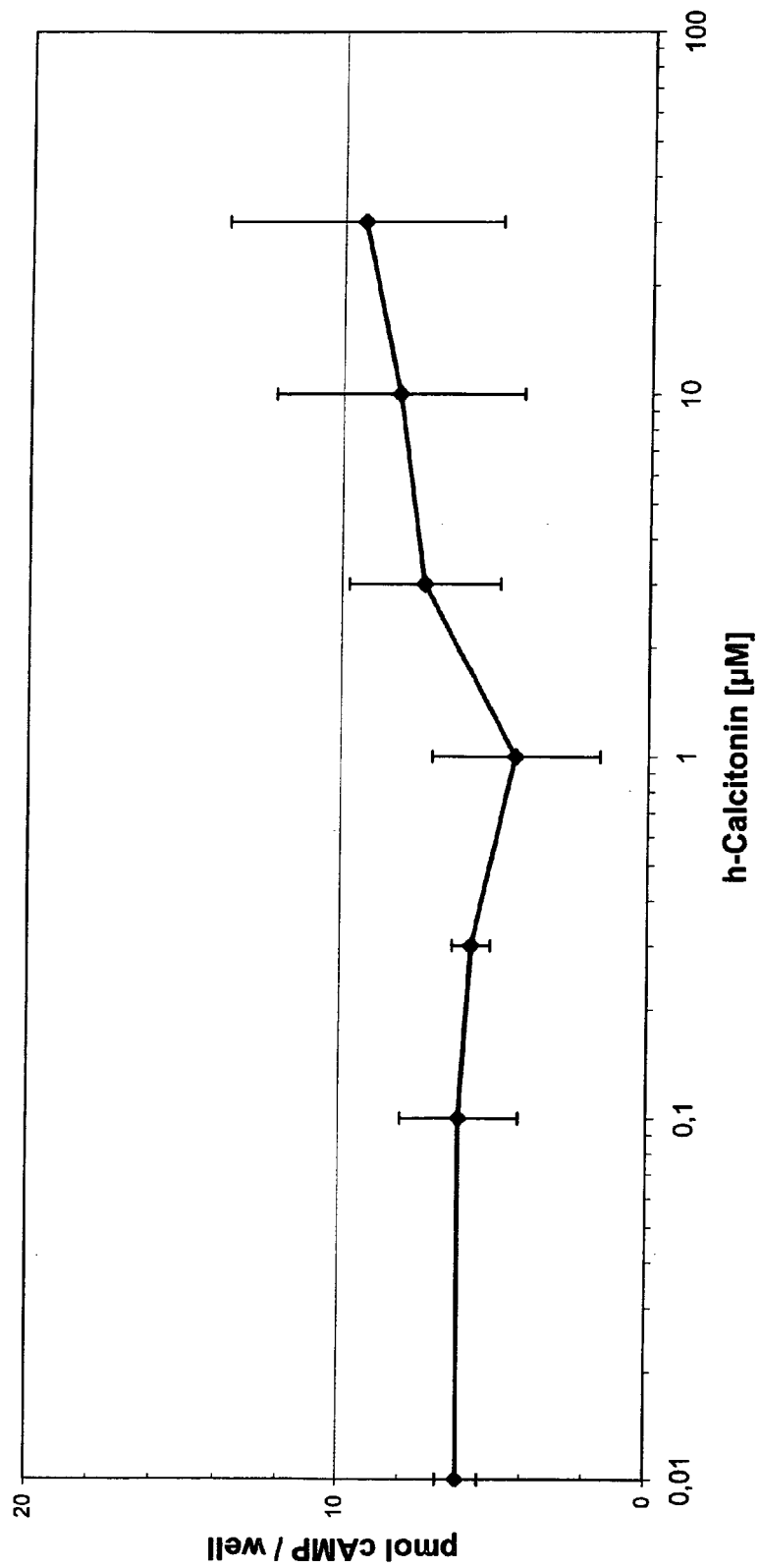
Figure 62:
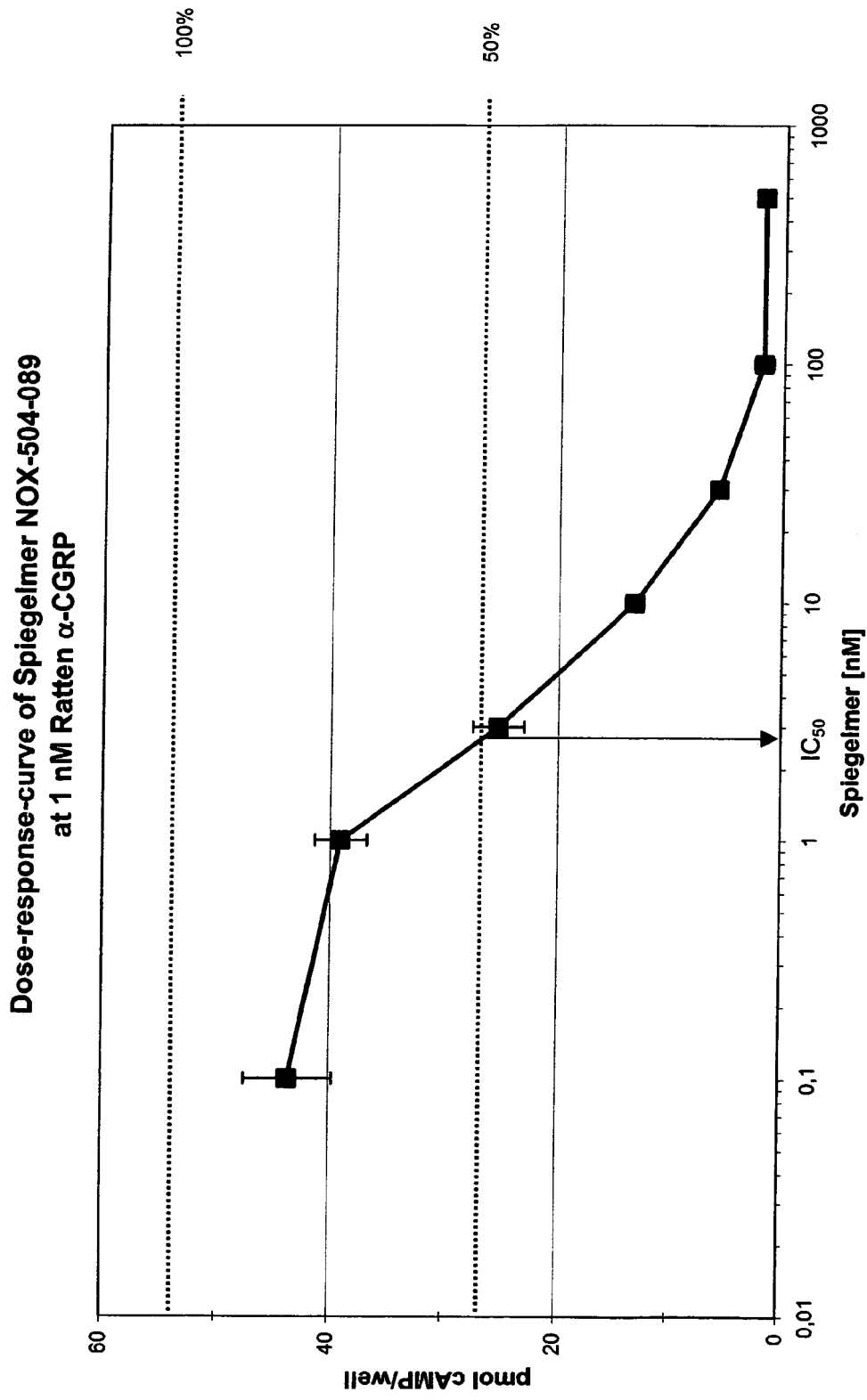
Figure 64:
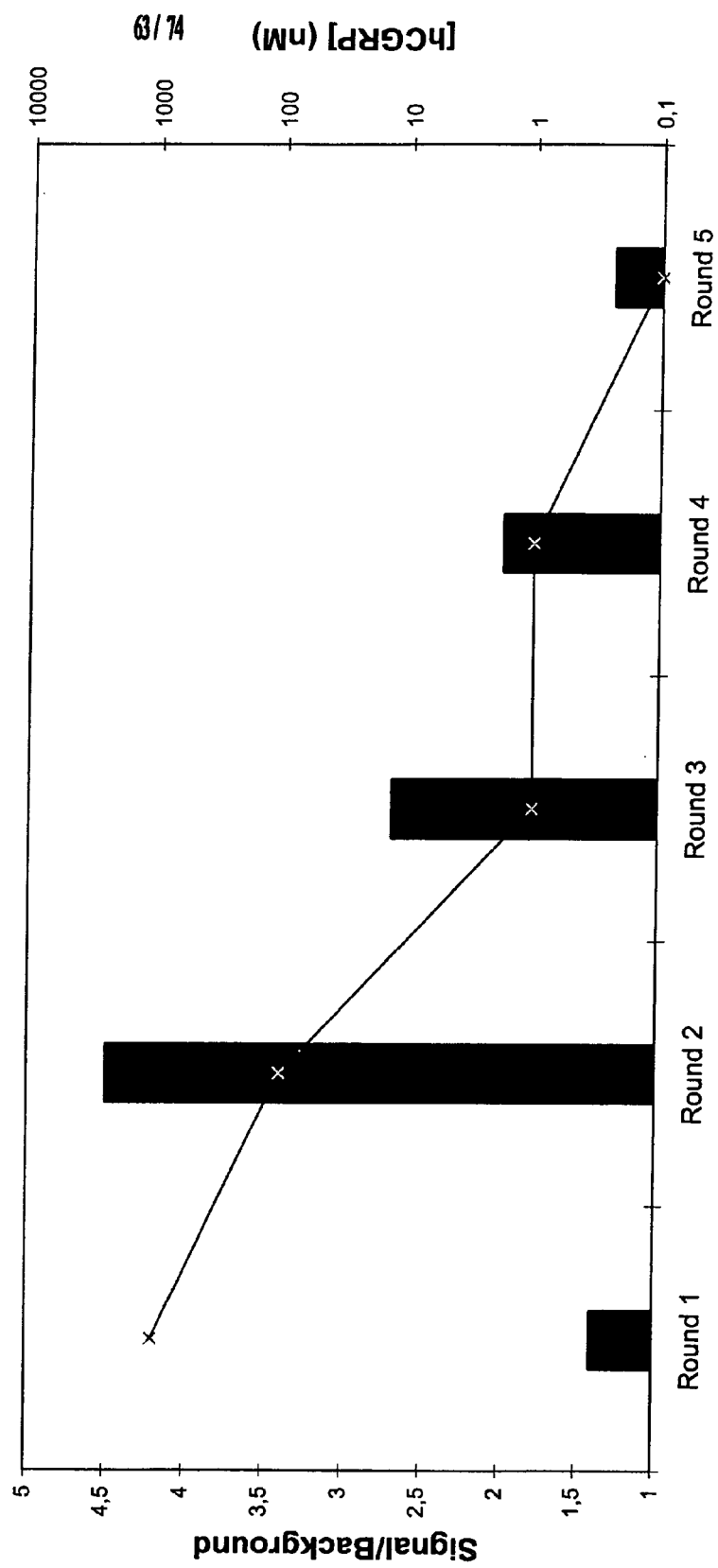
Figure 66A:
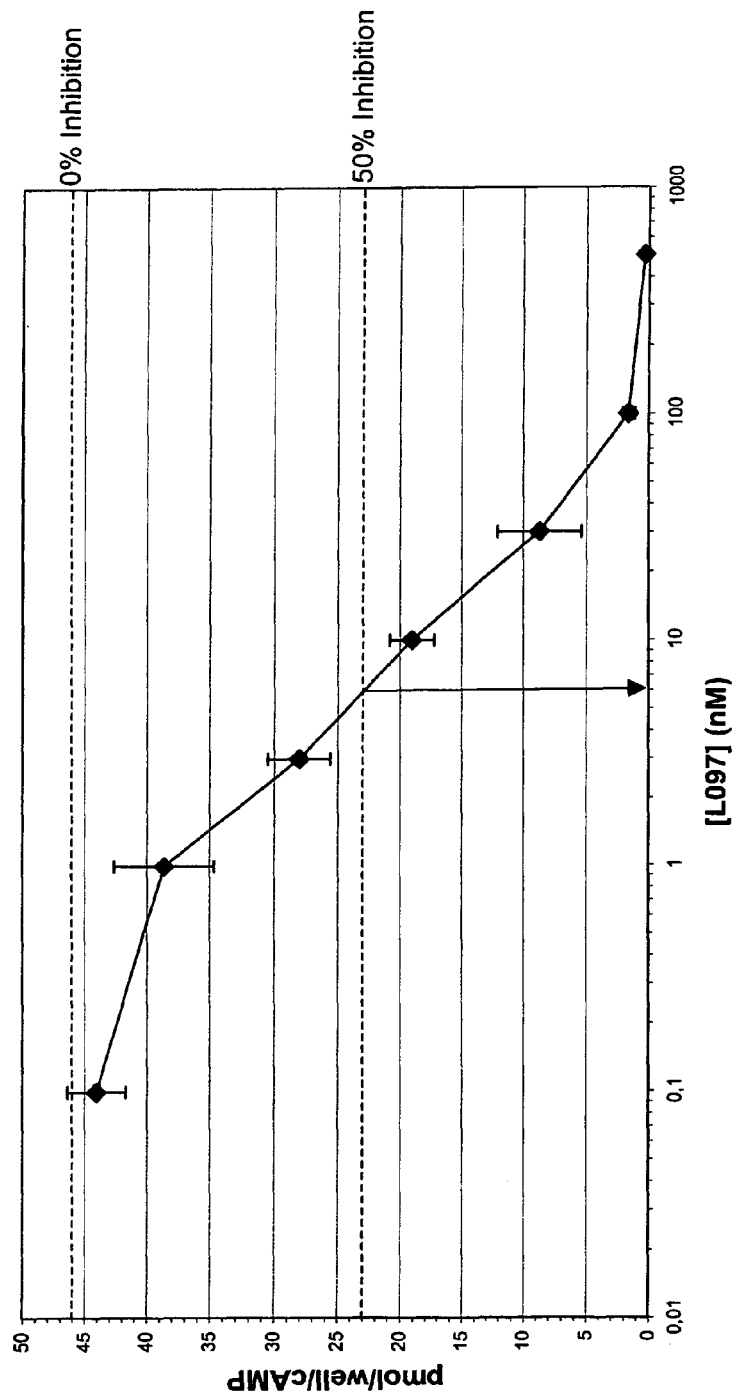
Figure 66B:
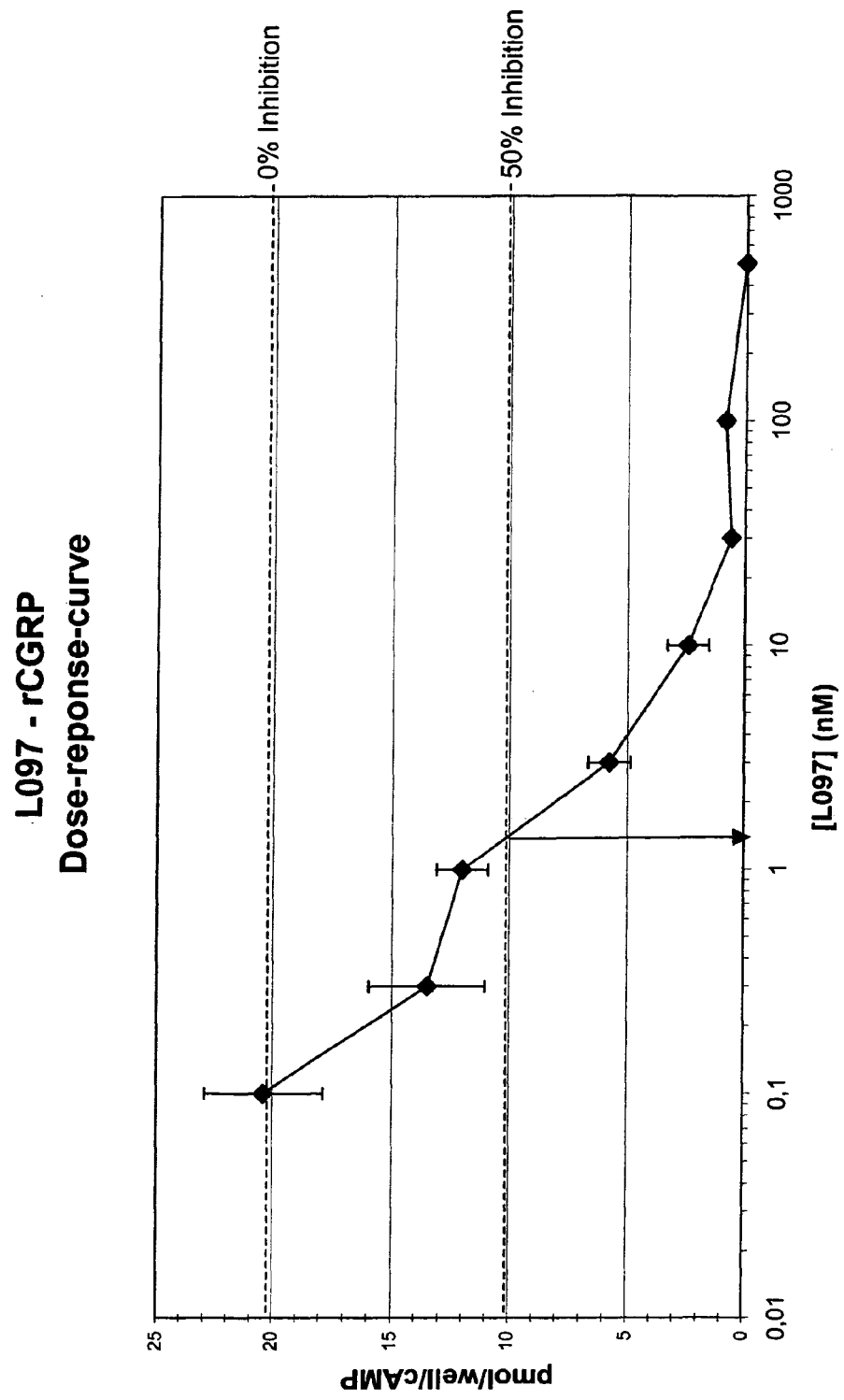
Figure 67:
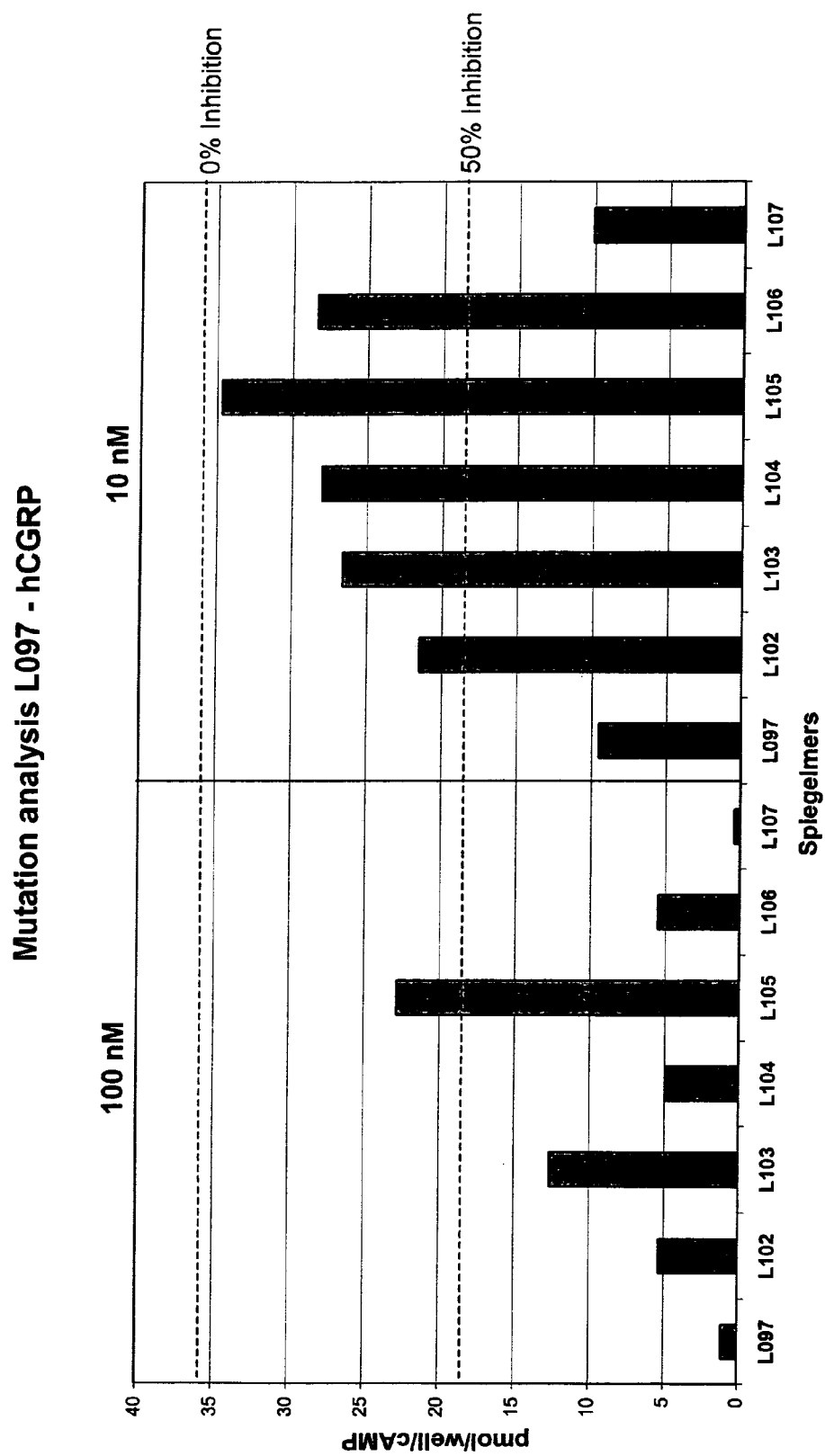
Figure 68:
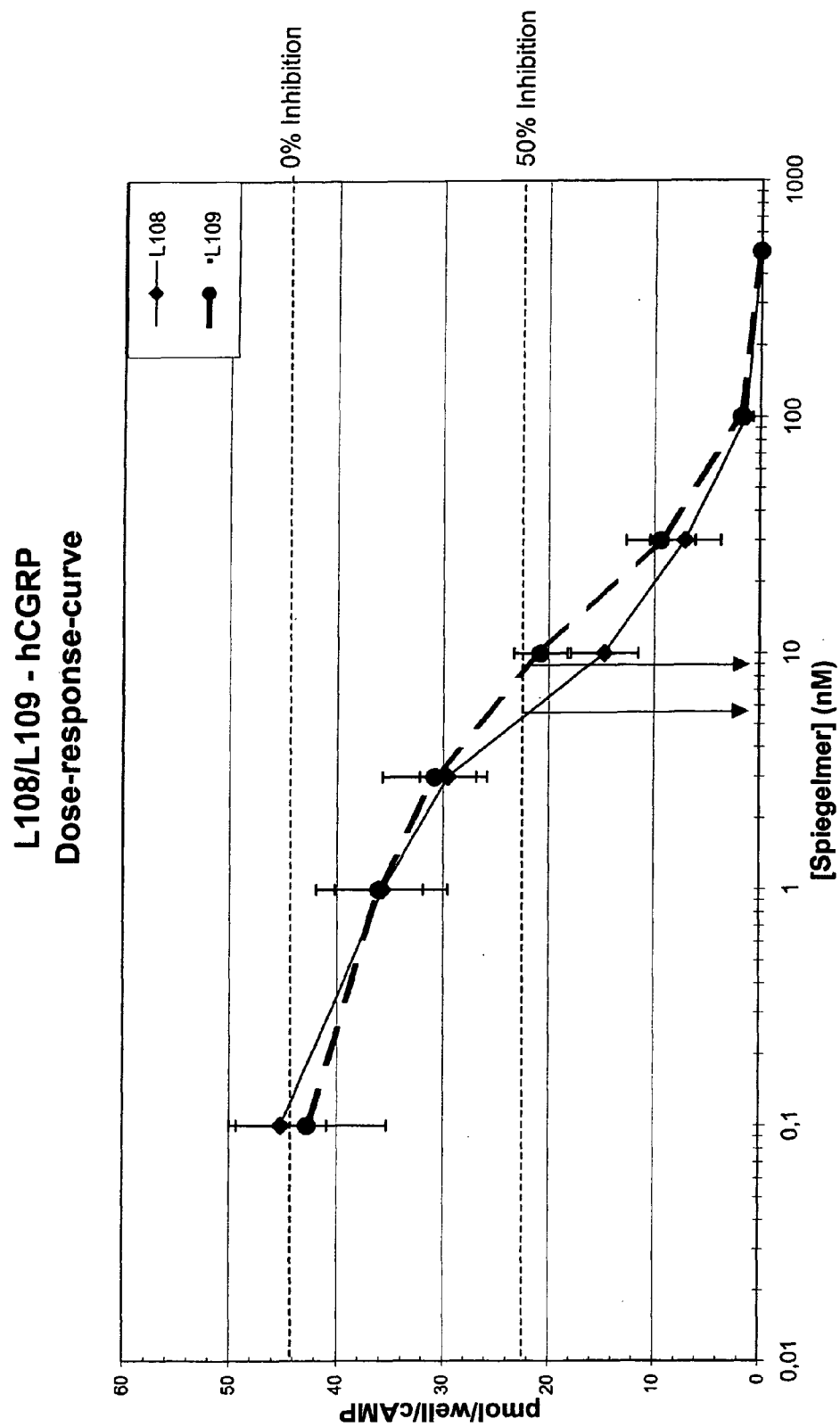
Figure 69:
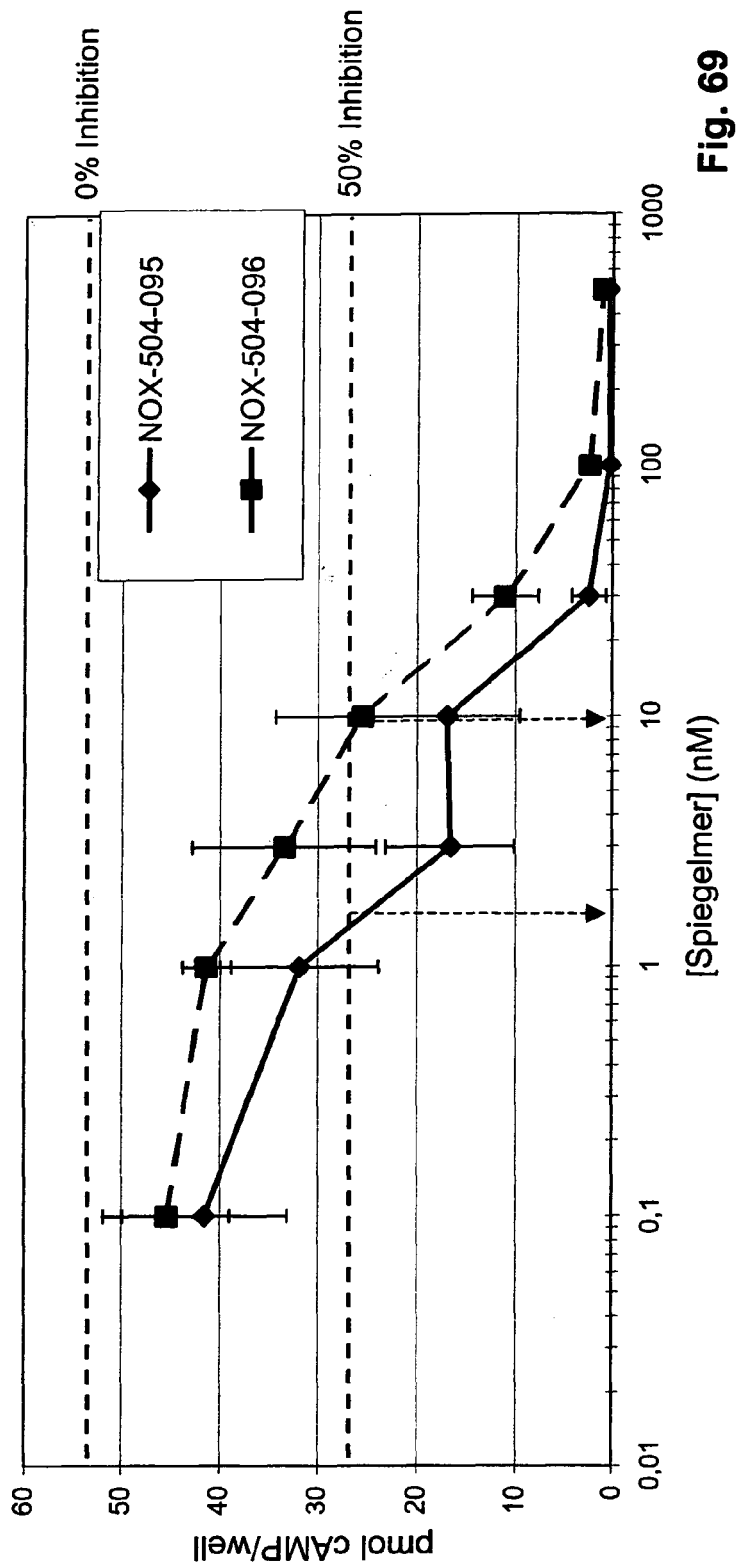
Figure 70:
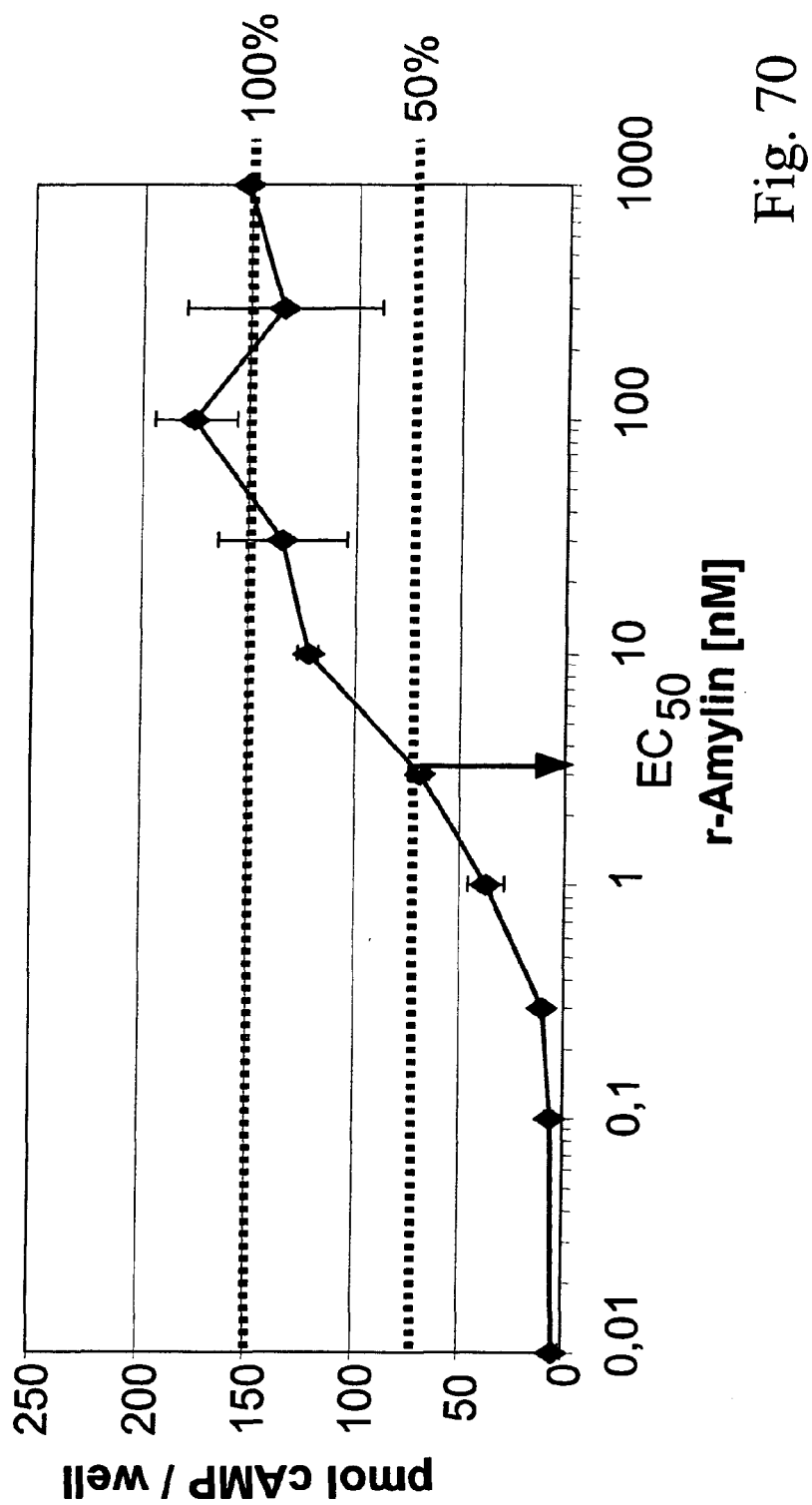
Figure 71:
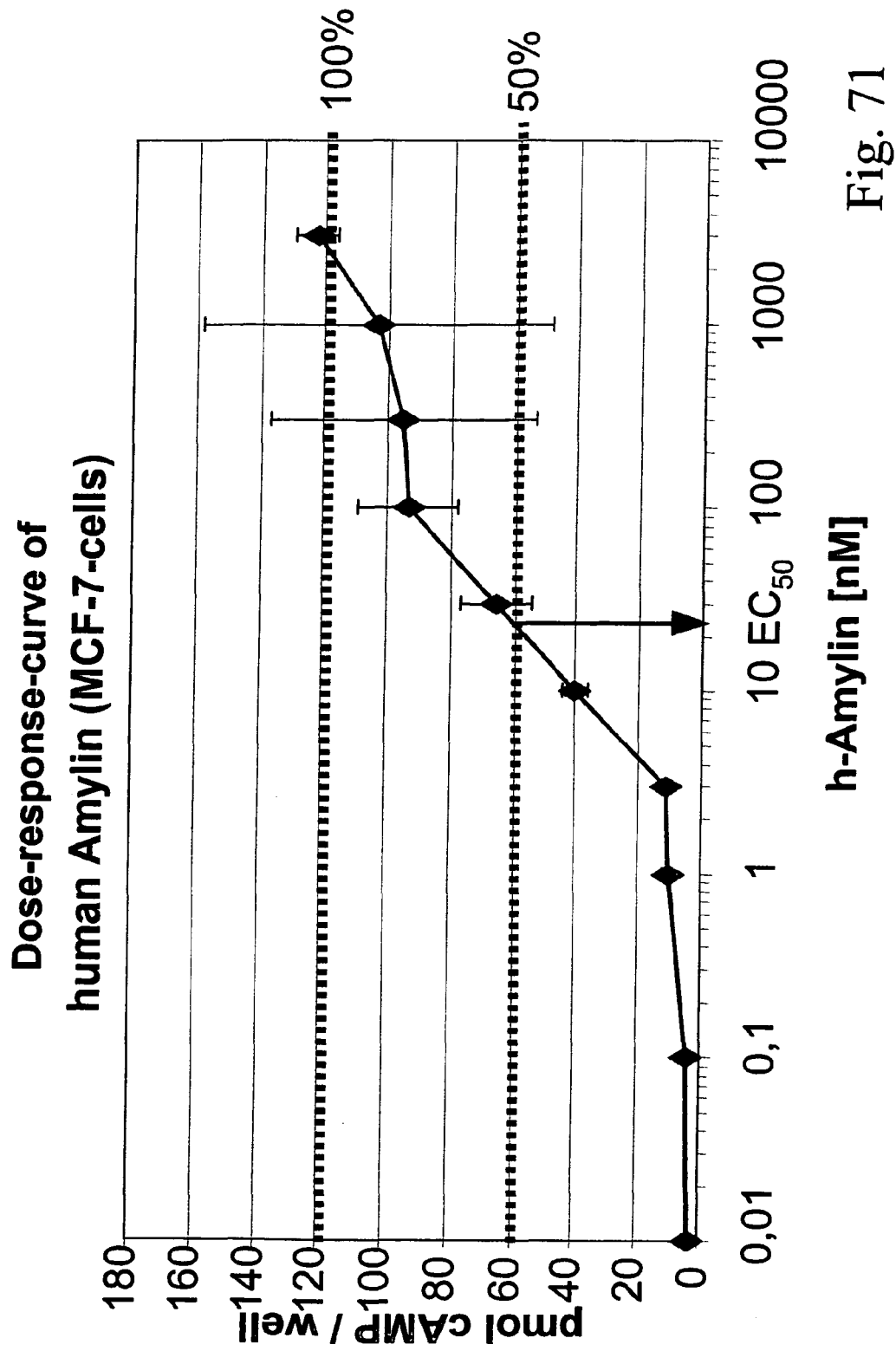
Figure 72:
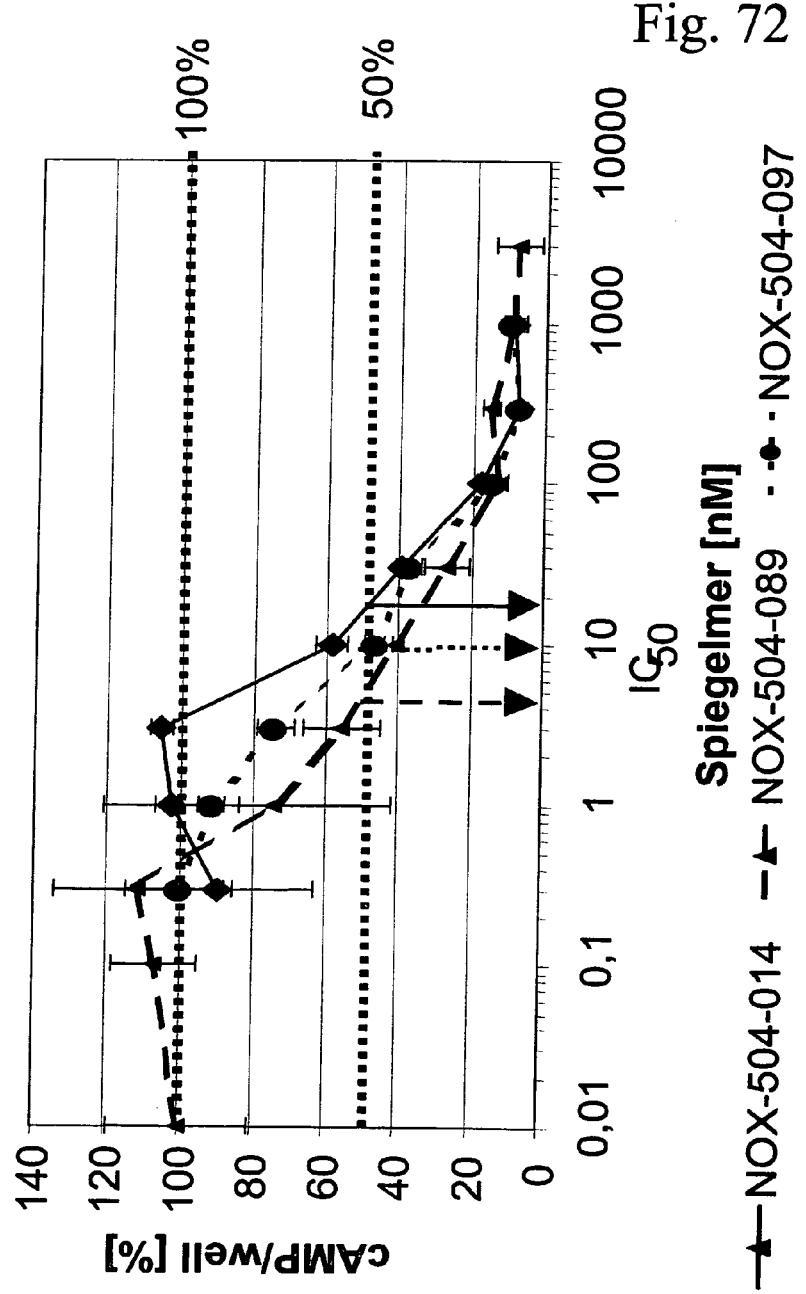
Figure 73:
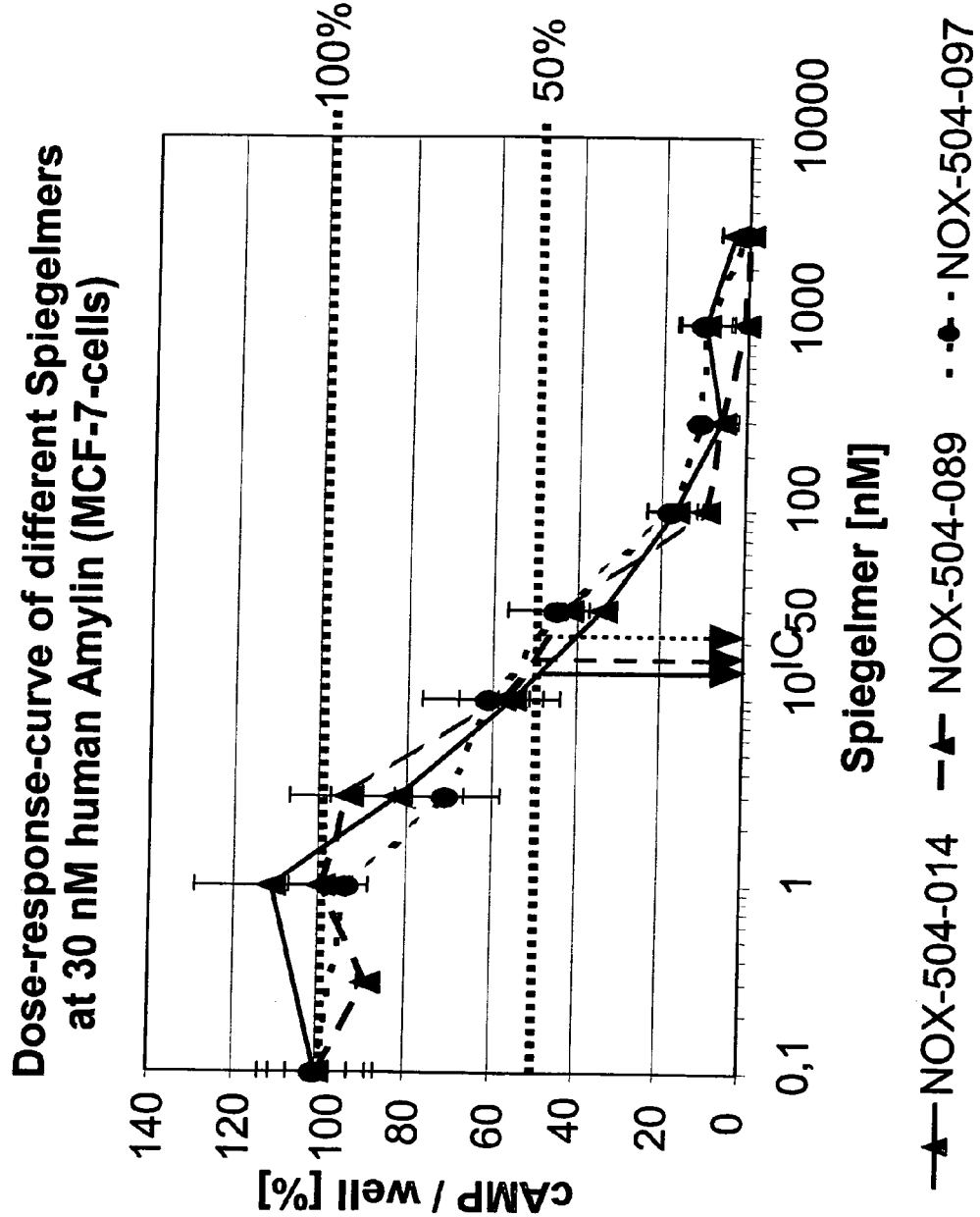
Figure 74:
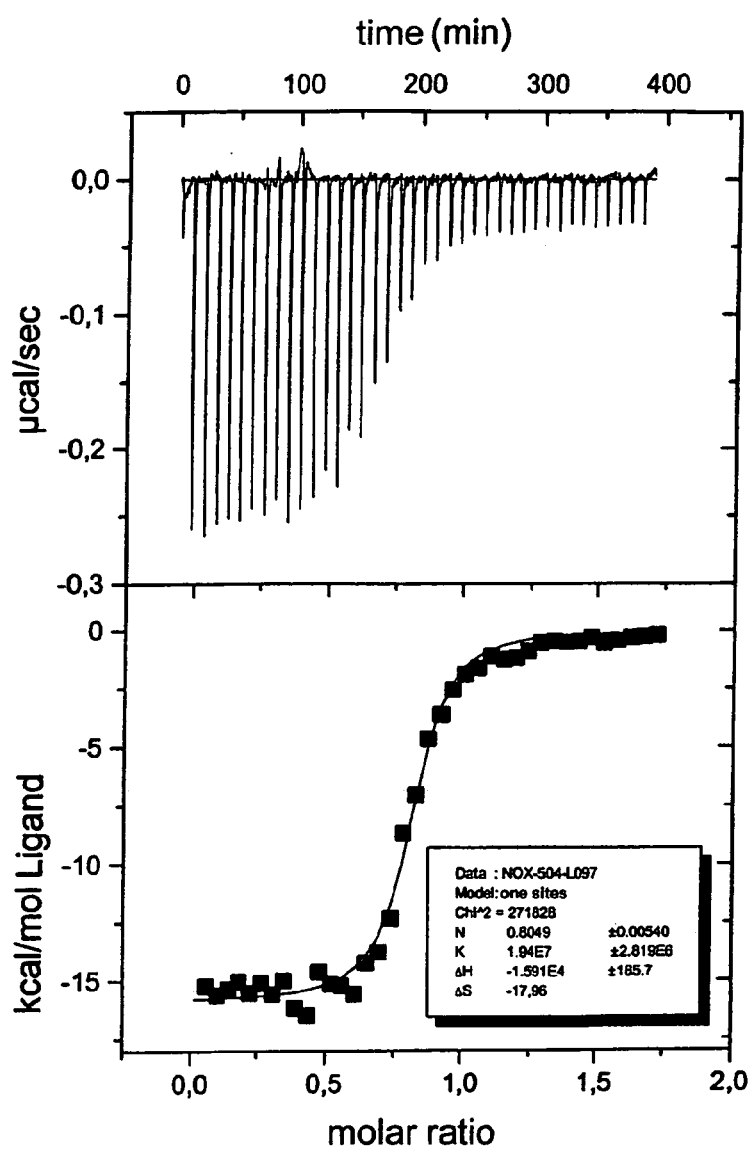

FIG. 50 shows the inhibiting of cAMP production by spiegelmer STAR-R02-15xx-F12 (NOX-504) with 1 μM rat α-CGRP at 37° C.;

FIG. 51 shows an enthalpy diagram for the binding of spiegelmer STAR-R02-15xx-F12 (NOX-504) to rat α-CGRP;

FIG. 52 shows a structural proposal for spiegelmer STAR-R02-lSxx-F12 (NOX-504) and the shortening site (in box);

FIG. 53 shows the dose effect curve of spiegelmer NOX-504-014 with 1 μM rat α-CGRP;

FIG. 54 shows the dose effect curve of spiegelmer NOX-504-014 with 1 μM human α-CGRP;

FIG. 55 shows the dose effect curve of spiegelmer NOX-504-014 with 1 μM human β-CGRP;

FIG. 56 shows the dose effect curve of spiegelmer NOX-504-014 at 30 μM rat adrenomedullin;

FIG. 57 shows the dose effect curve of spiegelmer NOX-504-014 with human adrenomedullin;

FIG. 58 shows the cAMP formation by competition with rat amylin at 1 μM rat α-CGRP and 100 μM spiegelmer NOX-504-014;

FIG. 59 shows the cAMP formation by competition with human amylin at 1 μM human α-CGRP and 100 μM spiegelmer NOX-504-014;

FIG. 60 shows the cAMP formation by competition with rat calcitonin at 1 μM rat α-CGRP and 100 μM spiegelmer NOX-504-014;

FIG. 61 shows the cAMP formation by competition with human calcitonin at 1 μM human α-CGRP and 100 μM spiegelmer NOX-504-014;

FIG. 62 shows the dose effect curve of spiegelmer NOX-504-089 with 1 μM rat α-CGRP;

FIG. 63 shows the sequences of RNA clones binding CGRP, and mutations of the reselected sequence (Grt2-STAR-504-5-BO.1-C10) as compared to the starting sequence of the 504-ad3-18% pool (NOX-504-ad3) are underlined;

FIG. 64 shows the course of reselection, with the peptide concentration characterised as line (right size axis) and the signal/background ratio as beam (left size axis);

FIG. 65 shows the sequences of the RNA spiegelmers for the cell culture trials, whereby mutations are highlighted by underlining;

FIG. 66A shows the dose effects curves of L097 with hCGRP, whereby the arrow indicates the concentration of 50% inhibition of the hCGRP effect ($IC_{50}$);

FIG. 66B shows the dose effects curves of L097 with rCGRP, whereby the arrow indicates the concentration of 50% inhibition of the rCGRP effect ($IC_{50}$);

FIG. 67 shows the mutation analysis of L097, illustrating the inhibition of the cAMP formation by different spiegelmers in the concentrations 10 μM and 100 μM;

FIG. 68 shows the dose effects curves of L108 and L109 with hCGRP, illustrating the inhibition of the cAMP formation depending on the spiegelmer concentration, whereby the arrow indicates the concentration of 50% inhibition of the hCGRP effect ($IC_{50}$);

FIG. 69 shows the dose effects curves of NOX-504-095 and NOX-504-096 with rat α-CGRP, illustrating the inhibition of the cAMP formation depending on the spiegelmer concentration, whereby the arrow indicates the concentration of 50% inhibition of the α-CGRP effect ($IC_{50}$);

FIG. 70 shows the dose effects curve for rat amylin;

FIG. 71 shows the dose effects curve for human amylin;

FIG. 72 shows the inhibition curve for the three spiegelmers NOX-504-014, NOX-504-089, NOX-504-097 and rat amylin;

FIG. 73 shows the inhibition curve for the three spiegelmers NOX-504-014, NOX-504-089, NOX-504-097 and human amylin; and FIG. 74 shows the course of the calorimetric determining of the binding constants of spiegelmer NOX-504-L097 with respect to hCGRP at 37° C.

EXAMPLE 1

Production of 2'-Fluoro-Modified Spiegelmers

Figure 1:
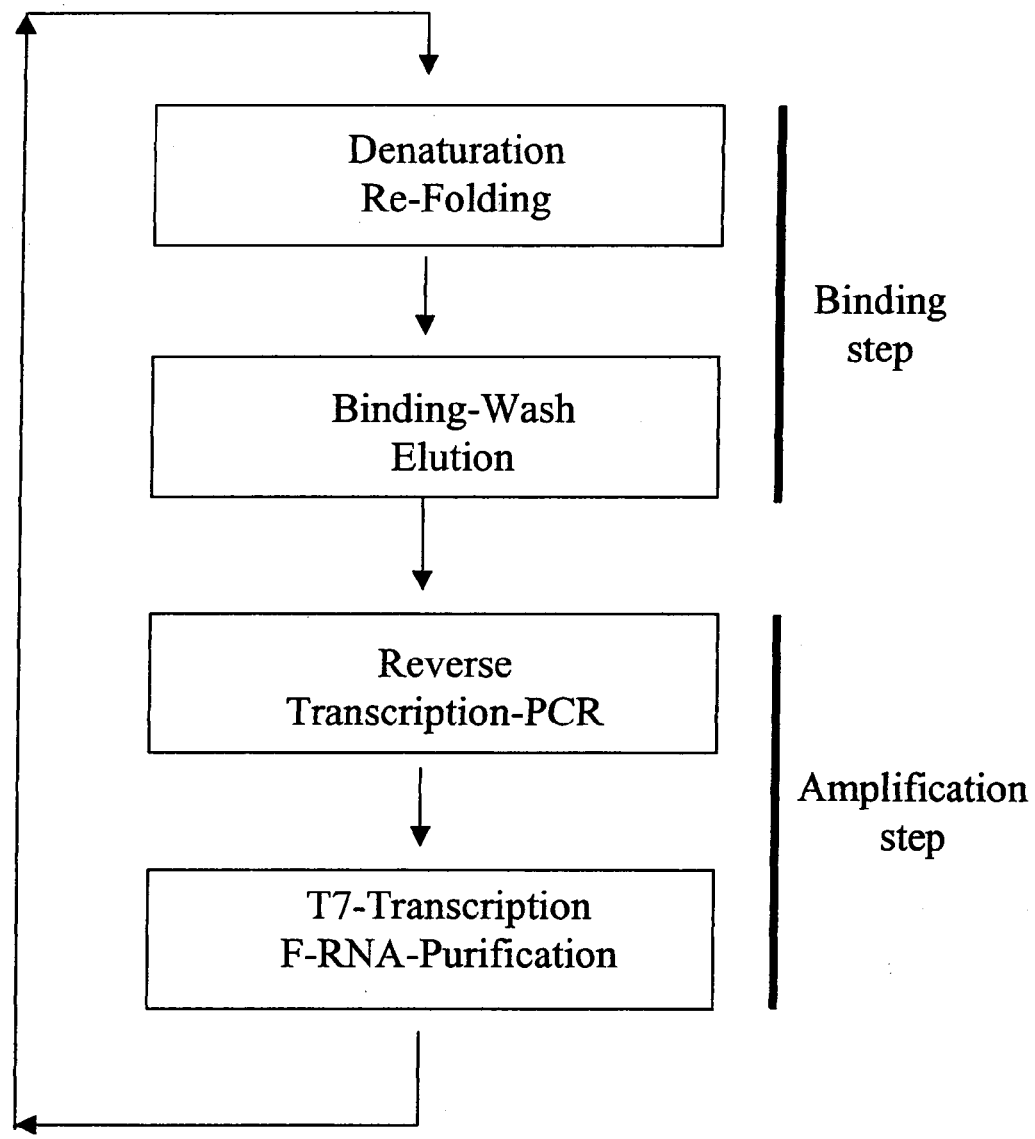
FIG. 1 shows the principle of RNA selection of nucleic acids binding to CGRP comprising a binding step with the partial sections of denaturing and folding as well as binding washing elution and the amplifying step comprising the step of reverse transcription PCR and T7 transcription and cleaning.

Starting out from the method for identifying nucleic acids, in particular D nucleic acids, which bind to a target molecule, such as for example illustrated in FIG. 1, 2'-fluoro-modified spiegelmers were employed using 2'-fluoridated RNA molecules.

The fluoro-modified nucleic acids (F-RNA) used in the selection process are distinguished from biologically occurring RNA by the presence of a fluoro group on the 2' carbon of the ribose. Fluorine here replaces the natural hydroxyl group of ribose. This modification was limited here to pyrimidine nucleotides. Such synthetic nucleic acids are replaced enzymatically with a mutated T7 polymerase (Epicentre, Madison, Wis., USA), which is more tolerant to modified nucleotides, using 2'-fluoro-UDP and 2'-fluoro-CTP. The mutation of the T7 polymerase enables efficient incorporation of fluoro-modified nucleoside triphosphates.

A. Materials

GTP, ATP, and dNTPs were sourced from Larova, Berlin; fluoro-dUTP and fluoro-dCTP from Tri-Link, San Diego, USA. The T7 DNA/RNA polymerase for the production of fluorinated RNA was sourced from Epicentre, USA. The enzyme Taq DNA polymerase and Superscript II Reverse transcriptase were sourced from Life Technologies, the kit for the Reverse transcriptase/Taq polymerase was from Qiagen. Radioactive $^{32}$[P]-α-GTP for marking the F-RNA was sourced from Hartmann, Braunschweig.

D-CGRP was first synthesised by JERINI AG, Berlin, and later by Bachem, Heidelberg. The peptide used for selection bears a biotin group on the carboxyl terminus to enable the separation of unbound nucleic acids by means of the biotin-streptavidin or biotin-NeutrAvidin interaction. For this purpose NeutrAvidin agarose from Pierce and streptavidin Paramagnetic Particles from Roche were used. Unbiotinylated peptide (likewise from JERINI, Berlin, and Bachem, Bubendorf, Switzerland) was used in the first seven rounds for affinity solution.

DNA-Pool

The DNA for the start pool was synthesised in-house and is based on the described pool PB40 with the sequence 5'-GGA GCT CAG CCT TCA CTGC-N40-GGC ACC ACG GTC GGA TCCAC-3' (SEQ ID NO:264) (Burgstaller & Famulok, 1994, Angew. Chem. [Applied Chem.] Int. Ed. 33, 1084).

The 5' and 3' primers had the sequence

PB40-R-For: 5'-TCT AAT ACG ACT CAC TAT AGG AGC TCA GCC TTC ACT GC-3' (SEQ ID NO:265) and PB40-R-Rev: 5'-GTG GAT CCG ACC GTG GTG CC-3' (SEQ ID NO:266).

The single-strand DNA was checked for its amplifying capacity with radioactive primers; a complexity of $1.41 \times 10^{14}$ molecules/nmol DNA was derived therefrom. The single-strand DNA in total volume was processed by means of PCR from 8 ml to double-strand DNA.

B. Selection Steps

Denaturing and Folding of the Fluorinated RNA

With the exception of denaturing, all non-enzymatic selection steps were performed in selection buffer (HEPES-KOH, pH 7.5; 150 mM NaCl, 1 mM MgCl2, 1 mM $CaCl_2$ and 0.1% Tween 20). The denaturing took place for 3 minutes at 94° C. in selection buffer without Tween 20, MgCl2 and $CaCl_2$. After denaturing the enzymatically produced F-RNA was first incubated in selection buffer for 30 minutes at 37° C., MgCl2 and $CaCl_2$ were added and the folding was then continued at 37° C. for 30 minutes.

Binding

On completion of folding the F-RNA was first incubated at 37° C. for 15 minutes without peptide with the matrix (NeutrAvidin agarose or streptavidin paramagnetic particles). This so-called preselection serves to pre-isolate potential matrix binders. Following this incubation step the F-RNA was separated from the matrix, replaced with the concentrations of biotinylated CGRP evident from FIG. 2A and left for at least 3 hours at 37° C. Then the biotin-binding matrix was added to the binding preparation and again incubated 5-10 minutes at 37° C. The matrix was separated from the solution and washed with selection buffer. The washing volume used here in the first rounds was at 5 to 10-fold the quantity of the matrix, in later rounds up to 60-fold washing volumes were used. The quantity of F-RNA remaining after washing on the matrix was detected and quantified by scintillation count. The binding value was expressed as a percentage of the used F-RNA.

Elution

In rounds 1-9 the binding F-RNA was eluted in three steps with non-biotinylated peptide. As a rule a 10-fold excess of the non-biotinylated relative to the biotinylated CGRP was used here and eluted first for one, then three hours and finally overnight at 37° C. The eluted F-RNA was extracted with phenol chloroform isoamyl alcohol, precipitated with ethanol and resuspended in water. The RNA remaining on the matrix after these affinity solution steps was not eluted but amplified directly on the matrix (see below).

From round 10 elution took place only in one step under denaturing conditions. For this purpose the F-RNA remaining after washing was incubated on the matrix in two steps with in each case 100 μl 8 M urea for 5 minutes at 65° C. The eluted F-RNA was extracted with phenol chloroform isoamyl alcohol, precipitated with ethanol and absorbed in water.

C. Amplification—Enzymatic Reactions

Transcription Compilation of Fluorinated RNA for use in Selection

Transcriptions were made with 150 U T7 RNA/DNA polymerase and the buffer supplied by the manufacturer (40 mM Tris-HCl pH 7.5; 10 mM NaCl; 6 mM $MgCl_2$; 2 mM spermidin; 10 mM DTT) in a total volume of 100 l. $MgCl_2$ at a final concentration of 11 mM was generally added to the reactions. The final concentrations of ATP and GTP were in each case 1 mM during the entire selection; 2'-fluoro-UTP and 2'-fluoro-CTP were used up to the 9th round with a concentration of in each case 3 mM, and from the 9th round only with 1.5 mM. Per reaction of 100 μl there were between 20 and 50 μmol template used, i.e. double-strand DNA template in the first round and in all subsequent rounds auf double-strand DNA, which was compiled by enzymatic preparation of the F-RNA selected in the previous cycle. $^{32}[P]$-α-GTP was used for the radioactive marking of the fluorinated RNA. The reactions were incubated overnight at 37° C. and added with DNase 1, to digest the template. The created F-RNA was then separated under denaturing conditions via a 8% polyacrylamide gel with 8 M urea from non-embodied NTPs. The transcribed F-RNA was eluted from the gel, precipitated with ethanol, dried and taken up in pure water.

Reverse Transcription Compilation of cDNA of Selected F-RNAs

Reverse transcription of eluted fluoro-RNA was carried out with Superscript II and the buffer conditions of the manufacturer in a volume of 20 μl with 200 units enzyme and a dNTP concentration of in each case 1 mM. As a rule up to 8 pmol of the eluted F-RNA were dissolved in 10 μl water and mixed with 2 μl of a 100 μM solution of the reverse primer.

This template primer mixture was denatured for 2 minutes at 94° C., transferred to ice and then adjusted in the thermocycler to a temperature of 50° C. After 2 minutes at 50° C. 8 μl of a mixture of buffer, dNTPs and enzyme were added and the sample was incubated for 15 minutes at 50° C., a further 15 minutes at 55° C. and finally 10 minutes at 68° C.

In rounds 1-9 the F-RNA remaining after the affinity solution on the matrix was also reverse-transcribed directly to the carrier and amplified by means of the PCR. The RT-PCR kit by Qiagen was used for this.

PCR Compilation of the Double-Strand DNA Template

The cDNA produced in the reverse transcription was used directly in the PCR. In the process 6.66 μl of the 20 μl RT preparation served as template for a 100 μl reaction with 5 units Taq DNA polymerase. The concentration of the primers was 2.5 μm. The DNA was first denatured for 2 minutes at 94° C. and then amplified with a PCR profile of 30 seconds at 94° C., 30 seconds at 55° C. and for 30 seconds at 72° C. The number of cycles was generally kept as low as possible and as a rule ran to approximately 5-10 cycles.

Results

Figure 2A:
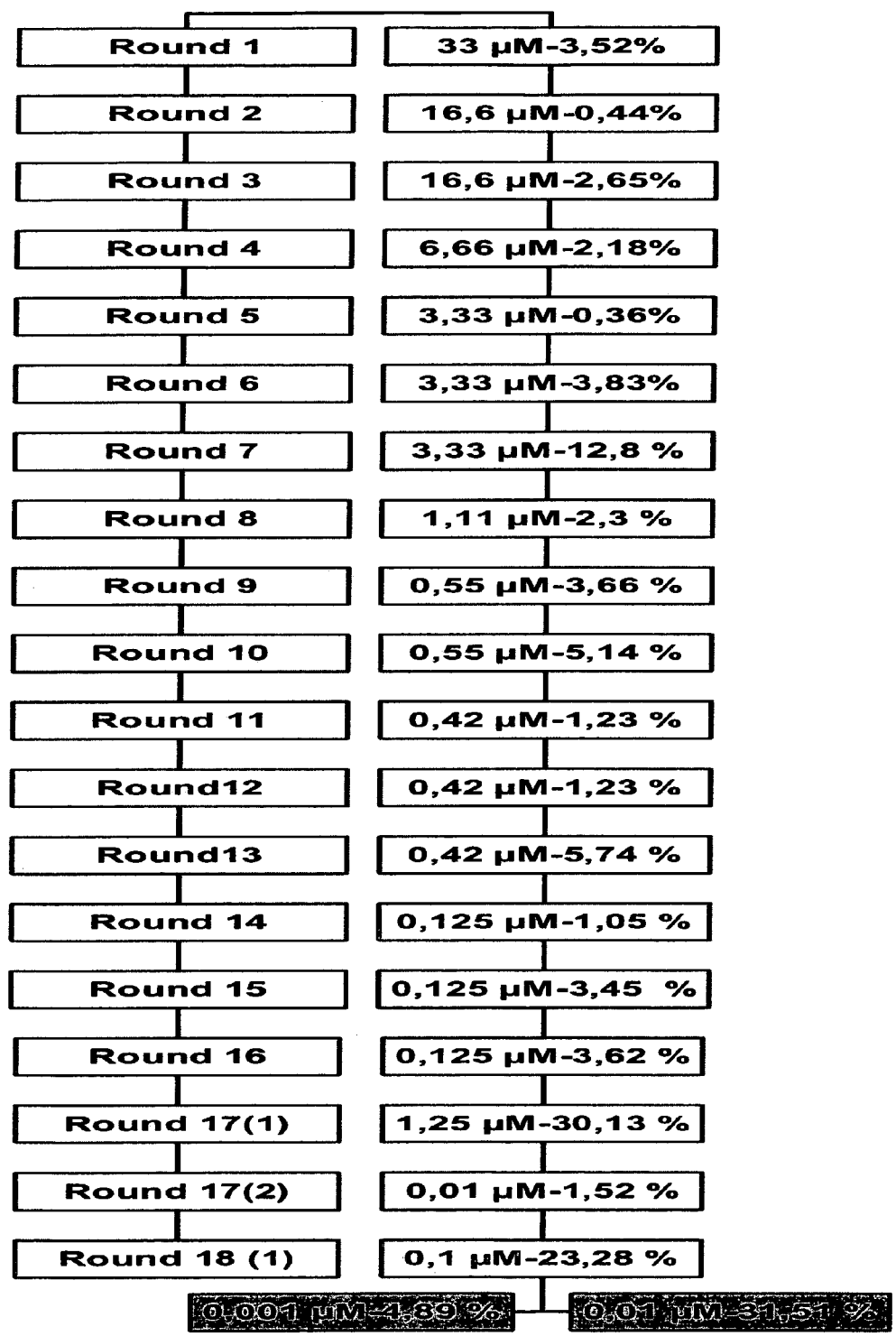
FIGS. 2A and 2B show the course of selection of 2'-fluoro-modified nucleic acids binding to CGRP, whereby in particular

The course of selection is illustrated in FIG. 2. The values specified in FIG. 2A constitute the CGRP concentrations used in each round and the associated percentage binding of the F-RNA pools.

Figure 2B:
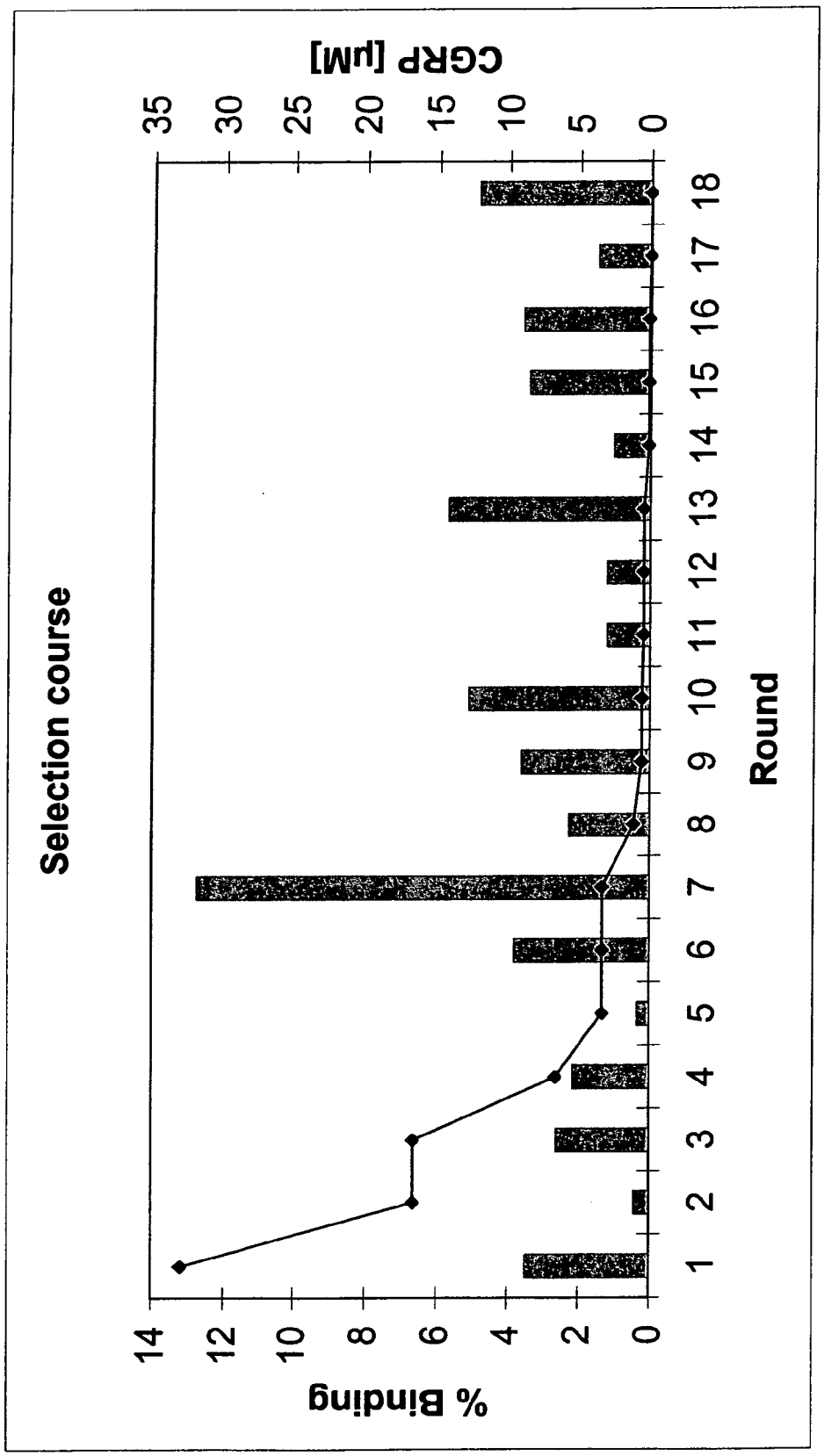

Only that strand which finally also produced the subsequent sequences is illustrated. In most of the rounds the binding was done with different peptide concentrations and a control selection without peptides (not illustrated). Generally the selected F-RNA of the most stringent strand, i.e. the least peptide concentration, which gave yet another significant signal on the zero control, was prepared as template for the next round. FIG. 2B is a graphic illustration of these data.

The first selection round was completed with 2.5 nmol F-RNA molecules, and the complexity had an order of magnitude of approximately $2.82 \times 10^{14}$ different sequences. Because under these conditions each sequence was represented only approximately five times, in the first round a relatively high percentage of selected sequences was transferred to the 2nd selection round. From the 2nd to the 5th round between 0.36% and 2.65% of the used F-RNA were placed in each subsequent round. During these five rounds the stringency was tightened by a decrease in the biotinylated D-CGRP offered for binding from 33 µM to 3.33 µM. In the 6th round a slight rise in the binding was to be indicated, which continued with a value of 12.8% of the used F-RNA in the 7th round.

Through continuous decreasing of the CGRP concentration in the subsequent rounds the stringency was increasingly sharpened, which lead to a breach of the binding of the inserted F-RNA to the peptide. Continuous increase in the binding values in round 8 and 9 of up to 5.14% in round 10 correlated with a rise in preselection (not illustrated) and was thus not attributable to peptide-caused binding. For this reason in round 11 the matrix was changed from NeutrAvidin agarose to streptavidin paramagnetic particles. This was reflected in a drop in percentage binding to now 1.23%. A peptide-caused rise to 5.74% was registered however in round 13. Over the next three rounds a value of approximately 3.5% binding at a CGRP concentration of 125 µM was adjusted. Since this value did not rise further despite uniform stringency in rounds 15, 16 and 17 (round 17 not illustrated), rounds 17 and 18 were completed as so-called double rounds. The consideration for this methodical approach is based on the assumption that stagnation of the percentage binding with uniform peptide concentration is the consequence of a type of equilibrium between the actual binding and the subsequent amplification. In order to shift this equilibrium in favour of binding, the F-RNA was subjected to a two-fold binding process: the F-RNA was first bound with the less stringent CGRP concentration of 1.25 uM, then eluted and purified. The F-RNA collected in this way was now not prepared as usual by enzymatic amplifying, but rather newly folded and inserted directly into a further selection round under more stringent conditions. As evident from FIGS. 2A and B, binding of the inserted F-RNA (as evident from FIG. 2A) was able to be achieved by this method in round 18 at peptide concentrations of 1 and 10 µM in each case 4.89% and 31.51%. This F-RNA was reverse-transcribed and amplified by PCR. The DNA was cloned, and there were 192 clones sequenced in total.

Sequences

The result of the sequence analysis is illustrated in FIG. 3. The cursively illustrated sequence (third sequence from the top) is that of clone 732 (SEQ ID NO:3). Mutations are in shown in bold type, while the contribution of the primer binding site is marked by underscoring. The following sequence was established for the different clones:

| Position in FIG. 3 | Clone description | Frequency | Seq. ID No. |
|---|---|---|---|
| 1 | 666 | 168 x | 1 |
| 2 | 711 | 1 x | 2 |
| 3 | 732 | 2 x | 3 |
| 4 | 669 | 5 x | 4 |

-continued

| Position in FIG. 3 | Clone description | Frequency | Seq. ID No. |
|---|---|---|---|
| 5 | 670 | 1 x | 5 |
| 6 | 781 | 1 x | 6 |
| 7 | 836 | 1 x | 7 |
| 8 | 748 | 1 x | 8 |

Of the 192 clones both primers could be found in 180 clones. Of these 180 sequences one sequence with 168 copies was clearly represented toe most frequently. The other twelve sequences are distinguished from the main sequence only through point mutations and base deletions: a point mutation occurred five times, five more for every one. deletion of two nucleotides occurred twice.

A comparison of the binding strength of these sequences was made using the Biacore device and showed that seven of the eight sequences display the same affinity for the target molecule. The $K_D$ of the clone shortened by two nucleotides was surveyed with ca. 10 µM. The binding constant was at 37° C. higher by the factor two. Binding constants were determined both with the Biacore device, and also with isothermal calorimetry (ITC). The calorimetry experiments were performed at 37° C. in a degassed selection buffer with a stirring speed of 300 rpm. The measuring cell was filled with a 10 µM solution of each 2° F. spiegelmer. The injection contained a 25 µM CGRP solution, which was injected in the measuring cell after an initial 5 µl injection in 7.5 µl fraction. The injection procedure lasted in each case 10 s, while the time interval between two injections was 300 s. The Biacore experiments were performed at 37° C. in a degassed selection buffer. Biotinylated CGRP was immobilised on the streptavidin chip (Blank-140 RU-640 RU-900 RU). Spiegelmer solution in a concentration of 500 provided a typical binding signal, which was evaluated with standard Biacore software (1:1 binding model).

EXAMPLE 2

Shortening of 2'-F-RNA Aptamers, which Bind Free D-CGRP

Starting out from the 2'-F-RNA aptamers binding D-CGRP described in Example 1 and the corresponding 2'-F-RNA spiegelmers, which can recognise free L-CGRP, it was attempted to shorten the length of each aptamer or respectively spiegelmer. Of the total of eight clones, as illustrated in Example 1, seven clones were distinguished by similar binding constants of 10 to 50 µM. The clone 670 (SEQ ID NO:5) recognised D-CGRP clearly poorer. As expected, the selected aptamers, the D oligonucleotides, which were expressed by plasmids correspondingly obtained from cloning and sequencing via an interposed PCR step, did not recognise natural L-CGRP, as measurements on the Biacore have shown.

Figure 4:
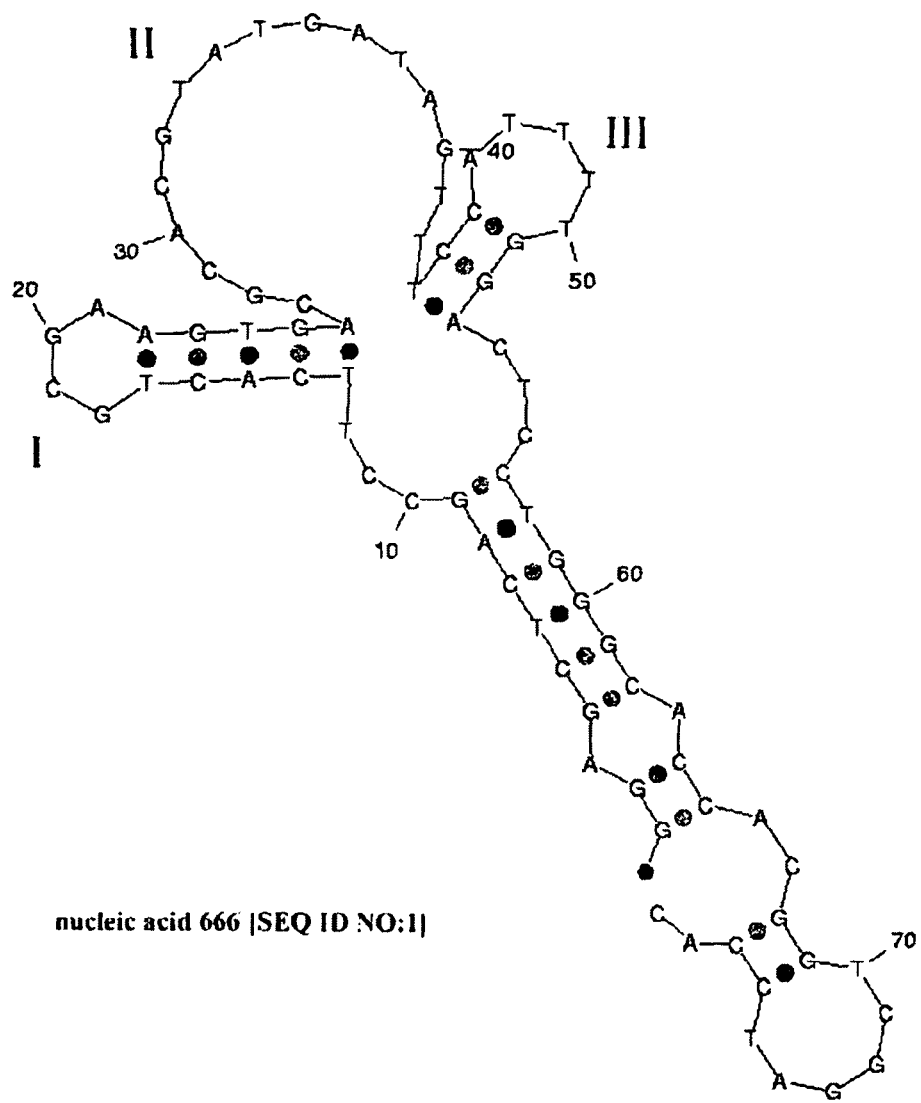
FIGS. 4-11 show the secondary structure of different nucleic acids binding to CGRP, as were created within the scope of Example 2.
Figure 5:
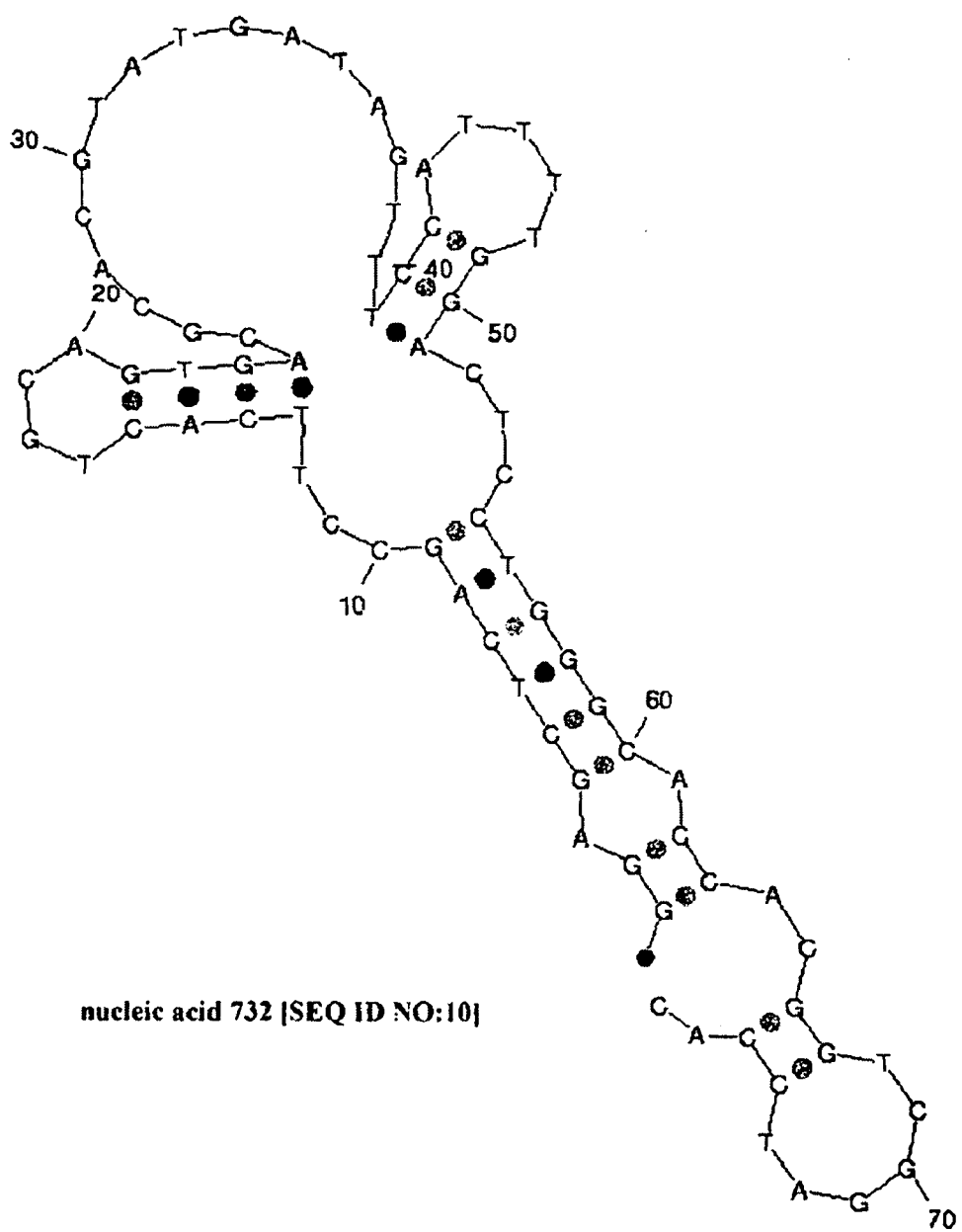
Figure 6:
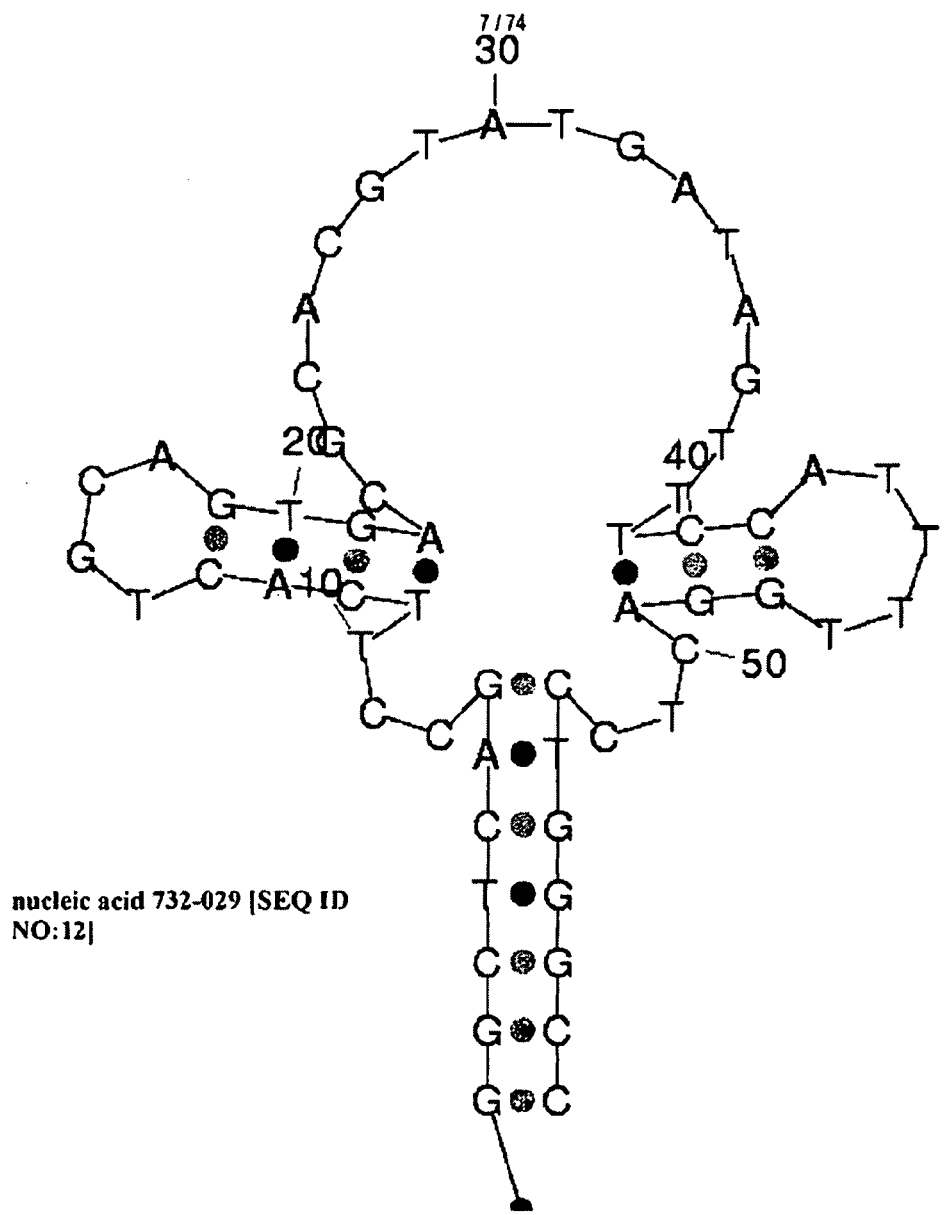
Figure 7:
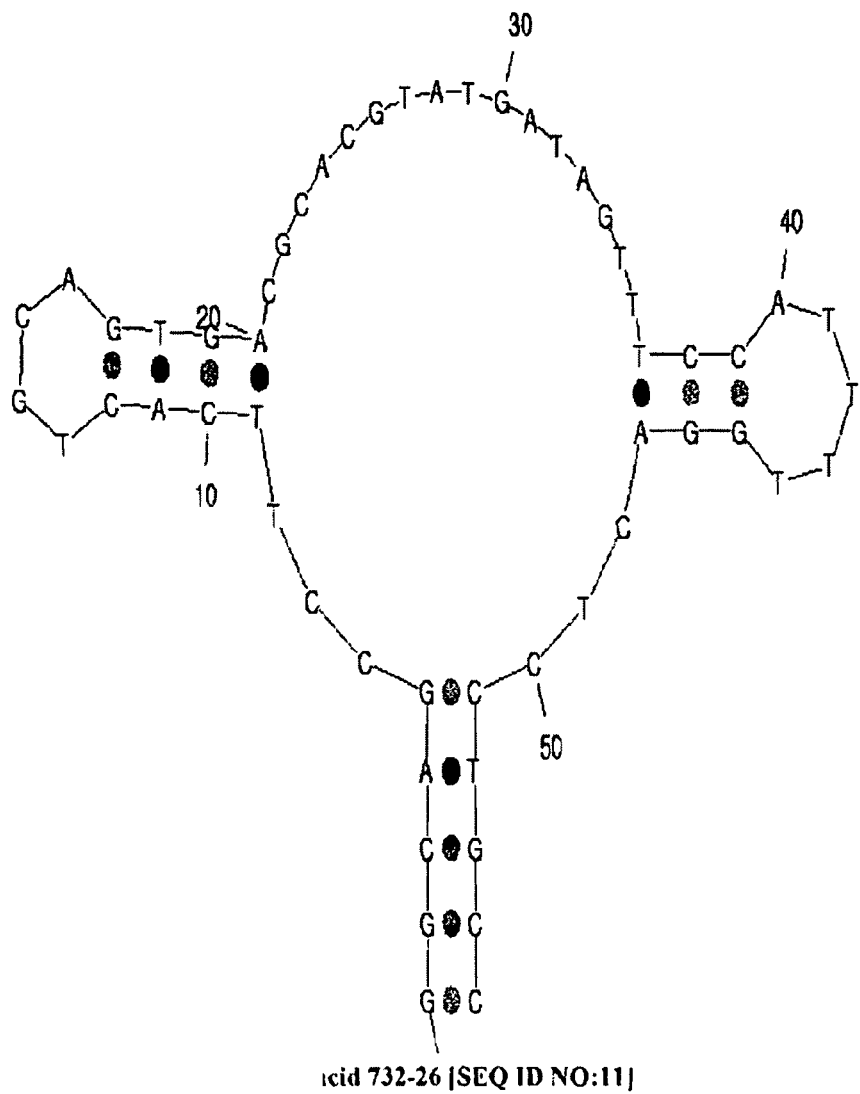

The secondary structure of a few of the aptamers and spiegelmers described in Example 1 was determined with the program rnafold (I. L. Hofacker, et al., 1994, Monatsh. Chem 125, 167-188). In particular the secondary structure models of the aptamers 666 (SEQ ID NO:9) and 732 (SEQ ID NO:10) as well as of the spiegelmers 732-029 (SEQ ID NO:12), 732-026 (SEQ ID NO:11), 732-100 (SEQ ID NO:15) and 732-108 (SEQ ID NO:18) are shown. The results are illustrated in FIGS. 4 and 5 and for the spiegelmers in FIGS. 6, 7, 8 and 9. The secondary structure models well matched the results of enzymatic probing experiments (Ehresmann, C., et al., 1987, Nucleic Acids Res 15 (22): p. 9109-28).

The secondary structures in each case comprise a stem, two hairpin loops and a 15- or 16-nt long bulge and thus form a clover leaf-like structure. The bulges in the structure core, formed by C(10)-C(11)-U(12) and C(54)-U(55)-C(56), and the hair pin loop U(13) to A(26) seem to be essential for recognition of the target molecule CGRP. For aptamers binding CGRP or respectively L-CGRP-binding spiegelmers a minimal binding determinant can therefore be recorded, which has a clover leaf-like structure. An alternative minimal binding determinant is the formation of a stem with two hair pin loops and a bulge comprising 15 or 16 nucleotides. Preferably the bulge is formed in the structure core by the nucleotide sequence C(10)-C(11)-U(12) and C(54)-U(55)-C(56) and the hair pin loop is formed by the nucleotide sequence U(13) to A(26), as illustrated in FIGS. 4 to 9.

On account of the measured binding affinity to the target molecule CGRP with a $K_d$ of 10 µM clone 666 (SEQ ID NO:9) was selected as starting clone for the shortening and optimising of 2'-F-RNA aptamers and spiegelmers. As described in Example 1, clone 666 (SEQ ID NO:9) was isolated from a N40 pool, i.e. a pool whereof the randomised sequence has a length of 40 nucleotides, and consisted of a 79-nt long sequence. The sequence has a particularly random U-rich region between the nucleotide position 41-50, in which 7 of 10 nucleobases are uracils. The secondary structure of the clone 666 (SEQ ID NO:9) was anticipated by the program rnafoldl. L. Hofacker, et al., 1994, Monatsh. Chem. 125, 167-188 and is illustrated in FIG. 4. In this case the secondary structural forecast also well matched the results of the enzymatic probing experiments (Ehresmann, C. et al., 1987, Nucleic Acids Res. 15 (22), 9109-28). The aptamer forms a characteristic clover leaf-like structure, comprising a stem with several small bulges, two hair pin loops (I and III) and a seemingly unstructured 16-nt bulge (II), connecting both hair pin loops. All four structural elements have their origin in two opposing bulges in each case comprising three bases. The primer binding sites, above all the 5'-primer binding site, are integrated in the stem.

For synthesis of 2'-F-RNA spiegelmers it was necessary to shorten and optimise the sequence of clone 666 (SEQ ID NO:9) to the extent that the resulting minimal binding determinant permits chemical synthesis with justifiable effort and at the same time preserving the high affinity to the target molecule.

A minimal binding determinant was identified using direct nucleotide point mutations and deletions. A series of deletions with tetranucleotide blocks resulted in a first overview of regions, which are essential for the binding of the target molecule. Deletions in all three double helix regions were possible and lead not to a significant reduction in the binding affinity, at least only as long as stem development was still possible. As soon as too many deletions resulted in the loss of stem development, there was no longer any binding to the target molecule CGRP observed. This was to be observed when the closing stem of the nucleic acid binder was shorted either to less than five base pairs or the hair pin loops I and III to less than 3 base pairs.

Deletions in the three loops lead to different outcomes.

Each of the embodiments of the following sequences described hereinbelow constitutes an inventive nucleic acid. Excision of the nucleotides G(20)-A(21) in hair pin loop I (in analogy to clone 732 (SEQ ID NO:10)) led to a nucleic acid binder which was further highly affine ($K_d$=20 µM), and each further tested deletion or mutation in loop 1 however led to a loss in complete binding. In loop III the nucleotides A(46) and U(47) could be withdrawn without binding loss. As was expected, the deletion of one of the bases U(48), U(49) or U(50) in combination with A(46) resulted in the same outcome.

Different shortenings were likewise possible in loop II, and especially removal of the bases G(28), U(29), A(30), U(31), A(33) and A(35) was tolerated, though it led to changes of various intensity in the binding affinity. A combination of these deletions was possible exclusively in the case of co-deletion of U(29)-A(30). The stem of the hair pin loop I allowed further shortening of the stem length to three base pairs with deletion of the base pair A(15) and U(24) (the stem length is already shortened with deletion of the nucleotides G(20)-A(21) in the loop I of 5 base pairs to 4 base pairs (clone 732 (SEQ ID NO:10), FIG. 5)). The bulges C(10) to U(12) and C(54) to C(56) seem to be essential for recognising the target molecule or respectively for the required tertiary structure, since the deletion of one of these nucleotides already leads to the complete loss of recognition of the target molecule CGRP.

In summary it can be said that in particular the loop of the hairpin loop 1 and the central bulge of the clover leaf structure are essential for the binding of the target molecule. The hair pin loop III, the smaller bulges in the centre of the clover leaf structure and the attached stem probably act to stabilise a special tertiary structure.

Additional shortenings could be achieved with the almost complete removal of the 3'-primer binding site C(64) to C(79) and the removal of the dinucleotide A(3)-G(4), a small part of the 5'-primer binding site from the final stem of the nucleic acid binder. Such shortening represents clone 732_029 (SEQ ID NO:12). This shortening was accompanied by only minimal loss of affinity ($K_d$=30 µM). The final stem could further be shortened by the deletions of the base pairs C(5): G(61) and U(6): G(60) to five base pairs ($K_d$=30 µM, as is described also in FIG. 7).

Figure 8:
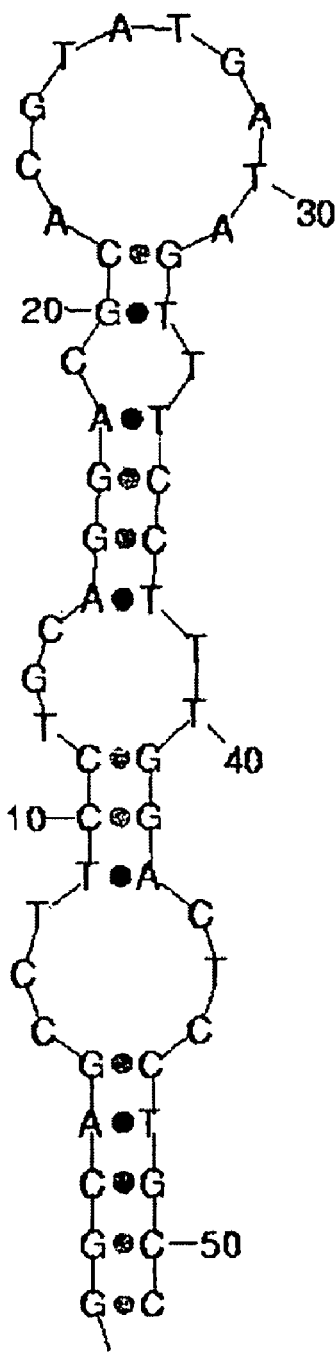
Figure 9:
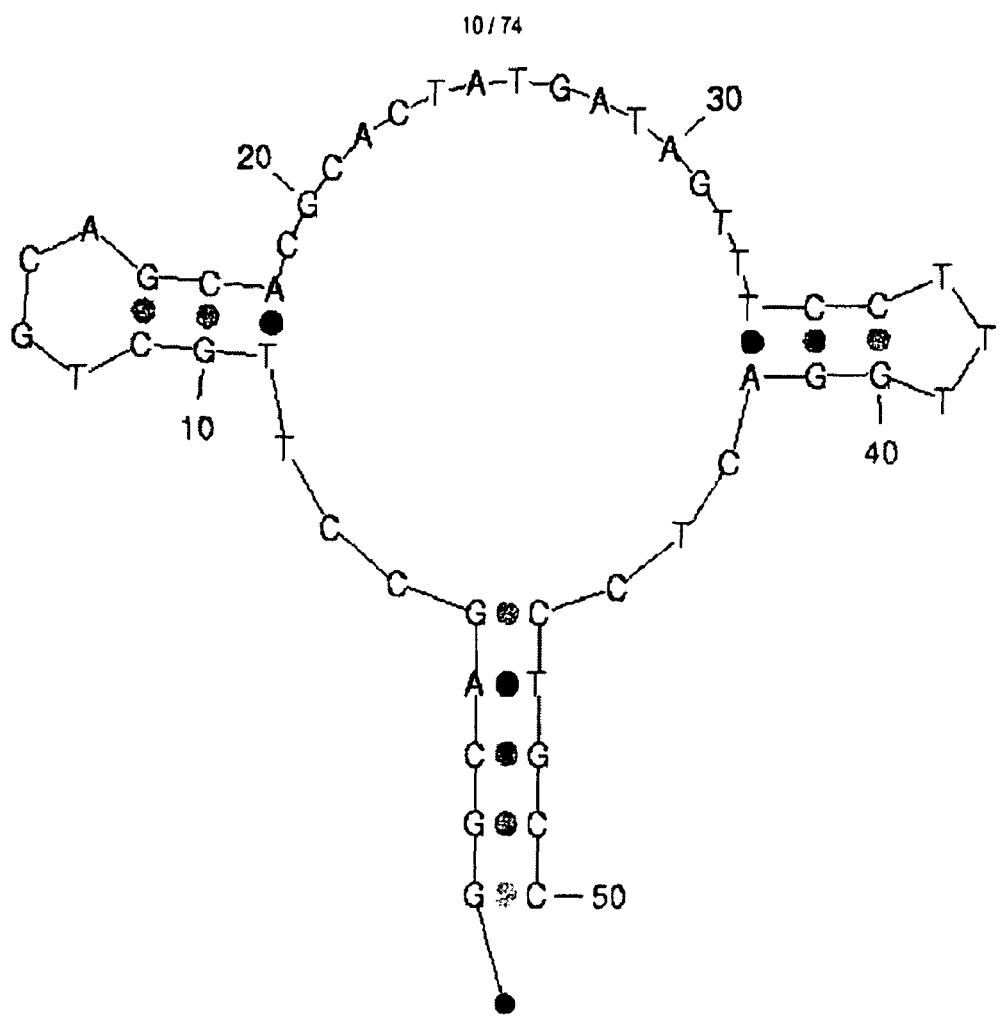

The testing of different combinations of these different deletions led to clone 732_100 (SEQ ID NO:15) (length 51 nt, $K_d$=75 µM, FIG. 8). Here the deletions A(3)-G(4), C(5): G(61), U(6): G(60), G(20)-A(21), A(15): U(24), A(46)-U(47) and C(64) to C(79) were combined with one another. This 51mer binds with a $K_d$ of 75 µM to the CGRP target molecule. Analysis of the structure forecast by means of the program rnafold however shows potential alternative folding, which can be prevented through mutation of the base pair C(14): G(25) to G(14): C(25) (clone 732_103 (SEQ ID NO:16)) or respectively of the base pair C(44): G(52) according to 0(44): C(52) (clone 732_104 (SEQ ID NO:17)). In actual fact both these clones also display a heightened affinity to CGRP with a $K_d$ of 20 or respectively 40 µM. Clone 732_104 (SEQ ID NO:17 (can be further combined with the deletion G(32), resulting in clone 732_108 (SEQ ID NO:18), a 50mer with a $K_d$ of 35 µM (FIG. 9).

Figure 10:
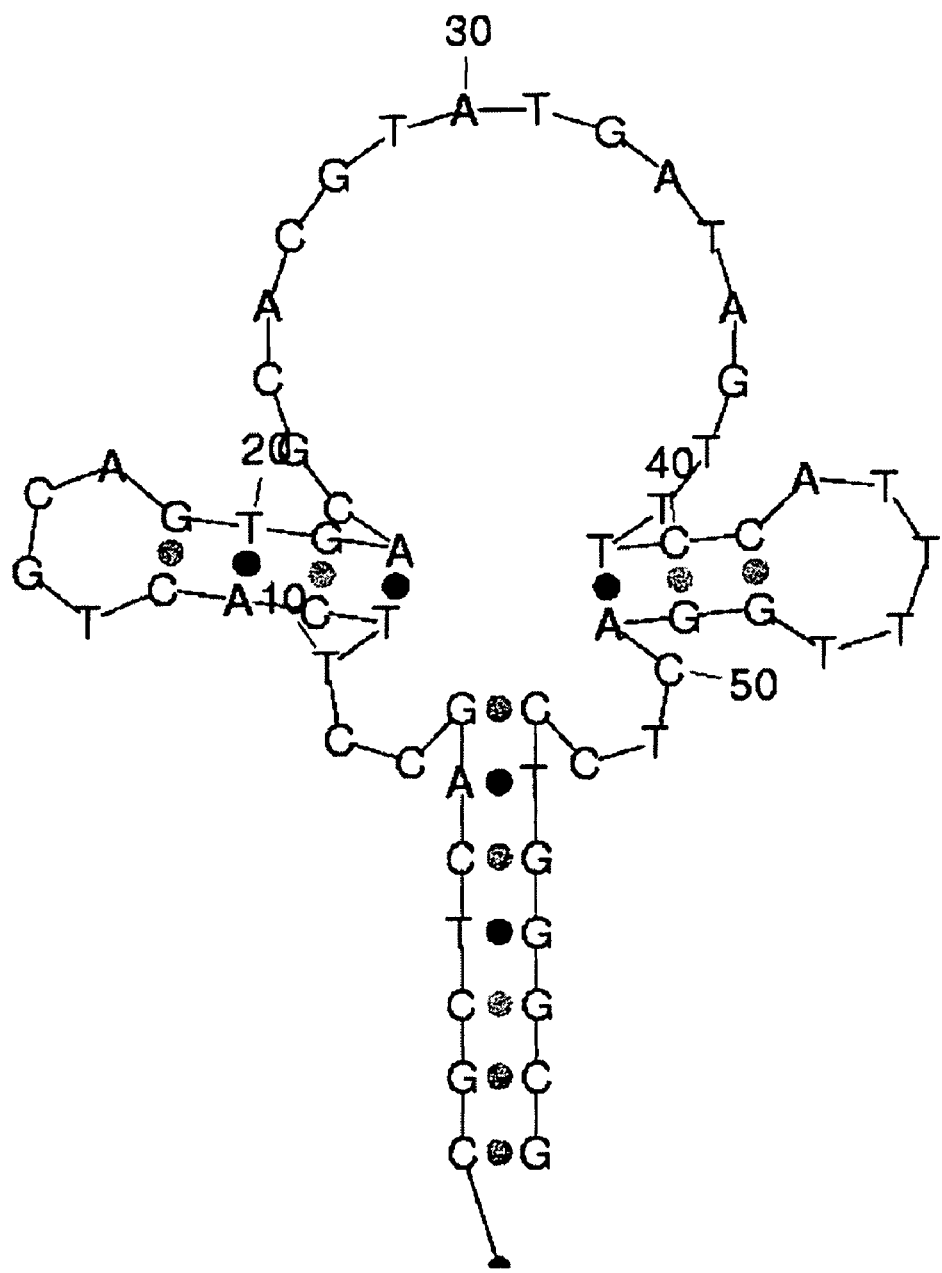
Figure 11:
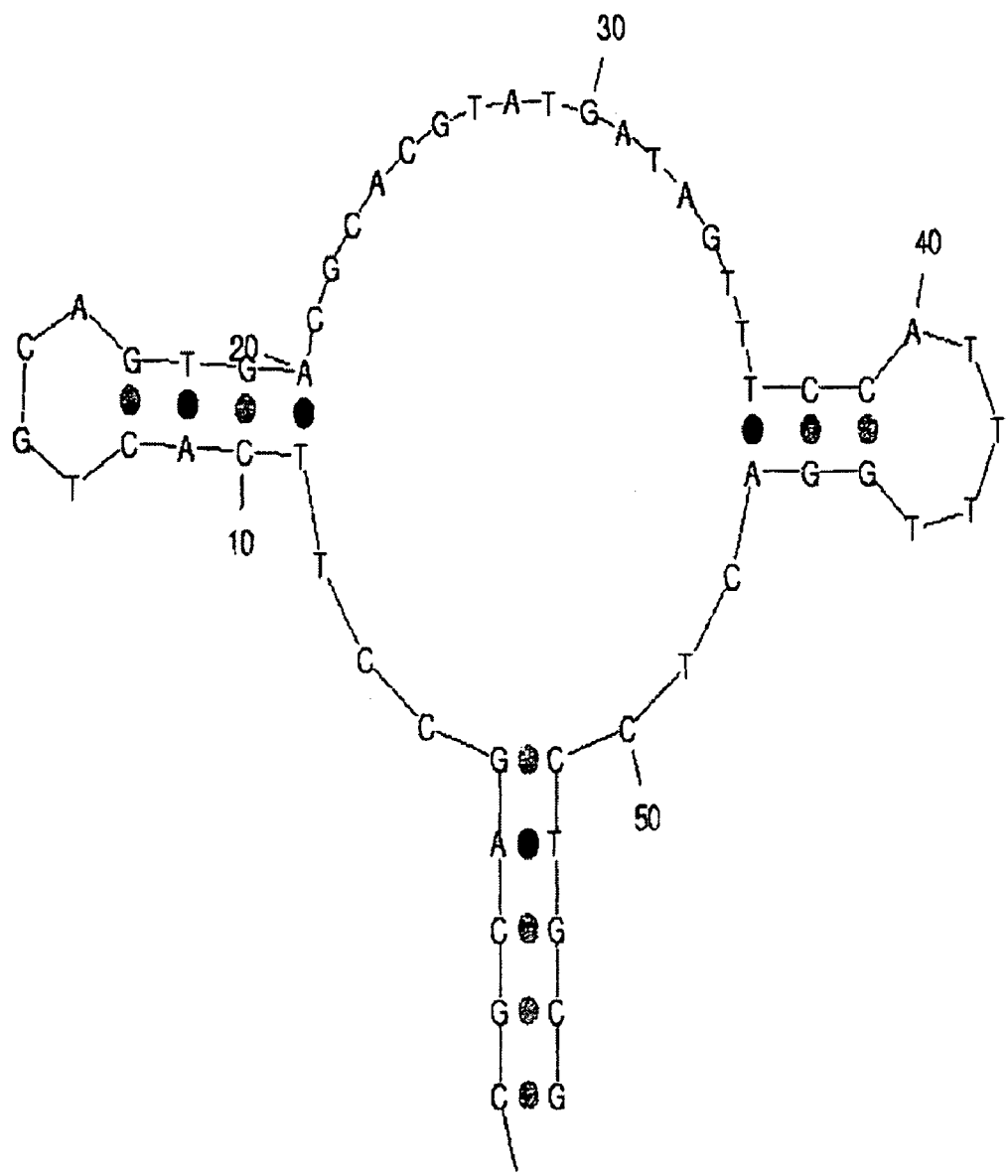

The sequences 732_026 (SEQ ID NO:11) and 732_029 (SEQ ID NO:12) were selected for the production of spiegelmers for determining their biological activities. Since no solid phase material with L-2'-F-modified C was available, it was first tested as to whether mutation of the GC-base pair terminal in each case was possible in a CG base pair corresponding to the clones 732_045 (SEQ ID NO:13) or respectively 732_096 (SEQ ID NO:14) (FIG. 10 and FIG. 11) without measurable loss of the binding affinity. Since almost identical $K_d$ values for 732_045 (SEQ ID NO:13) or respectively 732_096 (SEQ ID NO:14) compared to 732_026 (SEQ ID NO:11) or respectively 732_029 (SEQ ID NO:12) were obtained, these were selected for the production of spiegelmers to determine their biological activities.

Another method of finding a minimal binding determinant was pursued, as clone 666 (SEQ ID NO:9) or shortened forms thereof from two totally independent synthesised fragments were combined. In two pre-trials in each case fragmenting in one of the two hairpin loops I and III was tested. For one G(1) to C(19) and A(22) to C(79) (illustrated with clone 732070a (SEQ ID NO:19) and 732__070b (SEQ ID NO:20), FIG. 26) and for another G(1) to A(46)+AG and C+U(49) to C(79) (illustrated with clone 732_071a (SEQ ID NO:21) and 732__071b (SEQ ID NO:22), FIG. 27). The composed system 732__070ab (SEQ ID NOs:21 and 22) showed no measurable binding affinity to CGRP. This result strengthens the supposition that the hairpin loop 1 is involved in the binding process with CGRP, as suggested also by data of the enzymatic probing experiments. The fragments 732__071a (SEQ ID NO:21)+732__071b (SEQ ID NO:22) on the other hand form a nucleic acid binder, which binds to the CGRP target molecule with a $K_d$ of 100 µM. Further experiments point out that the stem of the former hair pin loop III must be at least five base pairs long to obtain a measurable binding result. The composition of a nucleic acid binder from two fragments is an efficient alternative for obtaining a minimal binding determinant. It permits synthesis and production of relatively long nucleic acid binders to a large synthesis extent with replaceable scientific and also economic expense. For generating combined CGRP-binding nucleic acid structures the same guidelines apply as for one-piece nucleic acid binder. The affinity and bioactivity of the resulting inventive nucleic acid binder 732__071ab (SEQ ID NOs:21 and 22) was comparable to that of the one-piece nucleic acid binders 732__108 (SEQ ID NO:18), 732__096 (SEQ ID NO:14) and 732__045 (SEQ ID NO:13) in the measured areas in the assays used (732__071ab (SEQ ID NOs:21 and 22), $K_d$=100 µM), 732__108 (SEQ ID NO:18) $K_d$=35 µM, 732__96 (SEQ ID NO:14) $K_d$=30 µM and 732__045 (SEQ ID NO:13) $K_d$=30 µM).

The spiegelmer/L-CGRP and aptamer/D-CGRP complexes gave agreeing equilibrium binding constants within the experimental error deviation.

The nucleic acid binder 732__045 (SEQ ID NO:13), 732__096 (SEQ ID NO:14) and 732__071ab (SEQ ID NOs:21 and 22) were selected for further biological studies and synthesised in the corresponding enantiomer forms.

The different sequences generated and used within the scope of this example are illustrated in FIG. 18. At the same time the following SEQ. ID. No. in each case can be assigned to the sequences illustrated in FIG. 18:

| Sequence | SEQ. ID. No. |
|---|---|
| 666 | 9 |
| 732 | 10 |
| 732__026 | 11 |
| 732__029 | 12 |
| 732__045 | 13 |
| 732__096 | 14 |
| 732__100 | 15 |
| 732__103 | 16 |
| 732__104 | 17 |
| 732__108 | 18 |
| 732__070a | 19 |
| 732__070b | 20 |
| 732__071a | 21 |
| 732__071b | 22 |

EXAMPLE 3

Selection of 2'-F-RNA Aptamers

Further selection was carried out with the aim of identifying 2'-F-RNA aptamers against D-CGRP. The applicable reaction conditions are the following:

The used target molecule is CGRP from rats. Sequence and preparation were similar to the method described in Example 1.

Selection Pool, Compiling the Start Pool

The selection pool SK60 comprises a randomised region of 60 nucleotides, flanked by the T7 primer (37 nucleotides) at the 5' end and by the reverse primer (20 nucleotides) at the 3' end. The T7 primer contains a transcription-initiating and a forward primer area. The forward primer begins with a guanosine triplet for improving the transcription efficiency.

```
SK60 pool:  5'-GGG AAT TCG AGC TCG GTACC-N60-CTG
            CAG GCA TGC AAG CTT GG-3'
            (SEQ ID NO: 267)

SK. 60T7:   5'-TAA TAC GAC TCA CTA TAG GGA ATT CGA
            GCT CGG TAC C-3' (SEQ ID NO: 268)

SK. 60F:    5'-GGG AAT TCG AGC TCG GTA CC-3'
            (SEQ ID NO: 269)

SK. 60R:    5'-CCA GCT TGC ATG CCT GC AG-3'
            (SEQ ID NO: 270)
```

The annealing temperature for the primer was theoretically calculated and then experimentally optimised in the calculated framework.

| | $T_m$ (° C.) | $T_p$ (° C.) | Used (° C.) | |
|---|---|---|---|---|
| For | 56.1 | 68.72 | RNA | 2'-F-RNA |
| Rev | 56.9 | 68.72 | 68-72 | 70-72 |

Tm = melting temperature,
Tp = 22 + 1.46 × [2 × (#GC) + (#AT)] = optimal annealing temperature with optimal amplification, according to Wu et al., 1991, DNA and Cell Biology 10, 233; without T7 promotor region.

The pool was manufactured synthetically, the base composition was determined and a complexity of $1 \times 10^{15}$ molecules was accordingly amplified and 1.78 nmol ssDNA was amplified via polymerase chain reaction (Engl. polymerase chain reaction [PCR]). 1.78 nmol of the double-strand DNA were transferred in the in-vitro transcription with fluorinated pyrimidine nucleotides (TriLink BioTechnologies, San Diego, Calif. 92121) in 2'-fluorinated RNA according to protocol 1. The resulting 2'-F-SK60 RNA start pool was placed in the first selection round.

| Component | Stock concentration | 100 1 preparation |
|---|---|---|
| T7 Buffer (Epicentre) | 5 x | 20 |
| DTT | 100 mM | 5 |
| $Mn^{2+}$ | 25 mM | 10 |
| 2'-F-CTP | 100 mM | 3 |
| 2'-F-UTP | 100 mM | 3 |
| RATP | 100 mM | 1 |
| RGTP | 100 mM | 1 |
| PCR template | ca. 100 mol/µl | 0.5 |
| T7 Polymerase | 5 U/µl | 2 |
| ddH20 | — | 54.5 |

Protocol 1. Preparation of the In Vitro Transcription for the 1st Round

Selection Buffer

The selection buffer (20 mM HEPES, 150 mM NaCl, 5 mM KCl, 1 mM $MgCl_2$ and 1 mM$CaCl_2$) follows physiological conditions of human blood and used during the entire selection. The pH value of 7.4 was set at 37° C.

Selection Strings and Stringencies

There were 2 different selection preparations carried out for identifying a 2'fluoro RNA-binding CGRP, whereof the characteristics are specified in the following table.

TABLE

Characteristics of the selection preparations against rCGRP-1

|  | Preparation 1 - NA-A/D | Preparation 2 - SA |
|---|---|---|
| Immobilising matrix | Neutravidin agarose | Streptavidin magnetic beads |
| Elution | in two steps 1. affinity elution 2. denaturing elution | denaturing elution |
| Amplification | separate amplification of the eluates | common amplification of the eluates |

The first preparation was made using Neutravidin agarose (Pierce) as matrix for immobilising the 2'-F-RNA/peptide complex. The bound 2'-fluoro RNA was eluted from the matrix in 2 steps. First, the binders were eluted via affinity solution by competition with an excess of non-biotinylated CGRP. Next, followed elution with 8 M urea by denaturing of the 2'-fluoro RNA peptide complex. The eluates were processed separately in amplification in order to limit a selection pressure on the part of the enzymatic reactions.

The second selection preparation was performed Steptavidin-derived magnetic particles as matrix for immobilising of the 2'-fluoro RNA peptide complex. elution occurred likewise with 8 M urea by denaturing of the RNA/peptide complex.

Folding the 2'Fluoro RNA

To obtain $Mg^{2+}$ and $Ca^{2+}$ ions-independent folding of the 2'-fluoro RNA, the denaturing and renaturing (folding) in selection buffer was carried into effect without $Ca^{2+}$ and $Mg^{2+}$ ions. The 2'-fluoro RNA was denatured in selection buffer without $Mg^{2+}/Ca^{2+}$ for 5 minutes at 95° C. and then folded for 30 minutes at 37° C. This was followed by addition of the ions and further folding for 10 minutes at 37° C. The preparation was given directly to a precolumn.

Precolumn

The precolumn was performed for counter-selection of potentially matrix-binding 2'F-RNA molecules and thus generally serves to enrich matrix-binding 2'-F-RNA within the selection process. Precolumn is understood as an uncharged column, which is placed upstream of the actual peptide column within a selection round. The precolumn was the same size as the main column. The 2'-F-RNA was incubated for 30 minutes at 37° C. with the matrix, and then the 2'-F-RNA was washed with a column volume selection buffer from the matrix. The marked RNA remaining on the matrix was determined and as documented precolumn. The eluted 2'-F-RNA was used again for the selection process.

Figure 12:
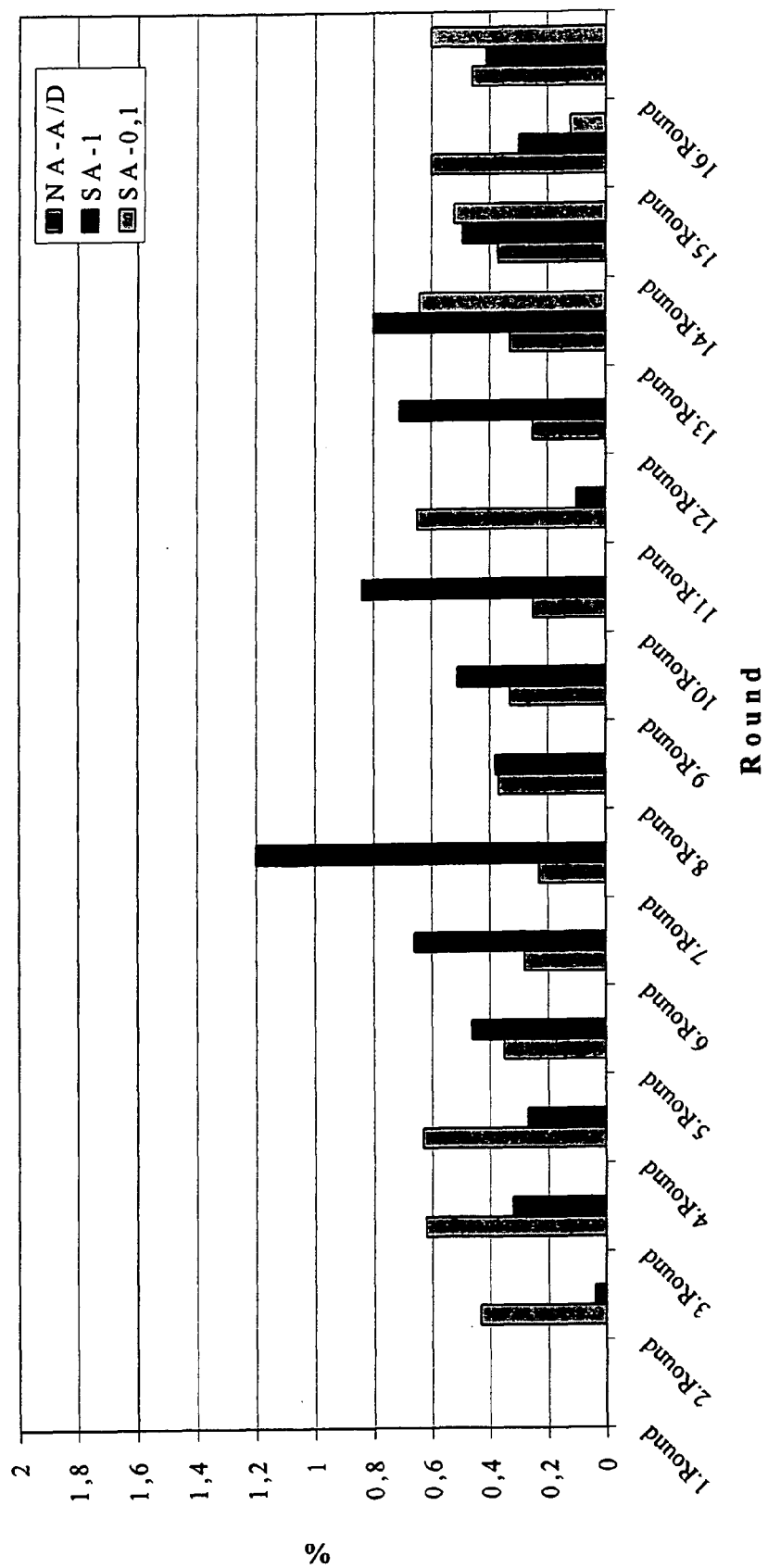
FIG. 12 shows the course of the precolumns during the selection of nucleic acids binding to CGRP.

The course of the precolumns during selection, i.e. the proportion of marked RNA remaining on the matrix, is illustrated in FIG. 12. It should be noted that from round 13 the selection SA was subdivided into two selection strands, namely selection strand SA-1 and SA-0,1, differing in peptide concentration. In the case of SA-1 the peptide concentration in round 13 was 10 μM and in rounds 14 to 16 1 μM, whereas in the selection preparation SA-0,1 the concentration of peptide in the 13th round was 10 μM and then in rounds 14 to 16 was only 0.1 μM.

Binding and Immobilising

The biotinylated D-CGRP was added directly to the 2'-F-RNA in solution. The concentration of the biotinylated peptide in the binding preparation was reduced successively over the course of the selection process, as illustrated in the following table.

TABLE

Decrease of the peptide concentration

|  | NA-AID | SA-1 | SA-0.1 |
|---|---|---|---|
| 1. round | 15 μM | 3.4 μM | 3.4 μM |
| 2. round | 3 μM | 1 μM | 1 μM |
| 3. round | 3 μM | 1 μM | 1 μM |
| 4. round | 1.5 μM | 500 nM | 500 nM |
| 5. round | 1.5 μM | 500 nM | 500 nM |
| 6. round | 1.5 μM | 500 nM | 500 nM |
| 7. round | 500 nM | 500 nM | 500 nM |
| 8. round | 500 nM | 500 nM | 500 nM |
| 9. round | 100 nM | 100 nM | 100 nM |
| 10. round | 100 nM | 100 nM | 100 nM |
| 11. round | 10 nM | 100 nm | 100 nM |
| 12. round | 10 nM | 50 nM | 50 nM |
| 13. round | 10 nM | 10 nM | 10 nM |
| 14. round | 10 nM | 1 nM | 0.1 nM |
| 15. round | 10 nM | 1 nM | 0.1 nM |
| 16. round | 10 nM | 1 nM | 0.1 nM |

Binding of the biotinylated rCGRP-2'-F-RNA preparation to the Neutravidin-derived or respectively streptavidin-derived matrix occurred by direct addition of the binding preparation to the matrix. Binding took place in the thermoshaker (Eppendorf) for 10 minutes at 37° C. with a shaking speed of 800 rpm.

Washing

The bio-CGRP-2'F-RNA complex immobilised on the matrix was washed with selection buffer so as to remove non-bound 2'F-RNA in individual washing stages from the column. CGRP-1 binding 2'F-RNA remains on the matrix. A washing volume was 100 μl of selection buffer. During selection the stringency of the selection was tightened by increasing the washing steps, as is also evident from following table.

TABLE

Washing steps sequence

|  | NA-A/D | SA-1 | SA-0.1 |
|---|---|---|---|
| 1. round | 400 μl | 400 μl | 400 μl |
| 2. round | 400 μl | 400 μl | 400 μl |
| 3. round | 600 μl | 600 μl | 600 μl |
| 4. round | 600 μl | 600 μl | 600 μl |
| 5. round | 600 μl | 1000 μl | 1000 μl |
| 6. round | 1000 μl | 1000 μl | 1000 μl |
| 7. round | 1000 μl | 1200 μl | 1200 μl |
| 8. round | 1000 μl | 1200 μl | 1200 μl |
| 9. round | 1000 μl | 1200 μl | 1200 μl |
| 10. round | 1000 μl | 1200 μl | 1200 μl |
| 11. round | 1000 μl | 1200 μl | 1200 μl |
| 12. round | 1000 μl | 1200 μl | 1200 μl |
| 13. round | 1000 μl | 1200 μl | 1200 μl |
| 14. round | 2000 μl | 1200 μl | 1200 μl |
| 15. round | 2000 μl | 5000 μl | 5000 μl |
| 16. round | 2000 μl | 5000 μl | 5000 μl |

Elution of the Bound 2'-fluoro RNA

Selection preparation NA-A: Elution of the 2'-FRNA bound to the matrix took place via the peptide first by competition with non-biotinylated CGRP in a 10-fold excess over the immobilised bio-CGRP. Incubation occurred over 12 hours at 37° C. in the overhead shaker. Then elution of the remaining 2-F-RNA took place by denaturing of the 2'-F-RNA/peptide complex by addition of 8 M urea. Incubation took place at 65° C. for 20 minutes in the thermoshaker at a shaking speed of 1200 rpm.

Selection preparation SA-1/0, 1: elution occurred by denaturing of the 2'-F-RNA/peptide complex by addition of 8 M urea. Incubation occurred at 65° C. for 20 minutes in a thermoshaker at a shaking speed of 1200 rpm.

Figure 13:
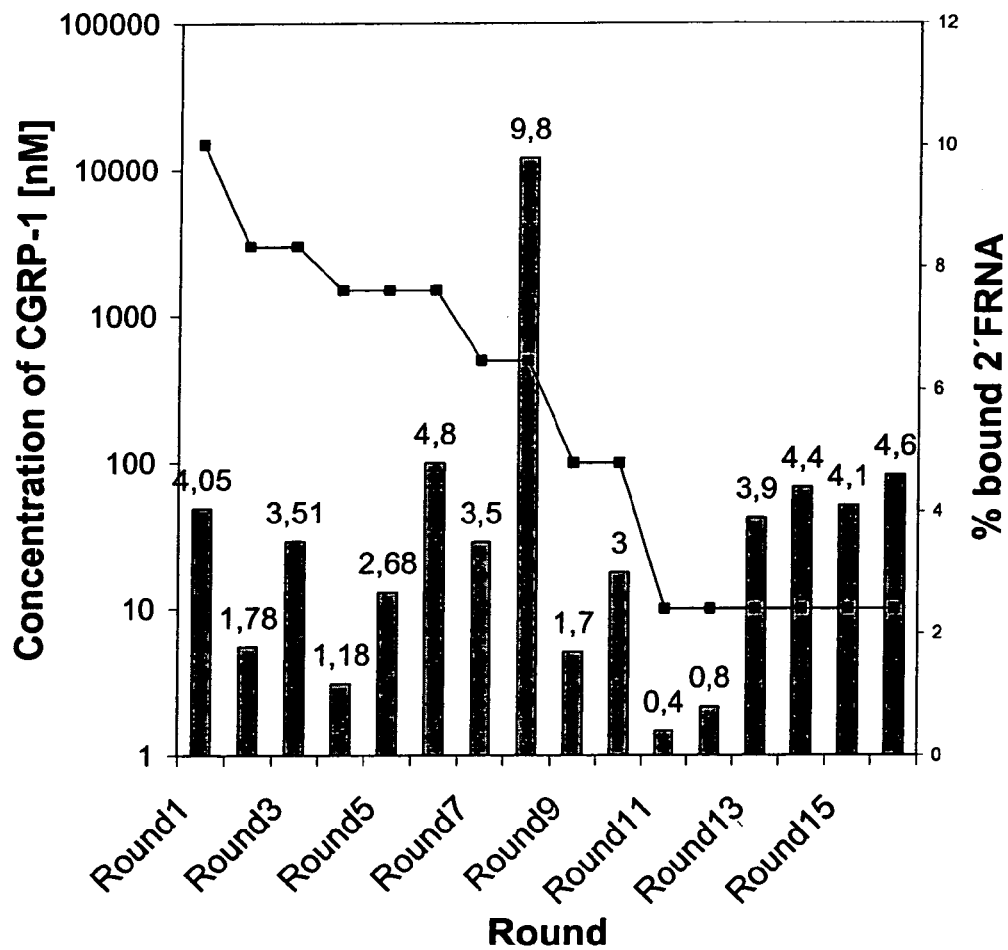
FIG. 13 shows the course of 2'-F-RNA binding CGRP and the peptide concentration of the selection preparation NA with use of neutravidin as selection matrix.
Figure 14:
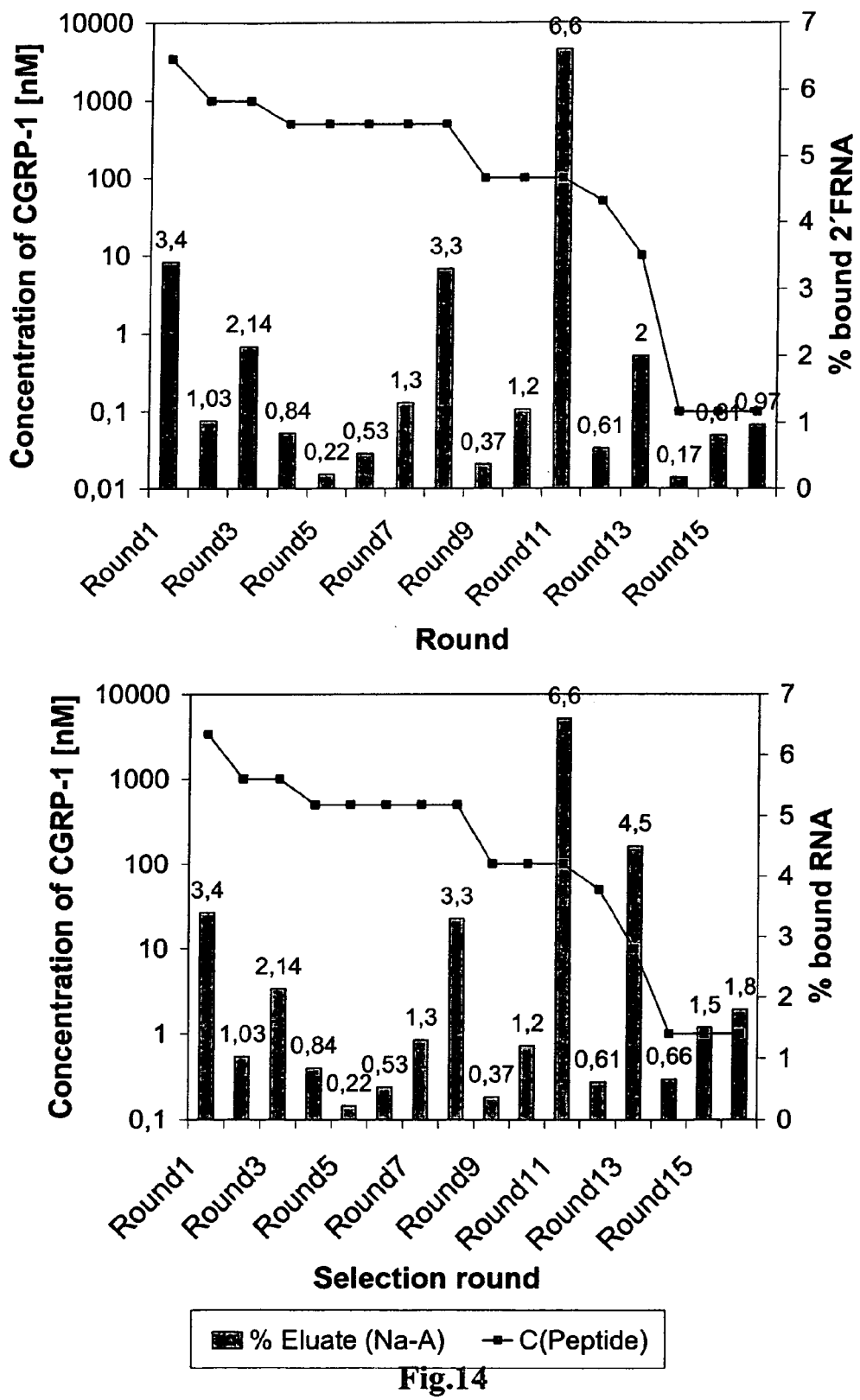
FIG. 14 shows the course of the 2'-F-RNA binding to CGRP and the peptide concentration of the selection preparation SA-1 and SA-0.1 using streptavidin derived magnetic beads as selection matrix.

The course of the eluted 2'-F-RNA and the peptide concentration of the selection preparation NA-A is illustrated in FIG. 13. Enriching of the binding 2-F-RNA could be shown in the sixth selection round at 1 µM peptide concentration. The peptide concentration was reduced continuously down to 10 µM. Reduction in the peptide concentration occurred in each case only after renewed enriching of the binding 2'-F-RNA at the given peptide concentration, as is illustrated in rounds 6, 8, 10 and 13. Selection was made from round 13 to 16 at 10 µM peptide in plateau, and the enriched nucleic acids were cloned and sequenced.

The sequence of the eluted 2'-F-RNA and the peptide concentration of the selection strands SA-1 and SA-0,1 is illustrated in diagram 14 A/B. The selections SA-1 and SA-0,1 were done to the 13th round together as one selection strand and then were placed, cloned and sequenced in the different selection strands SA-1 and SA-0,1 with different continuation of the peptide concentration up to round 16. A reduction in the peptide concentration occurred in each case only after renewed enriching of the binding 2'-F-RNA at a given peptide concentration, as is illustrated in rounds 8, 11 and 13.

Amplification

Extraction and Precipitation

The eluted 2'-F-RNA was purified by means of phenol chloroform extraction and then precipitated with glycogen as carrier, 0.3 M of sodium acetate pH 5.5 and 3 volumes 50:50 (v/v) ethanol isopropanol for 30 minutes at −80° C.

Reverse Transcription (RT)

The precipitated 2'-F-RNA was circumscribed by means of reverse transcription in single-strand DNA (ssDNA). There are <5 pmol 2'-F-RNA template per 40 µl preparation used. 10 µM SK60-reverse primer were first annealed after denaturing (5 minutes at 95° C.) of the 2'-F-RNA template in the presence of 0.8 M betaine by direct cooling of the sample on ice (so-called snap cooling). Then the first strand buffer (250 mM Tris/HCl, pH 8.3, 375 mM KCl, 15 mM MgCl$_2$), 10 mM DTT and deoxyribonucleic acid are added. The buffer conditions correspond to those for the enzyme Superscript II (standard conditions of the manufacturer). The preparation is heated for 2 minutes to 48° C., and 5 units of the reverse transcriptase are added. Incubation occurred over a temperature gradient (48° C. at 30 minutes, 50° C. at 20 minutes, 55° C. at 10 minutes, 70° C. at 15 minutes) in a PCR thermocycler.

Polymerase Chain Reaction

In each case 10 µl of the RT preparation were used as template for the PCR, corresponding to a template quantity of 1-5 pmol/100 µl PCR preparation. The nucleotide sequences of the primers are:

SK. 60T7: 5'-TAA TAC GAC TCA CTA TAG GGA ATT CGA GCT CGG TAC C-3' (SEQ ID NO: 268)

SK. EQR: 5'-CCA AGC TTG CAT GCC TGC AG-3' (SEQ ID NO: 270)

The PCR preparation was given as follows together and taken to a dsDNA yield of ca. 1 pmol/µl preparation at 1 minute 94° C. denaturing, 1 minute 72° C. annealing and 1 minute 72° C. elongation. The reaction was analysed on a denaturing 8% polyacrylamide gel.

| Component | Stock concentration | 100 µl preparation |
|---|---|---|
| T7 Buffer (Gibco) | 10 x | 10 |
| MgCl$_2$ | 50 mM | 5 |
| DNTP mix (A, T, G, C) | 10 mM per NTP | 2.5 |
| T7 primer (SEQ ID NO: 268) | 100 mM | 3 |
| Reverse primer (SEQ ID NO: 270) | 100 mM | 3 |
| template (from RT) | 1 - 5 pmol/100 µl | 10 |
| Taq Polymerase (Gibco) | — | 1 |
| ddH20 | — | 65.5 |

Protocol 2: PCR Reaction During Selection

The PCR preparations were precipitated with ethanol, resuspended in water, and 50-100 pmol of material were used for in-vitro transcription.

2'-fluoro Transcription 50 pmol dsDNA were used as template for transcription with fluoro pyrimidine nucleoside triphosphates. The ratio of the 2'-fluoro pyrimidine nucleoside triphosphates to the non-modified purin nucleoside triphosphates is 3:1. Incubation was performed overnight at 37° C. in a thermoblock.

4. Results

Course of Selections

The selections were laid in the first round as a collection round, in order as far as possible not to lose any binding F-RNA molecules. In the following rounds the stringency was continuously tightened with respect to the selection of high affine binding 2'-F-RNA by intensifying the washing steps, the reduction in peptide concentration, and the increase in the RNA:peptide ratio.

A first enriching of CGRP-binding 2-F-RNA could be shown in rounds 6 and 8 for the selection strand NA. After increasing the stringency factors and subsequent collapse of the signal in each case a renewed increase of binding 2'-F-RNA could be observed. The selection was finally brought to a plateau at a peptide concentration of 10 µM with respect to the signal, and the eluates (affinity solution and denaturing elution) were separately amplified, cloned and sequenced. NA-A designates the sequences of the eluates of the affinity solution and NA-D designates the eluates of the subsequent denaturing elution. The selection strand SA in round 8 showed enriching binding to CGRPr 2'-F-RNA. A reduction in peptide concentration always first led to a collapse of the signal with subsequent renewed enriching (rounds 11 and 13). After round 13 the selection strand was split into both strands SA-1 and SA-0,1. SA-1 was brought to a signal plateau at a peptide concentration of 1 µM, SA-0,1 at a peptide concentration of 100 µM; both strands were then separately amplified, cloned and sequenced.

Sequences:

Within the framework of selection the following sequences were obtained:

Families

| # | Sequence (shown from 5' to 3') |
|---|---|
| 1 | GGGAAUUCGAGCUCGGU-ACCUUAACCCGUAUGGGGUCACUGUWCGA UWCAWCGCCWAUCGAGCCGAWCACWGCGCUGCAGGCAUGAAGCUUGG (SEQ ID NO: 23) |
| 2 | GGGAAUUCGAGCUCGGU-ACCUUGUUACCCACUGUUUAGUAUCUCGC GAUACUCAUUACCGAGACACAGUCCCAUUACUGCCUGCAGGCAUGAA GCUUGG (SEQ ID NO: 24) |
| 3 | GGGAAUUCGAGCUCGGU-ACCGCACWUCGWACAUACGAUAUACUGGG CUAUAGUCUAUCCWGUGCCUACAGGUACUGCUGCAGGCAUGAAGCUU GG (SEQ ID NO: 25) |
| 4 | GGGAAUUCGAGCUCGGU-ACCUACUGCUCGACUAAUUGUCUAGUACA UAUGCUUACCACAUUAUCUGUUAGUGAGCUcccUGCAGGCAUGAAGC UUGG (SEQ ID NO: 26) |
| 5 | GGGAAUUCGAGCUCGGU-ACCUUGUUCUGACUCUGUUUAUGCGUUUU CCGCGUCUUUACCGGACUCCUUCUUCCCCAGUGCCUGCAGGCAUGAA GCUUGG (SEQ ID NO: 27) |
| 6 | GGGAAUUCGAGCUCGGU-ACCUAUCGUCGAACAUUCGAUCUGUUUUU ACGUAAGUAACUUUACCGUCCUCGUUUUUCCCGCCUGCAGGCAUGAA GCUUGG (SEQ ID NO: 28) |
| 7 | GGGAAUUCGAGCUCGGU-ACCAAACAUCACUUACAUGUGCUCUGCGU UUUUUGCAUAGUUUUUUGGUCGAGCGCUUCCuccUGCAGGCAUGAA GCUUGG (SEQ ID NO: 29) |
| 8 | GGGAAUUCGAGCUCGGU-ACCGCGGAGUCUGUCACAAGAUCUCGUCC UUAUCGUUGAUGUAUCGUACAAGUCUUUGCCCUGCAGGCAUGAAGCU UGG (SEQ ID NO: 30) |
| 9 | GGGAAUUCGAGCUCGGU-ACCUAAUACGACUNACUAUAGGGAAUUCG AGCUNGGUACCUUAACCCGUAUGGGGUUACU (SEQ ID NO: 31) |
| 10 | GGGAAUUCGAGCUCGGU-ACCAAUGCCUGCUUUGUUUGAGUUUUCC UUCACACUAGGGAUGGAUAAUACAGUCCUUACCCUGCAGGCAUGAAG CUUGG (SEQ ID NO: 32) |

Tab x.:

| Sequence | Origin from selection | No. of sequences | total sequenced | No. of mutated position |
|---|---|---|---|---|
| 1 | SA-1 | 18 | 33 | 7 |
|   | SA-0.1 | 14 | 33 |   |
|   | NA-A | 13 | 45 |   |
|   | NA-D | 13 | 26 |   |
| 2 | SA-1 | 2 | 33 | 0 |
| 3 | SA-1 | 2 | 33 | 9 |
|   | SA-0.1 | 2 | 33 |   |
|   | NA-A | 7 | 45 |   |
|   | NA-D | 3 | 26 |   |
| 4 | SA-1 | 2 | 33 | 0 |
| 5 | SA-0.1 | 6 | 33 | 3 |
| 6 | SA-0.1 | 3 | 33 | 3 |
|   | NA-D | 9 | 26 |   |
| 7 | SA-0.1 | 2 | 33 | 1 |
| 8 | SA-0.1 | 2 | 33 | 0 |
| 9 | NA-A | 5 | 45 | 6 |
| 10 | NA-D | 5 | 26 | 4 |

The abovementioned sequences correspond to the following SEQ. ID. No.:

| Sequence | SEQ. ID. No |
|---|---|
| 1 | 23 |
| 2 | 24 |
| 3 | 25 |
| 4 | 26 |
| 5 | 27 |
| 6 | 28 |
| 7 | 29 |
| 8 | 30 |
| 9 | 31 |
| 10 | 32 |

Ranking

Figure 19:
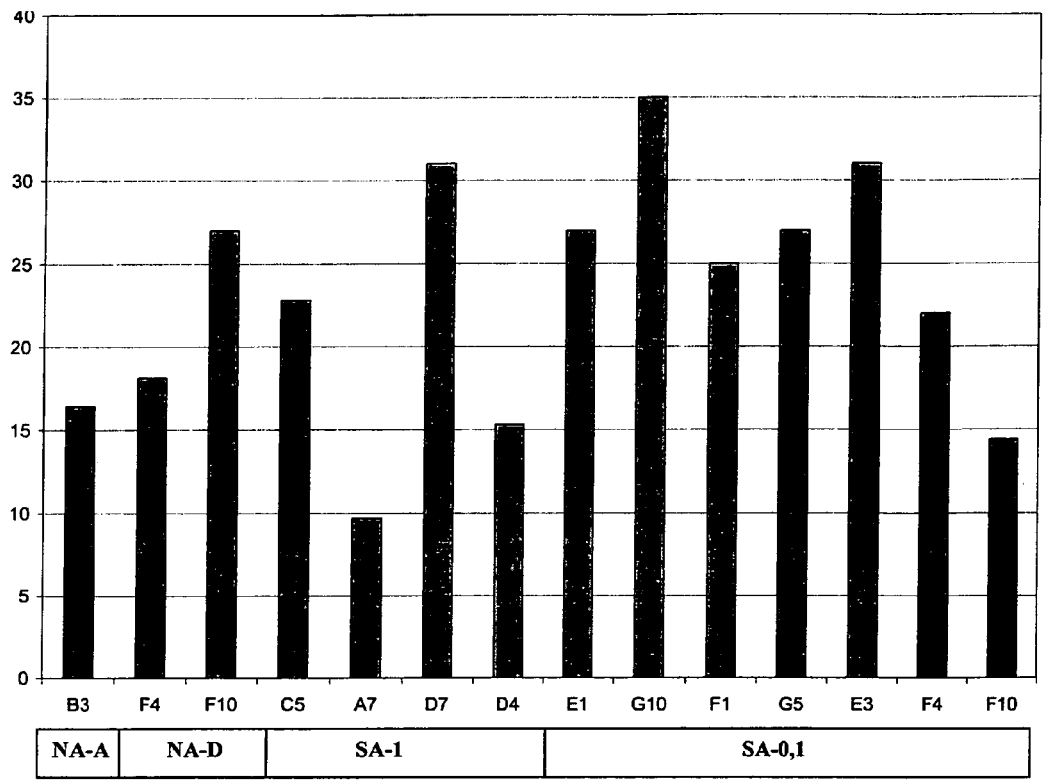
FIG. 19 shows the percentage binding of different nucleic acids recognising CGRP, as described in greater detail in Example 3; NA-A here means NeutrAvidin agarose with affinity solution, NA-D means NeutrAvidin agarose with denaturising elution, SA-1 means streptavidin beads with 1 µM peptide and SA 0.1 µM peptide concentration.

Ranking the clones was arranged by binding tests against 1 µM D-CGRP in solution. The folded, radioactive marked RNA was incubated for 2 hours at 37° C. with the peptide, immobilised and washed via Neutravidin agarose, and the percentage binding the 2'-F-RNA to CGRP was arranged. The clones D7, E1, G10 and E3 showed the highest percentage binding. The result is also illustrated in FIG. 19. The assignation of the origin of the clones from the respective selection strands NA-A (affinity solution), NA-D (denaturing elution), SA-1 and SA-0,1 is illustrated under the x axis.

Competition

Figure 20:
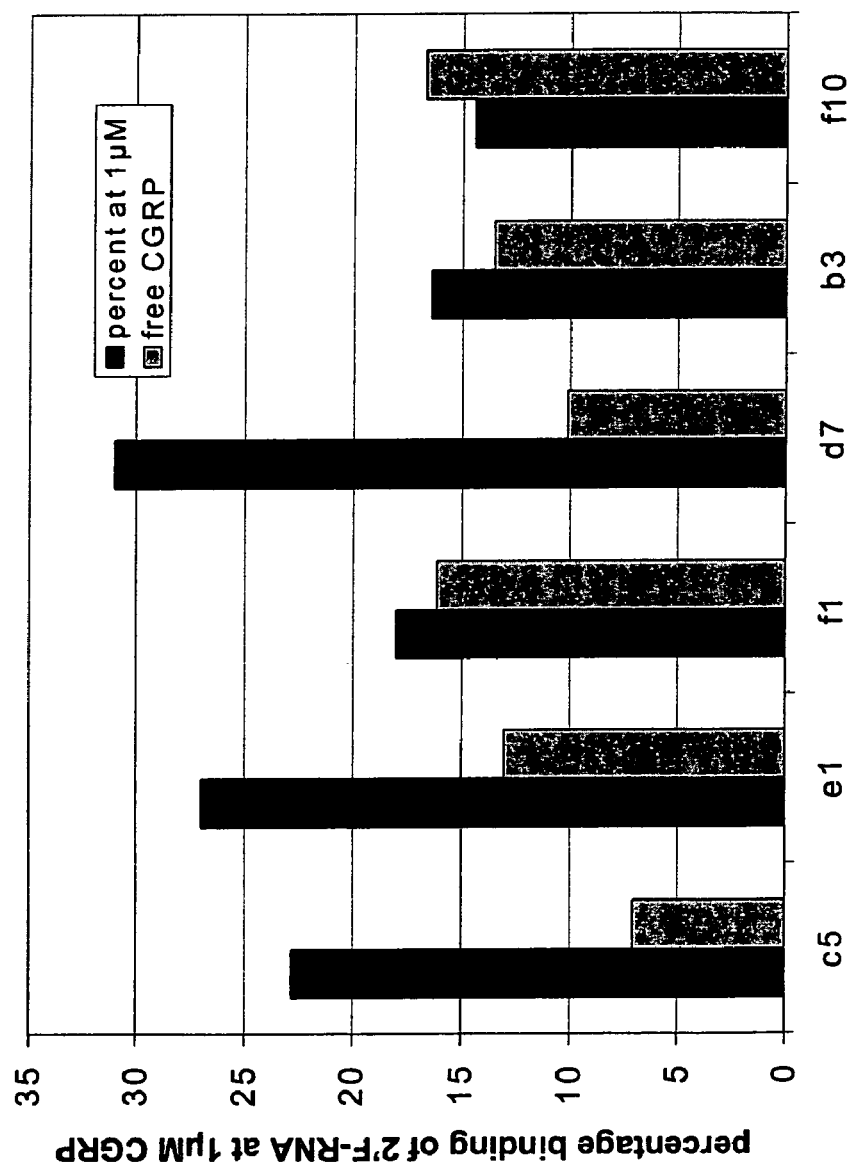
FIG. 20 shows the result of competition analysis of different nucleic acids binding CGRP selected according to Example 3.

Competition tests were carried out to further characterise the clones C5, E1, F1, D7, B3 and F10. The result is illustrated in FIG. 20. The competition by non-biotinylated D-CGRP was determined through incubation of the biotinylated D-CGRP(1 µM) and of the free CGRP (10 µM) at 37° C. with radioactively marked 2-F-RNA for 2 hours. It was shown that the clones C5, E1 and D7 competitive via free CGRP, whereas the clones F1, B3 and F10 do not recognise the non-biotinylated CGRP.

Bead Assay for Determining the Dissociation Constants

In each case 50 pmol of the marked 2'-F-RNA of clones E1, D7 and 732 (reference, origin of the 2'-F-RNA selection with pool PB40) were folded and incubated for 3 hours with different bio-CGRP concentrations in solution at 37° C. in the thermoshaker. Next, constant quantity of magnetic streptavidin beads (Roche) was added as matrix and the 2'-F-RNA/peptide complex was immobilised for 10 minutes at 37° C. and at a shaking speed of 800 rpm. The magnetic particle matrix was separated by means of a magnetic separator, the excess was taken off and the difference of the bound/unbound 2'F-RNA was determined. The control (0 µM bio-CGRP) was removed from the determined values as background. The determined values were input into the software program GraphFit (Erithacus Software Ltd.) and the dissociation constant was determined.

Figure 21:
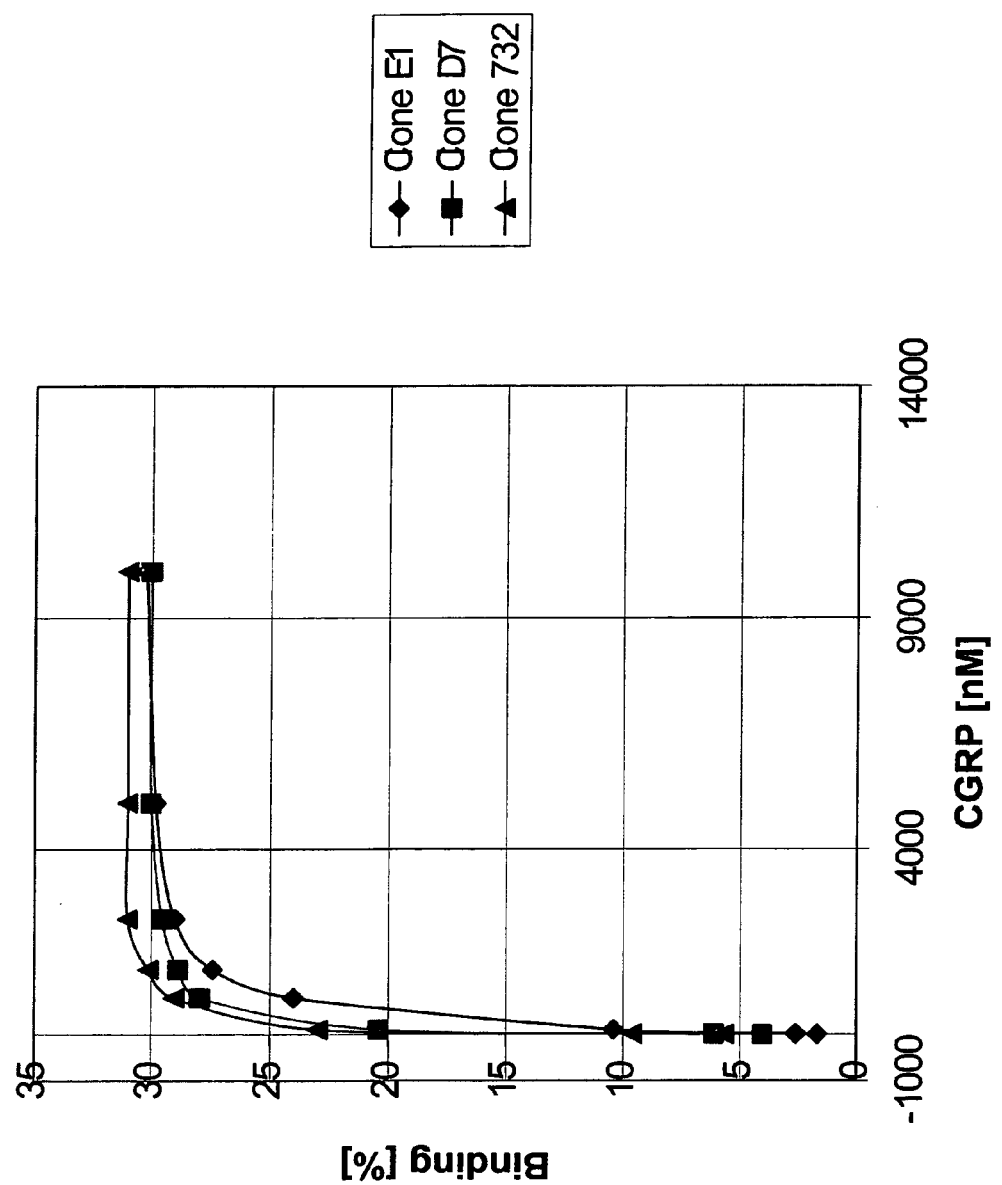
FIG. 21 shows an illustration of trials for determining the dissociation constants of different nucleic acids binding CGRP.
Figure 22:
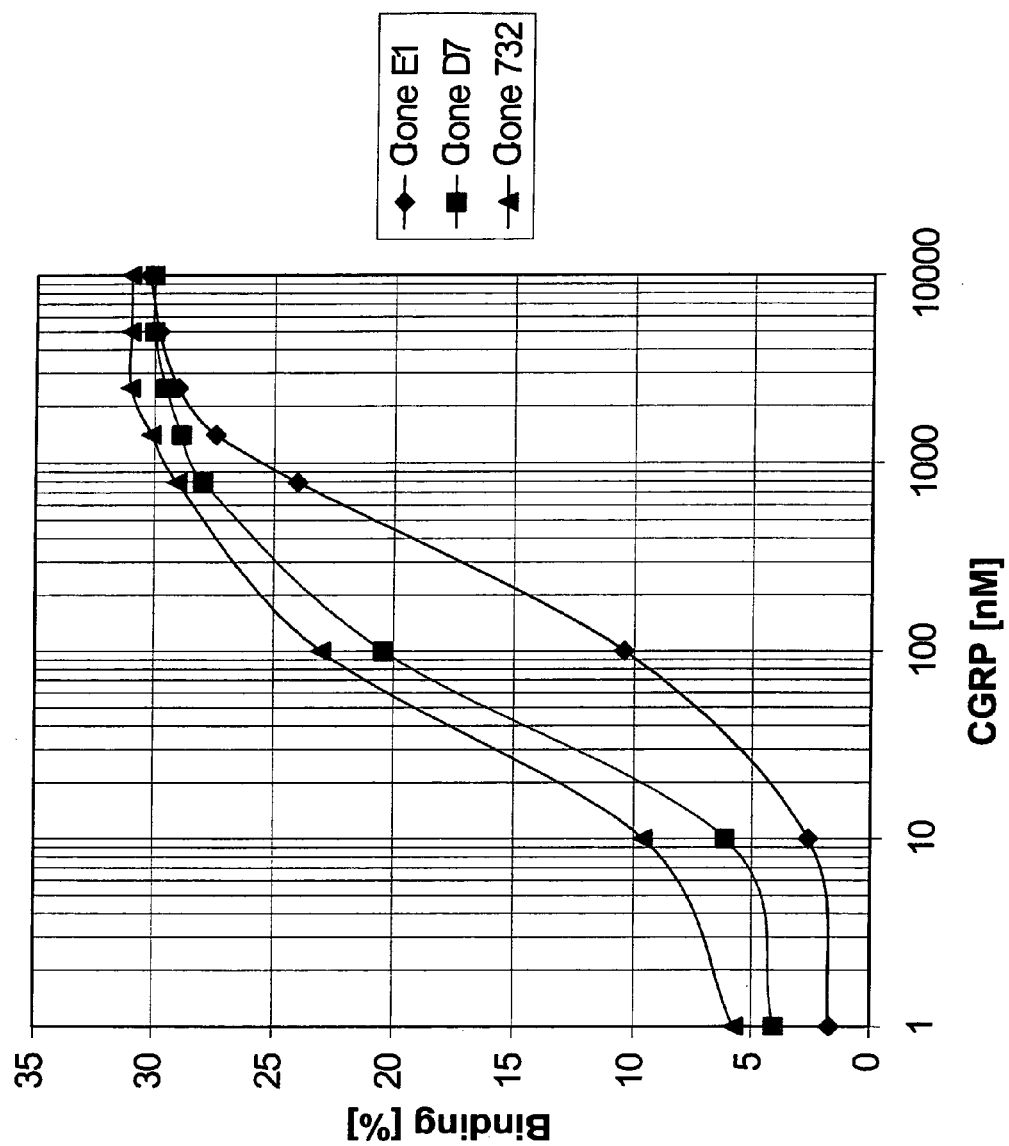
FIG. 22 shows a further illustration of trials for determining the dissociation constants of different nucleic acids binding CGRP.

After this the estimated dissociation constant is 196 µM for E1 and 42 µM for D7. The reference clone 732 (see application example 1) from the selection with the start pool PB40 as internal control for the bead assay used here yielded a dissociation constant of 23 µM. The result is illustrated in FIGS. 21 and 22. Other sequences obtained are illustrated in FIGS. 48 and 49.

EXAMPLE 4

Use of Nucleic Acids without Primer Binding Sites for the Selection of D-CGRP Binding Nucleic Acids The following materials were used for the tests described herein, whereby the details on the manufacturers of the substances, solutions and enzymes detailed hereinbelow were specified in the corresponding text passages. In all cases LiChromosolv water by Merck was used.

Rat α-D-CGRP was synthesised by Bachem, Heidelberg. The peptide used for selection carries a biotin group on the carboxyl terminus to enable the separating of unbound nucleic acids by means of the biotin-streptavidin or biotin-neutravidin binding. Neutravidin agarose and Ultralink Plus Immobilized streptavidin gel (both by Pierce) was used as matrix.

The oligonucleotides used, i.e. RNA and DNA nucleotides, such as primer, start pool, ligation constructs and the like were all synthesised with NOXXON Pharma AG with standard phosphoramidite chemistry. The sequences are found in the following overview.

Used and Tested Oligonucleotides

STAR-1 Oligonucleotides

The following applies for the sequences disclosed herein with respect to written style: details in cursive script designate nucleotides of the ligation matrices, which hybridise with the library.

The underlined area of a sequence means that this area corresponds to the T7 RNA polymerase promotor.

$N_{OH}$ generally designates a ribo-nucleotide.

$C_{Ome}$ designates a 2'-Omethyl-modified cytosine.

P designates a 5'-phosphate

Overview of the different sequences:

```
STAR-1-pool during selection:
pGGAC- (N)₄₀-GACAGG (SEQ ID NO: 271)

STAR-1-pool during ligation:
GCG ACU ACU AAT ACG ACU CAC UAUA' GGAC- (N)₄₀ -
GACAGG' ACG CTG AGC TGA ACT CGC TGC TGA GTG ATAT.
CCTG CTGTCC. UCG GAC UCG ACT TGA GC G
(mixture of SEQ ID NOs: 248, 271, 273, 275 and 277)

Library
STAR-1 initial pool, reverse strand:
5' C_OMeC_OMeT GTC- (dN)₄₀ -GTC CTA TAG TGA GTC GTA
TTA GTA GTG CGA AG 78 nt (SEQ ID NO: 272)

Forward
STAR-1 Forward Primer:
5' GCG ACT ACT AAT ACG ACT CAC TAT A GGAC 29 nt
(SEQ ID NO: 273)

STAR-1 Forward Ligate (RNA):
5' GCG ACU ACU AAU ACG ACU CAC UAU A 25nt
(SEQ ID NO: 274)

STAR-1 Forward matrix:
5' GTCC TA TAG TGA GTC G 3'dT 17 nt
(SEQ ID NO: 275)

Reverse
STAR-1 Reverse Primer Ribo U:
5' GCG AGT TCA GC U_OH CAG CG U_OH CCT GTC 24 nt
(SEQ ID NO: 248)

STAR-1 Reverse Primer:
only for amplification before sequencing
5' GCG AGT TCA GCT CAG CGT CCT GTC 24 nt
(SEQ ID NO: 276)

STAR-1 Reverse matrix corresponds to STAR-1
Reverse Primer

Reverse Ligate:
STAR-1 Reverse ligate:
pACG CTG AGC TGA ACT CG 3'dC 18 nt
(SEQ ID NO: 277)

STAR-1 N + 1 Reverse ligate
pCG CTG AGC TGA ACT CG 3'dC 17 nt
(SEQ ID NO: 278)

STAR-1 Reverse matrix = STAR-1 Rev Primer Ribo U:
5' GCG AGT TCA GC U_OH CAG CG U_OH CCT GTC 24 nt
(SEQ ID NO: 248)

STAR-1 N Reverse matrix ribo I:
5' GCG AGT TCA GCT CAG CG I_OH CCT GTC 24 nt
(SEQ ID NO: 279)
```

Production of the Start Pool

For a complexity of $1\times10^{15}$ molecules 1.67 nmol start pool were introduced to the selection. Accordingly 33.4 transcriptions with 50 µmol "STAR-1 initial pool, Reverse Strand" (5' $C_{OMe}C_{OMe}$T GTC-(dN)$_{40}$-GTC CTA TAG TGA GTC GTA TTA GTA GTG CGA AG, (SEQ ID NO:270)) was used as template of a 100 µl reaction. To achieve a DNA double strand in the region of the T7 promotor "STAR-1 Forward Primer" was added in 1.5 fold excess to "STAR-1 initial pool, Reverse Strand", the reaction preparation. The RNA was then gel-purified and precipitated (transcription and gel-purification, see below).

Selection Steps

Denaturing and Folding of RNA

All non-enzymatic steps of selection—with the exception of denaturing—were performed in selection buffer (10 mM Hepes-KOH pH 7.5 (Biochrom AG); 150 mM NaCl; 4 mM KCl; 1 mM MgCl$_2$; 1 mM CaCl$_2$ (all Ambion) and 0.05% Tween-20 (Sigma)). Denaturing occurred for 5 minutes at 95° C. in selection buffer without Tween-20, MgCl$_2$ and CaCl$_2$. After denaturing the RNA was first cooled for 15 minutes at 37° C. (or room temperature) to 37° C. (or room temperature). Tween-20, MgCl$_2$ and CaCl$_2$ were added and folding was continued at 37° C. (or room temperature) for 15 minutes.

Binding

Following folding the RNA was first incubated at 37° C. (or room temperature) for 30 minutes without peptide either with the matrix Neutravidin agarose or with Ultralink Plus Immobilized streptavidin gel. This so-called preselection acted as separation of potential matrix binders. After this incubation step the unbound RNA was separated out from the matrix by means of filtration by MobiTec column, mixed with different concentrations of biotinylated CGRP and left for at least 2 hours—at low peptide concentrations maybe also overnight—at 37° C. (or room temperature). At that point the biotin binding matrix was added to the binding preparation. The matrix with the bound RNA was separated after 30 min from the solution by centrifuging and washed with selection buffer. The washing volume used was 5-10 times the quantity of the matrix in the first rounds, and in later selection rounds was 25 times the washing volume.

Elution of the Binding RNA Molecules

For this purpose the RNA remaining on the matrix after washing was eluted twice from the matrix material with in each case with 400 µl 8 M urea with 10 mM EDTA (both from Ambion) for 15 minutes at 65° C. The eluted RNA was mixed with 400 µl phenol/(chloroform/isoamylalcohol) mixture (1:(1:1/24)) (Applichem), centrifuged for 5 min at 13000 rpm at room temperature, the aqueous phase (excess) was removed, the phenolic phase was re-extracted once with 100 µl water, the aqueous phases was cleaned and shaken with 500 µI chloroform—isoamyly alcohol mixture (24:1) (Applichem), centrifuged for 5 min at 13000 rpm to room temperature and the upper aqueous phase was removed.

The aqueous phase was then precipitated with 2.5 times volume 100% ethanol (Fluka), 0.3 M sodium acetate (Ambion) and 1 µI Glycogen (Roche) for 30 min at −80° C. and centrifuged for 30 min at 14,000 rpm (4° C.). The pellet was washed once with ice-cold 70% ethanol (Fluka).

Ligation and Amplification

Preparation for Ligation

Arrangement of the RNA quantity to be ligated was decisive for successful ligation. The eluted RNA quantity was determined via radioactivity and—if possible—via OD. The advantage of OD determining is that a minimal volume of 50 µl is necessary. The RNA was not meant to be absorbed in too large a volume for the ligation preparation however.

Therefore the specific activity [cpm/pmol] was determined at the beginning of each selection round. In this way the quantity of the eluted RNA was able to be well estimated.

Estimating the H₂O Quantity for Solution of the Pellet:

Since the ligation preparations were optimised for template quantities of up to 5 pmol template or respectively from 5 pmol template, the corresponding protocol was selected for the following calculation of the H₂O quantity. By means of the ligation protocol the maximum quantity H₂O was determined and the pellet correspondingly dissolved.

Ligation

For ligation 2 preparations were determined in pretrials with different (template quantity)/(reaction volume+enzyme quantity) ratios. The preparations vary since instead of the "simultaneous ligation" specified here "parallel 2-step ligation" was carried out (see below).

Preparations up to 5 pmol: "Simultaneous Ligation"

Volume of the preparation: 14 µl per 1 pmol RNA template

| [Stem sol.] | Component | [final] |
|---|---|---|
| | eluted RNA, dissolved in H₂O | All |
| 10x | Ligation buffer (MBI Fermentas) | 1x |
| 50% | PEG 4000 (MBI Fermenats) | 5% |
| 10 µM | ds F adapter (F ligate RNA (SEQ ID NO: 274)/F matrix) (SEQ ID NO: 275) | 20x [eluted RNA] |
| 10 µM | ds R adapter 1 (Rev ligate (SEQ ID NO: 277)/ Rev Primer Ribo U) (SEQ ID NO: 248)) | 10x [eluted RNA] |
| 10 µM | ds R adapter 2 (Rev ligate (SEQ ID NO: 278)/N + 1 matrix ribol (SEQ ID NO: 279)) | 10x [eluted RNA] |
| 5 min auf 50° C. + 5 min auf 25° C. | | |
| | RNAse out (Invitrogen) | 0.5 pl |
| 30 U/µl | T4 DNA ligase (MBI Fermentas) | 36 U/pmol RNA (1.2 µl) |

16 h to 25° C. + 15 min at 65° C.

"Parallel 2-step ligation": In this case the dissolved RNA was divided into two preparations. The first preparation was first ligated at the 5' end, while the second preparation was first ligated at the 3' end. Accordingly, in each case only the corresponding quantity "dsF or R adapter" was first added to the preparation. After the first ligation step correspondingly the "F or R adapter" still missing in each case were added, heated for 5 min. at 50° C. and then again RNAse-out and ligase added.

Preparations from 5 pmol: "Simultaneous Ligation"

Volume of the preparation: 14 µl pro 5 pmol RNA template

| [stock] | component | [final] |
|---|---|---|
| | eluted RNA, dissolved in H20 | all |
| 10x | Ligation buffer (MBI Fermentas) | 1x |
| 50% | PEG 4000 (MBI Fermentas) | 5% |
| 100 µM | ds F-Adapter (F Ligate RNA (SEQ ID NO: 274)/F Matrix (SEQ ID NO: 275)) | 20x eluted RNA |
| 100 µM | ds R-Adapter (Rev Ligate (SEQ ID NO: 277)/Rev Primer Ribo U) (SEQ ID NO: 248)) | 10x eluted RNA |
| 100 µM | ds R-Adapter n + l (Rev Ligate/N + 1 Matrix dl) | 10x eluted RNA |

5 min to 50° C. + 5 min at 25° C.

| [stock] | Component | [final] |
|---|---|---|
| | RNAse out (Invitrogen) | 0.5 µl |
| 30 U/µl | T4 DNA-Ligase (MBI Fermentas) | 7.2 U/pmol RNA (0.24 µl) |

16 h at 25° C. + 15 min at 65° C.

"Parallel 2-Step Ligation": (as Described Hereinabove)

Ligation After the First Round

Compared to the abovedescribed protocol after the 1st round the addition of ds R adapter 2 (for n+1 transcripts) is not necessary, as transcription was terminated clean prior to the 1st round by using two terminal 2'-O-methyl nucleotides. Accordingly following the first round only ds R adapter 1 (Rev Ligate/Rev Primer) was used in the 20x excess for eluted RNA.

Reverse Transcription

Reverse transcription took place-directly following ligation-with up to 15 pmol of ligated RNA in a volume of up to 100 µl. With larger quantities several parallel preparations must be made. The magnitude of the rT preparation is determined by the variously concentrated ligation preparations (simultaneous ligation/parallel 2-step ligation to or respectively from 5 pmol).

Standard values for the RT were:

| [stock] | component | [final] |
|---|---|---|
| 71.4 nM | RNA (with simultaneous ligation to 5 pmol) | 30 nM |
| 357 nM | RNA (with simultaneous ligation from 5 pmol) | 150 nM |
| 60 nM | RNA (with parallel 2-step ligation to 5 pmol) | 25 nM |
| 300 nM | RNA (with parallel 2-step ligation from 5 pmol) | 125 nM |
| 5x | 1st strand buffer (Invitrogen) | 1x |
| 5x | Q solution (Qiagen) | 1x |
| 100 mM | DTT (Invitrogen) | 10 mM |
| 25 mM | dNTPs (Larova) | 0.5 mM |
| 200 | Superscript (Invitrogen) | 200 U |

The temperature conditions were: 20 min to 51° C.+10 min to 54° C.; then 4° C.

PCR

PCR was performed with maximal 1 pmol template per 100 μl PCR. When a large quantity of RNA material was eluted, several PCRs had to be set parallel. If it is thought that prior to the commencement of an increase frequently only 1 pmol is eluted and thus the complexity cannot be greater then the number of molecules in a pmol, without doubt also only a part (>1 pmol) of the cDNA PCR can be amplified (the entire cDNA must not be put in PCR). This was implemented in this way from round 5.

Reason for the use of maximum 1 pmol ligation template in the PCR is the ligation matrix for the n+1 transcripts (3'-microheterogenities in the transcription). The used ligation matrix with the "universal" base (2'-desoxyinosine) is spread into the PCR and can also inevitably prime as Reverse Primer. This gives rise to an uncleavable PCR product. The more template is brought into the PCR, the more ligation adapters are spread and the more uncleavable PCR product there is. Accordingly, never more than 1 pmol template should be introduced to the PCR.

If on the other hand inosine is used as "universal base" for the ligation matrix, up to 5 pmol (or more, not tested) template can be placed in the PCR. In this case also the PCR products primed by the ligation matrices were alkaline digestible (was not used in this selection). As for ligation and reverse transcription there were two different PCR protocols for simultaneous ligation/parallel 2-step ligation to or respectively from 5 pmol.

Standard Values for the PCR were:

| [Stem | Component | [End |
|---|---|---|
| 30 nM | cDNA (with simultaneous ligation to 5 pmol) | 1-10 nM |
| 150 nM | cDNA (with simultaneous ligation from 5 pmol) | 1-10 nM |
| 25 nM | cDNA (with parallel 2-step ligation to 5 pmol) | 1-10 nM |
| 125 nM | cDNA (with parallel 2-step ligation to 5 pmol) | 1-10 nM |
| 10x | PCR buffer Roche) | 1x |
| 100 μM | Forward primer (SEQ ID NO: 273) | 5 μM |
| 100 μM | Reverse primer (RiboT) (SEQ ID NO: 248) | 5 μM |
| 10 μM | dNTPs (Larova) | 0.2 mM |
| 5 U/μl | Taq DNA polymerase (Roche) | 5 U |
| Temperature conditions for STAR-1 | | |
| Pool: | 1. | 95° C. 0 min |
| 15 cycles | 2. | 95° C. 4 min |
| | 3. | 95° C. 1 min |
| | 4. | 68° C. 1 min |
| | 5. | 72° C. 1 min |
| | 6. | Goto 3 14x |
| | 7. | 72° C. 6 min |
| | 8. | 4° C. infinite |

As a rule 13-15 PCR cycles were completed.

Alkaline Splitting of the Reverse Strand and Test Gel

First 10 μl PCR product were split alkaline as a test. The standard procedure for analytical alkaline splitting of the reverse strand was as follows:

| [Stem sol.] | Component | Final | V [μl] |
|---|---|---|---|
| | PCR product | | 10 |
| 2.5 M | NaOH (Merck) | ⅓ vol. of PCR prod. = 310 mM | 1.43 |

10 min to 95° C. in the PCR block, cooled to 4° C., processed further on ice

| [Stem sol.] | Component | Final | V [μl] |
|---|---|---|---|
| | PCR product | | 10 |
| 2.5 M | NaOH (Merck) | ⅓ vol. of PCR prod. = 310 | 1.43 |

Next, the pH value was checked by means of indicator paper. The pH value should be approximately pH 5-6.

The split PCR product was quantified by means of a ssDNA standard (length 78 nt, 3.55 pmol NaCl (Ambion) was added to the sample to equalise the salt effect) on a 10% denaturing PAGE, in order to determine which volume of alkaline split PCR product has to be placed in the following in vitro-transcription (target quantity: 50 pmol PCR product per 100-μl preparation). As a rule 100 pmol PCR product were digested alkaline (for two 100-μl in vitro-transcriptions).

Ethanol Precipitation with Sodium Acetate

Ethanol precipitation with sodium acetate (Ambion) acted at this point mainly to desalinise the samples.

¹⁄₁₀ volume of PCR was added to 3 M NaOAc (pH 5.3), 2.5 times the PCR volume was added to 100% ethanol and 1-2 μl glycogen (20 μg/ml). The preparation was precipitated for 30 min at −80° C., centrifuged for 30 min at 13,000-14,000 rpm at 4° C., the pellet was washed once with 500 μl 70% ethanol and centrifuged for 5 min at 13,000-14,000 rpm. The pellet was resuspended in water (¹⁄₁₀ of the original PCR volume) or the T7 transcription preparation was pipetted directly on the pellet (and then resuspended).

T7 Transcription

During the T7 transcription radioactive alpha-$^{32}$P-GTP (Hartmann) was incorporated. 50 pmol template (per 100 μl preparation) were introduced to the in-vitro transcription. An 8 times excess of guanosine-5'-monophosphate (8×GMP) was added via GTP as a special feature compared to other transcriptions, so that most transcripts may have carried a 5'-monophosphate.

Standard Values for the In Vitro Transcription were:

| [Stem sol.] | Component | final |
|---|---|---|
| | alkaline digestible PCR product | 50 pmol |
| 10x | Txn-Puffer (SK) | 1x |
| 100 mM | DTT (Invitrogen) | 10 mm |
| 10 mg/ml | BSA (Invitrogen) | 0.12 mg/ml |
| 25 mM | NTPs (Larova) | 4 mM |
| 250 mM | 5'-GMP (Sigma) | 32 mM |
| | RNAse out (Invitrogen) | 1 μl |
| 5 U/μl | T7-RNA polymerase (Invitrogen) | 2 μl |

The 10×Txn buffer (SK) contains 800 mM Hepes/KOH (Biochrom), 220 mM $MgCl_2$ (Ambion), 10 mM Spermidin (Fluka), pH 7.5.

The in vitro-transcription was carried out for 8-16 hours at 37° C. The remaining DNA was then digested with ca. 10 units DNAse I (Sigma) (20 min at 37° C.). The digesting was stopped by addition of EDTA (Ambion) (final concentration 25 mM).

Gel Purification of the Transcribed RNA

50 µl of concentrated urea solution (Roth) with blue marker (7.2 M urea, 10% bromphemol blue (Merck)) was added to the 100-µl transcription preparations, denatured for 5 min at 95° C. and fed to a preparative denaturing 10% PAA gel (run time approximately 1 hour at 50 watts). A RNA (50mer) and DNA (78mer) standard of magnitude (each 250 pmol) were additionally applied as standards of magnitude. The bands were made visible by means of "UV shadowing" (at 256 nm).

The excised gel band was eluted by means of "Crush & Soak". For this the gel pieces were absorbed in 360 µl $H_2O$ and 140 µl 5 M ammonium acetate (final concentration ca. 2 M). The crush-and-soak elution ran for 2×1.5 hours at 68° C. on the thermoshaker (1000 rpm). The excesses were filtered through Ultrafree MC column (Millipore) in the table centrifuge in 2 ml Eppis. Added to the Crush-and-Soak filtrate (500 µl) were 1-2 µl clycogen (20 µg/ml) and 1250 µl 100% ethanol, the RNA was precipitated for 30 min at room temperature, centrifuged for 30 min at 13,000-14,000 rpm, the pellet was washed once with 400 µl ice-cold 70% ethanol and finally centrifuged for 5 min at 13,000 to 14,000 rpm. The dried pellet was absorbed in 100 µl water and the RNA concentration was determined at 260 nm photometrically.

Results:

Simultaneous 5'- and 3'-Ligation: STAR-R02

Selection STAR-R02 was divided in round 6 into two strands. The first strand was guided to the plateau with a peptide concentration of 10 µM and a 2-fold peptide excess. Round 10 was cloned and sequenced. The result is illustrated graphically in FIG. 28 and as a table in FIG. 29.

Sequencing of Selection Round STAR-R02-10

Of 82 evaluable sequences there were 62 different sequences obtained. Of these, 19 bear the characteristic core determinant 1 (CAUACGGUGAAAGAAACGAU) (SEQ ID NO:280), however with slight modifications than in later selection rounds. Seven clones show a determinant 1/1, which permits any variability only at three successive positions, tensed over the entire randomised area. The determinant 1. contains in the centre (ggacGACAUGUUC NNN GAA-CAUACGGUGAAAGAAACGAUUGUCGgacagg (SEQ ID NO:281)). In addition to this two clones surface again in the sequencing from STAR-R02-12MW. Another is found in STAR-R02-15d.

Selection with Higher Stringency

Selection round 6 was repeated, whereby several parallel preparations were selected. These are distinguished only in a falling peptide concentration. In the following rounds the peptide concentration was reduced further and further. The choice of the peptide concentrations happened as follows: The highest peptide concentration corresponded to the concentration in which it still had been able to be successfully selected in the previous round (signal>1%, at least 3 times above empty selection). In addition, peptide concentrations decreased by a factor of 3.16 and a factor of 10 were employed. An empty selection completely without peptide served as control. Rounds 11-14 were selected with a reduced RNA:peptide ratio of 5:1, round 15 as double round (2× selection omitting amplification) The result is illustrated graphically in FIG. 30 and as a table in FIG. 31.

Sequencing of Selection Round STAR-R02-15d

Of 41 evaluable sequences there were 22 different sequences obtained, all of which exhibited the characteristic determinant 1 (CAUACGGUGAAAGAAACGAU (SEQ ID NO:280)). 14 of them showed the expanded determinant 1/1. 20 of the 41 clones also occur in selection STAR-RNA-03-11 with parallel 2-step ligation. 17 partly intersecting clones are rediscovered in STAR-R02-12 MW, 3 in the 37° C. selection STAR-R02-15xx. A single sequence is found in selection STAR-R02-10.

Matrix Change

From round 8 based on round 7 s (1 µM) a further, parallel selection strand was opened. This differs from the abovementioned selection strands by the repeated change of selection matrix (solid phase). The exchange was made between streptavidin ultralink Plus (Pierce/Perbio) and Neutravidin agarose (Pierce/Perbio). The result is illustrated graphically in FIG. 32 and as a table in FIG. 33.

Sequencing of Selection Round STAR-R02-12MW

From 35 evaluable sequences there were 22 different sequences obtained (1 of them has an N). 20 of the 22 (19 without N of the 22) sequences bear the characteristic determinant 1, already observed in selection STAR-R02-15d (CAUACGGUGAAAGAAACGAU (SEQ ID NO:280)). 11 clones comprise the expanded determinant 1/1. 2 of the 35 clones are known from selection STAR-R02-10, and 21 from STAR-R02-15d. 2 also occur in STAR-R02-15xx and 15 clones in STAR-R03-11.

Selection at 37° C.

From round 10 a further strand was branched off from the matrix exchange selection (RNA 02MW) and further selected at 37° C. Rounds 13xx, 14xx, 15xx were selected as double rounds. The result is illustrated graphically in FIG. 34 and as a table in FIG. 35.

Sequencing of Selection Round STAR-R02-15xx

Cloning and sequencing provided 40 evaluable clones with 17 different sequences (3 of them bear an N). 6 sequences (5 without a seq. with N) bear the typical determinant 1 (CA-UACGGUGAAAGAAACGAU (SEQ ID NO:280)). 4 (3 without N) sequences carry a partial determinant from the abovementioned: (GAAAG) and are practically identical. One clone shows the characteristic determinant 1/1. 7 clones (of which 6 are identical) carry the determinant 1/1 however with four successive variable positions (ggacGACAUGUUC NNNN GAACAUACGGUGAAAGAAACGAUUGUCG-gacagg (SEQ ID NO: 282)).

Clone R02-15xx-A11, which was characterised in Examples 9 and 11 in the cell culture and in Example 12 in the micro-calorimeter, came from this selection strand. Six (5 without, one with N) sequences with slight variations carry a newly identified determinant 2 (GAUGGCGCGGU-CUNAAAAAACGCCGNNNGGGNGAGGG (SEQ ID NO:283)). Another sequence carries a very similar determinant with a deviation (6 nt) in the centre of the determinant. Of the 40 clones there were already three identical in selection STAR-R02-10 to be found. Two appeared in STAR-R02-15d, one of which was also in STAR-R02-12MW. 7 clones were to be found in selection R03-11.

Parallel 2-Step Ligation: Selection STAR-R03

Selection, whereof the eluates were first divided and then ligated first 5' and then 3' or respectively first 3' and then 5', was placed with increasing stringency into round 11. The result is illustrated graphically in FIG. 36 and as a table in FIG. 37.

Sequencing of Selection Round STAR-R03-11

The cloning and sequencing provided 29 different sequences from 47 clones. 26 of these contained the characteristic determinant 1 (CAUACGGUGAAAGAAACGAU (SEQ ID NO:280)). One sequence is missing the 5'C(-->A). One sequence shows the shortened determinant (GAAAG, see STAR-R02-15xx). 14 of the 26 showed the expanded determinant 1/1. Two others showed the determinant 1/1 with four successive variable nucleotides, which also occurred in selection STAR-R02-15xx. One sequence is obviously an orphan.

There are no sequence overlaps with STAR-R02-10. 20 clones were also found in selection STAR-R02-15d, 19 clones in selection STAR-R02-12MW and 7 clones in STAR-R02-15xx.

In all, there is thus no difference between simultaneous and parallel 2-step ligation to be made at the sequence level on account of the major overlap. Modified molecules were already synthesised from two clones (shortened and terminal stem stabilised). These are: STAR-R03-11-F10-45-001 and STAR-R03-11-C12-48-001.

Originating from this selection was clone R03-11-F10, which was characterised in greater detail in Example 12 in the microcalorimeter.

The different resulting sequences are illustrated in FIGS. 43-47.

EXAMPLE 5

Selection of an Aptamer Binding to Biotinylated CGRP Using Non-Modified RNA

In this example the selection of aptamers is described, which bind against CGRP, more precisely biotinylated CGRP from rats. The CGRP was acquired from Jerini AG and has 37 amino acids at a pH according to SWISS PROT databank entry of 7.8. Neutravidin agarose was used as a matrix, and after round 9 was changed to magnetic streptavidin beads corresponding to the materials utilised in Example 3. Immobilising for the selection with pre-immobilised CGRP occurred of NeutrAvidin agarose using the following buffers, and was also used as selection buffer: 10 mM HEPES (pH 7.4), 1 mM Cal$_2$, 1 mM MgCl$_2$, 4 mM KCl, 150 mM NaCl, 0.1% Tween 20.

The complex formation occurred on the matrix, after round 9 in solution. The elution occurred via affinity solution for the pre-immobilised target, with 8 M urea for the streptavidin beads. The selection temperature was 37° C. and the RNA-pool was used as pool, as was used in connection with Example 1, with the exception here that no 2'-fluor-modified pyrimidine nucleotides were used.

Characteristics of Selection:

The selections were made at a constant concentration of the target molecule of 50 μM to round 9. From round 9 this concentration was lowered gradually to 10 μM to slowly increase the stringency of the selection. Over the course of selection based on a 2.5-fold washing volume of the washing proportion the washing volume was increased to 5 times (rounds 3-6) or respectively 10 times (from round 7). The target molecule was pre-immobilised in rounds 1-8 on NeutrAvidin agarose. In the following rounds (from round 9) the complex formation occurred in solution on magnetic streptavidin beads. This was eluted as an elution method in each case for 5 minutes with 7 M urea at 65° C.

Sequence of Selection:

Over the course of selection a first increase could be observed in round 4. This rise could however be successful in round 9 with 17% binding. Because an increase was observed on the precolumns in this round also, in this round the above-mentioned change occurred on the magnetic streptavidin beads, whereby another ca. 10% of RNA showed binding. By increasing the stringency of selection the attempt was made to constantly improve the quality of the binding molecules with respect to higher binding. In round 15 at a concentration of 500 μM of the target molecule a binding rate of 16% was achieved and the pool was cloned and sequenced. The sequencing produced 4 sequence families, strongly represented with 14 to 32 clones, and a further 13 sequences were present 2 to 7 times in the pool. In addition, 36 single sequences were found. Determining binding constants using the Biacore device produced affinities which were still too far removed from the target affinity of $K_d$<30 μM. The best binding constant was arranged for the single sequence G12. Based on this result the selection was continued by further increasing the stringency to round 19 (concentration of target molecule 10 μM). In round 18 binding occurred as control experiment at a concentration of the target molecule of 5 μM and a ratio of RNA to target molecule of 1:1; at the same time 50% binding was achieved. On completion of round 19 at 10 μM and a binding rate of 8.5% the resulting pool was sequenced. A sequence family could be identified from the sequencing outcome, making up over 60% of the pool. This sequence family corresponded to clone G 12, the best binder from sequencing after round 15 (whereby G12 was a single sequence). For clone G12 a $K_D$ of 100-200 μM at 25° C. was determined.

The results of the Biacore tests anticipate a bivalent binding behaviour of the clone. This could be shown in trials with non-biotinylated CGRP. The repetition of round 19 with affinity solution, in which elution of the RNA bound to biotinylated CGRP occurs with free non-biotinylated CGRP, shows only a minimal portion of elutable RNA. This round 19 with affinity solution was not sequenced. Furthermore, in the sequencing of round 19 with denaturing elution apart from the dominant G12 clone a further determinant family with 14 agents was found, as well as 30 new single sequences. The determining of the dissociation constant using the Biacore device meant that all these sequences have a lesser affinity and thus a poorer dissociation constant than clone G12.

The selection sequence is shown in the following table.

| Round | Temp. [° C.] | Pre-selection | Nucl. | Peptide [pmol] | Nucleic acid:peptide | Reaction | Volume Washing | Elutio | Σ Elution [%] | Control [%] | Commentary |
|---|---|---|---|---|---|---|---|---|---|---|---|
| 1 | 37 | — | 5000 | 10000 | 1:5 | 250 | 5 × 100 | 2 × 100 + column | 0.10 | — | 200 μl matrix |
| 2 | 37 | 100 μl; 1.83 | 1000 | 10000 | 1:10 | 200 | 5 × 100 | 2 × 100 + column | 0.17 | — | 200 μl matrix |
| 3 | 37 | 100 μl; 1.42 | 500 | 5000 | 1:10 | 100 | 5 × 100 | 2 × 100 + column | 0.17 | — | 100 μl matrix going from here |

-continued

| Round | Temp. [° C.] | Pre-selection | Nucl. [pmol] | Peptide acid:peptide | Nucleic Reaction | Volume Washing | Elutio | Σ Elution [%] | Control [%] | Commentary |
|---|---|---|---|---|---|---|---|---|---|---|
| 4 | 37 | 100 μl; 0.15 | 500 | 5000 | 1:10 | 100 | 5 × 100 | 2 × 100 + column | 2.45 | — | |
| 5 | 37 | 100 μl; 1.23 | 500 | 5000 | 1:10 | 100 | 5 × 100 | 2 × 100 + column | 1.16 | 0.05 | |
| 6 | 37 | 100 μl; 0.51 | 500 | 5000 | 1:10 | 100 | 5 × 100 | 2 × 100 + column | 2.55 | 0.11 | |
| 7 | 37 | 100 μl; 3.97 | 500 | 5000 | 1:10 | 100 | 10 × 100 | 2 × 100 + column | 3.66 | 0.16 | |
| 8 | 37 | 100 μl; 1.77 | 500 | 5000 | 1:10 | 100 | 10 × 100 | 2 × 100 + column | 6.25 | 0.26 | |
| 9a | 37 | 100 μl; 18.36 | 500 | 5000 | 1:10 | 100 | 10 × 100 | 2 × 100 + column | 17.16 | 0.07 | |
| 9b | 37 | 100 μl; 0.08 | 500 | 5000 | 1:10 | 100 | 10 × 100 | 2 × 100 | | 10.75 | | Reversal to binding in solution |
| 10 | 37 | 100 μl; 0.14 | 500 | 1000 | 1:2 | 100 | 10 × 100 | 2 × 100 | 4.89 | 2.15 | |
| 11 | 37 | 100 μl; 0.08 | 500 | 1000 | 1:2 | 100 | 10 × 100 | 2 × 100 | 2.15 | 0.25 | |
| 12 | 37 | 100 μl; 0.11 | 500 | 500 | 1:1 | 100 | 10 × 100 | 2 × 100 | 12.22 | 0.20 | |
| 13 | 37 | 100 μl; 0.15 | 500 | 500 | 1:1 | 100 | 10 × 100 | 2 × 100 | 14.15 | 0.15 | |
| 14a | 37 | 100 μl; 0.17 | 500 | 500 | 1:1 | 100 | 10 × 100 | 2 × 100 + column | 30.30 | — | |
| 14b | 37 | 100 μl; 0.17 | 500 | 100 | 5:1 | 100 | 10 × 100 | 2 × 100 | 12.24 | 0.92 | |
| 15a | 37 | 100 μl; 0.29 | 500 | 100 | 5:1 | 100 | 10 × 100 | 2 × 100 | 16.26 | 1.54 | Pool was sequenced, Occurrence of G12 as single sequence |
| 15b | 37 | 100 μl; 0.31 | 500 | 50 | 10:1 | 100 | 10 × 100 | 2 × 100 | 8.74 | 1.54 | Pool was sequenced |
| 16 | 37 | 100 μl; 0.29 | 500 | 10 | 501 | 100 | 10 × 100 | 2 × 100 | 2.55 | 0.84 | |
| 17a | 37 | 100 μl; 0.32 | 500 | 10 | 50:1 | 100 | 10 × 100 | 2 × 100 | 4.52 | 0.68 | |
| 17b | 37 | 100 μl; 0.27 | 500 | 5 | 100:1 | 100 | 10 × 100 | 2 × 100 | 1.07 | 0.68 | |
| 17c | 37 | 100 μl; 0.30 | 500 | 3 | 166:1 | 100 | 10 × 100 | 2 × 100 | 0.77 | 0.68 | |
| 17d | 37 | 100 μl; 0.28 | 500 | 1 | 500:1 | 100 | 10 × 100 | 2 × 100 | 1.12 | 0.68 | |
| 18 | 37 | 100 μl; 0.38 | 500 | 1 | 500:1 | 100 | 10 × 100 | 2 × 100 | 7.00 | 0.72 | Selection round |
| 18c | 37 | 100 μl; 0.38 | 500 | 500 | 1:1 | 100 | 10 × 100 | 2 × 100 | 50.08 | 0.72 | Control selection |
| 19 | 37 | 100 μl; 0.38 | 500 | 1 | 500:1 | 100 | 10 × 100 | 2 × 100 | 8.53 | 1.96 | Pool was sequenced, Occurrence of G12 as dominant sequence sequence |
| 19 verd | 37 | 100 μl; 0.38 | 500 | 1 | 500:1 | 500 | 10 × 100 | 2 × 100 | 1.40 | 0.56 | Low concentrations |
| 19 Aff. | 37 | 100 μl; 0.38 | 500 | 1 | 500:1 | 100 | 10 × 100 | 2 × 100 | 1.39 | 0.43 | Affinity elution as test for affinity against free target |

The preferred single sequences can be illustrated as follows.

```
GGAGCUCAGCCUUCACUGC-N40-GGCACCACGGUCGGAUCCAG
(SEQ ID NO: 284)
```

G12 group 12:

```
                                  (SEQ. ID NO. 234)
GAGCUCAGCCUUCACUGCAUCGAGGCGAUCCAAGWGUAGGAAUGGGGUGG
CUUGGAGGGCACCACGGUCGGAUCCAG(G 12) (SEQ. ID NO. 234)

+ Mutations:
                                  (SEQ. ID NO. 235)
GGAGCUCAGCCUUCACUGCAUCGAGGCAUCCAAGUUAUAGGAAUAGGGUG
GCUUGAAGGGCACCACGGUCGGAUCCAG(G 12a) (SEQ. ID NO. 235)

(SEQ. ID NO. 236)
GGAGCUCAGCCWCACUGCAUCGAGGCAUCCAAGWAUAGGAAUAGGGUGGC
WGAAGGGCACCACGGUCGGAUCCAG(G 12b) (SEQ. ID NO. 236)

(SEQ. ID NO. 237)
GGAGCUCAGCCWCACUGCAUCGAGGCGAUCCAAGWGAGGAAUGGGGUGGC
WGGAGGGCACCACGGUCGGAUCCAG(G 12c) (SEQ. ID NO. 237)

(SEQ. ID NO. 238)
GGAGCUCAGCCWCACUGCAUCGAAGGCGAUCCAAGWGUAAGAAUGGGGGU
```

```
-continued
GGCWGGAGGGCACCACGGUCGGAUCCAG(G 12d) (SEQ. ID NO.
238)

(SEQ. ID NO. 239)
GGAGCUCAGCCWCACUGCAUCGAGGCGAUCCAAGWGUAGGAAWGGAUGAC
WGGAGGGCACCACGGUCGGAUCCAG(G 12e) (SEQ. ID NO. 239)

(SEQ. ID NO. 240)
GGAGCUCAGCCUUCACUGCAUCGAGGGCGAUCCAAGWGUAGGAAUGGGGU
GGCWGGAGGGCACCACGGUCGGAUCCAG(G 12f) (SEQ. ID NO.
240)

(SEQ. ID NO. 241)
GGAGCUCAGCCUUCACUGCAUCGAAGCGAUCCAAGUUGUAGGAAUGGGGU
AGCUUGGAGGGCACCACGGUCGGAUCCAG(G 12g) (SEQ. ID NO.
241), whereby the K_D values vary only in a very narrow
band.
``` whereby the $K_D$ values vary only in a very narrow band.

H08 group 6:

```
                                     (SEQ. ID NO. 242)
GGAGCUCAGCCWCACUGCGGGUGGGAGGGUGGAUGGUGAAGAACGAGCGC
UGACCGCGGCACCACGGUCGGAUCCAG(H 08a)

(SEQ. ID NO. 243)
GGAGCUCAGCCWCACUGCGGGUGGGAGGGUGGAUGGUGGAGAACGAGCAC
UGACCUCGGCACCACGGUCGGAUCCAG(H 08b)
```

The binding nucleic acids of this group show $K_D$ values poorer than the nucleic acid according to clone G 12.

H03 group 6:

```
                                     (SEQ. ID NO. 244)
GGAGCUCAGCCUUCACUGCCAUUGAGGAUAUGCCGCGGGUCCGCAUGGAG

UGGGUGUUGGGCACCACGGUCGGAUCCAG(H 03a)
```

The binding nucleic acid of this group shows a $K_D$ value poorer than the nucleic acid according to clone G12.

EXAMPLE 6

Synthesis of L-2'-fluoro Phosphoramidites

Figure 15:
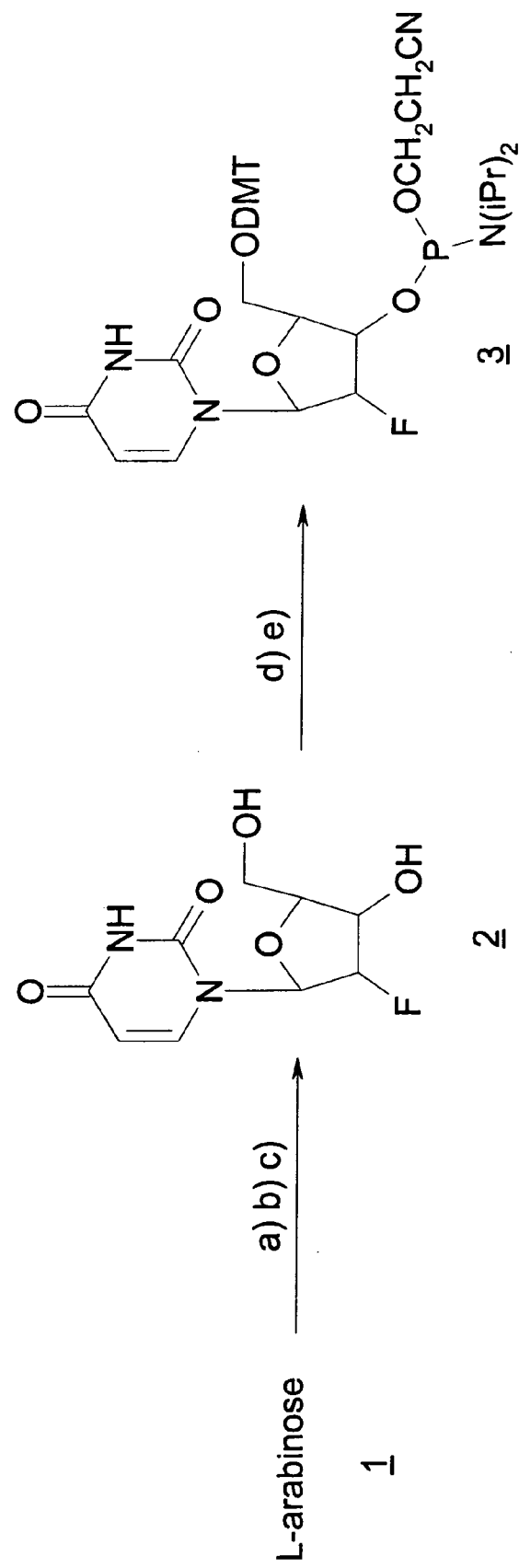
FIG. 15 shows the reaction diagram for synthesis of 5'-DMT-2'-fluoro-L-uridine phosphoramidite.
Figure 16:
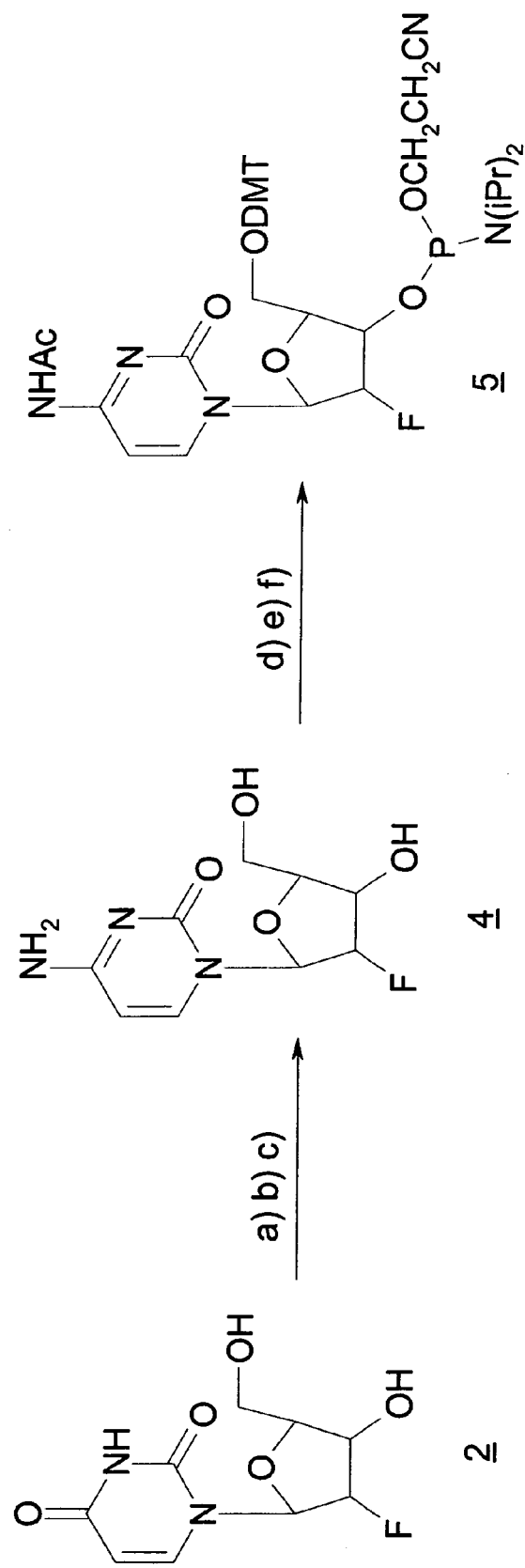
FIG. 16 shows the illustration of 2'-fluoro-L-cytidine phosphoramidite based on 2'-fluoro-L-uridine.
Figure 17:
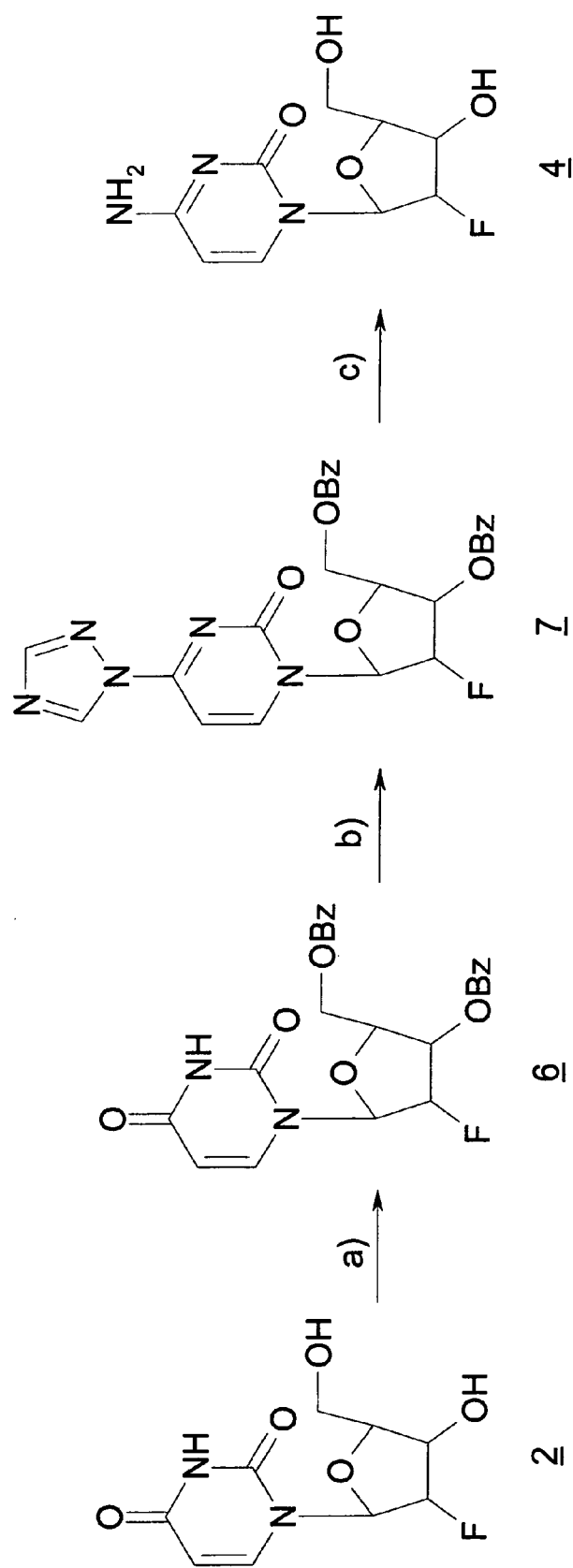
FIG. 17 shows the synthesis of 2'-fluoro-L-cytidine based on 2'-fluoro-L-uridine.

The synthesis of 5'-DMT-2'-fluoro-L-uridine and 5'-DMT-2'-fluoro-N (Ac)-L-cytidin phosphoramidites (3 and 5) is depicted in FIGS. 15 to 17:

2'-fluoro-L-uridine 2 was synthesised according to Codington, J. F., Doerr, I. L., & Fox, J. J. (1964) J. Org. Chem. 29, 558, from L-arabinose 1. Next, it was converted to 5'-DMT-2'-fluoro-L-uridine and phosphitylised (FIG. 15) to obtain the phosphoramidite (FIG. 17).

The references according to FIG. 15 mean:
a) cyanamide, MeOH, NH4OH; b) methylpropiolate, EtO-Haq; c) HF, dioxane, autoclave 120 C; d) DMTCI, DMAP, Pyr; e) Cl—P(OCH$_2$CH$_2$CN)N(iPr)$_2$, DIPEA, DMAP, THF.

For the conversion of D-uridine derivates to D-Cytidin derivates many synthesis methods are described in the literature (Sung W. L. (1982) J. Org. Chem. 47, 3623; Reese C. B., Ubasawa A. (1980) Tetrahedron Lett., 2265; Sung W. L. (1981) J. Chem. Soc. B, 1089; Krug A., Schmidt S., Lekschas J., Lemke K., Cech D. (1989) Journal f. prakt. Chemie, 331 (5), 835). These syntheses utilise as starting group 1,2,4-triazol (Sung W. L. (1982) J. Org Chem. 47, 3623) or 1-tetrazol (Reese C. B., Ubasawa A. (1980) Tetrahedron Lett., 2265; Sung W. L. (1981) J. Chem. Soc. B, 1089; Krug A., Schmidt S., Lekschas J., Lemke K., Cech D. (1989) Journal f prakt. Chemie, 331 (5), 835). The synthesis of 2'-fluoro-L-cytidin 4 was carried out with 1,2,4-triazol chemistry (Krug A., Schmidt S., Lekschas J., Lemke K., Cech D. (1989) Journal f prakt. Chemie, 331 (5), 835). The resulting 2'-fluoro-L-cytidine 4 was then aminoacetylated, tritylated and phosphorylated (FIG. 16) to obtain 5.

The references according to FIG. 16 mean:
a) BzCl, Pyr; b) 1,2,4-triazol, 4-chlorophenyl phosphordichloridate, Pyr; c) NH$_3$ (28% in water)/dioxane; d) Ac$_2$O, DMF; e) DMTCI, DMAP, Pyr; f) Cl—P(OCH$_2$CH$_2$CN)N (iPr)$_2$, DIPEA, DMAP, THF.

The details of the conversion of 2'-fluoro-L-uridine 2 into 2'-fluoro-L-cytidine 4 are described in the following diagram (FIG. 17):

The references according to FIG. 17 mean:
a) BzCl, Pyr; b) 1,2,4-triazol, 4-chlorophenyl phosphordichloridate, Pyr; c) NH$_3$ (28% in water)/dioxane; or NH$_3$ (28% in water)/dioxane and MeO/NH$_3$ sat.

2'-fluoro-L-uridine 2 was first benzoylated to obtain 6. The substance 6 was converted without cleaning directly with 1,2,4-triazol and 4-chlorophenyl phosphordichloridate to give 7. Following processing with ammonia/dioxane 2'-fluoro-L-cytidine can be obtained directly from the unpurified substance as beige brown crystallisation product.

Of particular interest with this type of synthesis is that no purifying of the intermediate substances is necessary. The final substance can be obtained from the raw substance with a high yield of approximately 70%.

Experimental Setup

2'-fluoro-L-uridine 2 (22.35 g, 57% purity, 90 mmol) was coevaporated three times with dry pyridine (3×40 ml). The raw substance was introduced to dry pyridine (150 ml, with molecular sieve) and cooled to 0° C. Benzoyl chloride was added dropwise, and the reaction was stirred for 1 h at 0° C. and stored overnight at room temperature (TLC (Hex/EE 1/2): Rf: 0.5). The reaction was stopped with methanol (5 ml) and concentrated to a dry substance. The residual substance was dissolved in DCM (250 ml) and diluted with NaHCO$_3$ (50%, 150 ml, three times). The organic phase was dried and concentrated via Na$_2$SO$_4$.

The raw substance was in dissolved dry pyridine (300 ml). The mixture was stirred with molecular sieve at 0° C. with N$_2$ for 30 minutes. 1,2,4-triazol (4.0 eq, 360 mmol, 29.9 g) was then added. This mixture was stirred at room temperature for 10 minutes. Then 4-chlorophenyl phosphodichloridate (2.0 eq, 180 mmol, 29.3 ml) was added slowly to the mixture. After 30 minutes the reaction became exothermal.

The mixture was stirred 2 h at 0° C. and stored overnight at room temperature. The unpurified product ran in on the thin-layer plate in a speck (TLC, hexane/ethyl acetate 1/2):Rf:0, 34). The residual substance was dissolved in DCM (250 ml) and the organic phase washed with diluted NaHCO$_3$ (50%, 300 ml) (exothermal). The organic phases were dried and evaporated via Na$_2$SO$_4$.

The raw substance was dissolved in dioxane (600 ml) and NH$_3$ (600 ml, 28% in water), then stirred for 72 h at room temperature. After TLC control (DCM/MeOH 9/1, Rf: 0.34) the mixture was concentrated to dry (brownish oil) and coevaporated with methanol (twice 50 ml). The brownish residual substance was dissolved in a mixture of water (200 ml) and DCM (200 ml). The aqueous phase was then washed three times with DCM (150 ml) and concentrated until a minimal volume (50 ml) was obtained. After a night in the refrigerator the substance was filtered, and washed with DCM (twice 25 ml) and Et20 (2×25 ml) (beige-brown crystals, 6.1 g (50% yield). A second yield (3.0 g, 23% yield) was obtained after brief chromatography of the original substance (storage on silica gel, course of MeOH in DCM (5-30%)) and second crystallising from water (total yield 73%).

An alternative method could result from the suspension of the raw substance in dioxane (300 ml) and NH3 (300 ml, 28% in water). The mixture was stirred 2 h at room temperature. After the TLC control (DCM/MeOH 9/1) the mixture was evaporated to dry (brownish oil) and coevaporated with methanol (twice 50 ml). The raw substance was dissolved in methanol (ca. 5 ml), and saturated methanolic ammonia (200 ml) was added. The mixture was stirred overnight.

EXAMPLE 7

Determining the Cytotoxicity of Binding to CGRP Selected L-Nucleic Acids

On the basis of the L nucleic acids selected in Example 2 one of the compounds, namely 732_096, was used to determine the toxicity of the L nucleic acid. The neuroblastoma cell line SK-N-MC with the accession number ACC 203 (DSMZ, Deutsche Sammlung von Mikroorganismen and Zellkulturen GmbH, Braunschweig) was used as cellular test system.

AlamarBlue Test

The AlamarBlue Test is an assay for detecting cell growth and cytotoxicity. AlamarBlue is an indicator dye for quantitative measuring of the proliferation of eukaryotic and prokaryotic cells. AlamarBlue is a non-toxic, water-soluble oxidation reduction indicator, which changes both its fluorescence and its colorimetric properties with completed chemical reduction. Chemical reduction of the indicator takes place in living cells proportional to the cellular metabolism and to the intracellular enzyme activity and is accordingly a measure for cytotoxicity of tested substances (Ahmend et al., 1994, J. Immunol. Methods 170, 211-224, Page et al., 1993, Int. J Oncology 3, 473-476. Absorption can be measured using a microtiter plate photometer at 570 nm (excitation) (600 nm emission; reference).

To carry this out AlamarBlue is diluted in culture medium to 5%, with 100 μl/well a microtiter plate (96th format) is given to the cells previously incubated with the test substances (spiegelmers) for 30 minutes and incubated for a certain time in the incubator. The incubation time is adapted to cell type and number. Two hours are valid as focus value for the used SK-N-MC cells (neuroblastoma cell line). On completion of the incubation time photometric measuring takes place.

As a measure for cytotoxicity the percentage change of the processed wells is ascertained against the respective controls. Inhibitions greater than 20% are considered as cytotoxic effects.

The result is expressed as a table in the following table.

| Spiegelmer concentration [M] | Inhibition [%] |
|---|---|
| $1 \times 10^{-5}$ | 0.51 |
| $5 \times 10^{-6}$ | 0 |
| $1 \times 10^{-6}$ | 1.93 |
| $5 \times 10^{-7}$ | 0.82 |
| $1 \times 10^{-7}$ | p |
| $5 \times 10^{-8}$ | 1.83 |
| $1 \times 10^{-8}$ | 2.91 |
| $5 \times 10^{-9}$ | 8.22 |
| $1 \times 10^{-9}$ | 0 |

-continued

| Spiegelmer concentration [M] | Inhibition [%] |
|---|---|
| $1 \times 10^{-10}$ | 0 |
| $1 \times 10^{-11}$ | 0 |
| $1 \times 10^{-12}$ | 0.001 |
| 0 (control) | 0 |
| 1 μM CGRP8-37 (Antagonist control) | 4.60 |
| IBMX (control) | 2.96 |

EXAMPLE 8

Inhibition of cAMP Production by Spiegelmers Binding Human CGRP

Analysis of the biological efficacy of CGRP-binding L nucleic acids, i.e. spiegelmers, was undertaken as follows.

Cells of the human neuroblastoma line SK-N-MC with the accession number ACC 203 (DSMZ, Deutsche Sammlung von Mikroorganismen and Zellkulturen GmbH, Braunschweig) are sown at the rate of 4×104 per well of a 96 well microtiter plate and at 37° C. and 5% $CO_2$ in DMEM (1000 mg/L glucose), additionally containing 10% heat-inactivated foetal calf serum (FCS), 4 mM L-alanyl-L-glutamine (GLUTAMAX), 50 units/ml penicillin, 50 μg/ml streptomycin and cultivated. 48 h after sowing the cells are 80-90% confluent and are used for the tests.

The spiegelmers are incubated together with 1 μM human or rat CGRP (Bachem) in Hank's balanced salt solution (HBSS)+1 mg/ml BSA for 15-60 min at RT or 37° C. in a 0.2 ml "low-profile 96-tube" plate. Shortly before addition to the cells 2 μl of a 50 mM IBMX solution are added. The cells are pre-treated for 20 min prior to addition of the CGRP/spiegelmer preparations with 1 mM IBMX.

For stimulation the medium is suctioned from the cells, and the pre-incubated preparations are added. After incubation for 30 min at 37° C. the cell excesses are suctioned off and the cells are lysated with 50 μl/well lysis buffer for 30 min at 37° C. The lysis buffer is a constituent of the "cAMP screen system" kit (Applied Biosystems), with which the cAMP content of the extracts is ascertained. In each case 10 μl of the extracts are added in to the test. The tests are carried into effect as described by the manufacturer: In an assay plate (coated with goat anti-rabbit IgG) 10 μl/well of the lysate are added to 50 μl of the lysis buffer and mixed with 30 μl/well of the cAMP alkalic phosphatase conjugate diluted according to the manufacturer data. After this 60 μl/well of the cAMP antibody delivered in the kit are added. Then follows an incubation period of 1 h with agitation at room temperature. Then the solutions are removed from the wells and washed six times with the supplied washing buffer. For detection 100 μl/well CSPD/Sapphire-II RTU substrate are added, incubated for 30 min at RT and the luminescence is measured in a POLARstar Galaxy multidetection plate reader unit (BMG).

In this test system two L nucleic acids were tested within the scope of Example 2 described herein. These are sequences 732_096 and 732_045 corresponding to SEQ. ID. No 14 and 13.

The spiegelmers 732_045 and 732_096 were pre-incubated prior to addition to the cells together with 1 μM human CGRP in medium (M199) without serum for 15 min. After 30 min at 37° C. lysis of the cells occurred. The extracts from in each case two identically processed "wells" were combined and the quantities of cAMP were determined as described.

Figure 23:
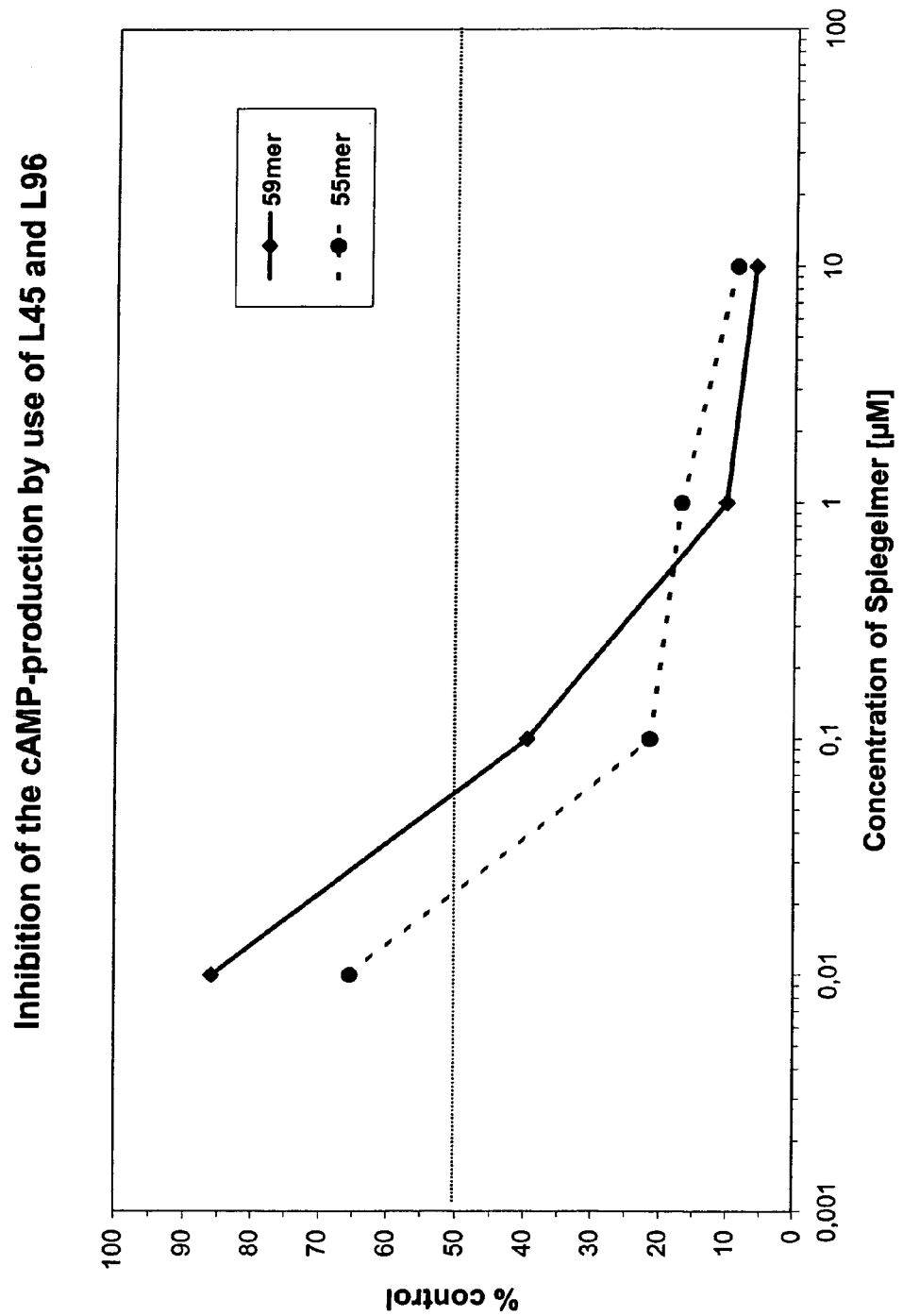
FIG. 23 shows the inhibition of cAMP production through spiegelmers binding to human CGRP.

The result is illustrated in FIG. 23. The developed quantities of cAMP were applied as percentage of the control. The graphic evaluation gives, as concentration of spiegelmer, in which still only 50% of the cAMP quantity available in the control is formed ($IC_{50}$), a value of ca. 60 µM for 732_096 (59mer) and of ca. 22 µM for 732_045 (55mer). These very good $IC_{50}$ values, which also correlate with the dissociation constants, clearly point out that the identified fluorospiegelmers are extremely potent, more potent than the unmodified RNA molecules to date selected with the same methods.

EXAMPLE 9

Inhibition of cAMP Production by Spiegelmers Binding Rat CGRP

The test was performed as described for Example 8. The spiegelmer L501L, which had been selected within the scope of Example 4, was pre-incubated prior to addition to the cells together with 1 µM rat CGRP in Hank's balanced salt solution (HBSS)+1 mg/ml BSA for 60 min at 37° C. After 30 min of sustained stimulation lysis of the cells occurred, as did determining of the cAMP quantities in the lysates as described. 3× determinations were effected and the formed quantities of cAMP were applied as percentage of the control (no spiegelmer in pre-incubation preparation)±standard deviation in FIG. 24. The graphic evaluation gives a value of ca. 60 µM as concentration of spiegelmer, in which still only 50% of the cAMP quantity available in the control is developed.

The result of a half-maximum stimulating concentration by CGRP of ca. 1 µM, as determined in Example 1 is a $K_d$ value of ca. 30 µM.

EXAMPLE 10

Binding Studies on Cellular CGRP Receptor

Membranes of CHO-K1 cells, which are transfixed with human calcitonin receptor-related receptor (CRLR, Genbank: U17473) and human receptor-associated modifying protein type 1 (RAMP1, Genbank: AJ001014) (Euroscreen, Brussels, Belgium), are swiftly thawed, diluted in 20 mM HEPES, 100 mM NaCl, 10 mM $MgCl_2$, 1 mM EDTA pH 7.4 and resuspended by homogenising. For every test preparation 2 µg membrane protein are incubated in 20 mM HEPES pH 7.4, 10 mM $MgCl_2$, 100 mM NaCl, 1 mM EDTA, 1 µM GDP and the spiegelmers in a volume of 150 µl. After 30 minutes of incubation at room temperature 50 µl 2 µM [35S] GTPγS (Amersham) are added and incubated for a further 30 minutes at room temperature. Then 25 µg WGA-PVT balls (wheat germ agglutinine-charged polyethylene imine-treated) (Amersham) are added to 50 µl by pipetting, incubated for 30 minutes at room temperature and the assay plate centrifuged for 10 min at 3200 rpm. The bound activity was determined with a Wallac1450 MicroBeta™ scintillation counter (Wallac).

Evaluation. The data are analysed by non-linear regression (GraphPad Prism, Vers. 3.02, Graphpad Software Inc., San Diego, Calif., USA).

The binding studies were carried out with both spiegelmers 732_045 and 732096, selected within the scope of Example 2. The result is illustrated in FIG. 25.

Both spiegelmers efficiently inhibit binding of the ligands to the receptor. This means that the spiegelmer specifically recognises the CGRP, and therefore no receptor binding and receptor activating occurs. As a consequence neither can [$^{35}$S] GTPγS be incorporated.

732_045 and 732_096 were purified in each case by means of HPLC or gel. FIG. 25 shows that the purification method within the scope of the error has only negligible influence on the biological activity of the fluoro-modified RNA spiegelmer.

EXAMPLE 11

Cell Culture Experiment Dose Effects Curve for CGRP

SK-N-MC cells were cultivated as described in Example 8 in 96-well plates. 20 min prior to stimulation with rat α-CGRP the medium was replaced in each case by 100 µl Hank's balanced salt solution (HBSS)+1 mg/ml BSA and mixed with 1 mM 3-isobutyl-1-methylxanthine (IBMX). Stimulation with CGRP occurred through addition from 100 or 30 times concentrated stem solutions of rat α-L-CGRP (Bachem) dissolved in PBS. After 30 min at 37° C. the excess was suctioned off and the cells were lysated with 50 µl lysis buffer. The cAMP content of the extracts was determined as described in Example 8. Applying the developed cAMP quantities to the CGRP concentration used for stimulation, as illustrated in FIG. 38, gave a half-maximum activation of ca. 1 nM.

EXAMPLE 12

Calorimetric Determining of the Binding Constants and the Activity

Execution

The binding of spiegelmers to rat α-CGRP was also determined by the method of isothermal titration calorimetry (ITC) with the VP ITC (Microcal).

To this end 1.465 ml of a 10 µM solution of the spiegelmers were introduced to the adiabatic measuring cell of the unit. The binding enthalpy released by addition of 7.5 µl of a 70 µM rat α-L-CGRP solution is registered by the unit. Through repeated addition of the peptides and measuring in each case of the released binding enthalpies binding constants and activities of the molecules can be determined.

Figure 39:
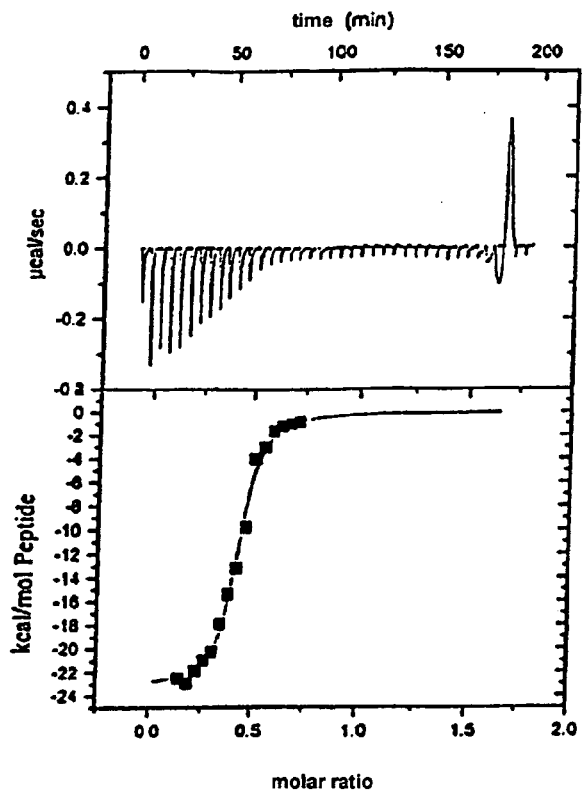
Figure 40:
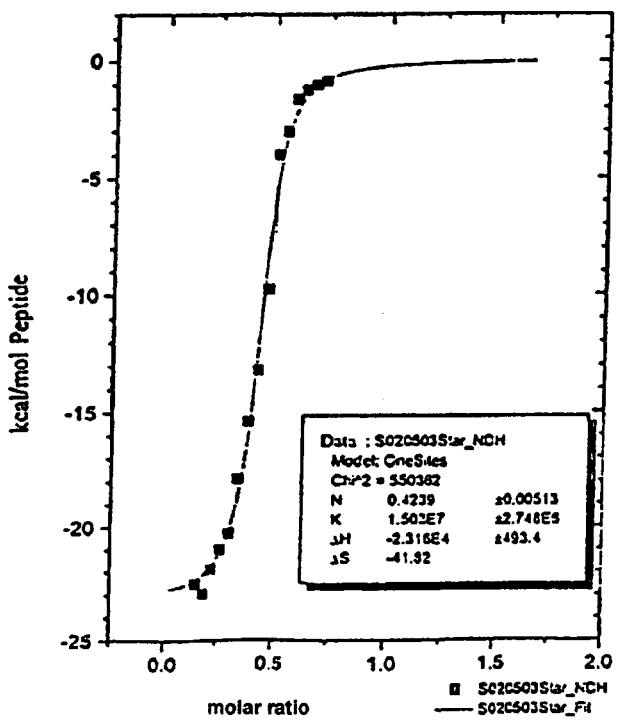

The spiegelmer STAR-R02-15xx-All was measured at 37° C. The result is illustrated in FIGS. 39 and 40.

Figure 42:
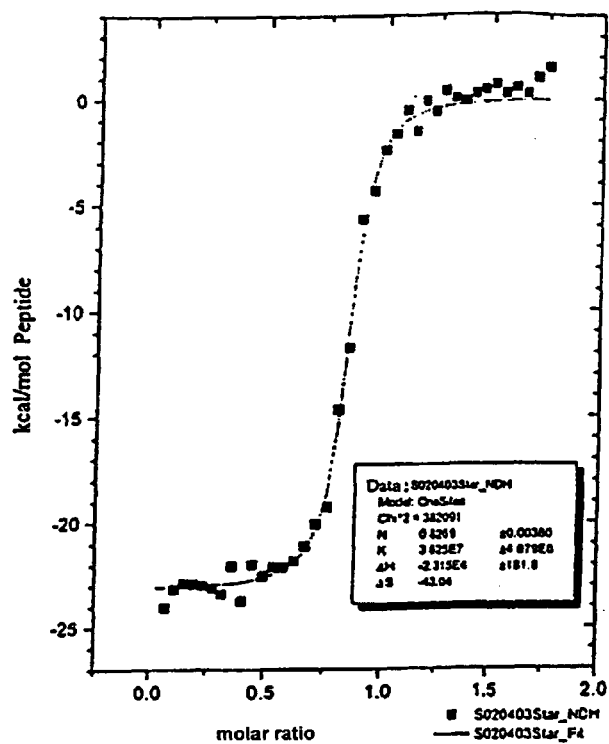
Figure 41:
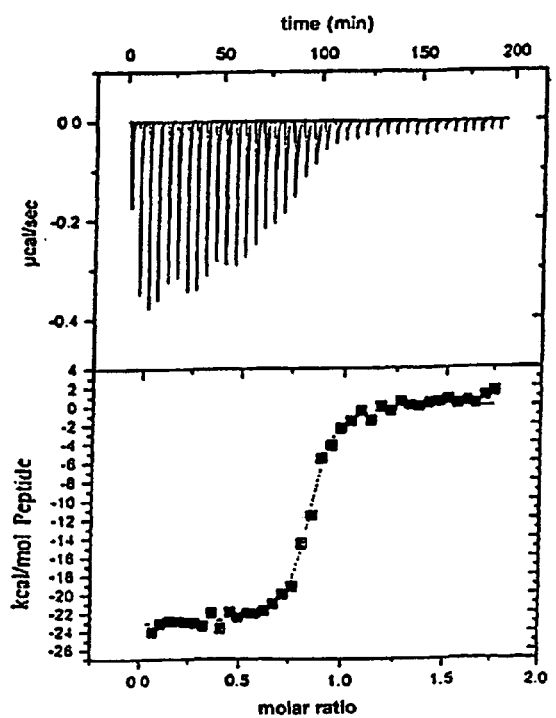

The spiegelmer STAR-R03-F10 was measured at 25° C. The result is illustrated in FIGS. 41 and 42.

Results of the ITC Measuring

The binding constant or dissociation constant $K_D$ is the reciprocal value of the association constant $K_A$ (K in the enthalpy diagram) and resulted for the spiegelmer STAR-R02-15xx-All at 65 µM. The activity was 42%. This is somewhat worse than the data of the cell culture, but in the same order of magnitude.

Spiegelmer STAR-R03-11-F10 showed at 25° C. a binding constant of 28 µM and an activity of 83%.

EXAMPLE 13

Characterising of Spiegelmer STAR-R02-15xx-F12 (NOX-504)

The trial was undertaken as described in connection with Example 8. Spiegelmer STAR-R02-15xx-F12 (also designated as NOX-504) was pre-incubated prior to addition to the cells together with 1 µM rat α-CGRP in Hank's balanced salt solution (HBSS)+1 mg/ml BSA 60 min at 37° C. After 30 min stimulation die lysis of the cells occurred and determining the cAMP quantities in the lysates as described. Double determinations were carried out and the resulting quantities of cAMP±standard deviation in FIG. 50 were applied. Graphic evaluation gave a value of ca. 7 µM as concentration of spiegelmer, in which still only 50% of the cAMP quantity available in the control (incubation of the cells with CGRP though without spiegelmer) is formed. With a half-maximum stimulating concentration by CGRP of ca.1 µM, as ascertained in Example 11, a $K_D$ value of ca. 3.5 µM results.

This spiegelmer too was characterised using the microcalorimetry method, as described in Example 12 for other spiegelmers. The binding constant or dissociation constant $K_D$ is the reciprocal value of the association constants $K_A$ (K in the enthalpy diagram, FIG. 51) and resulted for the spiegelmer STAR-R02-15xx-F12 at 44 µM. The activity was 47%.

EXAMPLE 14

Identification of Shortened Spiegelmers

Based on spiegelmer STAR-R02-15xx-F12 (48 nucleotides), which had demonstrated the best CGRP binding in cell culture (see Example 13), shortened variants were produced, since synthesis of shorter molecules is more cost-effective, which can turn out to be decisive in large-scale syntheses on the commercial success of a product. Important for the success of shortening however is the fact that the binding capacity to CGRP remains intact. FIG. 52 shows a structural suggestion for the spiegelmer. On account of this structural suggestion no rational shortening proposals can be worked out. Shortening from the 3' end surprisingly provided uniformly good binding properties when increasing the portion of active (binding) molecules, was could possibly be attributed to a favouring of binding conformation (folding) by reducing interfering influences of the 3'-terminal nucleotides. The sequence shortened by 6 nucleotides reads as follows: STAR-R02-15xx-014 (also designated as NOX-504-014): GGA CUG AUG GCG CGG UCC UAU UAC GCC GAA AGG GAG AGG GGA(SEQ ID No. 245).

A further rise in yield in spiegelmer synthesis is to be expected by dissolving the 3'-terminal purine region from G28. Therefore, focussed point mutations were introduced. The sequence, which despite two A-U mutations (A30U and A35U) still showed surprisingly uniformly high binding to CGRP, reads as follows: NOX-504-089: GGA CUG AUG GCG CGG UCC UAU UAC GCC GAU AGG GUG AGG GGA (SEQ ID No. 246).

EXAMPLE 15

Characterising the Shortened Variants

The shortened variants of spiegelmer STAR-R02-15xx-F12 were tested as described in Example 13.

In addition to this the specificity of the 42 nucleotide-long spiegelmer NOX-504-014 (abbreviated STAR-R02-15xx-F12) was tested at 37° C. for calcitonin (CT), calcitonin gene-related peptide I (α-CGRP), calcitonin gene-related peptide II (β-CGRP), adrenomedullin (AMD) and amylin.

First, the dose effect curves of the peptides were determined without addition of spiegelmers. For those peptides showing a good receptor response (measured over increased intracellular cAMP levels), direct tests were performed with increasing spiegelmer concentrations and the $IC_{50}$ values were determined. The following peptides were measured in direct trials:

α-CGRP from the rat and human α-CGRP (EC50 at 1 µM), illustrated in FIG. 53 and FIG. 54, human β-CGRP (EC50 at 1 µM), illustrated in FIG. 55 and adrenomedullin from rats and human adrenomedullin (EC50 at 30 nM), illustrated in FIG. 56 and FIG. 57.

Spiegelmer NOX-504-014 binds strongly to rat α-CGRP and human α-CGRP. The $IC_{50}$ values in each case were 2.8 µM and 25 µM (FIGS. 53 and 54).

As evident from FIGS. 53 to 55 spiegelmer NOX-504-014 binds human ssCGRP just as well as rat α-CGRP and therefore better than human α-CGRP. The $IC_{50}$ of approximately 1.5 µM. The tests were performed in each case with 1 µM CGRP, which corresponds to EC50. For this reason the following $K_I$s result for NOX-504-014: rat α-CGRP: 1.4 µM, human α-CGRP: 12.5 µM and β-CGRP: 750 pM.

Spiegelmer NOX-504-014 only slightly inhibits the interaction between rats or respectively human adrenomedullin with the calcitonin receptor-lie receptor (CRLR). The $IC_{50}$ was not able to be ascertained. In these trials 30 µM adrenomedullin was used, which corresponds to the EC50 of adrenomedullin on the CRLR. Even with 100 times excess of spiegelmer (3HM) there was no clear reduction in cAMP production observed.

The remaining peptides were tested in competition tests with α-CGRP. In these trials the concentration of α-CGRP and spiegelmer was kept constant, whereas the concentration of peptides was raised. In the event of cross-reactivity competitor spiegelmer complexes form. This effectively lowers the concentration of free spiegelmer.

Spiegelmers were then released from the α-CGRP spiegelmer complexes. The thus released α-CGRP leads consequently to the receptor stimulating. Peptides tested in competitive tests were:

amylin from rat and human amylin (EC50 in each case at 1 µM+3 µM), illustrated in FIG. 58 and FIG. 59 and calcitonin from rat and human calcitonin (EC50 not determinable), illustrated in FIG. 60 and FIG. 61.

Amylins stimulate the calcitonin receptor. This stimulating is very weak however with a EC50 of 1 µM and 3 µM in each case for rat and human amylin. To carry out direct tests very high spiegelmer concentrations had to be used. This could lead to unwanted unspecific effects. For this reason an indirect preparation was selected. We are confronted by the question of how much amylin is necessary to reduce the concentration of free spiegelmers by forming amylin spiegelmer complexes, so that CGRP might be released from CGRP spiegelmer complexes. The released free CGRP would then be proved by receptor stimulation and a strong cAMP response (CGRP has a EC50 of 1 nM). The graphs for rat amylin (FIG. 58) as well as human amylin (FIG. 59) show that amylin at a concentration of 100 µM is obviously capable of shifting the equilibrium in the direction of less free spiegelmers, and thus in the direction pf more free α-CGRP. At 100 µM amylin the stoichiometry between amylin and spiegelmers is 1:1.

In the rat amylin test at 100 µM the contribution of CGRP to the total signal 56 pmol cAMP is high. This is ca. 50% of the total signal. If the results of the rat α-CGRP graphs ($IC_{50}$ of 2 µM spiegelmer at 1 µM rat α-CGRP) are consulted, it could be decided that at the concentration of 100 µM amylin only 2 µM free spiegelmers are available for binding to CGRP. The remaining spiegelmers would have to be present therefore in the complex with rat amylin. Since the stoichiometry of amylin and spiegelmer is 1:1, this points to a low binding constant of the spiegelmer for amylin. Supposedly it is in the nanomolar range.

In the same test with human peptides the level of cAMP production induced exclusively by human α-CGRP is at 26% of the maximum, if 100 µM human amylin is used. If the dose effect curve of human α-CGRP is consulted (FIG. 54), this matches a spiegelmer concentration of almost 100 µM. At 300 µM h-amylin already 50% of the maximum cAMP production is achieved by CGRP receptor interaction. Here the concentration of free spiegelmers must be comparable to the $IC_{50}$ for human CGRP (i.e. 25 µM). 75 µM (75%) of the spiegelmers must therefore be in the complex with the present 300 µM human amylin. The interaction is accordingly slightly weaker, though supposedly still in the nanomolar range.

Neither rat nor human calcitonin stimulates the intracellular cAMP production of SK-N-MC cells. Therefore a competition experiment with 1 µM α-CGRP and 100 µM spiegelmer was performed to obtain a cAMP signal. In this case the quantity of cAMP, which is produced by the direct effect of calcitonin, is insignificant. Even with an increasing quantity of competitor (calcitonin) no additional cAMP was formed. Calcitonin is thus obviously not capable of binding spiegelmers and thus freeing CGRP from CGRP spiegelmer complexes through a shift in equilibrium, which would have resulted in a cAMP response. As evident from FIGS. 60 and 61, the experiments showed that there is no cross-reactivity of the spiegelmers with calcitonin.

In another trial a dose effect curve for the spiegelmer NOX-504-089 was recorded with the A-U mutations in cell culture. The sequence of the spiegelmer NOX-504-089 is illustrated in Example 14. And as shown in FIG. 62 the mutations were able to be incorporated surprisingly without loss of the binding quality.

EXAMPLE 16

Reselection of STAR-R02-15xx-F12 (NOX-504)

The RNA-sequence NOX-504 (SEQ ID No. 250) (FIG. 63) obtained in the selection with biotinylated rat CGRP acted as a starting point for reselection with human biotinylated D-CGRP (D-hCGRP).

To avoid reciprocal contamination of RNA pools during reselection the six 3'-terminal nucleotides (positions 43-48) of the starting sequence were modified (Grt2-STAR-504-ad3, also known as NOX-504-ad3 (SEQ ID NO:251); see FIG. 63). The modification consists of a change in the sequence at the 3' end, more precisely the last six nucleotides, which were changed from GACACG to GCACGG to prevent contamination of the reaction preparation.

An 18% mutation library of molecules based on NOX-504-ad3 was generated. The four 5'-terminal and six 3'-terminal positions of the sequence were kept constant for this purpose, while in positions 5 to 42 the bases preselected in the sequence are incorporated only to 82%, the other bases in each case to 6%; the library thus represents sequence NOX-504-ad3 with a mutation rate of 0.18 in positions 5 to 42.

Reselection should supply references on the variability of the sequence and also on the structure of the RNA molecules. For this reason, both a comparatively minimal mutation rate of the RNA pool and a low number of rounds for selection were selected.

The execution of selection follows the description in Example 4, whereby the RNA pool and its production, a few oligonucleotides, and elution and ligation of the eluted RNA molecules were altered as follows:

Use of a Mutation Pool

The mutation pool with upstream T7 promotor is synthesised as reverser ssDNA strand, converted enzymatically to dsDNA and then transcribed in a RNA library:

504-ad3-18%-library (reverser ssDNA-strand)

5'-$C_{OMe}C_{OMe}$G TGC TCC CCT CTC CCT TTCGGC GTAA TA GGA CCG CGC CA T CAG TCC TAT AGT GAG TCG TAT TAG TAG TCG C-3' (SEQ ID NO:247)

(the desoxy nucleotides (A, T, G, C) deviating from the sequence are incorporated in italicised positions at 6%).

504-ad3-18%-library (RNA sequence after transcription)
5'-GGA CUG AUG GCG CGG UCC UAU UAC GCC GAA AGG GAG AGG GGA GCA CGG-3' (SEQ ID NO:285)

(the ribonucleotides deviating from the sequence (A, T, G, C) are incorporated in italicised positions at 6%).

Oligonucleotides for Ligation of the Primer Sequences "Primer Ligation"

STAR-1 Reverse Primer Ribo U (=STAR-1 reverse matrix)
5'-GCG AGT TCAGCU$_{OH}$ CAG CGU$_{OH}$ CCG TGC-3' 24 nt (SEQ ID NO:248)

STAR-1 N+1 reverse matrix ribo 15'-GCG AGT TCAGCU$_{OH}$ CAG CG$_{OH}$ CCG TGC-3' 24 nt (SEQ ID NO:249)

Production of the Initial RNA Library

The reverse ssDNA strand of the 504-ad3-18%-library was mixed with a three-fold molar excess STAR-1 Forward Primer (see Example 4) and transferred enzymatically by AmpliTaq DNA polymerase Stoffel Fragment (Applied Biosystems) to double-strand DNA. This was placed as template in the T7 transcription (see Example 4).

Elution of the Binding RNA Molecules

The RNA remaining on the matrix after washing is eluted twice with in each case 100 µl guanidinium isothiocyanate (Roti-Quick 1; Roth) in 15 min at 37° C.

Ligation

The ligates are linked with the eluted RNA according to the protocol of simultaneous ligation.

There were 5 rounds (R1 to R5) of reselection carried out. The stringency was increased by the peptide concentration of 1 µM (R1) being lowered via 100 µM (R2) and 1 µM (R3, R4) to 0.1 µM (R5). At the same time the RNA:peptide ratio of 1:2 (R1, R2, R3) was raised over 1:1 (R4) to 10: 1 (R5). After the initial rise of the signal in rounds R1 and R2 to a signal/background ratio of 4.5 the quotient was reduced with increasing stringency to a value of ca. 1.3. The selection sequence is illustrated in FIG. 64.

The CGRP binding RNA of round 5 was amplified, cloned and sequenced. In the process 22 sequences were obtained: the starting sequence of reselection and another 16 sequences with different mutations. Amongst these is the sequence Grt2-STAR-504-5-B0.1-C10 (SEQ ID No. 252), which is characterised by the substitution A37U, as well as two insertions of guanosine between positions 29/30 and 41/42 (ins[29G30]; A37U; ins[41G42]; see FIG. 63).

EXAMPLE 17

Biological Efficacy of Grt2-STAR-504-5-B0

1-C10 Grt2-STAR-504-5-B0.1-C10 was selected as D-RNA by means of biotinylated D-hCGRP. In order to analyse the biological activity of the corresponding spiegelmer (L-RNA) with L-hCGRP, reference was made to the cell culture model described in Example 8.

The starting sequence of reselection (NOX-504-ad3) with the modified 3'-terminal nucleotides is barely altered compared to NOX-504 with respect to the binding of CGRP. It was accordingly supposed that the varying sequence range for peptide binding is simply nit significant. Spiegelmer L097 shortened by six nucleotides (FIG. 65) was correspondingly used for the cell culture studies.

In the cell culture experiment the dose effects curves of L097 (SEQ ID No. 253) were determined with hCGRP and rCGRP. In the process $IC_{50}$ of [L097]=6 µM was ascertained for inhibition of hCGRP and [L097]=1.5 µM for inhibition of rCGRP (FIGS. 66A and 66B).

EXAMPLE 18

Mutation Analysis of L097 in the Cell Culture Model

The three mutations, which distinguish L097 from the starting sequence of reselection, lead to an approximately five-fold improvement in binding to hCGRP. For the purpose of analysing which of these three mutations is necessary for binding improvement spiegelmers were synthesised with the individual mutations (ins [29G30]; A37U; ins [41G42]), and their combinations and their biological activity were examined in the cell culture model. The execution of the experiments follows the description in Example 8. The sequences of L-RNA are detailed in FIG. 65, whereby L097 corresponds to SEQ ID No. 253, L102 to SEQ ID No. 254, L103 to SEQ ID No. 255, L104 to SEQ ID No. 256, L105 to SEQ ID No. 257, L106 to SEQ ID No. 258, L107 to SEQ ID No. 259, L108 to SEQ ID No. 260, L109 to SEQ ID No. 261.

Each of the spiegelmers was used both in a concentration of 10 µM, and also 100 µM and in its biological effect measured for hCGRP (FIG. 67). It eventuated that none of the individual mutations (L102, L103, L104) inhibits the CGRP effect as strongly as L097 (cf. L097, L102, L103, L104). The same applies for the combination of mutations (cf. L097, L105, L106) with the exception of clone L107: insertion of the two nucleotides between positions 29/30 and 41/42 is adequate for improved binding of the RNA spiegelmer to hCGRP.

The 3 terminus of L097 is strongly purine-rich. To simplify chemical synthesis and increase the yield of the spiegelmer it should be checked as to whether further A-U substitutions can be introduced without the biological activity being influenced.

For this purpose the additional mutations A30U (=L108) or A35U (=L109) (sequences cf. FIG. 65) were introduced to the sequence of L097 and in the cell culture model a dose effect curve of the corresponding spiegelmers was compiled (FIG. 68).

At the same time $IC_{50}$ values of [L108]=5.5 µM and [L109]= 9 µM were ascertained for hCGRP. Compared to spiegelmer L097 the biological effect is not substantially aggravated by the introduction of additional mutations.

EXAMPLE 19

Characterising of Reselection Variants

In the reselection of NOX-504 (see Example 16) substitutions A30U (4 of 22), A30G (5 of 22) and A37U (5 of 22) were observed in the 22 sequences as most frequent mutations.

The tolerated mutation A30U was already known (cf. NOX-504-089, Example 14).

For characterising both other variants the following sequences were generated:

NOX-504-095:
(SEQ. ID. No. 262)
GGA CUG AUG GCG CGG UCC UAU UAC GCC GAG AGG GAG

UGG GGA

This sequence differs from NOX-504-014 by substitutions A30G and A37U.

NOX-504-096:
(SEQ.ID. No. 263)
GGA CUG AUG GCG CGG UCC UAU UAC GCC GAU AGG

GUG UGG GGA

Here sequence NOX-504-089 is expanded through substitution A37U.

Spiegelmers (L-RNA) of both sequences were synthesised and their biological activity examined in the cell culture model. To this end dose effects curves of the spiegelmers were compiled against rat α-CGRP (method, see Example 9), and the ascertained $IC_{50}$ values were compared to those of NOX-504-014 and NOX-504-089. The dose effects curve is illustrated in FIG. 69.

$IC_{50}$ values of [NOX-504-095]=1-2 µM and [NOX-504-096]=10 µM were ascertained for rat CGRP. NOX-504-095 thus binds approximately as well as NOX-504-014 and NOX-504-089 (cf. Example 15), whereas the $IC_{50}$ value of NOX-504-096 is poorer by approximately a factor of 5. As a consequence simplification of the synthesis of the spiegelmer NOX-504-089 is not possible through introducing another AOU substitution (cf. Example 14).

EXAMPLE 20

Binding Spiegelmers NOX-504-014, NOX-504-089, NOX-504-097 to Rat and Human Amylin and Effect as Amylin Antagonists in Cell Culture As already described in Example 15 binding of spiegelmer 504-014 to amylin with a $IC_{50}$ in the nanomolar range is probable. For clearer understanding direct tests were carried out with MCF-7 cells (DSZM-Deutsche Sammlung von Mikroorganismen and Zellkulturen GmbH, Braunschweig, access number 115).

MCF-7-cells were cultivated in the following medium: Ham's F12 nutrient mix and DMEM (1:1) and addition of 10% FBS and 50 units/ml penicillin and 50 µg/ml streptomycin. All further parameters of cultivating, sowing and sequence of the assay for stimulating cAMP production and cAMP measuring are identical to those described in Example 8.

But in the experiments described here it was not CGRP, but amylin, from rats or respectively amylin from humans (both from BACHEM, Bubendorf, Switzerland), which served to stimulate the intracellular cAMP production.

First, dose effect curves of both amylins were recorded to determine the sensitive and the linear range of the assay.

As evident from FIGS. 70 and 71 the die EC50 values are 3.1 µM for rat amylin and 22 µM for human amylin.

The amylin concentrations in the experiments for determining the biological efficacy of the spiegelmers were fixed at 3 µM rat amylin and 30 µM human amylin.

The results are illustrated in FIG. 72 and FIG. 73.

The following spiegelmer concentrations led to half-maximum inhibition of cAMP production:

| Spiegelmer\Peptide | IC$_{50}$ at 3 nM Amylin (Rat) | IC$_{50}$ at 30 nM Amylin (human) |
|---|---|---|
| NOX-504-014 | 19 nM | 15 nM |
| NOX-504-089 | 5 nM | 16 nM |
| NOX-504-097 | 10 nM | 21 nM |

Since here the IC$_{50}$ is in the area of concentration of the stimulating peptide, as a result the portion of the spiegelmer present as free spiegelmer, on the IC$_{50}$ is already clearly under the used concentration. However, for assessing the dissociation constant K$_D$ the portion of free spiegelmer must be employed.

The dissociation constant is calculated from the IC$_{50}$ according to the following formula:

$$K_D = IS_5 - 0.5 \ast [amylin]$$

The following dissociation constants result therefrom:

| Spiegelmer\Peptide | K$_D$ | K$_D$ |
|---|---|---|
| NOX-504-014 | 17.5 nM | <1 nM |
| NOX-504-089 | 3.5 nM | 1 nM |
| NOX-504-097 | 8.5 nM | 6 nM |

EXAMPLE 21

Calorimetric Determining of the Binding Constants and the Activity of NOX-504-L097

Execution

The binding of spiegelmers to human α-CGRP was also determined via the method of isothermal titration calorimetry (ITC) with the VP ITC (Microcal).

For this, 1.465 ml of a 10 μM solution of the spiegelmer was placed in the adiabatic measuring cell of the unit. The binding enthalpy released with addition of 7.5 μl of a 70 μM human α-L-CGRP solution is registered by the device. Through repeated addition of the peptide and measuring in each case of the released binding enthalpies binding constants and activities of the molecules can be determined.

The spiegelmer NOX-504-L097 was measured at 37° C. The result is illustrated in FIG. 74.

Results of ITC Measuring

The binding constant or dissociation constant K$_D$ is the reciprocal value of the association constant K$_A$ (K in the enthalpy diagram) and resulted for binding of the spiegelmer NOX-504-L097 to human α-CGRP at 52 nM. The activity was 80% (FIG. 74).

The features disclosed in the preceding description, claims and diagrams of the invention can be essential both individually and in any combination for carrying out the invention in its various embodiments.

The invention claimed is:

1. An antagonist of CGRP, wherein the antagonist is an L-nucleic acid which binds to CGRP with a $K_D$ of less than 100 nM, wherein said L-nucleic acid comprises SEQ ID NO:246 or an L-nucleic acid at least 85% homologous thereto.

2. The antagonist of CGRP as claimed in claim 1, wherein the CGRP is α-CGRP.

3. The antagonist as claimed in claim 1, wherein the CGRP is β-CGRP.

4. An antagonist of the CGRP receptor, wherein the antagonist is an L-nucleic acid which binds to a ligand of the receptor with a $K_D$ of less than 100 nM, wherein said L-nucleic acid comprises SEQ ID NO:246 or an L-nucleic acid at least 85% homologous thereto.

5. The antagonist as claimed in claim 4, wherein the ligand is α-CGRP.

6. The antagonist as claimed in claim 4, wherein the ligand is β-CGRP.

7. An L-nucleic acid which binds to CGRP with a $K_D$ of less than 100 nM, wherein said L-nucleic acid comprises SEQ ID NO:246 or an L-nucleic acid at least 85% homologous thereto.

8. The nucleic acid as claimed in claim 7, wherein the CGRP is α-CGRP.

9. The nucleic acid as claimed in claim 7, wherein the CGRP is β-CGRP.

10. The nucleic acid as claimed in claim 7, wherein the nucleic acid is selected from the group consisting of DNA, RNA and combinations thereof.

11. The nucleic acid as claimed in claim 7, wherein the $K_D$ value of the nucleic acid is selected from the group consisting of less than 0.05 μM and less than 0.01 μM.

12. The nucleic acid as claimed in claim 7, wherein the $K_D$ value of the nucleic acid is selected from the group consisting of more than 10 nM, more than 1 nM and more than 0.01 nM.

13. The nucleic acid as claimed in claim 7, wherein the nucleic acid comprises a minimal binding motif.

14. The nucleic acid as claimed in claim 7, wherein said nucleic acid has a length selected from the group consisting of 15 to 150 nucleotides, 20 to 100 nucleotides, 20 to 80 nucleotides, 20 to 60 nucleotides, 20 to 50 nucleotides and 30 to 50, and 25 to 45 nucleotides.

15. The nucleic acid as claimed in claim 7, wherein the nucleic acid has a two-, three- or multi-partite structure.

16. A method of inhibiting CGRP, the CGRP receptor system or both comprising exposing CGRP or a CGRP receptor system to the nucleic acid as claimed in claim 7.

17. A composition comprising the nucleic acid of claim 7, 8 or 9 and a pharmaceutically acceptable carrier.

18. A complex comprising CGRP and the nucleic acid of claim 7, 8 or 9.

19. The antagonist of CGRP of claim 1, wherein said L-nucleic acid is at least 90% homologous to SEQ ID NO:246.

20. The antagonist of CGRP of claim 19, wherein said L-nucleic acid is at least 95% homologous to SEQ ID NO:246.

21. The antagonist of the CGRP receptor of claim 4, wherein said L-nucleic acid is at least 90% homologous to SEQ ID NO:246.

22. The antagonist of the CGRP receptor of claim 21, wherein said L-nucleic acid is at least 95% homologous to SEQ ID NO:246.

23. The L-nucleic acid of claim 7, wherein said L-nucleic acid is at least 90% homologous to SEQ ID NO:246.

24. The L-nucleic acid of claim 23, wherein said L-nucleic acid is at least 95% homologous to SEQ ID NO:246.

25. The nucleic acid of claim 13, where said motif comprises the sequence, GGACUGAUGGCGCGGUCCUA-UUACGCCGAXDAGGGWGWGGGGR (SEQ ID NO:286), wherein X is G or absent; D is G, U or A; W is A or U and R is G or A.

* * * * *